United States Patent
Sato et al.

(10) Patent No.: US 7,799,775 B2
(45) Date of Patent: Sep. 21, 2010

(54) PYRIMIDINE DERIVATIVES

(75) Inventors: Michitaka Sato, Kawasaki (JP); Teruaki Matsui, Kawasaki (JP); Akira Asagarasu, Machida (JP); Hiroyuki Hayashi, Kawasaki (JP); Sei-ichi Araki, Kawasaki (JP); Satoru Tamaoki, Kamakura (JP); Nobuyuki Takahashi, Handa (JP); Yukinao Yamauchi, Kawasaki (JP); Yoshiko Yamamoto, Kawasaki (JP); Norio Yamamoto, Kawasaki (JP); Chisato Ogawa, Kawasaki (JP)

(73) Assignee: ASKA Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/590,707

(22) PCT Filed: Feb. 25, 2005

(86) PCT No.: PCT/JP2005/003691

§ 371 (c)(1), (2), (4) Date: Aug. 25, 2006

(87) PCT Pub. No.: WO2005/082887

PCT Pub. Date: Sep. 9, 2005

(65) Prior Publication Data

US 2007/0197551 A1  Aug. 23, 2007

(30) Foreign Application Priority Data

Feb. 26, 2004 (JP) ............................. 2004-052040
Nov. 5, 2004 (JP) ............................. 2004-322858

(51) Int. Cl.
| | |
|---|---|
| *A01N 43/54* | (2006.01) |
| *A01N 43/90* | (2006.01) |
| *A01N 43/04* | (2006.01) |
| *A01N 43/58* | (2006.01) |
| *A01N 43/60* | (2006.01) |
| *A61K 31/54* | (2006.01) |
| *A61K 31/505* | (2006.01) |
| *A61K 31/519* | (2006.01) |
| *A61K 31/535* | (2006.01) |
| *A61K 31/675* | (2006.01) |
| *A61K 31/50* | (2006.01) |
| *A61K 31/495* | (2006.01) |

(52) U.S. Cl. ............. 514/222.2; 514/228.8; 514/260.1; 514/264.1; 514/267; 544/55; 544/88; 544/249; 544/250; 544/255

(58) Field of Classification Search ................. 514/267, 514/260.1, 264.1, 228.8, 222.2; 544/55, 544/88, 250, 255, 249, 253
See application file for complete search history.

(56) References Cited

FOREIGN PATENT DOCUMENTS

| CA | 2431406 | * | 6/2002 |
|---|---|---|---|
| EP | 0 364 598 | * | 4/1990 |
| GB | 99/17755 | | 4/1999 |
| IE | 02/30406 | | 4/2002 |
| JP | 2001-518495 | | 10/2001 |
| WO | 02/48117 | | 6/2002 |

OTHER PUBLICATIONS

Cryan, J., et al., 5-HT1A and Beyond: The Role of Serotonin and its Receptors in Depression and the Antidepressant Response, Hum. Psychopharmacol. Clin. Exp. 15, 113-135 (2000).*

(Continued)

*Primary Examiner*—James O Wilson
*Assistant Examiner*—Erich A Leeser
(74) *Attorney, Agent, or Firm*—Wenderoth, Lind & Ponack, L.L.P.

(57) ABSTRACT

This invention provides pyrimidine derivatives represented by a formula,

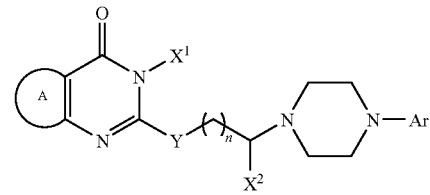

(I)

in the formula,
ring A stands for carbocyclic group or heterocyclic group,
$X^1$ stands for hydrogen, lower alkyl, amino, etc.,
$X^2$ stands for hydrogen or lower alkyl,
Y stands for a direct bond or sulfur or nitrogen,
n stands for an integer of 0-4, and
Ar stands for a group of the following formula,

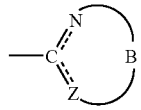

or a salt thereof, which concurrently exhibit $5\text{-HT}_{1A}$ agonistic activity and $5\text{-HT}_3$ antagonistic activity and are useful for therapy and treatments of diseases such as IBS.

The invention furthermore provides a therapeutic method of IBS, characterized by having $5\text{-HT}_{1A}$ agonistic activity and $5\text{-HT}_3$ antagonistic activity work simultaneously and cooperatively in vivo, which comprises either administering $5\text{-HT}_3$ antagonistic agent which concurrently exhibits $5\text{-HT}_{1A}$ agonistic activity, or administering $5\text{-HT}_{1A}$ agonistic agent and $5\text{-HT}_3$ antagonistic agent simultaneously, in sequence or at an interval.

19 Claims, No Drawings

OTHER PUBLICATIONS

Modica et al., High Potent and Selective Arylpiperazine Derivatives as Ligands for the 5-HT1A Receptor, Bioorganic & Medicinal Chemistry Letters, 10(10), 1089-1092 (2000).*

3D-QSAR Using "Multiconformer" Alignment: The Use of HASL in the Analysis of 5-HT1A Thienopyrimidinone Ligands, Journal of Computer-Aided Molecular Design, 14(7), 647-657 (2000).*

Modica, et al., [[(Arylpiperazinyl)alkyl]thio]thieno[2,3-d]pyrimidinone Derivatives as High-Affinity, Selective 5-HT1A Receptor Ligands, J. Med. Chem. 40, 574-585 (1997).*

Modica Marie et al., "[[(Arylpiperazinyl)alkyl]thio]thieno[2,3-d]pyrimidinone Derivatives as High-Affinity, Selective 5-HT$_{1A}$ Receptor Ligands", J. Med. Chem. 1997, 40, 574-585.

Modica Maria et al., "High affinity and selectivity of [[(Arylpiperazinyl)alkyl]thio]thieno[2,3-d]pyrimidinone derivatives for the 5-HT$_{1A}$ receptor. Synthesis and structure-affinity relationships", Eur. J. Med. Chem. 35 (2000) 677-689.

López-Rodríguez Maria L. et al., "Design and Synthesis of New Benzimidazole-Arylpiperazine Derivatives Acting as Mixed 5-HT$_{1A}$/5-HT$_3$ Ligands", Bioorganic & Medicinal Chemistry Letters 13 (2003) 3177-3180.

Abe Michikazu et al., "Reduction of Wrap Restraint Stress-Induced Defecation by MKC-242, a Novel Benzodioxan Derivative, via 5-HT$_{1A}$-Receptor Agonist Action in Rats", Jpn. J. Pharmacol. 77, 211-217 (1998).

Merino Isidro, "Synthesis and anti-HIV-1 activities of new pyrimido [5,4-b]indoles", Il Farmaco 54 (1999) 255-264.

Supplementary European Search Report issued Mar. 25, 2009 in counterpart European Application No. 05 71 9969.

* cited by examiner

PYRIMIDINE DERIVATIVES

TECHNICAL FIELD

This invention relates to pyrimidine derivatives or salts thereof which exhibit serotonin receptor subtype 1A ("5-HT$_{1A}$") agonistic activity and serotonin receptor subtype 3 ("5-HT$_3$") antagonistic activity concurrently, and which are useful as treating agent of irritable bowel syndrome ("IBS") and the like.

The invention also relates to therapy of IBS and the like, which comprises having the 5-HT$_{1A}$ agonistic activity and HT$_3$ antagonistic activity synergistically and simultaneously work in vivo.

BACKGROUND ART

IBS is a functional disease of which main symptoms are evacuation abnormalities such as diarrhea or constipation and bellyache, and is not caused by intestinal organic lesion. This disease is developed as the result of mutual association of intestinal motion disorder, viscerosensory anaphylaxis and psychological and social factors.

Because 5-HT$_3$ in intestine participates in intestinal contraction, secretion of intestinal juice, peristalsis and content transport, diarrheal symptoms can be improved by administration of 5-HT$_3$ antagonist. In the United States, alosetron which is a 5-HT$_3$ antagonist has been approved as an IBS treating agent. Also other 5-HT$_3$ antagonists, for example, ondansetron, alosetron, tropisetron, granisetron and so on are disclosed in WO 99/17755 Pamphlet and U.S. Pat. No. 6,284,770, which publications disclose that 5-HT$_3$ antagonistic medicines are useful for IBS treating agent.

On the other hand, because psychological and social factors are recognized to be one of the origins of IBS, administration of benzodiazepine antianxiety agent in IBS therapy has been experimented. Recently, novel serotonin agonistic antianxiety agent, for example, non-benzodiazepine compounds showing less adverse effect are under development and of which application for IBS therapy is expected.

J. Med. Chem., 40, 574-585 (1997) and Eur. J. Med. Chem., 35, 677-689 (2000) disclose pyrimidinone derivatives having selective affinity to 5-HT$_{1A}$. In these literature references, the derivatives' selectivity for 5-HT$_{1A}$ over α$_1$ receptor was investigated. Also EP 343,050, WO 01/32659 Pamphlet, JP 2001-97978A and J. Med. Chem., 32, 1147-1156 (1989) disclose piperazinyl isoquinoline derivatives, piperazinyl thienopyridine derivatives and piperazinyl furopylidine derivatives which exhibit affinity to 5-HT$_{1A}$ and the like. While these references describe psychic action based on 5-HT$_{1A}$ agonistic activity, they are silent on 5-HT$_3$. They contain no disclosure or suggestion on the named derivatives' application to IBS or associated diseases based on their activities on the two receptors.

J. Med. Chem., 42, 4362-4379 (1999) discloses piperazinyl-pyrazine derivatives having selective affinity to 5-HT$_3$, but their action is agonistic.

In Japan, tandospirone which is a 5-HT$_{1A}$ agonist is marketed, of which indication is stress-caused dyspeptic ulcer. This indication is attributable to removal of stress by the antianxiety action of tandospirone, and IBS is not included in its indications.

As above, currently many 5-HT$_3$ antagonists and 5-HT$_{1A}$ agonists are developed or marketed, but all of these 5-HT$_3$ antagonists and 5-HT$_{1A}$ agonists have unilateral activities. Because IBS has plural origins, therapeutic effect of these compounds on IBS is insufficient.

Only recently, Bioorg. Med. Chem. Lett., 13, 3177-3180 (2003) disclosed compounds which exhibit affinity to both of the receptors 5-HT$_3$ and 5-HT$_{1A}$. These compounds, however, are benzimidazole-arypiperazine derivatives, and the literature refers only to the compounds' action on nervous system, containing no disclosure or suggestion on combination of 5-HT$_3$ antagonistic activity and 5-HT$_{1A}$ agonistic activity on IBS or the effect based on the combination.

We have engaged in concentrative studies to discover simultaneous expression in vivo of 5-HT$_3$ antagonistic activity and 5-HT$_{1A}$ agonistic activity is very effective for treating the diseases associated with both hyperactivity or expression enhancement of 5-HT$_3$ and hypoactivity of 5-HT$_{1A}$, in particular, treating IBS.

DISCLOSURE OF THE INVENTION

Thus, the present invention provides novel pyrimidine derivatives represented by the following formula (I)

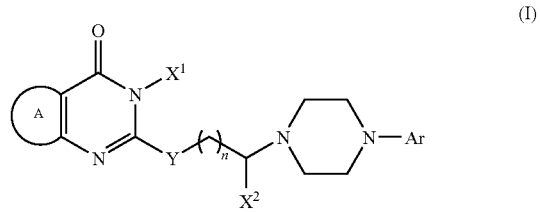

(I)

in which ring A stands for a carbocyclic group or heterocyclic group,

X$^1$ stands for hydrogen, amino, lower alkylamino, di-lower alkylamino, lower alkylideneamino, lower alkyl, phenyl lower alkyl or substituted or unsubstituted phenyl, X$^2$ stands for hydrogen or lower alkyl, Y stands for a direct bond, sulfur or nitrogen, n is 0 or an integer of 1-4, Ar stands for a group represented by the following formula,

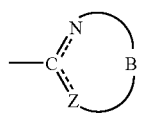

which is either unsubstituted or substituted with substituent(s) selected from halogen, lower alkyl, hydroxyl, lower alkoxy and phenyl, and in which Z stands for carbon, oxygen or sulfur, B stands for the residual member(s) necessary for completing a monocyclic or polycyclic, nitrogen-containing heterocyclic ring group, which may form a condensed ring together with the remainder of the group of the above formula, and the dotted lines indicate optionally existing bonds, or their pharmaceutically acceptable salts, which concurrently possess 5-HT$_{1A}$ agonistic activity and 5-HT$_3$ antagonistic activity.

The invention also provides a therapeutic method of IBS characterized by exerting 5-HT$_{1A}$ agonistic activity and 5-HT$_3$ antagonistic activity in vivo simultaneously and cooperatively, which comprises administering to human being or other mammals who require IBS treatment, 5-HT$_3$ antagonistic agent concurrently exhibiting 5-HT$_{1A}$ agonistic activity, or administering 5-HT$_{1A}$ agonistic agent and 5-HT$_3$ antagonistic agent simultaneously, or in sequence, or at an interval.

Hereinafter the invention is explained in further details.

In the present specification, the term "lower" means that the groups referred to by this term have not more than six carbons, preferably not more than 4 carbons.

"Lower alkyl" has either straight chain or branched chain structure, examples of which including methyl, ethyl, n-propyl, isopropyl, n-butyl, isobutyl, sec-butyl, tert-butyl, n-pentyl and n-hexyl. Of those, C$_1$-C$_4$ alkyl such as methyl, ethyl, n-propyl, isopropyl and n-butyl are preferred. As "lower alkoxy", for example, methoxy, ethoxy, n-propoxy, isopropoxy, n-butoxy, isobutyloxy, sec-butyloxy, n-pentyloxy and n-hexyloxy can be named, among which C$_1$-C$_4$ alkoxy such as methoxy, ethoxy, n-propoxy, isopropoxy and n-butoxy are preferred.

"Phenyl lower alkyl" in the definition of X$^1$ signifies lower alkyl as exemplified in the above, which are substituted with phenyl, examples of which including benzyl, phenylethyl, phenylpropyl and phenylbutyl. Of these, benzyl is particularly preferred. Also as the substituent on phenyl of "substituted or unsubstituted phenyl" in the definition of X$^1$, for example, halogen, lower alkyl and lower alkoxy can be named, among which lower alkoxy is preferred.

"Lower alkylamino" in the definition of X$^1$ signifies amino which is mono-substituted with lower alkyl as above exemplified, specific examples including N-methylamino, N-ethylamino, N-n-propylamino, N-isopropylamino, N-n-butylamino, N-isobutylamino, N-sec-butylamino, N-tert-butylamino, N-n-pentylamino and N-n-hexylamino. Of these, C$_1$-C$_4$ alkylamino such as N-methylamino, N-ethylamino, N-n-propylamino, N-isopropylamino and N-n-butylamino are particularly preferred. "Di-lower alkylamino" in the definition of X$^1$ signifies amino which is di-substituted with same or different lower alkyl as above exemplified, specific examples including N,N-dimethylamino, N,N-diethylamino, N,N-di-n-propylamino, N,N-diisopropylamino, N-methyl-N-ethylamino, N-methyl-N-n-propylamino, N-ethyl-N-isopropylamino, N-methyl-N-n-butylamino, N-ethyl-N-isobutylamino, N-isopropyl-N-sec-butylamino, N-n-propyl-N-n-pentylamino and N-methyl-N-n-hexylamino. Of these, di-C$_1$-C$_4$ alkylamino such as N,N-dimethylamino, N-methyl-N-ethylamino, N-ethyl-N-isopropylamino and N-methyl-N-n-butylamino are particularly preferred. "Lower alkylideneamino" in the definition of X$^1$ signifies amino which is substituted with lower alkylidene, specific examples including N-isopropylideneamino.

"Halogen" includes fluorine, chlorine, bromine and iodine, among which fluorine, chlorine and bromine are particularly preferred.

Where the ring A in the formula (I) stands for carbocyclic group, preferred examples of the carbocyclic group include those represented by the following formulae i)-iv),

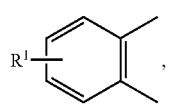

i)

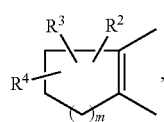

ii)

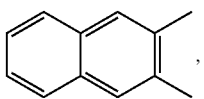

iii)

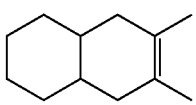

iv)

in which

R$^1$ stands for hydrogen, halogen, lower alkyl, halogenated lower alkyl, lower alkoxy, carboxyl, lower alkoxycarbonyl, phenyl, amino, hydrazino or nitro, R$^2$, R$^3$ and R$^4$ either stand for, independently from each other, hydrogen, halogen, lower alkyl, lower alkoxy, phenyl or hydroxyl; or two out of R$^2$, R$^3$ and R$^4$ together stand for oxo or lower alkylenedioxy, and m is an integer of 1-3.

Where the ring A in the formula (I) stands for heterocyclic group, the heterocyclic group may be a monocycle or may form a condensed ring with another ring, preferred examples of which include those of the following formulae v)-xv),

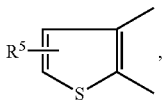

v)

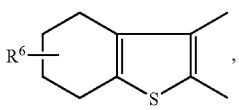

vi)

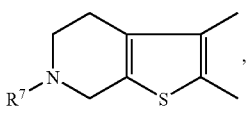

vii)

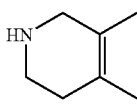

viii)

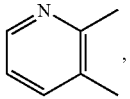

ix)

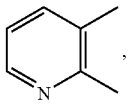

x)

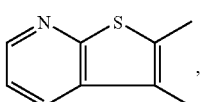

xi)

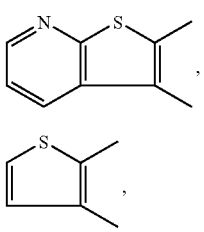

xii)

-continued

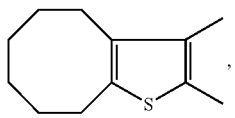

xiii)

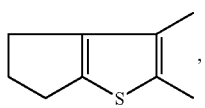

xiv)

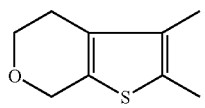

xv)

in which
R[5] stands for hydrogen, lower alkyl, carboxyl or lower alkoxycarbonyl,
R[6] stands for hydrogen or lower alkyl, and
R[7] stands for hydrogen, lower alkyl, lower alkanoyl, lower alkoxycarbonyl or phenyl lower alkoxycarbonyl.

As the ring A, groups of the formula i) or ii) are preferred, those of the formula ii) being particularly preferred.

In the above definition of ring A, "halogenated lower alkyl" signifies lower alkyl whose at least one hydrogen is substituted with halogen, examples of which including chloromethyl, 2-bromoethyl, 3-fluoropropyl, 4-iodoisopentyl, dichloromethyl, 1,2-dibromoethyl, trifluoromethyl and 2,2,2-trichloroethyl. Of these, chloromethyl and trifluoromethyl are particularly preferred.

"Lower alkoxycarbonyl" in the definition of ring A signifies lower alkoxy-CO-group, for example, methoxycarbonyl, ethoxy-carbonyl, isopropoxycarbonyl and tert-butoxycarbonyl. Of these, methoxycarbonyl and ethoxycarbonyl are particularly preferred.

As examples of "lower alkylenedioxy" in the definition of ring A, methylenedioxy, ethylenedioxy and trimethylenedioxy can be named, ethylenedioxy being particularly preferred.

"Lower alkanoyl" in the definition of ring A signifies lower alkyl-CO-group, for example, acetyl, propionyl, butyryl, isobutyryl, valeryl, isovaleryl or pivaloyl. Of these, acetyl and propionyl are particularly preferred.

"Phenyl lower alkoxycarbonyl" in the definition of ring A signifies lower alkoxycarbonyl as explained in the above, which is substituted with phenyl, for example, benzyloxycarbonyl, 1-phenylethoxycarbonyl, 2-phenylethoxycarbonyl, 3-phenylpropoxy-carbonyl, 1-benzylethoxycarbonyl or 1-benzyl-1-methylethoxy-carbonyl. Of these, benzyloxycarbonyl, 2-phenylethoxycarbonyl and 3-phenylpropoxycarbonyl are preferred.

The group represented by the formula,

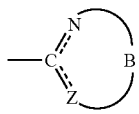

in which Z and B have the previously given significations, in the definition of Ar in the formula(I) includes, for example, monocyclic or polycyclic, nitrogen-containing heterocyclic groups which are either unsubstituted or substituted with a substituent selected from halogen, lower alkyl, hydroxyl, lower alkoxy and phenyl.

As the skeletal structure of the nitrogen-containing heterocyclic group, those of the following formulae,

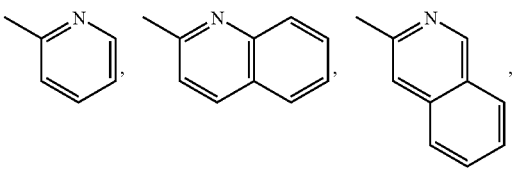

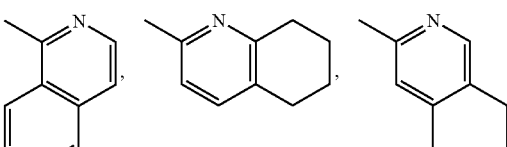

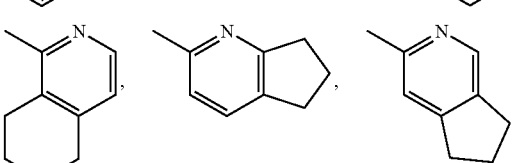

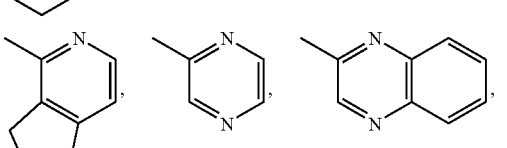

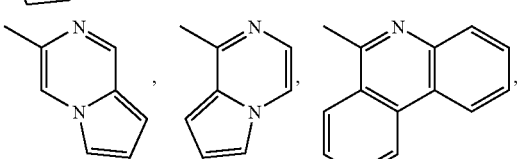

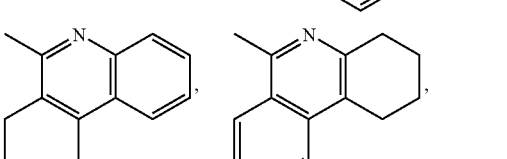

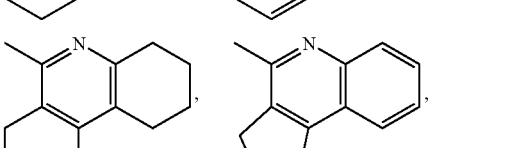

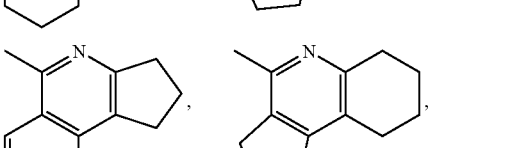

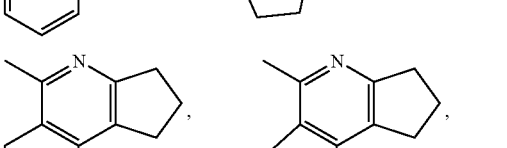

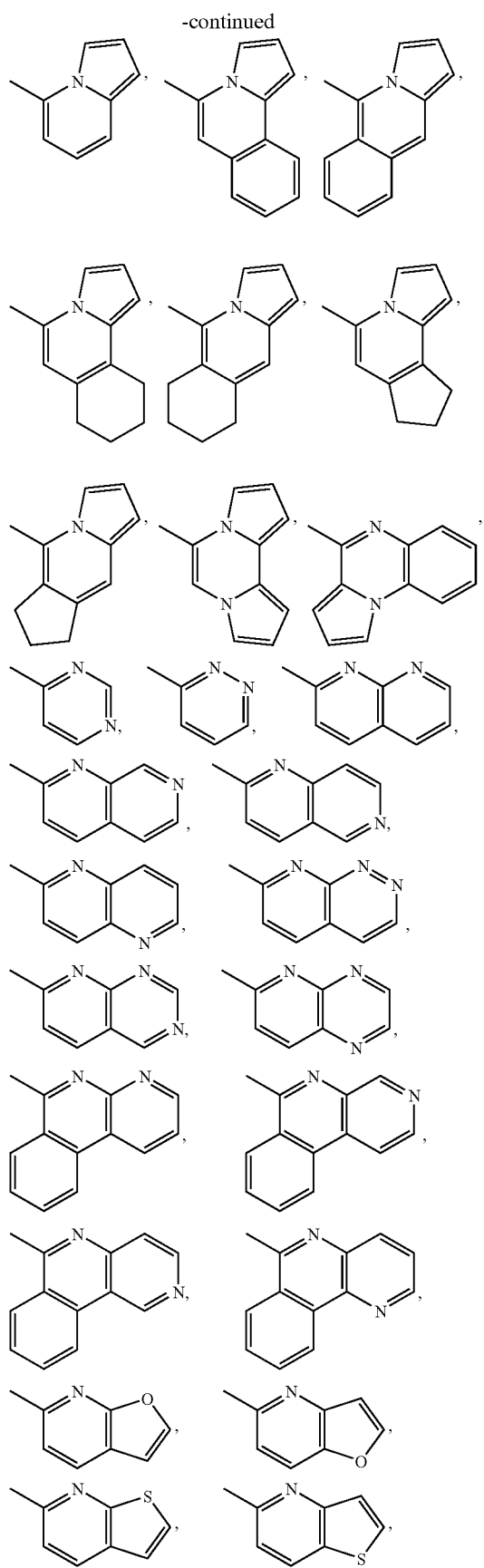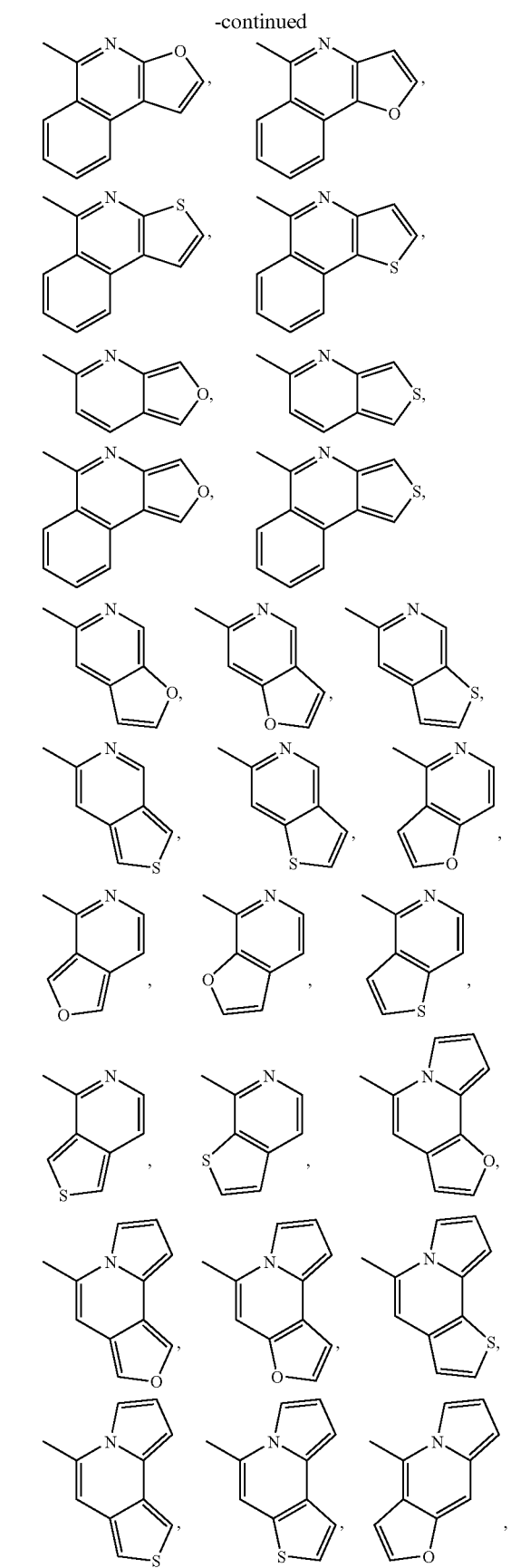

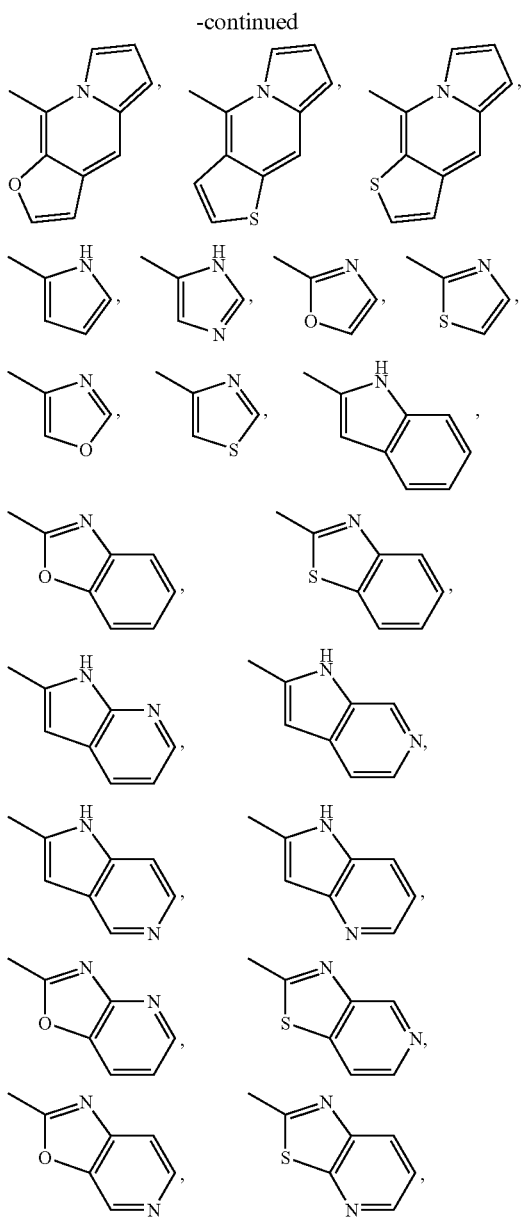

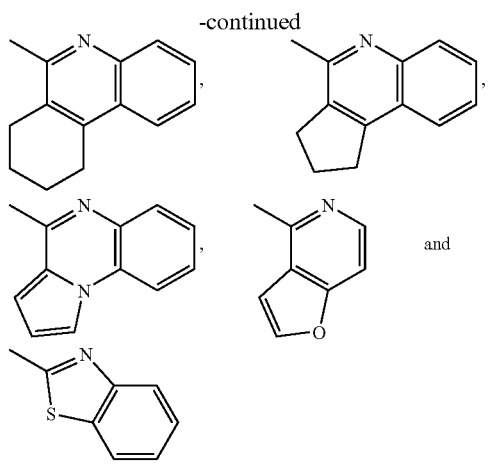

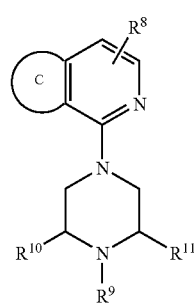

can be named. Of these, those of the following formulae,

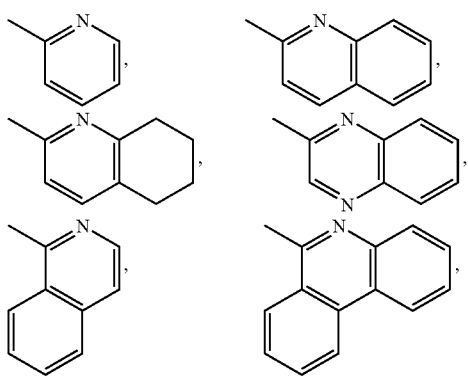

are particularly preferred.

"5-HT$_3$ antagonistic agent concurrently exhibiting 5-HT$_{1A}$ agonistic activity" in the present specification may have still other pharmacological activity(ies) in addition to 5-HT$_{1A}$ agonistic activity and 5-HT$_3$ antagonistic activity. More specifically, as examples of such antagonistic agent, pyrimidine derivatives represented by the given formula (I) and pharmaceutically acceptable salts thereof, and piperazinylpyridine derivatives represented by the following formula (II), (II)

in which ring C stands for unsubstituted benzene ring or an unsubstituted heterocyclic group selected from pyridine, furan and thiophene; benzene ring substituted with substituent(s) selected from halogen, lower alkyl, phenyl, hydroxyl, lower alkoxy, phenyl lower alkoxy (the phenyl moiety being either unsubstituted or halogen-substituted), amino, lower alkylamino, di-lower alkylamino, lower alkylthio, lower alkylsulfinyl and aminosulfonyloxy; or heterocyclic group selected from halogen- or lower alkyl-substituted pyridine, furan and thiophene, R$^8$ stands for hydrogen, halogen or lower alkyl, R$^9$ stands for hydrogen, lower alkyl, phenyl lower alkyl (the phenyl moiety being unsubstituted or substituted with substituent(s) selected from halogen, lower alkyl and lower alkoxy), amino lower alkyl (the amino moiety being either unsubstituted or mono- or di-substituted with lower alkyl, or optionally forming a cyclic imido group) or phenyl cycloalkyl (the phenyl moiety being either unsubstituted or substituted with substituent(s) selected from halogen, lower alkyl and lower alkoxy), $R^{10}$ stands for hydrogen or lower alkyl, or $R^9$ and $R^{10}$ may together form the residual members of pyrrolidine ring or piperidine ring (which may be unsubstituted or substituted with substituent(s) selected from hydroxyl, lower alkoxy and phenyl lower alkoxy), and $R^{11}$ stands for hydrogen or lower alkyl, or their pharmaceutically acceptable salts can be named.

"Phenyl lower alkoxy (the phenyl moiety being either unsubstituted or halogen-substituted)" in the definition of ring C in the formula (II) signifies lower alkoxy which is substituted with unsubstituted or halogen-substituted phenyl, examples of which including benzyloxy, phenylethoxy, phenylpropyloxy, phenylbutoxy, 2-chlorobenzyloxy, 2-bromobenzyloxy, 2-fluorobenzyloxy, 3-bromobenzyloxy, 4-fluorobenzyloxy, 2,4-dichlorobenzyloxy and 1-(4-fluorophenylmethyl)ethoxy. Of these, unsubstituted benzyloxy and benzyloxy substituted with one halogen atom are particularly preferred.

"Lower alkylamino" in the definition of ring C in the formula (II) signifies amino which is mono-substituted with lower alkyl, examples of which including N-methylamino, N-ethylamino, N-n-propylamino and N-sec-butylamino. Of these, N-methylamino and N-ethylamino are particularly preferred. Also "di-lower alkylamino" in the definition of ring C signifies amino which is di-substituted with same or different lower alkyl groups, examples of which including N,N-dimethylamino, N,N-diethylamino, N,N-diisopropylamino, N-methyl-N-ethylamino and N-methyl-N-tert-butylamino. Of these, N,N-dimethylamino and N,N-diethylamino are particularly preferred.

"Lower alkylthio" in the definition of ring C in the formula (II) signifies lower alkyl-S-group, examples of which including methylthio, ethylthio and isobutylthio. Of these, methylthio is particularly preferred. "Lower alkylsulfinyl" in the definition of ring C signifies lower alkyl-SO— group, examples of which including methylsulfinyl, ethylsulfinyl and isopropylsulfinyl. Of these, methylsulfinyl is particularly preferred.

Furthermore, where the ring C in the formula (II) stands for "unsubstituted heterocyclic group selected from pyridine, furan and thiophene" or "heterocyclic group selected from pyridine, furan and thiophene", as the heterocyclic ring formed by condensation of such ring C with the pyridine ring in the formula (II), for example, 1,6-naphthyridine, 2,6-naphthyridine, 2,7-naphthyridine, 1,7-naphthyridine, furo[3,2-c]pyridine, furo[3,4-c]pyridine, furo[2,3-c]pyridine, thieno[3,2-c]pyridine, thieno[3,4-c]pyridine and thieno[2,3-c]pyridine can be named. Of these, 1,6-naphthyridine, 2,6-naphthyridine, 2,7-naphthyridine, 1,7-naphthyridine, furo[3,2-c]pyridine, furo[2,3-c]pyridine, thieno[3,2-c]pyridine and thieno[2,3-c]pyridine are preferred, in particular, 1,6-naphthyridine, 1,7-naphthyridine, furo[2,3-c]pyridine and thieno[2,3-c]pyridine are preferred.

"Phenyl lower alkyl (the phenyl moiety being unsubstituted or substituted with a substituent selected from halogen, lower alkyl and lower alkoxy)" in the definition of $R^9$ in the formula (II) signifies lower alkyl which is substituted with substituted or unsubstituted phenyl. As the substituent on the phenyl, for example, 2-fluoro, 3-fluoro, 4-fluoro, 2-chloro, 4-chloro, 3-bromo, 4-bromo, 4-iodo, 2-methyl, 3-methyl, 4-methyl, 2-ethyl, 3-ethyl, 3-n-propyl, 4-isopropyl, 2-methoxy, 3-methoxy, 4-methoxy, 3-ethoxy and 4-isopropyloxy can be named. Of these, 4-fluoro, 4-chloro, 4-bromo, 3-methyl, 3-ethyl, 3-methoxy and 3-ethoxy are preferred. Also as the lower alkyl in the above definition, for example, methyl, ethyl, n-propyl and n-butyl are preferred. Thus, as preferred specific examples of "phenyl lower alkyl (the phenyl moiety being either unsubstituted or substituted with a substituent selected from halogen, lower alkyl and lower alkoxy)", benzyl, 4-fluorobenzyl, 2-(4-chlorophenyl)ethyl, 3-(4-bromophenyl)-n-propyl, 3-methylbenzyl, 3-(3-ethylphenyl)butyl, 3-methoxybenzyl and 4-(3-methoxyphenyl)butyl can be named.

"Amino lower alkyl (the amino moiety being either unsubstituted or mono- or di-substituted with lower alkyl, or may form cyclic imido)" in the definition of $R^9$ in the formula (II) signifies lower alkyl substituted with amino, wherein the "amino" includes not only unsubstituted amino but also amino which is substituted with one or two lower alkyl groups and amino which formed cyclic imido. As preferred lower alkyl substituent on the amino, methyl, ethyl, n-propyl and n-butyl can be named. Thus, as preferred specific examples of "amino lower alkyl (the amino moiety being either unsubstituted or mono- or di-substituted with lower alkyl, or may form cyclic imido)", aminomethyl, 2-aminoethyl, 3-aminopropyl, 4-aminobutyl, 2-(N-methylamino)ethyl, 3-(N,N-dimethylamino)propyl and 3-phthaliminopropyl can be named.

Again, "phenyl cycloalkyl (the phenyl moiety being either unsubstituted or substituted with a substituent selected from halogen, lower alkyl and lower alkoxy)" in the definition of $R^9$ of the formula (II) signifies cycloalkyl which is substituted with unsubstituted phenyl or substituted phenyl with a substituent selected from halogen, lower alkyl and lower alkoxy, wherein the substituent on the phenyl can be any of those named as examples of substituents on the phenyl group in "phenyl lower alkyl" in the definition of $R^9$. As the cycloalkyl, cyclopentyl, cyclohexyl, cycloheptyl, cyclooctyl and the like can be named, among which cyclohexyl is preferred. As the substitution site of the phenyl in the "phenyl cycloalkyl", 3-position is preferred for cyclopentyl, 4-position is preferred for cyclohexyl and cycloheptyl, and 5-position is preferred for cyclooctyl. Thus, as preferred specific examples of "phenyl cycloalkyl (the phenyl moiety being either unsubstituted or substituted with a substituent selected from halogen, lower alkyl and lower alkoxy)", 4-(4-fluorophenyl)cyclohexyl, 4-(4-chlorophenyl)cyclohexyl, 4-(4-bromophenyl)cyclohexyl, 4-(3-methylphenyl)cyclohexyl, 4-(3-ethylphenyl)cyclohexyl, 4-(3-methoxyphenyl)cyclohexyl and 4-(3-ethoxyphenyl)cyclohexyl can be named.

As the substituent on the benzene ring in the isoquinoline ring which is formed when ring C in the formula (II) stands for benzene ring, for example, 5-chloro, 6-chloro, 7-chloro, 8-chloro, 5-fluoro, 7-fluoro, 5-bromo, 7-bromo, 5-iodo, 5-methyl, 6-methyl, 7-methyl, 8-methyl, 5-ethyl, 5-n-propyl, 5-sec-butyl, 5-phenyl, 6-phenyl, 7-phenyl, 8-phenyl, 5-hydroxy, 6-hydroxy, 7-hydroxy, 8-hydroxy, 5-methoxy, 6-methoxy, 7-methoxy, 8-methoxy, 5-ethoxy, 7-ethoxy, 5-isopropyloxy, 5-tert-butyloxy, 5-benzyloxy, 7-benzyloxy, 5-(2-phenyl)ethoxy, 5-(4-fluorophenyl)methoxy, 7-(4-fluorophenyl)-methoxy, 5-(2-chlorophenyl)methoxy, 5-(3-bromophenyl)methoxy, 5-(2-fluoro-4-chlorophenyl)methoxy, 6-(2,4-dichlorophenyl)ethoxy, 5-amino, 6-amino, 7-amino, 8-amino, 5-(N-methylamino), 7-(N-methylamino), 5-(N-ethylamino), 5-(N-isobutylamino), 6-(N-tert-butylamino), 5-(N,N-dimethylamino), 7-(N,N-dimethyl-amino), 5-(N,N-diisopropylamino), 6-(N-methyl-N-n-butylamino), 5-methylthio, 6-methylthio, 7-methylthio, 8-methylthio, 5-ethylthio, 5-n-propylthio, 5-isobutylthio, 6-isopropylthio, 5-methylsulfinyl, 6-methylsulfinyl, 7-methylsulfinyl, 8-methylsulfinyl, 5-ethylsulfinyl, 6-isopropylsulfinyl, 7-tert-butylsulfinyl, 8-n-pentylsulfinyl, 5-aminosulfonyloxy, 6-aminosulfonyloxy, 7-aminosulfonyloxy and 8-aminosulfonyloxy can be named. Of these, 5-chloro, 6-chloro, 7-chloro, 7-fluoro, 7-bromo, 7-methyl, 7-phenyl, 7-hydroxy, 5-methoxy, 6-methoxy, 7-methoxy, 7-ethoxy, 7-benzyloxy, 7-(4-fluorophenyl)-methoxy, 7-(N-methylamino), 7-(N,N-dimethylamino), 7-methylthio, 7-methylsulfinyl and 7-aminosulfonyloxy are preferred. In particular, 6-chloro, 7-chloro, 7-fluoro, 7-bromo, 7-methyl, 7-hydroxy, 7-methoxy, 7-ethoxy, 7-benzyloxy, 7-(4-fluorophenyl)methoxy, 7-(N,N-dimethylamino) and 7-methylthio are preferred.

Also as the substituent on the pyridine ring in the isoquinoline ring which is formed when the ring C in the formula (II) stands for benzene ring, i.e., as the group $R^8$ in the formula (II), for example, 3-fluoro, 4-fluoro, 3-chloro, 4-chloro, 3-bromo, 4-bromo, 3-iodo, 4-iodo, 3-methyl, 4-methyl, 3-ethyl, 4-ethyl, 3-n-propyl, 4-isopropyl, 3-tert-butyl, 4-n-butyl, 3-isopentyl and 4-(1,2-dimethyl-butyl) can be named. Of these, 3-chloro, 4-chloro, 3-methyl and 4-methyl are preferred. Thus, as the preferred substituent on the isoquinoline ring which is formed when the ring C in the formula (II) stands for benzene ring, 5-chloro, 6-chloro, 7-chloro, 7-fluoro, 7-bromo, 7-methyl, 7-phenyl, 7-hydroxy, 5-methoxy, 6-methoxy, 7-methoxy, 7-ethoxy, 7-benzyloxy, 7-(4-fluorophenyl)methoxy, 7-(N-methylamino), 7-(N,N-dimethylamino), 7-methylthio, 7-methylsulfinyl, 7-aminosulfonyloxy, 3-methyl-5-chloro, 4-methyl-6-chloro, 3-methyl-7-chloro, 3-methyl-7-fluoro, 3,7-dimethyl, 3-methyl-7-hydroxy, 4-chloro-7-methoxy, 4-methyl-7-benzyloxy, 3-chloro-7-(4-fluoro-phenyl)methoxy, 3-chloro-7-(N-methylamino), 4-chloro-7-(N,N-dimethylamino), 3-methyl-7-methoxy, 4-methyl-7-methoxy and 3-chloro-7-methyl can be named.

Where the heterocyclic ring which is formed when the ring C in the formula (II) stands for pyridine ring is 1,6-naphthyridine ring, as substituent on the 1,6-naphthyridine ring, for example, 2-chloro, 3-chloro, 4-chloro, 2-fluoro, 3-fluoro, 2-bromo, 3-bromo, 2-iodo, 2-methyl, 3-methyl, 4-methyl, 2-ethyl, 2-n-propyl, 2-sec-butyl, 2,7-dichloro, 2,8-dichloro, 3,7-dichloro, 3,8-dichloro, 4,7-dichloro, 4,8-dichloro, 8-chloro-4-fluoro, 2,7-dimethyl, 2,8-dimethyl, 3,7-dimethyl, 3,8-dimethyl, 4,7-dimethyl, 4,8-dimethyl, 2-methyl-7-ethyl, 2-chloro-7-methyl, 3-chloro-7-methyl, 7-chloro-2-methyl and 7-chloro-3-methyl can be named. Of these, 2-chloro, 3-chloro, 3-fluoro, 3-bromo, 3-methyl and 3-chloro-7-methyl are preferred.

Where the heterocyclic ring which is formed when the ring C in the formula (II) stands for pyridine ring is 2,6-naphthyridine ring, as substituent on the 2,6-naphthyridine ring, for example, 5-chloro, 7-chloro, 8-chloro, 5-fluoro, 7-fluoro, 5-bromo, 7-bromo, 5-iodo, 5-methyl, 7-methyl, 8-methyl, 5-ethyl, 7-n-propyl, 8-sec-butyl, 3,5-dichloro, 3,7-dichloro, 3,8-dichloro, 4,5-dichloro, 4,7-dichloro, 4,8-dichloro, 4-chloro-8-fluoro, 3,5-dimethyl, 3,7-dimethyl, 3,8-dimethyl, 4,5-dimethyl, 4,7-dimethyl, 4,8-dimethyl, 3-chloro-5-methyl, 3-chloro-7-methyl, 3-chloro-8-methyl, 4-chloro-5-methyl, 4-chloro-7-methyl, 4-chloro-8-methyl, 5-chloro-3-methyl, 5-chloro-4-methyl, 7-chloro-3-methyl, 7-chloro-4-methyl, 8-chloro-3-methyl and 8-chloro-4-methyl can be named. Of these, 5-chloro, 7-chloro, 7-fluoro, 7-bromo, 7-methyl and 3,7-dichloro are preferred.

Where the heterocyclic ring which is formed when the ring C in the formula (II) stands for pyridine ring is 2,7-naphthyridine ring, as substituent on the 2,7-naphthyridine ring, for example, 5-chloro, 6-chloro, 8-chloro, 5-fluoro, 6-fluoro, 5-bromo, 6-bromo, 5-iodo, 5-methyl, 6-methyl, 8-methyl, 5-ethyl, 6-n-propyl, 8-sec-butyl, 3,5-dichloro, 3,6-dichloro, 3,8-dichloro, 4,5-dichloro, 4,6-dichloro, 4,8-dichloro, 4-chloro-8-fluoro, 3,5-dimethyl, 3,6-dimethyl, 3,8-dimethyl, 4,5-dimethyl, 4,6-dimethyl, 4,8-dimethyl, 5-chloro-3-methyl, 5-chloro-4-methyl, 6-chloro-3-methyl, 6-chloro-4-methyl, 8-chloro-3-methyl, 8-chloro-4-methyl, 3-chloro-5-methyl, 3-chloro-6-methyl, 3-chloro-8-methyl, 4-chloro-5-methyl, 4-chloro-6-methyl and 4-chloro-8-methyl can be named. Of these, 5-chloro, 6-chloro, 6-fluoro, 6-bromo, 6-methyl, 3,6-dichloro and 3,6-dimethyl are preferred.

Where the heterocyclic ring which is formed when the ring C in the formula (II) stands for pyridine ring is 1,7-naphthyridine ring, as substituent on the 1,7-naphthyridine ring, for example, 2-chloro, 3-chloro, 4-chloro, 2-fluoro, 4-fluoro, 2-bromo, 4-bromo, 4-iodo, 2-methyl, 3-methyl, 4-methyl, 4-ethyl, 3-n-propyl, 2-sec-butyl, 2,5-dichloro, 2,6-dichloro, 3,5-dichloro, 3,6-dichloro, 4,5-dichloro, 4,6-dichloro, 5-chloro-2-fluoro, 2,5-dimethyl, 2,6-dimethyl, 3,5-dimethyl, 3,6-dimethyl, 4,5-dimethyl, 4,6-dimethyl, 2-chloro-5-methyl, 2-chloro-6-methyl, 3-chloro-5-methyl, 3-chloro-6-methyl, 4-chloro-5-methyl, 4-chloro-6-methyl, 5-chloro-2-methyl, 6-chloro-2-methyl, 5-chloro-3-methyl, 6-chloro-3-methyl, 5-chloro-4-methyl and 6-chloro-4-methyl can be named. Of these, 2-chloro, 4-chloro, 2-fluoro, 2-bromo, 2-methyl and 2,6-dichloro are preferred.

Where the heterocyclic ring which is formed when the ring C in the formula (II) stands for furan ring is furo[3,2-c]pyridine, as substituent on the furo[3,2-c]pyridine, besides those named as examples of "substituent on the pyridine ring in the isoquinoline ring where the ring C stands for benzene ring", for example, 2-chloro, 3-chloro, 2-fluoro, 2-bromo, 2-iodo, 2-methyl, 3-methyl, 2-ethyl, 3-n-propyl, 2,6-dichloro, 2,7-dichloro, 3,6-dichloro, 3,7-dichloro, 2,6-dimethyl, 2,7-dimethyl, 3,6-dimethyl, 3,7-dimethyl, 7-chloro-3-fluoro, 2-chloro-6-methyl, 3-chloro-6-methyl, 2-chloro-7-methyl, 3-chloro-7-methyl, 6-chloro-2-methyl, 6-chloro-3-methyl, 7-chloro-2-methyl and 7-chloro-3-methyl can be named. Of these, 2-chloro, 3-chloro, 2-bromo, 2-methyl, 3-methyl, 6-chloro-2-methyl, 6-chloro-3-methyl, 2,6-dimethyl, 3,6-dimethyl and 7-chloro-3-methyl are preferred.

Where the heterocyclic ring which is formed when the ring C in the formula (II) stands for furan ring is furo[3,4-c]pyridine, as substituent on the furo[3,4-c]pyridine, for example, 1-chloro, 3-chloro, 1-fluoro, 1-bromo, 1-iodo, 1-methyl, 3-methy, 1-ethyl, 3-n-propyl, 1,6-dichloro, 3,6-dichloro, 1,7-dichloro, 3,7-dichloro, 7-chloro-3-fluoro, 1,6-dimethyl, 1,7-dimethyl, 3,6-dimethyl, 3,7-dimethyl, 1-chloro-6-methyl, 1-chloro-7-methyl, 3-chloro-6-methyl, 3-chloro-7-methyl, 6-chloro-1-methyl, 6-chloro-3-methyl, 7-chloro-1-methyl and 7-chloro-3-methyl can be named. Of these, 1-chloro, 3-chloro, 1-bromo, 1-methyl, 3-methyl, 6-chloro-1-methyl, 3-chloro-6-methyl and 6-chloro-3-methyl are preferred.

Where the heterocyclic ring which is formed when the ring C in the formula (II) stands for furan ring is furo[2,3-c]pyridine, as substituent on the furo[2,3-c]pyridine, for example, 2-chloro, 3-chloro, 3-fluoro, 3-bromo, 3-iodo, 2-methyl, 3-methyl, 3-ethyl, 2-n-propyl, 2,4-dichloro, 2,5-dichloro, 3,4-dichloro, 3,5-dichloro, 4-chloro-2-fluoro, 2,4-dimethyl, 2,5-dimethyl, 3,4-dimethyl, 3,5-dimethyl, 2-chloro-4-methyl, 2-chloro-5-methyl, 3-chloro-4-methyl, 3-chloro-5-methyl, 4-chloro-2-methyl, 4-chloro-3-methyl, 5-chloro-2-methyl and 5-chloro-3-methyl can be named. Of these, 2-chloro, 3-chloro, 3-bromo, 3-methyl, 2-methyl, 2-chloro-5-methyl, 5-chloro-2-methyl and 5-chloro-3-methyl are preferred.

Where the heterocyclic ring which is formed when the ring C in the formula (II) stands for thiophene ring is thieno[3,2-c]-pyridine, as substituent on the thieno[3,2-c]pyridine, for example, 2-chloro, 3-chloro, 2-fluoro, 2-bromo, 2-iodo, 2-methyl, 3-methyl, 2-ethyl, 3-n-propyl, 2,6-dichloro, 2,7- dichloro, 3,6-dichloro, 3,7-dichloro, 2,6-dimethyl, 2,7-dimethyl, 3,6-dimethyl, 3,7-dimethyl, 7-chloro-3-fluoro, 2-chloro-6-methyl, 3-chloro-6-methyl, 2-chloro-7-methyl, 3-chloro-7-methyl, 6-chloro-2-methyl, 6-chloro-3-methyl, 7-chloro-2-methyl and 7-chloro-3-methyl can be named. Of these, 2-chloro, 3-chloro, 2-bromo, 2-methyl, 3-methyl, 6-chloro-2-methyl, 6-chloro-3-methyl, 2,6-dimethyl, 3,6-dimethyl and 7-chloro-3-methyl are preferred.

Where the heterocyclic ring which is formed when the ring C in the formula (II) stands for thiophene ring is thieno[3,4-c]-pyridine, as substituent on the thieno[3,4-c]pyridine, for example, 1-chloro, 3-chloro, 1-fluoro, 1-bromo, 1-iodo, 1-methyl, 3-methyl, 1-ethyl, 3-n-propyl, 1,6-dichloro, 3,6-dichloro, 1,7-dichloro, 3,7-dichloro, 7-chloro-3-fluoro, 1,6-dimethyl, 1,7-dimethyl, 3,6-dimethyl, 3,7-dimethyl, 1-chloro-6-methyl, 1-chloro-7-methyl, 3-chloro-6-methyl, 3-chloro-7-methyl, 6-chloro-1-methyl, 6-chloro-3-methyl, 7-chloro-1-methyl and 7-chloro-3-methyl can be named. Of these, 1-chloro, 3-chloro, 1-bromo, 1-methyl, 3-methyl, 6-chloro-1-methyl, 3-chloro-6-methyl and 6-chloro-3-methyl are preferred.

Where the heterocyclic ring which is formed when the ring C in the formula (II) stands for thiophene ring is thieno[2,3-c]-pyridine, as substituent on the thieno[2,3-c]pyridine, for example, 2-chloro, 3-chloro, 3-fluoro, 3-bromo, 3-iodo, 2-methyl, 3-methyl, 3-ethyl, 2-n-propyl, 2,4-dichloro, 2,5-dichloro, 3,4-dichloro, 3,5-dichloro, 4-chloro-2-fluoro, 2,4-dimethyl, 2,5-dimethyl, 3,4-dimethyl, 3,5-dimethyl, 2-chloro-4-methyl, 2-chloro-5-methyl, 3-chloro-4-methyl, 3-chloro-5-methyl, 4-chloro-2-methyl, 4-chloro-3-methyl, 5-chloro-2-methyl and 5-chloro-3-methyl can be named. Of these, 2-chloro, 3-chloro, 3-bromo, 3-methyl, 2-methyl, 2-chloro-5-methyl, 5-chloro-2-methyl and 5-chloro-3-methyl are preferred.

As the preferred ring where "$R^9$ and $R^{10}$ together form the residual members of pyrrolidine ring or piperidine ring (which may be unsubstituted or substituted with a substituent selected from hydroxyl, lower alkoxy and phenyl lower alkoxy)", pyrrolidine ring can be named, and as the substituent on the pyrrolidine ring or piperidine ring, for example, hydroxyl, methoxy, ethoxy, n-propoxy, benzyloxy and (2-phenyl)ethoxy can be named. Of these, hydroxyl, methoxy and benzyloxy are particularly preferred.

In the therapeutic method of IBS of the present invention, "$5HT_{1A}$ agonistic agent", which is useful in the occasion of administering 5-$HT_{1A}$ agonistic agent and 5-$HT_3$ antagonistic agent simultaneously, in sequence or at an interval, is not subject to any particular limitation, which may be either known compound or novel compound so long as it exhibits 5-$HT_{1A}$ agonistic activity. As a specific example, tandospirone can be named. According to the invention, furthermore, besides those compounds having 5-$HT_{1A}$ agonistic activity alone, those concurrently having pharmacological activity(ies) other than 5-$HT_{1A}$ agonistic activity can be used as the 5-$HT_{1A}$ agonistic agent.

Again, "5-$HT_3$ antagonistic agent" to be used in combination with the 5-$HT_{1A}$ agonistic agent in the therapy of IBS following the present invention is not particularly restricted, so long as it exhibits 5-$HT_3$ antagonistic activity, which may be either known or novel compound. Specifically, for example, alosetron, granisetron, azasetron, tropisetron, ramosetron, ondansetron, lerisetron, cilansetron, itasetron, indisetron, dolasetron and (R)-zacopride can be named. Of these, particularly alosetron and cilansetron are preferred. According to the invention, furthermore, as such 5-$HT_3$ antagonistic agent, besides those having 5-$HT_3$ antagonistic activity alone, compounds which concurrently possess pharmacological activity(ies) other than 5-$HT_3$ antagonistic activity can be similarly used.

The time at which 5-$HT_{1A}$ agonistic agent and 5-$HT_3$ antagonistic agent manifest their activities in vivo differs according to the kind of active ingredient compounds and form of preparations. Their activity-manifesting time can be readily known by investigating the change in blood concentration or pharmacokinetics after administration of individual medicine. In the therapy following the present invention, it is desirable to administer 5-$HT_{1A}$ agonistic agent and 5-$HT_3$ antagonistic agent in such a manner that the two activities of 5-$HT_{1A}$ agonistic activity and 5-$HT_3$ antagonistic activity are substantially simultaneously expressed in vivo. Where a 5-$HT_{1A}$ agonistic agent and 5-$HT_3$ antagonistic agent whose activity-manifestation time after administration is about the same are used, the two agents can be administered simultaneously or in sequence. Whereas, where a 5-$HT_{1A}$ agonistic agent and 5-$HT_3$ antagonistic agent having different activity-manifestation time are used, they can be administered at an interval corresponding to the difference, whereby enabling simultaneous manifestation of the two agents' activities in vivo.

In the present invention, a preferred group of compounds among those represented by the formula (I) are those in which the ring A stands for the group of the formula i) or ii). In particular, the compounds of the formula (I) in which the ring A stands for groups of the formula ii) are more preferable. Furthermore, those of the formula (I) in which the ring A stands for a group of the formula ii) and m is 2 and/or all of $R^2$, $R^3$ and $R^4$ stand for hydrogen are the most preferred.

Another preferred group of compounds among those represented by the formula (I) of the present invention are those of the formula (I) in which $X^1$ stands for hydrogen, amino or lower alkyl. Of those, the compounds of the formula (I) in which $X^1$ stands for amino or lower alkyl are more preferable. In particular, those of the formula (I) in which $X^1$ stands for amino, methyl or ethyl are the most preferred. Still another preferred group of compounds among those represented by the formula (I) are the compounds of the formula (I) in which $X^2$ stands for hydrogen.

Another preferred group of compounds among those represented by the formula (I) of the present invention are the compounds of the formula (I) in which Y stands for a direct bond or sulfur atom.

Another preferred group of compounds among those represented by the formula (I) of the present invention are the compounds of the formula (I) in which n stands for 2 or 3.

Still another preferred group of compounds among those represented by the formula (I) of the present invention are the compounds of the formula (I) in which Ar is unsubstituted quinolyl or quinolyl which is substituted with substituent(s) selected from halogen, lower alkyl, hydroxyl, lower alkoxy and phenyl. Of these, the compounds of the formula (I) in which Ar stands for unsubstituted quinolin-2-yl or quinolin-2-yl which is substituted with a substituent selected from halogen, lower alkyl, hydroxyl, lower alkoxy and phenyl are particularly preferred.

In the therapeutic method of IBS provided by the present invention, a group of preferred compounds in the occasions of administering 5-$HT_3$ antagonistic agent concurrently having 5-$HT_{1A}$ agonistic activity are the pyrimidine derivatives represented by the formula (I) or pharmaceutically acceptable salts thereof, or the piperazinylpyridine derivatives represented by the formula (II) or pharmaceutically acceptable salts thereof. As those preferred among the pyrimidine derivatives represented by the formula (I) or pharmaceutically acceptable salts thereof, same compounds as specified in the above as "a group of preferred compounds in the present invention" "another preferred group of compounds in the present invention" and "still another preferred group of compounds in the present invention" can be named. Also as those preferred among the piperazinylpyridine derivatives represented by the formula (II) or pharmaceutically acceptable salts thereof, the following compounds can be named:
7-piperazin-1-ylfuro[2,3-c]pyridine,
6-methyl-7-piperazin-1-ylfuro[2,3-c]pyridine,
7-(3-methylpiperazin-1-yl)furo[2,3-c]pyridine,
7-(4-methylpiperazin-1-yl)furo[2,3-c]pyridine,
4-piperazin-1-ylfuro[3,2-c]pyridine,
4-(3-methylpiperazin-1-yl)furo[3,2-c]pyridine,
3-chloro-4-(3-methylpiperazin-1-yl)furo[3,2-c]pyridine,
4-(4-methylpiperazin-1-yl)furo[3,2-c]pyridine,
4-piperazin-1-ylfuro[3,4-c]pyridine,
7-piperazin-1-ylthieno[2,3-c]pyridine,
7-(3-methylpiperazin-1-yl)thieno[2,3-c]pyridine,
3-chloro-7-(3-methylpiperazin-1-yl)thieno[2,3-c]pyridine,
7-(4-methylpiperazin-1-yl)thieno[2,3-c]pyridine,
4-piperazin-1-ylthieno[3,2-c]pyridine,
4-piperazin-1-ylthieno[3,4-c]pyridine,
4-(3-methylpiperazin-1-yl)thieno[3,2-c]pyridine,
6-chloro-4-(3-methylpiperazin-1-yl)thieno[3,2-c]pyridine,
4-(4-methylpiperazin-1-yl)thieno[3,2-c]pyridine,
2-bromo-4-piperazin-1-ylthieno[3,2-c]pyridine dihydrochloride,
2-bromo-4-(3-methylpiperazin-1-yl)thieno[3,2-c]pyridine,
2-bromo-6-methyl-4-(3-methylpiperazin-1-yl)thieno[3,2-c]-pyridine,
2-bromo-4-(4-methylpiperazin-1-yl)thieno[3,2-c]pyridine,
2-methyl-4-piperazin-1-ylthieno[3,2-c]pyridine dihydrochloride,
2-methyl-4-(3-methylpiperazin-1-yl)thieno[3,2-c]pyridine dihydrochloride,
2-methyl-4-(4-methylpiperazin-1-yl)thieno[3,2-c]pyridine dihydrochloride,
3-bromo-4-piperazin-1-ylthieno[3,2-c]pyridine dihydrochloride,
3-bromo-4-(3-methylpiperazin-1-yl)thieno[3,2-c]pyridine,
3-bromo-4-(4-methylpiperazin-1-yl)thieno[3,2-c]pyridine,
7-((8aS)-octahydropyrrolo[1,2-a]pyrazin-2-yl)thieno[2,3-c]-pyridine,
7-((8aS)-octahydropyrrolo[1,2-a]pyrazin-2-yl)furo[2,3-c]-pyridine,
2-methyl-4-((8aS)-octahydropyrrolo[1,2-a]pyrazin-2-yl)-thieno[3,2-c]pyridine,
2-methyl-piperazin-1-ylfuro[3,2-c]pyridine,
7-(4-ethylpiperazin-1-yl)thieno[2,3-c]pyridine,
4-(4-ethylpiperazin-1-yl)thieno[3,2-c]pyridine,
5-piperazin-1-yl-1,6-naphthyridine,
7-chloro-5-piperazin-1-yl-1,6-naphthyridine,
5-(4-ethylpiperazin-1-yl)-1,6-naphthyridine,
8-piperazin-1-yl-1,7-naphthyridine,
8-(4-ethylpiperazin-1-yl)-1,7-naphthyridine,
1-piperazin-1-yl-2,6-naphthyridine,
1-piperazin-1-yl-2,7-naphthyridine,
3-chloro-1-piperazin-1-ylisoquinoline dihydrochloride,
3-chloro-7-methoxy-1-piperazin-1-ylisoquinoline,
3-chloro-1-(4-methylpiperazin-1-yl)isoquinoline dihydrochloride,
7-methoxy-3-methyl-1-piperazin-1-yl-isoquinoline,
7-methoxy-3,4-dimethyl-1-(4-methylpiperazin-1-yl)-isoquinoline,
7-methoxy-4-methyl-1-piperazin-1-ylisoquinoline,
7-methoxy-4-methyl-1-(4-methylpiperazin-1-yl)isoquinoline,
7-bromo-1-piperazin-1-ylisoquinoline,
7-bromo-1-(4-methylpiperazin-1-yl)isoquinoline,
7-methoxy-1-(4-methylpiperazin-1-yl)isoquinoline,
1-(4-ethylpiperazin-1-yl)-7-methoxyisoquinoline,
7-methoxy-1-piperazin-1-ylisoquinoline,
1-piperazin-1-ylisoquinoline,
1-(4-methylpiperazin-1-yl)isoquinoline,
1-(4-ethylpiperazin-1-yl)isoquinoline,
7-methoxy-1-(3-methylpiperazin-1-yl)isoquinoline,
1-(3,5-dimethylpiperazin-1-yl)-7-methoxy-isoquinoline,
6-methoxy-1-piperazin-1-ylisoquinoline,
6-methoxy-1-(4-methylpiperazin-1-yl)isoquinoline,
1-(4-ethylpiperazin-1-yl)-6-methoxyisoquinoline,
5-methoxy-1-piperazin-1-ylisoquinoline,
5-methoxy-1-(4-methylpiperazin-1-yl)isoquinoline,
1-(4-ethylpiperazin-1-yl)-5-methoxyisoquinoline,
7-methyl-1-piperazin-1-ylisoquinoline,
7-methyl-1-(4-methylpiperazin-1-yl)isoquinoline,
1-(4-ethylpiperazin-1-yl)-7-methylisoquinoline,
7-chloro-1-piperazin-1-ylisoquinoline,
7-chloro-1-(4-methylpiperazin-1-yl)isoquinoline,
7-chloro-1-(4-ethylpiperazin-1-yl)isoquinoline,
7-fluoro-1-(4-methylpiperazin-1-yl)isoquinoline,
1-(4-ethylpiperazin-1-yl)-7-fluoroisoquinoline,
1-(4-methylpiperazin-1-yl)-7-phenylisoquinoline,
1-(4-ethylpiperazin-1-yl)-7-phenylisoquinoline,
7-phenyl-1-piperazin-1-ylisoquinoline,
6-chloro-1-piperazin-1-ylisoquinoline,
6-chloro-1-(4-methylpiperazin-1-yl)isoquinoline,
6-chloro-1-(4-ethylpiperazin-1-yl)isoquinoline,
5-chloro-1-piperazin-1-ylisoquinoline,
5-chloro-1-(4-methylpiperazin-1-yl)isoquinoline,
5-chloro-1-(4-ethylpiperazin-1-yl)isoquinoline,
7-fluoro-1-piperazin-1-ylisoquinoline,
7-chloro-1-[4-[4-(3-methoxyphenyl)butyl]piperazin-1-yl]-isoquinoline,
7-methoxy-1-[4-[4-(3-methoxyphenyl)butyl]piperazin-1-yl]-isoquinoline,
7-chloro-1-[4-[trans-4-(3-methoxyphenyl)cyclohexan-1-yl]-piperazin-1-yl]isoquinoline,
7-methoxy-1-[4-[trans-4-(3-methoxyphenyl)cyclohexan-1-yl]-piperazin-1-yl]isoquinoline,
1-((8aS)-octahydropyrrolo[1,2-a]pyrazin-2-yl)-7-methoxy-isoquinoline,
7-chloro-1-((8aS)-octahydropyrrolo[1,2-a]pyrazin-2-yl)-isoquinoline,
8-((8aS)-octahydropyrrolo[1,2-a]pyrazin-2-yl)-1,7-naphthyridine,
5-((8aS)-octahydropyrrolo[1,2-a]pyrazin-2-yl)-1,6-naphthyridine,
7-chloro-1-((8aR)-octahydropyrrolo[1,2-a]pyrazin-2-yl)-isoquinoline,
1-((8aR)-octahydropyrrolo[1,2-a]pyrazin-2-yl)-7-methoxy-isoquinoline,
3-chloro-1-((8aS)-octahydropyrrolo[1,2-a]pyrazin-2-yl)-isoquinoline,
3-chloro-1-((8aS)-octahydropyrrolo[1,2-a]pyrazin-2-yl)-7-methylisoquinoline,
7-chloro-1-octahydropyrido[1,2-a]pyrazin-2-ylisoquinoline,
7-methoxy-1-octahydropyrido[1,2-a]pyrazin-2-ylisoquinoline,
7-methylthio-1-(S)-octahydropyrido[1,2-a]pyran-2-ylisoquinoline,
7-methylsulfinyl-1-(S)-octahydropyrido[1,2-a]pyran-2-yl-isoquinoline, 7-hydroxy-1-octahydropyrido[1,2-a]pyrazin-2-ylisoquinoline,
1-(S)-octahydropyrido[1,2-a]pyran-2-yl-7-hydroxy-isoquinoline,
1-octahydropyrido[1,2-a]pyrazin-2-yl-7-sulfamoyloxy-isoquinoline,
1-(S)-octahydropyrido[1,2-a]pyran-2-yl-7-sulfamoyloxyisoquinoline,
1-(4-benzylpiperazin-1-yl)-7-chloroisoquinoline,
1-(4-benzylpiperazin-1-yl)-7-dimethylaminoisoquinoline,
7-methylamino-1-piperazin-1-ylisoquinoline,
7-ethylamino-1-piperazin-1-ylisoquinoline,
7-dimethylamino-1-piperazin-1-ylisoquinoline,
7-dimethylamino-1-(4-methylpiperazin-1-yl)isoquinoline,
7-methylamino-1-(4-methylpiperazin-1-yl)isoquinoline,
1-[4-(4-fluorobenzyl)piperazin-1-yl]-7-methoxyisoquinoline,
1-[4-(4-fluorobenzyl)piperazin-1-yl]isoquinoline,
7-hydroxy-1-piperazin-1-ylisoquinoline hydrochloride,
7-hydroxy-1-(4-methylpiperazin-1-yl)isoquinoline,
7-ethoxy-1-piperazin-1-ylisoquinoline,
7-(4-fluorobenzyloxy)-1-piperazin-1-ylisoquinoline,
7-benzyloxy-1-piperazin-1-ylisoquinoline, and
7-sulfamoyloxy-1-piperazin-1-ylisoquinoline hydrochloride.

Of these, particularly the following compounds are preferred:
7-chloro-1-(4-methylpiperazin-1-yl)isoquinoline,
7-((8aS)-octahydropyrrolo[1,2-a]pyrazin-2-yl)thieno[2,3-c]-pyridine,
7-((8aS)-octahydropyrrolo[1,2-a]pyrazin-2-yl)furo[2,3-c]pyridine,
2-methyl-4-((8aS)-octahydropyrrolo[1,2-a]pyrazin-2-yl)-thieno[3,2-c]pyridine,
7-methoxy-1-((8aR)-octahydropyrrolo[1,2-a]pyrazin-2-yl)-isoquinoline, and
2-bromo-4-(4-methylpiperazin-1-yl)thieno[3,2-c]pyridine.

In the therapeutic method provided by the present invention, wherein 5-HT$_{1A}$ agonistic agent and 5-HT$_3$ antagonistic agent are administered simultaneously, in sequence or at an interval, preferred 5-HT$_{1A}$ agonistic agent is tandospirone, and preferred 5-HT$_3$ antagonistic agents are alosetron, granisetron, azasetron, tropisetron, ramosetron, ondansetron, lerisetron, cilansetron, itasetron, indisetron, dolasetron and (R)-zacopride. Of these, particularly preferred 5-HT$_3$ antagonistic agents are alosetron and cilansetron.

As representative examples of the compounds of the formula (I) which are provided by the present invention, besides those in the later appearing Examples, the following can be named:
3-amino-6-benzyl-2-[4-(4-quinolin-2-ylpiperazin-1-yl)butyl]-5,6,7,8-tetrahydro-3H-pyrido[4,3-d]pyrimidin-4-one,
3-amino-6-benzyl-8-methyl-2-[4-(4-quinolin-2-ylpiperazin-1-yl)butyl]-5,6,7,8-tetrahydro-3H-pyrido[4,3-d]pyrimidin-4-one,
3-amino-6-benzoyl-2-[4-(4-quinolin-2-ylpiperazin-1-yl)butyl]-5,6,7,8-tetrahydro-3H-pyrido[4,3-d]pyrimidin-4-one,
3-amino-6-methyl-2-[4-(4-quinolin-2-ylpiperazin-1-yl)butyl]5,6,7,8-tetrahydro-3H-pyrido[4,3-d]pyrimidin-4-one,
3-amino-7-benzyl-2-[4-(4-quinolin-2-ylpiperazin-1-yl)butyl]-5,6,7,8-tetrahydro-3H-pyrido[3,4-d]pyrimidin-4-one,
3-amino-7-methyl-2-[4-(4-quinolin-2-ylpiperazin-1-yl)butyl]-5,6,7,8-tetrahydro-3H-pyrido[3,4-d]pyrimidin-4-one,
3-amino-5-chloro-2-[4-(4-quinolin-2-ylpiperazin-1-yl)butyl]-5,6,7,8-tetrahydro-3H-quinazolin-4-one,
3-amino-6-chloro-2-[4-(4-quinolin-2-ylpiperazin-1-yl)butyl]-5,6,7,8-tetrahydro-3H-quinazolin-4-one,
3-amino-7-chloro-2-[4-(4-quinolin-2-ylpiperazin-1-yl)butyl]-5,6,7,8-tetrahydro-3H-quinazolin-4-one,
3-amino-8-chloro-2-[4-(4-quinolin-2-ylpiperazin-1-yl)butyl]-5,6,7,8-tetrahydro-3H-quinazolin-4-one,
3-amino-6-fluoro-2-[4-(4-quinolin-2-ylpiperazin-1-yl)butyl]-5,6,7,8-tetrahydro-3H-quinazolin-4-one,
3-amino-7-fluoro-2-[4-(4-quinolin-2-ylpiperazin-1-yl)butyl]-5,6,7,8-tetrahydro-3H-quinazolin-4-one,
3-amino-6-bromo-2-[4-(4-quinolin-2-ylpiperazin-1-yl)butyl]-5,6,7,8-tetrahydro-3H-quinazolin-4-one,
3-amino-7-bromo-2-[4-(4-quinolin-2-ylpiperazin-1-yl)butyl]-5,6,7,8-tetrahydro-3H-quinazolin-4-one,
3-amino-5-methoxy-2-[4-(4-quinolin-2-ylpiperazin-1-yl)-butyl]-5,6,7,8-tetrahydro-3H-quinazolin-4-one,
3-amino-6-methoxy-2-[4-(4-quinolin-2-ylpiperazin-1-yl)-butyl]-5,6,7,8-tetrahydro-3H-quinazolin-4-one,
3-amino-6-cyclohexyl-2-[4-(4-quinolin-2-ylpiperazin-1-yl)-butyl]-5,6,7,8-tetrahydro-3H-quinazolin-4-one,
3-amino-2-[4-(4-quinolin-2-ylpiperazin-1-yl)butyl]-7-trifluoromethyl-5,6,7,8-tetrahydro-3H-quinazolin-4-one,
3-amino-6-benzyl-2-[4-(4-quinolin-2-ylpiperazin-1-yl)butyl]-5,6,7,8-tetrahydro-3H-quinazolin-4-one,
3-amino-6-phenethyl-2-[4-(4-quinolin-2-ylpiperazin-1-yl)-butyl]-5,6,7,8-tetrahydro-3H-quinazolin-4-one,
3-amino-6-propyl-2-[4-(4-quinolin-2-ylpiperazin-1-yl)butyl]-5,6,7,8-tetrahydro-3H-quinazolin-4-one,
3-amino-2-[4-(4-quinolin-2-ylpiperazin-1-yl)butyl]-7,8-dihydro-3H,6H-thiopyrano[3,2-d]pyrimidin-4-one,
3-amino-2-[4-(4-quinolin-2-ylpiperazin-1-yl)butyl]-7,8-dihydro-3H, 5H-thiopyrano[4,3-d]pyrimidin-4-one,
3-amino-6,6-dioxo-2-[4-(4-quinolin-2-ylpiperazin-1-yl)butyl]-7,8-dihydro-3H, 5H-thiopyrano[4,3-d]pyridine-4-one,
3-amino-6-oxo-2-[4-(4-quinolin-2-ylpiperazin-1-yl)butyl]-7,8-dihydro-3H, 5H-thiopyrano[4,3-d]pyridine-4-one,
3-amino-2-[4-(4-quinolin-2-ylpiperazin-1-yl)butyl]-5,8-dihydro-3H,6H-thiopyrano[3,4-d]pyrimidin-4-one,
3-amino-2-[4-(4-quinolin-2-ylpiperazin-1-yl)butyl]-7,8-dihydro-3H, 5H-pyrano[4,3-d]pyrimidin-4-one,
3-amino-4-oxo-2-[4-(4-quinolin-2-ylpiperazin-1-yl)butyl]-3,4,5,6,7,8-hexahydroquinazolinone-6-carboxylic acid,
ethyl 3-amino-4-oxo-2-[4-(4-quinolin-2-ylpiperazin-1-yl)butyl]-3,4,5,6,7,8-hexahydroquinazolinone-6-carboxylate,
3-amino-4-oxo-2-[4-(4-quinolin-2-ylpiperazin-1-yl)butyl]-3,4,5,6,7,8-hexahydroquinazolinone-6-carbonitrile,
3-amino-4-oxo-2-[4-(4-quinolin-2-ylpiperazin-1-yl)butyl]-3,4,5,6,7,8-hexahydroquinazolinone-7-carbonitrile,
3,6-diamino-2-[4-(4-quinolin-2-ylpiperazin-1-yl)butyl]-5,6,7,8-tetrahydro-3H-quinazolin-4-one,
3-amino-6-methylamino-2-[4-(4-quinolin-2-ylpiperazin-1-yl)-butyl]-5,6,7,8-tetrahydro-3H-quinazolin-4-one,
3-amino-6,6-dimethylamino-2-[4-(4-quinolin-2-ylpiperazin-1-yl)butyl]-5,6,7,8-tetrahydro-3H-quinazolin-4-one,
3-amino-6-nitro-2-[4-(4-quinolin-2-ylpiperazin-1-yl)butyl]-5,6,7,8-tetrahydro-3H-quinazolin-4-one,
3-amino-6-methyl-2-[4-(4-quinolin-2-ylpiperazin-1-yl)butyl]-5,6-dihydro-3H,7H-cyclopenta[d]pyrimidin-4-one,
3-amino-6-chloro-2-[4-(4-quinolin-2-ylpiperazin-1-yl)butyl]-5,6-dihydro-3H,7H-cyclopenta[d]pyrimidin-4-one,
3-amino-6-hydroxy-2-[4-(4-quinolin-2-ylpiperazin-1-yl)-butyl]-5,6-dihydro-3H,7H-cyclopenta[d]pyrimidin-4-one,
3-amino-5-methyl-2-[4-(4-quinolin-2-ylpiperazin-1-yl)butyl]-5,6-dihydro-3H,7H-cyclopenta[d]pyrimidin-4-one, 3-amino-6-methyl-2-[4-(4-quinolin-2-ylpiperazin-1-yl)butyl]-5,6,7,8-tetrahydro-3H,9H-cyclohepta[d]pyrimidin-4-one,
3-amino-6-phenyl-2-[4-(4-quinolin-2-ylpiperazin-1-yl)butyl]-5,6-dihydro-3H,7H-cyclopenta[d]pyrimidin-4-one,
3-amino-2-[4-(4-quinolin-2-ylpiperazin-1-yl)butyl]-3H,7H-pyrrolo[2,3-d]pyrimidin-4-one,
3-amino-2-[4-(4-quinolin-2-ylpiperazin-1-yl)butyl]-3H,5H-pyrrolo[3,2-d]pyrimidin-4-one,
3-amino-6-methyl-2-[4-(4-quinolin-2-ylpiperazin-1-yl)butyl]-3H,5H-pyrrolo[3,2-d]pyrimidin-4-one,
3-amino-6-ethyl-2-[4-(4-quinolin-2-ylpiperazin-1-yl)butyl]-3H,5H-pyrrolo[3,2-d]pyrimidin-4-one,
3-amino-6,7-dimethyl-2-[4-(4-quinolin-2-ylpiperazin-1-yl)butyl]-3H,5H-pyrrolo[3,2-d]pyrimidin-4-one,
3,5-dimethyl-2-[4-(4-quinolin-2-ylpiperazin-1-yl)butyl]-5,6,7,8-tetrahydro-3H-quinazolin-4-one,
3,7-dimethyl-2-[4-(4-quinolin-2-ylpiperazin-1-yl)butyl]-5,6,7,8-tetrahydro-3H-quinazolin-4-one,
3,8-dimethyl-2-[4-(4-quinolin-2-ylpiperazin-1-yl)butyl]-5,6,7,8-tetrahydro-3H-quinazolin-4-one,
3-methyl-2-[4-[4-(5-methylquinolin-2-yl)piperazin-1-yl]butyl]-5,6,7,8-tetrahydro-3H-quinazolin-4-one,
3-methyl-2-[4-[4-(6-methylquinolin-2-yl)piperazin-1-yl]butyl]-5,6,7,8-tetrahydro-3H-quinazolin-4-one,
3-methyl-2-[4-[4-(7-methylquinolin-2-yl)piperazin-1-yl]butyl]5,6,7,8-tetrahydro-3H-quinazolin-4-one,
2-[4-[4-(6-bromoquinolin-2-yl)piperazin-1-yl]butyl]-3-methyl-5,6,7,8-tetrahydro-3H-quinazolin-4-one,
2-[4-[4-(6-chloroquinolin-2-yl)piperazin1-yl]butyl]-3-methyl-5,6,7,8-tetrahydro-3H-quinazolin-4-one,
2-[4-[4-(6-hydroxyquinolin-2-yl)piperazin1-yl]butyl]-3-methyl-5,6,7,8-tetrahydro-3H-quinazolin-4-one,
2-[4-[4-(3-hydroxyquinolin-2-yl)piperazin1-yl]butyl]-3-methyl-5,6,7,8-tetrahydro-3H-quinazolin-4-one,
6-methoxy-3-methyl-2-[4-(4-quinolin-2-ylpiperazin-1-yl)butyl]-3H-quinazolin-4-one,
6-methoxy-3-methyl-2-[4-[4-(4-methylquinolin-2-yl)-piperazin-1-yl]butyl]-3H-quinazolin-4-one,
2-[4-[4-(4-chloroquinolin-2-yl]piperazin-1-yl]butyl]-6-methoxy-3-methyl-3H-quinazolin-4-one,
3-ethyl-6-methoxy-2-[4-(4-quinolin-2-ylpiperazin-1-yl)-butyl]-3H-quinazolin-4-one,
3,6-dimethyl-2-[3-(4-quinolin-2-ylpiperazin-1-yl)propylthio]-5,6,7,8-tetrahydro-3H-quinazolin-4-one,
3-ethyl-6-methyl-2-[3-(4-quinolin-2-ylpiperazin-1-yl)-propylthio]-5,6,7,8-tetrahydro-3H-quinazolin-4-one,
3-ethyl-6-methyl-2-[3-[4-(5-methylquinolin-2-yl)piperazin-1-yl]propylthio]-5,6,7,8-tetrahydro-3H-quinazolin-4-one,
2-[3-[4-(4-chloroquinolin-2-yl)piperazin-1-yl]propylthio]-3,6-dimethyl-5,6,7,8-tetrahydro-3H-quinazolin-4-one,
3,6-dimethyl-2-[3-[4-(4-methylquinolin-2-yl)piperazin-1-yl]-butylthio]-5,6,7,8-tetrahydro-3H-quinazolin-4-one,
3,6-dimethyl-2-[3-(4-quinolin-2-yl)propylamino]-5,6,7,8-tetrahydro-3H-quinazolin-4-one,
3,6-dimethyl-2-[3-(4-quinolin-2-ylpiperazin-1-yl)-butylamino]-5,6,7,8-tetrahydro-3H-quinazolin-4-one,
2-[3-[4-(4-chloroquinolin-2-yl)piperazin-1-yl]butylamino]-3,6-dimethyl-5,6,7,8-tetrahydro-3H-quinazolin-4-one,
3,6-dimethyl-2-[4-(4-quinolin-2-ylpiperazin-1-yl)butyl]-3H-quinazolin-4-one,
2-[4-[4-(4-chloroquinolin-2-yl)piperazin-1-yl]butyl]-3-ethyl-6-methyl-3H-quinazolin-4-one,
3-methyl-2-[4-(4-quinolin-2-ylpiperazin-1-yl)pentyl]-3H-quinazolin-4-one,
6-methoxy-3-methyl-2-[3-(4-quinolin-2-ylpiperazin-1-yl)-propylthio]-3H-quinazolin-4-one,
3-ethyl-6-methoxy-2-[3-(4-quinolin-2-ylpiperazin-1-yl)-butylthio]-3H-quinazolin-4-one,
3-benzyl-2-[3-(4-quinolin-2-ylpiperazin-1-yl)-butylamino]-3H-quinazolin-4-one,
6,7-dichloro-3-methyl-2-[3-(4-quinolin-2-ylpiperazin-1-yl)-butylamino]-3H-quinazolin-4-one,
3,5,6-trimethyl-2-[3-(4-quinolin-2-ylpiperazin-1-yl)-butylamino]-3H-thieno[2,3-d]pyrimidin-4-one,
3-ethyl-5,6-dimethyl-2-[3-[4-(4-methylquinolin-2-yl)-piperazin-1-yl]butylthio]-3H-thieno[2,3-d]pyrimidin-4-one,
2-[4-(4-benzothiazol-2-ylpiperazin-1-yl)pentyl]-3-methyl-5,6,7,8-tetrahydro-3H-quinazolin-4-one,
2-[4-(4-benzothiazol-2-ylpiperazin-1-yl)pentyl]-3-ethyl-6-methyl-5,6,7,8-tetrahydro-3H-quinazolin-4-one,
2-[3-(4-benzothiazol-2-ylpiperazin-1-yl)butylthio]-3-ethyl-5,6,7,8-tetrahydro-3H-quinazolin-4-one,
2-[4-(4-benzothiazol-2-ylpiperazin-1-yl)butyl]-6-chloro-3-methyl-3H-quinazolin-4-one, and 2-[3-(4-benzothiazol-2-ylpiperazin-1-yl)butylthio]-3-methyl-3H-quinazolin-4-one.

Those compounds of the formula (I) provided by the present invention and those that are used in therapy of IBS following the present invention can also be present in the form of salts when occasions demand. As such salts, for example, those with inorganic acid such as hydrochloric acid, hydrobromic acid, sulfuric acid, nitric acid, phosphoric acid and the like; and those with organic acid such as acetic acid, oxalic acid, citric acid, lactic acid, tartaric acid, p-toluenesulfonic acid and the like can be named. Of those, pharmaceutically acceptable salts are preferred.

According to the present invention, those compounds of the formula (I) can be prepared by, for example, any of the methods as described in the following (a)-(e), depending on the kind of $X^1$ and Y.

Method (a):

Compounds of the formula (I) wherein $X^1$ stands for amino, lower alkyl, phenyl lower alkyl or substituted or unsubstituted phenyl and Y is direct bond, i.e., the pyrimidine derivatives represented by the following formula,

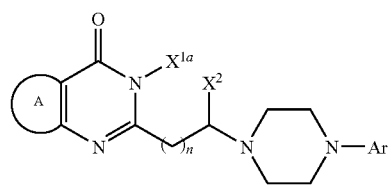

(I-1)

in the formula, ring A, n, $X^2$ and Ar have the previously given significations, and $X^{1a}$ stands for amino, lower alkyl, phenyl lower alkyl or substituted or unsubstituted phenyl, can be prepared by, for example, treating a compound of the formula,

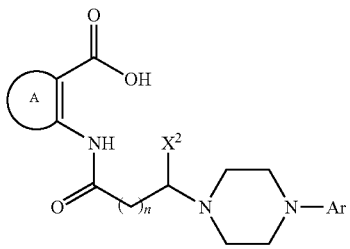

(III)

in the formula, ring A, n, $X^2$ and Ar have the previously given significations, with acetic anhydride, and successively reacting the reaction product with a compound of the formula,

 (IV)

$H_2N-X^{1a}$ in which $X^{1a}$ has the previously given signification, without intervening isolation of the reaction product.

Method (b):

Compounds of the formula (I) wherein $X^1$ stands for lower alkylamino, di-lower alkylamino or lower alkylideneamino and Y is direct bond, i.e., the pyrimidine derivatives represented by the following formula,

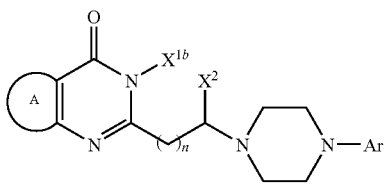

(I-2)

in which ring A, n, $X^2$ and Ar have the previously given significations and $X^{1b}$ stands for lower alkylamino, di-lower alkylamino or lower alkylideneamino, can be prepared by, for example, either N-alkylating, N,N-dialkylating or N-alkylidenating the compounds of the formula (I-1) wherein $X^{1a}$ stands for amino, as obtained by the method (a); or further N-alkylating the compounds of the formula (I-2) wherein $X^{1b}$ stands for lower alkylamino.

Method (c):

Compounds of the formula (I) wherein $X^1$ stands for hydrogen and Y is direct bond, i.e., the pyrimidine derivatives of the following formula,

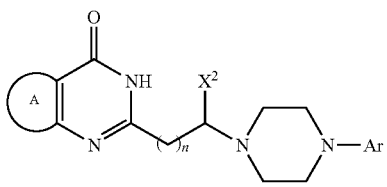

(I-3)

in which ring A, n, $X^2$ and Ar have the previously given significations, can be prepared by, for example, treating the compounds of the formula (I-1) wherein $X^{1a}$ stands for amino, as obtained by the method (a), with sodium nitrite.

Alternative Method (c-1):

The compounds of the formula (I-3) in which $X^2$ stands for hydrogen, in the above method (c), i.e., the pyrimidine derivatives of the following formula,

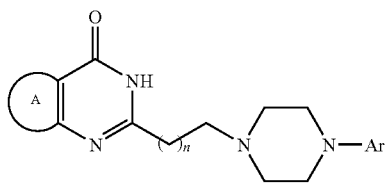

(I-3-1)

in which ring A, n and Ar have the previously given significations, may also be prepared by reacting a compound of the formula,

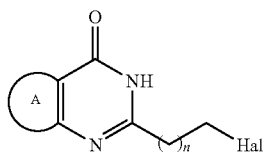

(V)

in which ring A and n have the previously given significations, and Hal stands for halogen, with a compound of a formula,

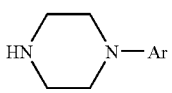

(VI)

in which Ar has the previously given signification.

Method (d):

The compound of the formula (I) in which Y stands for sulfur, i.e., the pyrimidine derivatives of the following formula,

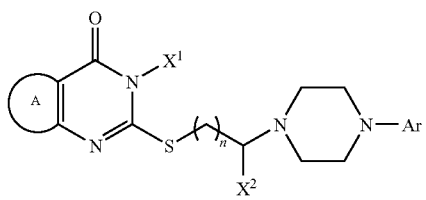

(I-4)

in which ring A, $X^1$, n, $X^2$ and Ar have the previously given significations, can be prepared by, for example, reacting a compound of a formula

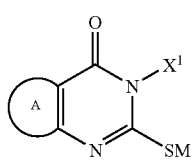

(VII)

in which ring A and $X^1$ have the previously given significations,

M stands for alkali metal or alkaline earth metal, and

SM means that the sulfur atom is in the form of a salt of the metal, with a compound of the formula,

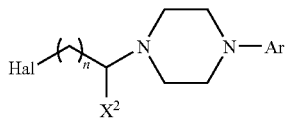

in which n, $X^2$, Ar and Hal have the previously given significations.

Method (e):

The compounds of the formula (I) in which Y stands for nitrogen atom, i.e., the pyrimidine derivatives of the following formula,

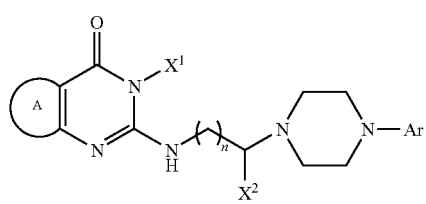

in which ring A, $X^1$, n, $X^2$ and Ar have the previously given significations, can be prepared by, for example, reacting a compound of the formula,

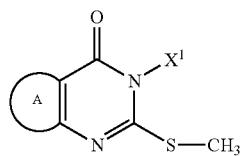

in which ring A and $X^1$ have the previously given significations, with a compound of the formula,

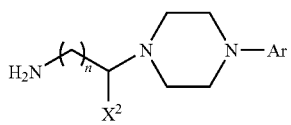

in which n, $X^2$ and Ar have the previously given significations.

The treatment with acetic anhydride of a compound of the formula (III) in the above method (a) can be conducted using generally about 1-10 mols, preferably about 1.3-5 mols, of acetic anhydride per mol of the compound of the formula (III), in an inert organic solvent such as amides, e.g., N,N-dimethylformamide, N,N-dimethylacetamide and the like; alcohols, e.g., methanol, ethanol, isopropanol and the like; or ethers, e.g., tetrahydrofuran, dioxane and the like; at 0° C.—reflux temperature of the reaction mixture, preferably room temperature—reflux temperature of the reaction mixture.

Then adding a compound of the formula (IV) to the reaction mixture to carry out the reaction at 0° C.—reflux temperature of the reaction mixture, the object compound of the formula (I-1) can be obtained.

The use rate of the compound of the formula (IV) to that of the formula (III) is not particularly limited. Whereas, in general terms it is preferred to use the compound of the formula (IV) within a range of the mol number of the residual acetic anhydride, i.e., the remaining mol number after subtracting the mol number of the formula (III) compound from that of the used acetic anhydride, plus at least 1 mol, preferably 1.2-10 mols, inter alia, 1.3-5 mols, per mol of the formula (III) compound.

N-alkylation reaction of the formula (I-1) compound in the above method (b) can be carried out by nucleophilic substitution reaction using alkyl halide or the like, or by reductive alkylation reaction using aldehydes or the like; and the N-alkylidenation reaction can be conducted by dehydration reaction using aldehydes or the like. Those reactions can be generally conducted in inert organic solvent such as amides, e.g., N,N-dimethylformamide, N-N-dimethyl-acetamide and the like; alcohols, e.g., methanol, ethanol, isopropanol and the like; or ethers, e.g., tetrahydrofuran, dioxane and the like; at 0° C.—reflux temperature of the reaction mixture, preferably room temperature—reflux temperature of the reaction mixture.

The use rate of alkylation agent or alkylidenation agent such as alkyl halides or aldehydes used for N-alkylation or N-alkylidenation of compounds of the formula (I-1) is not particularly limited. In general terms, in case of leading a formula (I-1) compound whose $X^{1a}$ stands for amino to a formula (I-2) compound whose $X^{1b}$ stands for lower alkylamino or lower alkylideneamino, or of leading a formula (I-2) compound whose $X^{1b}$ stands for lower alkylamino to another formula (I-2) compound whose $X^{1b}$ stands for di-lower alkylamino (in which the lower alkyl groups may be same or different), either of the agents can be used within a range of at least 1 mol, preferably 1.2-10 mols, inter alia, 1.3-5 mols, per mol of the formula (I-1) compound whose $X^{1a}$ stands for amino or of the formula (I-2) compound whose $X^{1b}$ stands for lower alkylamino. Again, in case of leading a formula (I-1) compound whose $X^{1a}$ stands for amino to a formula (I-2) compound whose $X^{1b}$ stands for di-lower alkylamino in which the lower alkyl groups are the same, the agent can be used within a range of at least 2 mols, preferably 2.2-10 mols, inter alia, 3-5 mols, per mol of the formula (I-1) compound whose $X^{1a}$ stands for amino.

The reaction in the above method (c) of treating a formula (I-1) compound whose $X^{1a}$ stands for amino with sodium nitrite can generally be conducted in mixed solvent of acetic acid and water, at 0° C.—reflux temperature of the reaction mixture, preferably room temperature—reflux temperature of the reaction mixture.

The use rate of sodium nitrite to the formula (I-1) compound whose $X^{1a}$ stands for amino is not particularly limited, while generally it can be at least 1 mol, preferably 1.5-10 mols, inter alia, 2-5 mols, of sodium nitrite per mol of the formula (I-1) compound whose $X^{1a}$ stands for amino.

The reaction of a formula (V) compound with a formula (VI) compound in the alternative method (c-1) can be generally conducted in an inert organic solvent such as amides, e.g., N,N-dimethyl-formamide, N,N-dimethylacetamide and the like; alcohols, e.g., methanol, ethanol, isopropanol and the like; ethers, e.g., tetrahydrofuran, dioxane and the like;

ketones, e.g., acetone, diethyl ketone; or aromatic hydrocarbon, e.g., benzene, toluene; and where necessary, in the presence of alkalis such as sodium hydride, sodium methoxide, potassium butoxide, potassium carbonate, potassium hydroxide and the like or organic base such as triethylamine, 2,6-di-tert-butyl-4-methylpyridine and the like, at temperatures ranging −20° C.—reflux temperature of the reaction mixture, preferably 0° C.-60° C.

The use rate of the formula (VI) compound to the formula (V) compound is not particularly limited. Generally, the formula (VI) compound can be used in the range of at least 1 mol, preferably 1.05-4 mols, inter alia, 1.2-2 mols, per mol of the formula (V) compound.

The reaction of a formula (VII) compound with a formula (VIII) compound in the above method (d) can be generally conducted in an inert organic solvent such as amides, e.g., N,N-dimethyl-formamide, N,N-dimethylacetamide and the like; alcohols, e.g., methanol, ethanol, isopropanol and the like; ethers, e.g., tetrahydrofuran, dioxane and the like; or organic base, e.g., pyridine and the like; where necessary in the presence of alkalis such as sodium hydride, sodium methoxide, potassium butoxide, potassium carbonate, potassium hydroxide and the like or organic base such as triethylamine, 2,6-di-tert-butyl-4-methylpyridine and the like, at temperatures ranging −20° C.—reflux temperature of the reaction mixture, preferably 0° C.-60° C.

The use rate of the formula (VIII) compound to the formula (VII) compound is not particularly limited. Generally, the formula (VIII) compound can be used in the range of at least 1 mol, preferably 1.1-5 mols, inter alia, 1.2-2 mols, per mol of the formula (VII) compound. Also it is adequate to use 1.2-10 mols of the alkalis or organic bases per mol of the formula (VII) compound.

The reaction of a formula (IX) compound with a formula (X) compound in the above method (e) can be generally conducted by heating them in pyridine to the reflux temperature of the reaction mixture.

The use rate of the formula (X) compound to the formula (IX) compound is not particularly limited. In general terms, at least 1 mol, preferably 1.1-5 mols, inter alia, 1.2-2 mols of the formula (X) compound can be used per mol of the formula (IX) compound.

Thus, compound of the above formulae (I-1), (I-2), (I-3), (I-4) or (I-5), i.e., compounds of the formula (I) intended by the present invention, can be prepared.

The compounds of the formula (III) which are used as the starting material in the above method (a) can be readily synthesized by following per se known method of synthesis, for example, by following the route as illustrated in the following reaction scheme 1. Concerning the particulars about the reaction scheme 1 such as reaction conditions, Steps 7-1-A to D in later appearing Example 7-1 are to be referred to.

Reaction scheme 1:

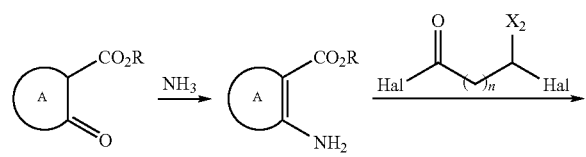

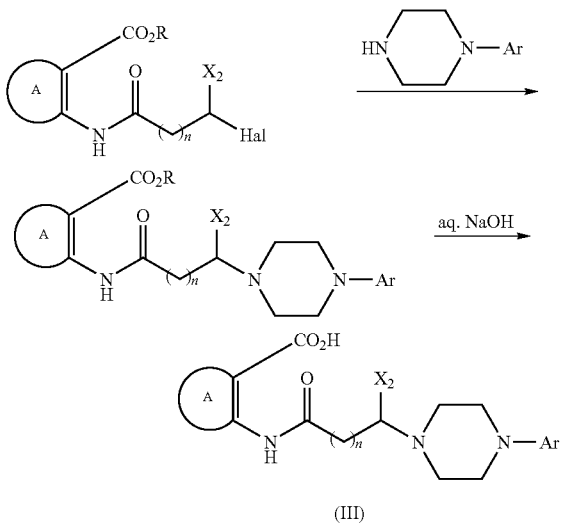

in the above formulae, ring A, n, $X^2$, Ar, Hal and R have the previously given significations, and R stands for lower alkyl.

Compounds of the formula (III) which are used as the starting material in the above method (a) can also be synthesized by the following the route illustrated in reaction scheme 2. Concerning the particulars of the reaction scheme 2 such as the reaction conditions, later appearing Examples 7-14 are to be referred to.

Reaction scheme 2:

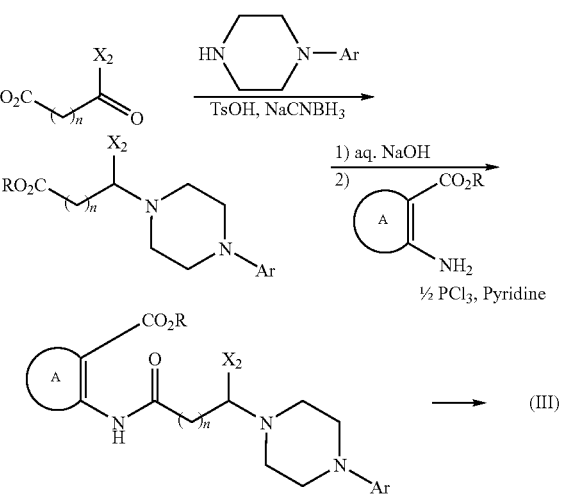

in the above formulae, ring A, n, $X^2$, Ar and R have the previously given significations.

Compounds of the formula (V) which are used as the starting material in the alternative method (c-1) can be synthesized by following per se known methods of synthesis, for example, through the route as illustrated in the following reaction scheme 3. Concerning further particulars of the reaction scheme 3 such as the reaction conditions, Step 3-1-A in later appearing Example 3-1 is to be referred to.

Reaction scheme 3:

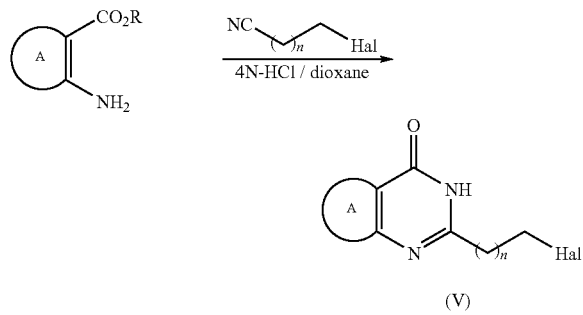

in the above formulae, ring A, n, Hal and R have the previously given significations.

Compounds of the formula (VII) which are used as the starting material in the above method (d) can be synthesized in accordance with per se known synthesis methods, for example, following the method as described in *J. Med. Chem.*, 40, 574-585 (1997), via the route as illustrated by the following reaction scheme 4.

Reaction scheme 4:

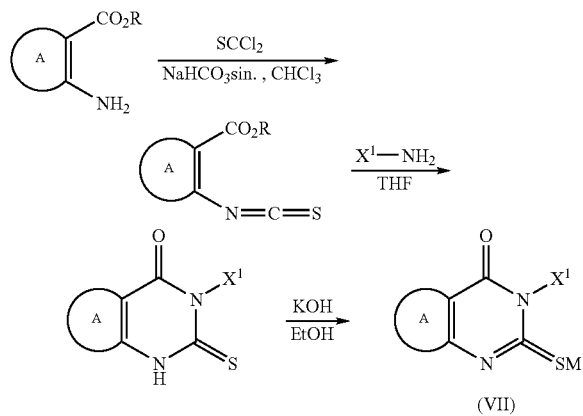

in the above formulae, ring A, $X^1$, R and M have the previously given significations.

Compounds of the formula (IX) which are used as the starting material in the above method (e) can be synthesized by, for example, methylating compounds of the formula (VII) via a route as illustrated in the following reaction scheme 5. Concerning the particulars of the reaction scheme such as the reaction conditions, Step 7-29-A in the later appearing Example 7-29 is to be referred to.

Reaction scheme 5:

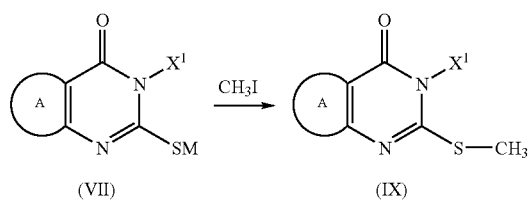

in the above formulae, ring A, $X^1$ and M have the previously given significations.

Those compounds of the formula (I) of the present invention which are prepared by above-described methods can be isolated from the reaction mixtures and purified by the means known per se, for example, recrystallization, column chromatography, preparative chromatography and the like.

Again, while most of the compounds of the formula II which are used in therapy of IBS following the present invention are known from literature (e.g., *J. Med. Chem.*, 42, 4362-4379 (1999)), even when they are novel compounds, they can be readily synthesized by synthesis methods disclosed in literature references or by following later given production examples.

The pyrimidine derivatives of the formula (I) of the present invention or their pharmaceutically acceptable salts concurrently possess $5\text{-HT}_{1A}$ agonistic activity and $5\text{-HT}_3$ antagonistic activity, and are effective for treatment and therapy of diseases associated with $5\text{HT}_{1A}$ and/or $5\text{HT}_3$ receptors in human beings and other mammals, for example, IBS, functional dyspepsia (FD), anxiety, urinary incontinence, anischuria, depression, prostate cancer, asyndesis, pollakiuria, schizophrenia, overactive bladder syndrome, psychosis, lower urinary tract symptom, senile dementia, bladder outlet obstruction associated with benign prostatic hyperplasia, Alzheimer disease, interstitial cystitis, addiction/withdrawal symptom, chronic prostatitis, cognitive impairment, acute ischemic stroke, Huntington's disease, transient ischemic attack, Parkinson's disease, head or spinal cord trauma, amyotrophic lateral sclerosis, fetal hypoxemia, AIDS dementia complex, nonulcer dyspepsia, chronic neurodegenerative disease, for example, retinal disease, reflux esophagitis, alcohol or cocaine addiction, hypersensitive bowel syndrome, extrapyramidal disorder, apnea/hypopnea syndrome, panic disorder, tremor, disturbance of short-term memory, nausea or emesis, alcoholism, epilepsy, nicotine dependence, sleep disorder, drug addiction, pain, eating disorder, sexual dysfunction, posttraumatic stress disorder, obesity, autism, cough, nerve root compression syndrome, myofascial syndrome, neuropathy, tendomyosis, algetic dystrophy, tendinosis, agitation, tendopathy, hostility, synovial bursa related disease, obsessive-compulsive disorder, periarthropathy, cognition enhancement, myofascial pain syndrome, premenstrual tension syndrome, autonomic imbalance, essential hypertension, psychophysiologic disorder, convulsion, peptic ulcer, mania, gastritis, migraine, meniscal lesion, polyarthritis, traumatic arthritis, paraneoplastic syndrome, osteochondritis dissecans, tumor-elicited inflammatory disease, osteonecrosis, inflammatory exudation, articularis chondromatosis, connective tissue disease, chronic obstructive pulmonary disease (COPD), infectious arthritis, acute respiratory distress syndrome (ARDS), seronegative spondyloarthropathy, bronchitis, vasculitis, pneumoconiosis, sarcoid arthropathy, laryngospasm, pulmonary angiitis, pulmonary granuloma, extrinsic allergic alveolitis, chronic fatigue syndrome, contact hypersensitivity, glaucoma, and so on. In particular, they are very useful for therapy and treatment of the diseases on which exertion of both $5\text{-HT}_{1A}$ agonistic action and $5\text{-HT}_3$ antagonistic action is effective, such as, for example, IBS, FD, reflux esophagitis, anxiety, psychophysiologic disorder, emesis, pain, urinary incontinence, anischuria and pollakiurea.

$5\text{-HT}_{1A}$ agonistic activity and $5\text{-HT}_3$ antagonistic activity of the compounds of the formula (I) provided by the present invention and the compounds of the formula (II) which are used in therapy of IBS following the present invention can be demonstrated by the following experiments.

(1) Affinity Measurement of the Compounds to Human 5-$HT_{1A}$ Receptor (in Vitro)

CHO cell membrane sample in which human 5-$HT_{1A}$ receptor was expressed (purchased from Packard Bioscience) 0.25 mL (about 50 units) was added to 24.75 mL of incubation buffer solution A (an aqueous solution of a mixture of 50 mmols/L of Tris-hydrochloric acid, 10 mmols/L of magnesium sulfate, 0.5 mmols/L of EDTA and 0.1% ascorbic acid, whose pH was adjusted to 7.4 at 27° C. with 1N-aqueous sodium hydroxide solution), and labeled as membrane sample suspension A. Separately, each test compound was made into 270 μmols/L DMSO solution and diluted to a prescribed concentration with the incubation buffer solution A, to provide a compound solution.

A piece of polypropylene tube was charged with 20 μL of [$^3$H]8-OH-DPAT (8-hydroxy-2-(di-n-propylamino)tetralin; purchased from Daiichi Pure Chemicals Co., Ltd.) (The concentration of the [$^3$H]8-OH-DPAT had been advancedly adjusted to render its concentration in the reaction mixture to 0.25 nmols/L) and 20 μL of one of the compound solutions. Further 500 μL of the membrane sample suspension A was added into the tube, followed by 60 minutes' incubation at 27° C. The reaction was terminated by rapid filtration of the reaction mixture through GF/C filter which had been advancedly immersed in a solution formed by adding to the incubation buffer solution A polyethyleneimine to a concentration of 0.3%, using Brandel cell harvester. Then the filter was washed with about 5 mL of 50 mmols/L of Tris-hydrochloric acid which had been cooled to 4° C. The filter was once again washed after similar operation.

Residual radioactivity on the filter was measured with liquid scintillation counter (Aloka Co., LSC-5100). Percent inhibition (%) of each test compound to binding of [$^3$H]8-OH-DPAT to 5-$HT_{1A}$ receptor at a concentration of 0.25 nmols/L, i.e., affinity of each test compound to 5-$HT_{1A}$ receptor, can be calculated according to the following expression. The ratio of non-specific binding was calculated by measuring the radioactivity in case of using 8-OH-DPAT at a concentration of 10 μmols/L, with which value the measured value of each test compound was compensated.

$$\left[1 - \frac{\text{radioactivity when each test compound was used}}{\text{radioactivity in the control experiment}} \times 100\right]$$

(2) Measurement of Affinity of Each Test Compound to Human 5-$HT_3$ Receptor (in Vitro):

HEK-293 cell membrane sample in which human 5-$HT_3$ receptor was expressed (purchased from BIOLINKS K.K.) 0.05 mL (about 50 microassay) was added to 24.95 mL of incubation buffer solution B (an aqueous solution of a mixture of 50 mmols/L of Tris-hydrochloric acid, 5 mmols/L of magnesium chloride and 1 mmol/L of EDTA, whose pH was adjusted to 7.5 at 25° C. with 1N-aqueous sodium hydroxide solution) and homogenized, to provide a membrane sample suspension B. Separately, each test compound was made into 270 μmols/L of DMSO solution and diluted to a prescribed concentration with the incubation buffer solution B to provide a compound solution.

A piece of polypropylene tube was charged with 20 μL of [$^3$H]BRL-43694 (purchased from Daiichi Pure Chemicals Co., Ltd.) (The concentration of [$^3$H]BRL-43694 had been advancedly adjusted to render its concentration in the reaction mixture to 0.5 nmols/L.) and 20 μL of one of the compound solutions. Further 500 μL of the membrane sample suspension B was added into the tube, followed by 60 minutes' incubation at 25° C. The reaction was terminated by rapid filtration of the reaction mixture through GF/B filter which had been advancedly immersed in a solution formed by adding to the incubation buffer solution B polyethyleneimine to a concentration of 0.5%, using Brandel cell harvester. Then the filter was washed with about 5 mL of 50 mmols/L of Tris-hydrochloric acid which had been cooled to 4° C. The filter was once again washed after similar operation.

Residual radioactivity on the filter was measured with liquid scintillation counter (ALOKA CO., LTD. LSC-5100). Percent inhibition (%) of each test compound to binding of [$^3$H]BRL-43694 to 5-$HT_3$ receptor at a concentration of 0.5 nmols/L, i.e., affinity of each test compound to 5-$HT_3$ receptor, can be calculated according to the following expression. The ratio of non-specific binding was calculated by measuring the radioactivity in case of using tropisetron: (ICS 205-930) at a concentration of 10 μmols/L, with which value the measured value of each test compound was compensated.

$$\left[1 - \frac{\text{radioactivity when each test compound was used}}{\text{radioactivity in the control experiment}} \times 100\right]$$

Affinity of each test compound to 5-$HT_{1A}$ receptor and 5-$HT_3$ receptor at a concentration of 100 nmols/L were as shown in the following Tables A-1 and A-2. BRL-43694 and tropisetron (ICS 205-930), which were used in measuring affinity of those compounds to 5-$HT_3$ receptor, have the following structures:

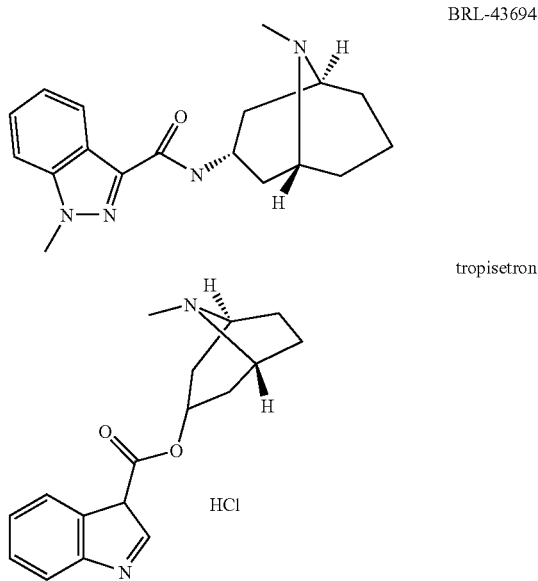

BRL-43694 tropisetron

TABLE A-1

| | Percent Inhibition (%) on Each Receptor's Binding at $10^{-7}$M | |
|---|---|---|
| Compound | 5-$HT_{1A}$ | 5-$HT_3$ |
| Example 1-1 | 94.5 | 94.0 |
| Example 1-4 | 96.6 | 93.2 |
| Example 1-5 | 85.0 | 82.6 |
| Example 1-14 | 99.8 | 95.9 |
| Example 1-24 | 95.7 | 79.6 |

TABLE A-1-continued

| Compound | Percent Inhibition (%) on Each Receptor's Binding at $10^{-7}$M | |
|---|---|---|
| | 5-HT$_{1A}$ | 5-HT$_3$ |
| Example 1-31 | 97.9 | 92.4 |
| Example 1-33 | 94.0 | 94.2 |
| Example 1-59 | 100.3 | 50.0 |
| Example 2-1 | 60.8 | 52.6 |
| Example 2-12 | 41.9 | 34.6 |
| Example 2-14 | 57.7 | 51.9 |
| Example 2-20 | 81.6 | 52.8 |
| Example 3-1 | 77.0 | 96.9 |
| Example 3-16 | 92.5 | 74.3 |
| Example 4-1 | 100.7 | 81.2 |
| Example 4-3 | 98.2 | 83.6 |
| Example 4-4 | 98.7 | 78.6 |
| Example 4-18 | 98.0 | 50.9 |
| Example 4-20 | 94.3 | 87.8 |
| Example 4-22 | 58.2 | 93.9 |
| Example 4-23 | 97.0 | 79.3 |
| Example 4-25 | 99.4 | 43.3 |
| Example 4-28 | 97.6 | 45.1 |
| Example 4-35 | 98.0 | 96.9 |
| Example 4-36 | 90.4 | 87.7 |
| Example 4-42 | 95.8 | 58.5 |
| Example 4-56 | 96.9 | 50.2 |
| Example 4-60 | 96.9 | 91.5 |
| Example 4-61 | 96.8 | 88.7 |
| Example 4-70 | 96.1 | 92.5 |
| Example 5-1 | 74.0 | 94.8 |
| Example 5-3 | 76.0 | 74.5 |
| Example 5-8 | 54.5 | 85.5 |
| Example 6-2 | 92.4 | 39.3 |
| Example 7-1 | 97.5 | 94.2 |
| Example 7-2 | 93.3 | 94.5 |
| Example 7-3 | 85.8 | 84.7 |
| Example 7-4 | 85.0 | 61.2 |
| Example 7-5 | 53.0 | 6.3 |
| Example 7-6 | 97.4 | 93.8 |
| Example 7-7 | 96.9 | 95.0 |
| Example 7-8 | 93.4 | 78.8 |
| Example 7-9 | 91.0 | 32.0 |
| Example 7-10 | 16.1 | 7.1 |
| Example 7-11 | 45.0 | 24.7 |
| Example 7-12 | 96.0 | 93.2 |
| Example 7-13 | 90.2 | 93.6 |
| Example 7-14 | 77.8 | 16.7 |
| Example 7-15 | 62.1 | 35.0 |
| Example 7-16 | 72.2 | 66.8 |
| Example 7-17 | 50.6 | 1.9 |
| Example 7-18 | 93.1 | 68.8 |
| Example 7-19 | 85.0 | 7.4 |
| Example 7-20 | 101.2 | 92.9 |
| Example 7-21 | 97.4 | 95.0 |
| Example 7-22 | 82.4 | 5.3 |
| Example 7-23 | 77.0 | 74.8 |
| Example 7-24 | 78.3 | 30.0 |
| Example 7-25 | 97.5 | 99.7 |
| Example 7-26 | 85.2 | 71.6 |
| Example 7-27 | 87.0 | 90.2 |
| Example 7-28 | 74.7 | 87.3 |
| Example 7-29 | 80.8 | 93.6 |
| Example 7-30 | 73.5 | 92.4 |

TABLE A-2

| Compound | Percent Inhibition (%) on Each Receptor's Binding at $10^{-7}$M | |
|---|---|---|
| | 5-HT$_{1A}$ | 5-HT$_3$ |
| Production Example 1 | 86.7 | 80.8 |
| Production Example 4 | 72.4 | 65.6 |
| Production Example 6 | 90.1 | 97.5 |
| Production Example 8 | 78.3 | 93.3 |

TABLE A-2-continued

| Compound | Percent Inhibition (%) on Each Receptor's Binding at $10^{-7}$M | |
|---|---|---|
| | 5-HT$_{1A}$ | 5-HT$_3$ |
| Production Example 10 | 98.5 | 73.8 |
| Production Example 16 | 61.1 | 99.2 |
| Production Example 17 | 83.6 | 82.9 |
| Production Example 23 | 83.2 | 85.8 |
| Production Example 25 | 83.2 | 65.5 |
| Production Example 28 | 23.9 | 92.5 |
| Production Example 30 | 92.8 | 93.4 |
| Production Example 32 | 91.7 | 94.4 |
| Production Example 37 | 57.3 | 70.2 |
| Production Example 38 | 94.8 | 93.1 |
| Production Example 40 | 42.9 | 99.3 |
| Production Example 47 | 90.6 | 93.6 |
| Production Example 49 | 88.7 | 96.3 |
| Production Example 52 | 84.1 | 97.0 |
| Production Example 57 | 88.9 | 96.5 |
| Production Example 61 | 25.3 | 94.1 |
| Production Example 63 | 80.4 | 96.8 |
| Production Example 71 | 94.8 | 42.2 |
| Production Example 72 | 96.7 | 99.8 |
| Production Example 73 | 98.3 | 99.3 |
| Production Example 74 | 94.6 | 98.9 |
| Production Example 76 | 96.6 | 94.4 |
| Production Example 77 | 98.9 | 97.9 |
| Production Example 81 | 95.8 | 74.4 |
| Production Example 82 | 99.3 | 90.3 |
| Production Example 85 | 99.9 | 98.9 |
| Production Example 87 | 96.4 | 96.9 |
| Production Example 89 | 92.1 | 83.5 |
| Production Example 98 | 88.2 | 60.8 |
| Production Example 102 | 95.4 | 98.9 |
| Production Example 103 | 91.4 | 99.5 |
| Production Example 104 | 85.5 | 99.3 |
| Production Example 105 | 72.7 | 96.4 |
| Production Example 106 | 100.7 | 98.3 |
| Production Example 107 | 98.5 | 95.9 |
| Production Example 108 | 90.6 | 100.1 |
| Production Example 109 | 75.4 | 92.5 |
| Production Example 110 | 98.9 | 97.9 |
| Production Example 111 | 48.0 | 95.5 |
| Production Example 112 | 53.9 | 98.8 |
| Production Example 113 | 56.4 | 82.4 |
| Production Example 114 | 16.7 | 91.0 |
| Production Example 115 | 82.0 | 74.3 |
| Production Example 116 | 70.6 | 25.6 |
| Production Example 117 | 57.7 | 10.6 |
| Production Example 118 | 76.0 | 84.9 |
| Production Example 119 | 33.7 | 71.9 |
| Production Example 120 | 81.0 | 99.4 |
| Production Example 121 | 69.3 | 85.6 |

(3) Measurement of 5-HT$_{1A}$ Receptor Agonistic Action on Rats (in Vivo):

Seven weeks old SD male rats were divided into 4-5 rats per group which were accustomized to the experimental environments twice. A week after the second accustomization, the rats were put into a transparent plastic case, and 10 mg/kg of a test compound (as dissolved in 1N-hydrochloric acid and diluted with suitable amount of saline) was intraperitoneally administered thereto. Immediately before the administration and 5, 10, 20 and 30 minutes after the administration, behaviors of the rats were observed as to lower lip retraction (LLP) and flat body posture (FBP). The results were evaluated in 4 grades (0: no reaction, 1: feeble reaction, 2: medium reaction, 3: maximum reaction). The maximum value of the evaluation points of each group was determined, with the result as shown in the following Tables B-1 and B-2.

TABLE B-1

| | 5-HT$_{1A}$ Receptor Agonistic Action on Rats | |
|---|---|---|
| Compound | LLR | FBP |
| Example 4-1 | 1.5 | 1.8 |
| Example 4-3 | 1.8 | 1.8 |
| Example 4-4 | 2.8 | 2.6 |
| Example 4-18 | 2.2 | 2.8 |
| Example 4-25 | 0.8 | 1.0 |
| Example 7-1 | 2.2 | 1.8 |
| Example 7-2 | 0.2 | 0.4 |
| Example 7-6 | 2.4 | 2.0 |
| Example 7-7 | 2.2 | 2.2 |
| Example 7-20 | 1.6 | 1.8 |

TABLE B-2

| | 5-HT$_{1A}$ Receptor Agonistic Action on Rats | |
|---|---|---|
| Compound | LLR | FBP |
| Production Example 6 | 2.8 | 2.4 |
| Production Example 8 | 2.0 | 0.8 |
| Production Example 34 | 3.0 | 2.8 |
| Production Example 49 | 2.2 | 1.8 |
| Production Example 72 | 3.0 | 3.0 |
| Production Example 73 | 2.4 | 2.2 |
| Production Example 102 | 3.0 | 3.0 |
| Production Example 103 | 3.0 | 0.4 |
| Production Example 104 | 1.6 | 0.2 |
| Production Example 107 | 2.8 | 3.0 |
| Production Example 108 | 2.4 | 0.4 |

(4) Measurement of 5-HT$_3$ Receptor Antagonistic Action on Rats (in Vivo)

SD male rats (weighing 270-410 g) were anesthetized by peritoneal administration of 1.25 g/kg of urethane (as dissolved in distilled water), and then catheters for measuring blood pressure and heart rate were inserted into their left carotid artery and a catheter for administration of test compound was inserted into their right carotid artery. After their blood pressure and heart rate were stabilized, 300 µg/kg of 5-hydroxytryptamine creatinine sulfate (serotonin) was rapidly intravenously administered and thereby induced transient bradycardiac reaction (BC 1) was observed. When the blood pressure and heart rate were re-stabilized after the serotonic administration, the test compounds were intravenously administered to the rats. Ten minutes thereafter, 300 µg/kg of serotonin was once again rapidly intravenously administered and thereby induced transient bradycardiac reaction (BC 2) was observed. Percent inhibition of bradycardia manifestation of each test compound, i.e., BJ reflex inhibition, can be calculated according to the following expression:

$$\left[\frac{BC1 - BC2}{BC1} \times 100\right]$$

Bradycardia manifestation inhibition of each test compound was as shown in the following Tables C-1 and C-2.

TABLE C-1

| Compound | Dose (mg/kg) | BC Inhibition (%) |
|---|---|---|
| Example 4-1 | 0.1 | 70.4 |
| Example 4-3 | 1.0 | 90.1 |
| Example 4-4 | 0.1 | 68.7 |
| Example 4-18 | 0.1 | 35.6 |
| Example 4-25 | 0.1 | 49.1 |
| Example 7-1 | 0.1 | 90.3 |
| Example 7-6 | 0.01 | 58.5 |
| Example 7-7 | 1.0 | 85.4 |
| Example 7-20 | 0.01 | 64.7 |

TABLE C-2

| Compound | Dose (mg/kg) | BC Inhibition (%) |
|---|---|---|
| Production Example 34 | 1.0 | 92.0 |
| Production Example 35 | 1.0 | 94.6 |
| Production Example 38 | 1.0 | 82.9 |
| Production Example 46 | 1.0 | 94.4 |
| Production Example 47 | 1.0 | 89.9 |
| Production Example 49 | 1.0 | 96.8 |
| Production Example 50 | 1.0 | 86.8 |
| Production Example 72 | 0.3 | 72.5 |
| Production Example 73 | 0.01 | 52.2 |
| Production Example 95 | 1.0 | 96.0 |
| Production Example 102 | 3.0 | 61.5 |
| Production Example 103 | 3.0 | 57.6 |
| Production Example 104 | 10.0 | 46.1 |

(5) Measurement of Defecation Acceleration in Rats under Restraint Stress

Six weeks old SD male rats were divided into 6-8 rats per groups, which were separately bred in five chained cages starting a day before the test, to accustomize them to the environments. Feed and drinking water were left for their free ingestion until the morning of the day on which the test was given. On the day of the experiment, test compounds were orally administered and positive control solution (the used compounds were dissolved in 1N-hydrochloric acid and diluted with a suitable amount of saline) was administered intraperitoneally. Five (5) minutes thereafter, under lightly anesthetized condition, the rats were placed under restraint stress, with their upper half of the bodies including the front feet immobilized with gum tape. The restraint stress loading was conducted for an hour, and the number of excrements discharged during that period was counted.

The average values in each group of the action of the compounds of the present invention on the stress defecation are shown in the following Table D, in comparison with average values in each group of the actions of combinations of various 5-HT$_{1A}$ agonistic agents and 5-HT$_3$ antagonistic agents, wherein the animal group administered with saline and not loaded with the restraint stress was labeled as normal group, and that administered with saline and loaded with the restraint stress, as control group.

Those compounds which were used as the positive control chemicals used in the acceleration of defecation in rats under restraint stress are identified with the following structures.

TABLE D

| Action of Compounds of Present Invention on Defecation Under Stress | | |
|---|---|---|
| Compound | Dose | Number of excrements |
| Normal | | 1.7 |
| Control | | 6.8 |
| Example 4-1 | 0.3 mg/kg | 5.3 |
| (intraperitoneal | 1 mg/kg | 4.3 |

TABLE D-continued

Action of Compounds of Present Invention on Defecation Under Stress

| Compound | Dose | Number of excrements |
|---|---|---|
| administration) | 3 mg/kg | 2.1 |
| Example 7-1 | 1 mg/kg | 5.8 |
| (oral administration) | 3 mg/kg | 3.8 |
| | 10 mg/kg | 2.3 |
| Example 7-6 | 1 mg/kg | 5.4 |
| (oral administration) | 3 mg/kg | 4.0 |
| | 10 mg/kg | 2.9 |
| Example 7-20 | 1 mg/kg | 5.4 |
| (oral administration) | 3 mg/kg | 3.6 |
| | 10 mg/kg | 2.4 |
| tandospirone | 1 mg/kg | 5.7 |
| (intraperitoneal | 3 mg/kg | 4.3 |
| administration) | 10 mg/kg | 3.8 |
| buspirone (intraperitoneal | 1 mg/kg | 4.3 |
| administration) | | |
| alosetron | 0.3 mg/kg | 5.2 |
| (intraperitoneal | 1 mg/kg | 4.1 |
| administration) | 3 mg/kg | 3.7 |
| granisetron (intraperitoneal | 0.3 mg/kg | 4.3 |
| administration) | | |
| cilansetron (intraperitoneal | 1 mg/kg | 4.0 |
| administration) | | |
| tandospirone (3 mg/kg) + alosetron (1 mg/kg) | | 2.4 |
| (intraperitoneal administration) | | |
| tandospirone (3 mg/kg) + granisetron (0.3 mg/kg) | | 2.6 |
| (intraperitoneal administration) | | |
| tandospirone (3 mg/kg) + cilansetron (1 mg/kg) | | 2.3 |
| (intraperitoneal administration) | | |
| buspirone (1 mg/kg) + alosetron (1 mg/kg) | | 2.8 |
| (intraperitoneal administration) | | |
| buspirone (1 mg/kg) + granisetron (0.3 mg/kg) | | 2.3 |
| (intraperitoneal administration) | | |
| buspirone (1 mg/kg) + cilansetron (1 mg/kg) | | 2.9 |
| (intraperitoneal administration) | | |

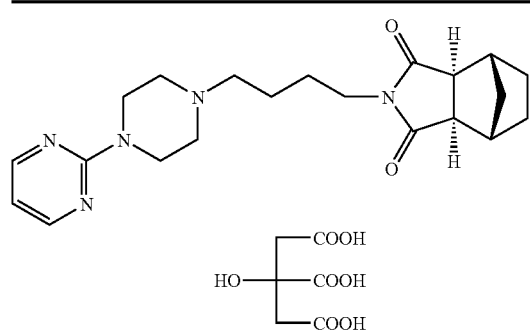

tandospirone

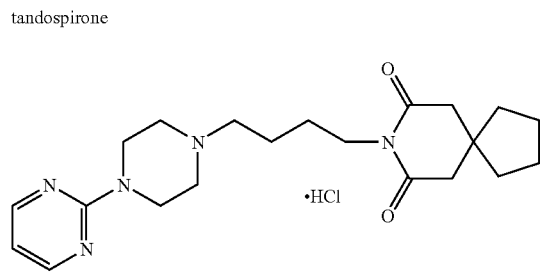

buspirone

TABLE D-continued

Action of Compounds of Present Invention on Defecation Under Stress

| Compound | Dose | Number of excrements |
|---|---|---| alosetron granisetron cilansetron

Thus the pyrimidine derivatives represented by the formula (I) of the present invention or their pharmaceutically acceptable salts can be orally or parenterally (e.g., intramuscular injection, intravenous injection, intraperitoneal administration, rectal administration, subcutaneous injection or the like) administered to human beings and other mammals for therapy or treatment, as 5-$HT_3$ antagonistic agents having 5-$HT_{1A}$ agonistic action. Also in the IBS-therapeutic method following the present invention, the 5-$HT_3$ antagonistic agent concurrently exhibiting 5-$HT_{1A}$ agonistic activity can be orally or parenterally (e.g., intramuscular injection, intravenous injection, intraperitoneal administration, rectal administration, endermic administration or the like) administered, or 5-$HT_{1A}$ agonistic agent and 5-$HT_3$ antagonistic agent can be similarly administered simultaneously, in sequence or at an interval, with the view to have cooperatively express 5-$HT_{1A}$ agonistic activity and 5-$HT_3$ antagonistic activity on human beings or other mammals in vivo.

Where compounds of the present invention and the active compounds which are used in therapy of IBS following the present invention are used as medicine, they can be formulated into medical preparations with non-toxic adjuvants, of such forms suitable for intended utilities such as solid (e.g., tablet, hard capsule, soft capsule, granule, powder, grain, pill, troche and the like); semi-solid (e.g., suppository, ointment and the like); or liquid (e.g., injection, emulsion, suspension, lotion, spray and the like). As non-toxic adjuvants useful for the preparations, for example, starch, gelatin, glucose, lactose, fructose, maltose, magnesium carbonate, talc, magnesium stearate, methyl cellulose, carboxymethyl cellulose or salts thereof, gum Arabic, polyethylene glycol, p-hydroxybenzoic acid alkyl esters, syrup, ethanol, propylene glycol, Vaseline, Carbowax, glycerine, sodium chloride, sodium sulfite, sodium phosphate, citric acid and the like can be named. The medical preparations may also contain therapeutically useful other medicines.

Content of compounds of the present invention or active compounds used in the therapy of IBS following the present invention in the medical preparations differs depending on the form of preparations. In general terms, for solid and semi-solid preparations it is desirable to use them at concentration levels of 0.1-50% by weight, and for liquid preparations, at the concentration levels of 0.05-10% by weight.

Dosage of compounds of the present invention or active compounds used in the therapy of IBS according to the present invention is variable over a broad range depending on the kind of object warm-blooded patients represented by human being, administration route, seriousness of symptoms, doctor's diagnosis and so on. In general terms, the dosage can be within a range of 0.01-5 mg/kg, preferably 0.02-2 mg/kg, per day. Whereas, of course dosages less than the above lower limit or more than the upper limit may be administered according to seriousness of individual patient, doctor's diagnosis and so on. Such a dosage can be administered once a day or in plural times as divided portions.

EXAMPLES

Hereinafter the present invention is more specifically explained, referring to working examples and formulation examples.

Example 1

Syntheses of Compounds of the Formula (I) in which $X^1$ Stands for Amino, Lower Alkylamino, Di-Lower Alkylamino or Lower Alkylideneamino; and Y Stands for Sulfur

Example 1-1

Step 1-1-A

To a solution formed by dissolving 4.31 g of anhydrous piperazine in 30 ml of ethylene glycol, 818 mg of 2-chloroquinoline was added, and stirred at 140° C. for 2 hours. After cooling, saturated aqueous sodium hydrogencarbonate solution was added, and the system was extracted with chloroform. The organic layer was dried over anhydrous magnesium sulfate and the solvent was distilled off under reduced pressure. The residue was purified on silica gel column chromatography (chloroform:methanol=2:1) to provide 1.09 g (100%) of 2-piperazin-1-ylquinoline.

$^1$H-NMR(CDCl$_3$) δ: 7.89 (d, J=9.2 Hz, 1H), 7.70 (d, J=8.4 Hz, 1H), 7.59 (dd, J=1.5 Hz, 8.0 Hz, 1H), 7.53 (ddd, J=1.5 Hz, 7.0 Hz, 8.4 Hz, 1H), 7.26~7.22 (m, 1H), 6.97 (d, J=9.2 Hz, 1H), 3.70 (t, J=5.0 Hz, 4H), 3.01 (t, J=5.0 Hz, 4H)

Mass, m/e: 213 (M$^+$), 145 (base)

Step 1-1-B

Dissolving 853 mg of 2-piperazin-1-ylquinoline as prepared in above Step 1-1-A in 5 ml of acetone, 5 ml of an aqueous solution containing 160 mg of sodium hydroxide was added to the solution, and into which 0.5 ml of 1-bromo-3-chloropropane was dropped, followed by stirring for an overnight at room temperature. Then diethyl ether was added, followed by washing with saturated aqueous sodium hydrogencarbonate solution, and the organic layer was dried over anhydrous magnesium sulfate. The solvent was distilled off under reduced pressure, and the residue was purified on silica gel column chromatography (chloroform:methanol=50:1) to provide 1.10 g (95%) of 2-[4-(3-chloropropyl)piperazin-1-yl]quinoline.

1H-NMR(CDCl$_3$) δ: 7.89 (d, J=9.2 Hz, 1H), 7.70 (d, J=8.4 Hz, 1H), 7.59 (dd, J=1.4 Hz, 8.0 Hz, 1H), 7.53 (ddd, J=1.5 Hz, 7.1 Hz, 8.5 Hz, 1H), 7.22 (ddd, J=1.1 Hz, 6.9 Hz, 8.0 Hz, 1H), 6.98 (d, J=9.2 Hz, 1H), 3.75 (t, J=5.1 Hz, 4H), 3.61 (t, J=6.5 Hz, 2H), 2.63~2.43 (m, 6H), 2.04~1.97 (m, 2H)

Mass, m/e: 289 (M$^+$), 157 (base)

Step 1-1-C

A mixture of 80 mg of potassium 3-amino-5,6-dimethyl-4-oxo-3,4-dihydrothieno[2,3-d]pyrimidine-2-thiolate, which was prepared from ethyl 2-amino-4,5-dimethylthiophene-3-carboxylate; 104 mg of 2-[4-(3-chloropropyl)piperazin-1-yl]quinoline as prepared in the Step 1-1-B; and 5 ml of ethanol, was heated under reflux for 4.5 hours. After cooling off the reaction mixture, chloroform was added, followed by washing with saturated brine. The organic layer was dried over anhydrous magnesium sulfate, and the solvent was distilled off under reduced pressure. The residue was purified on silica gel column chromatography (chloroform:methanol=100: 1) to provide 72 mg (50%) of 3-amino-5,6-dimethyl-2-[3-(4-quinolin-2-ylpiperazin-1-yl)-propylthio]-3H-thieno[2,3-d]pyrimidin-4-one.

$^1$H-NMR(CDCl$_3$) δ: 7.89 (d, J=8.7 Hz, 1H), 7.70 (d, J=8.4 Hz, 1H), 7.59 (d, J=8.1 Hz, 1H), 7.54-7.52 (m, 1H), 7.23-7.20 (m, 1H), 6.99 (d, J=9.2 Hz, 1H), 4.77 (s, 2H), 3.79 (t, J=5.1 Hz, 4H), 3.19 (t, J=7.3 Hz, 2H), 2.62 (t, J=5.1 Hz, 4H), 2.56 (t, J=7.0 Hz, 2H), 2.45 (s, 3H), 2.36 (s, 3H), 2.00 (q, J=7.3 Hz, 2H)

IR(KBr)vmax: 3308, 2916, 1668, 1604, 1506 cm$^{-1}$

Mass, m/e: 480 (M$^+$), 157 (base)

Example 1-2

In the manner similar to Example 1-1, 3-amino-5,6-dimethyl-2-[3-(4-pyridin-2-ylpiperazin-1-yl)propylthio]-3H-thieno[2,3-d]pyrimidin-4-one was obtained.

melting point: 183.1-184.8° C.

$^1$H-NMR(CDCl$_3$) δ: 8.19 (ddd, J=0.6 Hz, 1.9 Hz, 4.9 Hz, 1H), 7.48 (ddd, J=1.9 Hz, 7.2 Hz, 8.9 Hz, 1H), 6.65 (d, J=8.5 Hz, 1H), 6.62 (ddd, J=0.8 Hz, 4.9 Hz, 7.1 Hz, 1H), 4.77 (s, 2H), 3.57 (t, J=5.0 Hz, 4H), 3.18 (t, J=7.1 Hz, 2H), 2.59 (t, J=5.1 Hz, 4H), 2.54 (t, J=7.0 Hz, 2H), 2.44 (s, 3H), 2.36 (s, 3H), 1.98 (q, J=7.2 Hz, 2H)

IR(KBr)vmax: 3500, 2920, 1660, 1592, 1504 cm$^{-1}$

Mass, m/e: 430 (M$^+$), 107 (base)

Example 1-3

In the manner similar to Example 1-1, 3-amino-2-[3-(4-pyridin-2-ylpiperazin-1-yl)propylthio]-5,6,7,8-tetrahydro-3H-benzo[4,5]thieno[2,3-d]pyrimidine-4-one was obtained.

$^1$H-NMR(CDCl$_3$) δ: 8.19 (ddd, J=0.8 Hz, 2.1 Hz, 4.9 Hz, 1H), 7.49~7.47 (m, 1H), 6.65 (d, J=8.8 Hz, 1H), 6.63~6.61 (m, 1H), 4.77 (s, 2H), 3.57 (t, J=5.2 Hz, 4H), 3.17~3.15 (m, 2H), 2.97~2.94 (m, 2H), 2.77~2.73 (m, 2H), 2.59 (t, J=4.9 Hz, 4H), 1.98 (q, J=7.2 Hz, 2H), 1.89~1.78 (m, 4H)

IR(KBr)vmax: 3104, 2940, 1594, 1506 cm$^{-1}$

Mass, m/e: 456 (M$^+$), 107 (base)

Example 1-4

In the manner similar to Example 1-1, 3-amino-2-[3-(4-quinolin-2-ylpiperazin-1-yl)propylthio]-5,6,7,8-tetrahydro-3H-benzo[4,5]thieno[2,3-d]pyrimidin-4-one was obtained.

$^1$H-NMR(CDCl$_3$) δ: 7.88 (d, J=8.7 Hz, 1H), 7.70 (d, J=7.8 Hz, 1H), 7.59 (dd, J=1.3 Hz, 8.0 Hz, 1H), 7.53 (m, 1H), 7.24~7.20 (m, 1H), 6.99 (d, J=9.2 Hz, 1H), 4.77 (s, 2H), 3.79 (t, J=5.1 Hz, 4H), 3.21~3.17 (m, 2H), 2.99~2.95 (m, 2H), 2.75~2.71 (m, 2H), 2.62 (t, J=5.1 Hz, 4H), 2.56 (t, J=7.0 Hz, 2H), 1.99 (q, J=7.3 Hz, 2H), 1.91~1.80 (m, 4H)

Mass, m/e: 506 (M$^+$), 157 (base)

Example 1-5

In the manner similar to Example 1-1, 3-amino-5,6-dimethyl-2-[3-(4-pyrrolo[1,2-a]quinoxalin-4-ylpiperazin-1-yl)propylthio]-3H-thieno[2,3-d]pyrimidin-4-one was obtained.

$^1$H-NMR(CDCl$_3$) δ: 7.82~7.81 (m, 1H), 7.73 (dd, J=1.5 Hz, 8.0 Hz, 1H), 7.67 (dd, J=1.5 Hz, 8.0 Hz, 1H), 7.34~7.25 (m, 2H), 6.80 (dd, J=1.3 Hz, 3.9 Hz, 1H), 6.77~6.75 (m, 1H), 4.78 (s, 2H), 3.85 (t, J=4.9 Hz, 4H), 3.20 (t, J=7.2 Hz, 2H), 2.68 (t, J=4.9 Hz, 4H), 2.68 (t, J=7.2 Hz, 2H), 2.44 (s, 3H), 2.36 (s, 3H), 2.04~1.96 (m, 2H)

IR(KBr)vmax: 3468, 1662, 1510 cm$^{-1}$

Mass, m/e: 519 (M$^+$), 196 (base)

Example 1-6

In the manner similar to Example 1-1, 3-amino-2-[3-(4-benzothiazol-2-ylpiperazin-1-yl)propylthio]-5,6-dimethyl-3H-thieno[2,3-d]pyrimidin-4-one was obtained.

Melting point; 200.5-201.2° C.

$^1$H-NMR(CDCl$_3$) δ: 7.61~7.59 (m, 1H), 7.57~7.55 (m, 1H), 7.29 (ddd, J=1.4 Hz, 7.5 Hz, 7.9 Hz, 1H), 7.08 (ddd, J=1.2 Hz, 7.5 Hz, 7.9 Hz, 1H), 4.77 (s, 2H), 3.68 (t, J=5.1 Hz, 4H), 3.18 (t, J=7.4 Hz, 2H), 2.62 (t, J=5.1 Hz, 4H), 2.56~2.54 (m, 2H), 2.44 (d, J=0.7 Hz, 3H), 2.36 (d, J=0.9 Hz, 3H), 2.00~1.94 (m, 2H)

IR(KBr)vmax: 3200, 2920, 1666, 1512 cm$^{-1}$

Mass, m/e: 486 (M$^+$), 128 (base)

Example 1-7

In the manner similar to Example 1-1, 3-amino-2-[3-(4-quinolin-2-ylpiperazin-1-yl)propylthio]-3H-thieno-[3,2-d]pyrimidin-4-one was obtained.

$^1$H-NMR(CDCl$_3$) δ: 7.90 (d, J=5.1 Hz, 1H), 7.70 (d, J=8.4 Hz, 1H), 7.61~7.58 (m, 1H), 7.53 (ddd, J=1.5 Hz, 7.0 Hz, 8.4 Hz, 1H), 7.23~7.21 (m, 1H), 7.20 (d, J=5.1 Hz, 1H), 6.98 (d, J=9.1 Hz, 1H), 4.83 (s, 2H), 3.79 (t, J=4.9 Hz, 4H), 3.22 (t, J=7.3 Hz, 2H), 2.63 (t, J=4.9 Hz, 4H), 2.59 (t, J=7.3 Hz, 2H), 2.03 (q, J=7.3 Hz, 2H)

Mass, m/e: 452 (M$^+$), 157 (base)

Example 1-8

In the manner similar to Example 1-1, 3-amino-2-[3-(4-quinolin-2-ylpiperazin-1-yl)propylthio]-3H-quinazolin-4-one was obtained.

$^1$H-NMR(CDCl$_3$) δ: 8.22~8.19 (m, 1H), 7.89 (d, J=9.2 Hz, 1H), 7.73~7.69 (m, 1H), 7.61~7.51 (m, 3H), 7.41~7.36 (m, 1H), 7.24~7.20 (m, 1H), 6.99 (d, J=9.2 Hz, 1H), 4.82 (s, 2H), 3.79 (t, J=4.8 Hz, 4H), 3.26 (t, J=7.3 Hz, 2H), 2.65~2.58 (m, 6H), 2.05 (q, J=7.0 Hz, 2H)

Mass, m/e: 446 (M$^+$), 157 (base)

Example 1-9

In the manner similar to Example 1-1, 3-amino-5,6-dimethyl-2-[4-(4-quinolin-2-ylpiperazin-1-yl)but-2-enylthio]-3H-thieno-[2,3-d]pyrimidin-4-one was obtained.

$^1$H-NMR(CDCl$_3$) δ: 7.88 (d, J=9.2 Hz, 1H), 7.69 (d, J=8.3 Hz, 1H), 7.61~7.56 (m, 1H), 7.55~7.50 (m, 1H), 7.23~7.20 (m, 1H), 6.95 (d, J=9.2 Hz, 1H), 5.92~5.85 (m, 1H), 5.83~5.76 (m, 1H), 4.76 (s, 2H), 3.78 (d, J=6.7 Hz, 2H), 3.74 (t, J=5.1 Hz, 4H), 3.06 (d, J=6.4 Hz, 2H), 2.57 (t, J=5.1 Hz, 4H), 2.44 (s, 3H), 2.35 (s, 3H)

Mass, m/e: 492 (M$^+$), 157 (base)

Example 1-10

In the manner similar to Example 1-1, ethyl 3-amino-4-oxo-2-[3-(4-quinolin-2-ylpiperazin-1-yl)propylthio]-3,4-dihydroquinazoline-7-carboxylate was obtained.

$^1$H-NMR(CDCl$_3$) δ: 8.25 (d, J=5.5 Hz, 1H), 8.24 (d, J=0.7 Hz, 1H), 7.99 (dd, J=1.5 Hz, 8.4 Hz, 1H), 7.88 (d, J=9.2 Hz, 1H), 7.70 (d, J=8.1 Hz, 1H), 7.61~7.58 (m, 1H), 7.53 (ddd, J=1.8 Hz, 7.0 Hz, 8.8 Hz, 1H), 7.22 (ddd, J=1.1 Hz, 7.0 Hz, 8.1 Hz, 1H), 7.00 (d, J=4.2 Hz, 1H), 4.84 (s, 2H), 4.44 (q, J=7.3 Hz, 2H), 3.80 (t, J=5.1 Hz, 4H), 3.28 (t, J=7.0 Hz, 2H), 2.65 (t, J=5.1 Hz, 4H), 2.60 (t, J=7.0 Hz, 2H), 2.08~2.01 (m, 2H), 1.43 (t, J=7.3 Hz, 3H)

Mass, m/e: 518 (M$^+$), 157 (base)

Example 1-11

In the manner similar to Example 1-1, 3-amino-5,6-dimethyl-2-[3-(4-phenanthridin-6-ylpiperazin-1-yl)propylthio]-3H-thieno[2,3-d]pyrimidin-4-one was obtained.

$^1$H-NMR(CDCl$_3$) δ: 8.55 (d, J=8.4 Hz, 1H), 8.42 (dd, J=1.1 Hz, 8.1 Hz, 1H), 8.21 (d, J=7.3 Hz, 1H), 7.92 (dd, J=1.1 Hz, 8.1 Hz, 1H), 7.79~7.75 (m, 1H), 7.63~7.60 (m, 2H), 7.50~7.46 (m, 1H), 3.56 (br s, 4H), 3.21 (t, J=7.0 Hz, 2H), 2.79 (br s, 4H), 2.64 (t, J=7.0 Hz, 2H), 2.44 (s, 3H), 2.35 (s, 3H)

Mass, m/e: 530 (M$^+$), 207 (base)

Example 1-12

In the manner similar to Example 1-1, 3-amino-2-[3-(4-quinolin-2-ylpiperazin-1-yl)propylthio]-3,4,5,6,7,8-hexahydro-4,7-dioxa-9-thia-1,3-diaza-9H-fluorene was obtained.

$^1$H-NMR(CDCl$_3$) δ: 7.89 (d, J=9.1 Hz, 1H), 7.70 (d, J=8.1 Hz, 1H), 7.69 (d, J=7.9 Hz, 1H), 7.53 (ddd, J=1.3 Hz, 6.9 Hz, 8.2 Hz, 1H), 7.24~7.20 (m, 1H), 4.78 (s, 4H), 4.02~4.00 (m, 2H), 3.79 (t, J=5.0 Hz, 4H), 3.22~3.07 (m, 2H), 2.62 (t, J=5.0 Hz, 4H), 2.57 (t, J=6.8 Hz, 2H), 2.04~1.96 (m, 2H)

Mass, m/e: 508 (M$^+$), 157 (base)

Example 1-13

In the manner similar to Example 1-1, 3-amino-7-tert-butoxycarbonyl-2-[3-(4-quinolin-2-ylpiperazin-1-yl)propylthio]-3,4,5,6,7,8-hexahydro-4-oxa-9-thia-1,3,7-triaza-9H-fluorene was obtained.

$^1$H-NMR(CDCl$_3$) δ: 7.89 (d, J=9.2 Hz, 1H), 7.70 (d, J=8.4 Hz, 1H), 7.61~7.58 (m, 1H), 7.53 (ddd, J=1.5 Hz, 7.0 Hz, 8.4 Hz, 1H), 7.24~7.20 (m, 1H), 6.99 (d, J=9.2 Hz, 1H), 4.78 (s, 2H), 4.60 (br s, 2H), 3.79 (t, J=5.1 Hz, 4H), 3.73~3.70 (m, 2H), 3.22~3.18 (m, 2H), 3.06 (br s, 2H), 2.62 (t, J=5.1 Hz, 4H), 2.58~2.54 (m, 2H), 2.00 (q, J=7.3 Hz, 2H)

Mass, m/e: 607 (M$^+$), 157 (base)

Example 1-14

In the manner similar to Example 1-1, 3-amino-5-methyl-4-oxo-2-[3-(4-quinolin-2-ylpiperazin-1-yl)-propylthio]-3,4-dihydrothieno[2,3-d]pyrimidine-6-carboxylic acid ethyl ester was obtained.

$^1$H-NMR(CDCl$_3$) δ: 7.89 (d, J=8.8 Hz, 1H), 7.70 (d, J=8.4 Hz, 1H), 7.61~7.55 (m, 1H), 7.53 (ddd, J=1.5 Hz, 7.0 Hz, 8.4 Hz, 1H), 7.22 (ddd, J=1.1 Hz, 7.0 Hz, 8.1 Hz, 1H), 6.99 (d, J=9.2 Hz, 1H), 4.78 (s, 2H), 4.36 (q, J=7.3 Hz, 2H), 3.79 (t, J=5.1 Hz, 4H), 3.23~3.19 (m, 2H), 2.91 (s, 3H), 2.66~2.63 (m, 4H), 2.61~2.57 (m, 2H), 2.05~1.98 (m, 2H), 1.40 (t, J=7.3 Hz, 3H)

Mass, m/e: 538 (M$^+$), 157 (base)

Example 1-15

In the manner similar to Example 1-1, 3-amino-2-[3-(4-benzothiazol-2-ylpiperazin-1-yl)propylthio]-5,6,7,8-tetrahydro-3H-benzo[4,5]thieno[2,3-d]pyrimidin-4-one was obtained.

$^1$H-NMR(CDCl$_3$) δ: 7.59 (dd, J=1.2 Hz, 7.7 Hz, 1H), 7.54 (dd, J=1.2 Hz, 8.1 Hz, 1H), 7.29~7.27 (m, 1H), 7.07~7.05 (m, 1H), 4.76 (s, 2H), 3.68~3.66 (m, 4H), 3.19~3.15 (m, 2H), 2.97~2.94 (m, 2H), 2.73 (t, J=5.8 Hz, 2H), 2.60 (t, J=5.1 Hz, 4H), 2.55 (t, J=6.9 Hz, 2H), 1.96 (q, J=7.0 Hz, 2H), 1.90~1.83 (m, 4H)

Mass, m/e: 512 (M$^+$), 163 (base)

Example 1-16

In the manner similar to Example 1-1, 3-amino-7-nitro-2-[3-(4-quinolin-2-ylpiperazin-1-yl)propylthio]-3H-quinazolin-4-one was obtained.

$^1$H-NMR (DMSO-d$_6$) δ: 8.29 (d, J=8.9 Hz, 1H), 8.23 (d, J=2.2 Hz, 1H), 8.12 (dd, J=2.2 Hz, 8.9 Hz, 1H), 8.02 (d, J=9.2 Hz, 1H), 7.67 (d, J=7.2 Hz, 1H), 7.56~7.40 (m, 2H), 7.23~7.18 (m, 2H), 5.84 (s, 2H), 3.72 (t, J=4.8 Hz, 4H), 3.17 (t, J=7.3 Hz, 2H), 2.55~2.48 (m, 6H), 1.93 (t, J=7.3 Hz, 2H)

Mass, m/e: 491 (M$^+$), 157 (base)

Example 1-17

In the manner similar to Example 1-1, 3-amino-2-[3-(4-benzothiazol-2-ylpiperazin-1-yl)propylthio]-7-nitro-3H-quinazolin-4-one was obtained.

$^1$H-NMR (DMSO-d$_6$) δ: 8.30 (d, J=8.5 Hz, 1H), 8.23 (d, J=2.2 Hz, 1H), 8.14 (dd, J=2.2 Hz, 8.8 Hz, 1H), 7.75 (d, J=6.9 Hz, 1H), 7.45 (d, J=7.5 Hz, 1H), 7.29~7.25 (m, 1H), 7.08~7.04 (m, 1H), 5.85 (s, 2H), 3.62~3.59 (m, 4H), 3.19~3.15 (m, 2H), 2.51~2.49 (m, 6H), 1.93 (t, J=7.3 Hz, 2H)

Mass, m/e: 497 (M$^+$), 163 (base)

Example 1-18

In the manner similar to Example 1-1, 3-amino-2-[3-(4-benzothiazol-2-ylpiperazin-1-yl)propylthio]-3,4,5,6,7,8-hexahydro-4,7-dioxa-9-thia-1,3-diaza-9H-fluorene was obtained.

$^1$H-NMR(CDCl$_3$) δ: 7.65~7.51 (m, 2H), 7.38~7.13 (m, 2H), 4.78 (s, 2H), 4.00 (t, J=5.5 Hz, 2H), 3.74~3.54 (m, 4H), 3.27~3.02 (m, 4H), 2.67~2.49 (m, 6H), 2.13~1.88 (m, 2H), 1.62 (m, 2H),

Mass, m/e: 514 (M$^+$), 163 (base)

Example 1-19

In the manner similar to Example 1-1, 3-amino-2-[3-(4-quinolin-2-ylpiperazin-1-yl)propylthio]-3H-pyrido-[2,3-d]pyrimidin-4-one was obtained.

$^1$H-NMR(CDCl$_3$) δ: 8.77 (dd, J=1.5 Hz, 4.4 Hz, 1H), 7.92 (dd, J=1.5 Hz, 8.4 Hz, 1H), 7.89 (d, J=9.2 Hz, 1H), 7.70 (d, J=8.4 Hz, 1H), 7.64~7.59 (m, 2H), 7.54 (ddd, J=1.5 Hz, 7.0 Hz, 8.4 Hz, 1H), 7.25~7.21 (m, 1H), 6.99 (d, J=9.2 Hz, 1H), 4.94 (s, 2H), 3.79 (t, J=5.1 Hz, 4H), 3.27 (t, J=7.3 Hz, 2H), 2.64 (t, J=5.1 Hz, 4H), 2.60 (t, J=7.3 Hz, 2H), 2.05 (q, J=7.3 Hz, 2H)

Mass, m/e: 447 (M$^+$), 157 (base)

Example 1-20

In the manner similar to Example 1-1, 3-amino-7-tert-butoxycarbonyl-2-[3-(4-benzothiazol-2-ylpiperazin-1-yl)propylthio]-3,4,5,6,7,8-hexahydro-4-oxa-9-thia-1,3,7-triaza-9H-fluorene was obtained.

$^1$H-NMR(CDCl$_3$) δ: 7.60 (dd, J=0.7 Hz, 7.7 Hz, 1H), 7.56 (d, J=8.1 Hz, 1H), 7.31~7.29 (m, 1H), 7.10~7.06 (m, 1H), 4.78~4.76 (m, 2H), 4.61~4.59 (m, 2H), 3.73~3.68 (m, 6H), 3.21~3.18 (m, 2H), 3.06 (br s, 2H), 2.63~2.61 (m, 4H), 2.57 (t, J=7.0 Hz, 2H), 2.05~1.96 (m, 2H), 1.50 (s, 9H)

Mass, m/e: 613 (M$^+$), 56 (base)

Example 1-21

In the manner similar to Example 1-1, 3-amino-2-[3-(4-quinolin-2-ylpiperazin-1-yl)propylthio]-3H-pyrido[3,2-d]pyrimidin-4-one was obtained.

$^1$H-NMR(CDCl$_3$) δ: 8.92 (dd, J=1.8 Hz, 4.4 Hz, 1H), 8.55 (dd, J=1.8 Hz, 8.1 Hz, 1H), 7.88 (d, J=8.8 Hz, 1H), 7.70 (d, J=8.4 Hz, 1H), 7.59 (dd, J=1.1 Hz, 8.1 Hz, 1H), 7.53 (ddd, J=1.5 Hz, 7.0 Hz, 8.4 Hz, 1H), 7.37~7.34 (m, 1H), 7.24~7.20 (m, 1H), 6.98 (d, J=9.1 Hz, 1H), 4.84 (s, 2H), 3.78 (t, J=5.1 Hz, 4H), 3.38 (t, J=7.3 Hz, 2H), 2.64~2.59 (m, 6H), 2.07 (q, J=7.3 Hz, 2H)

Mass, m/e: 447 (M$^+$), 157 (base)

Example 1-22

In the manner similar to Example 1-1, 3-amino-2-[3-(4-benzothiazol-2-ylpiperazin-1-yl)propylthio]-3H-pyrido[2,3-d]pyrimidin-4-one was obtained.

$^1$H-NMR (DMSO-d$_6$) δ: 8.69 (dd, J=1.5 Hz, 4.4 Hz, 1H), 7.95~7.92 (m, 1H), 7.76~7.71 (m, 2H), 7.44~7.42 (m, 2H), 7.28~7.24 (m, 2H), 7.07~7.03 (m, 2H), 5.81 (s, 2H), 3.57 (t, J=5.1 Hz, 4H), 3.15~3.11 (m, 2H), 2.55~2.52 (m, 4H), 2.50~2.44 (m, 2H), 1.92~1.89 (m, 2H)

Mass, m/e: 453 (M$^+$), 163 (base)

Example 1-23

In the manner similar to Example 1-1, 3-amino-2-[3-(4-benzothiazol-2-ylpiperazin-1-yl)propylthio-3H-pyrido[3,2-d]pyrimidin-4-one was obtained.

$^1$H-NMR (DMSO-d$_6$) δ: 8.87 (dd, J=1.8 Hz, 5.3 Hz, 1H), 8.45 (dd, J=1.8 Hz, 8.1 Hz, 1H), 7.73 (d, J=8.1 Hz, 1H), 7.45~7.42 (m, 2H), 7.28~7.24 (m, 1H), 7.07~7.03 (m, 1H), 5.76 (s, 2H), 3.59~3.57 (m, 4H), 3.17~3.14 (m, 2H), 2.56 (br s, 4H), 2.53~2.48 (m, 2H), 1.94~1.90 (m, 2H)

Mass, m/e: 453 (M$^+$), 163 (base)

Example 1-24

In the manner similar to Example 1-1, 3-amino-2-[3-(4-quinolin-2-ylpiperazin-1-yl)propylthio]-3,4,5,6,7,8,9,10-octahydro-4-oxa-11-thia-1,3-diaza-11H-cycloocta[a]-indene was obtained.

$^1$H-NMR(CDCl$_3$) δ: 7.99 (d, J=9.0 Hz, 1H), 7.70 (d, J=9.0 Hz, 1H), 7.59 (d, J=8.0 Hz, 1H), 7.54~7.53 (m, 1H), 7.24~7.22 (m, 1H), 6.99 (d, J=9.2 Hz, 1H), 4.78 (s, 2H), 3.79 (t, J=5.1 Hz, 4H), 3.21~3.18 (m, 2H), 3.09 (t, J=6.4 Hz, 2H), 2.64~2.62 (m, 2H), 2.63 (t, J=5.1 Hz, 4H), 2.59~2.55 (m, 2H), 2.04~1.99 (m, 2H), 1.72~1.69 (m, 4H), 1.57~1.47 (m, 2H), 1.34~1.26 (m, 2H)

Mass, m/e: 534 (M$^+$), 157 (base)

Example 1-25

In the manner similar to Example 1-1, 3-amino-2-[3-(4-benzothiazol-2-ylpiperazin-1-yl)propylthio]-3,4,5,6,7,8,9,10-octahydro-4-oxa-11-thia-1,3-diaza-11H-cycloocta[a]-indene was obtained.

$^1$H-NMR(CDCl$_3$) δ: 7.58 (d, J=0.7 Hz, 1H), 7.56 (d, J=2.1 Hz, 1H), 7.32~7.28 (m, 1H), 7.10~7.08 (m, 1H), 4.79 (s, 2H), 3.73 (br s, 4H), 3.20~3.17 (m, 2H), 3.08~3.04 (m, 2H), 2.85~2.82 (m, 2H), 2.68 (br s, 4H), 2.62 (br s, 2H), 2.04~2.02 (m, 2H), 1.72~1.69 (m, 4H), 1.47~1.43 (m, 2H), 1.36~1.37 (m, 2H)

Mass, m/e: 540 (M$^+$), 163 (base)

Example 1-26

In the manner similar to Example 1-1, 3-amino-2-[3-(4-quinolin-2-ylpiperazin-1-yl)propylthio]-3,4,5,6,7-pentahydro-4-oxa-8-thia-1,3-diaza-8H-cyclopenta[a]indene was obtained.

$^1$H-NMR(CDCl$_3$) δ: 7.89 (d, J=9.2 Hz, 1H), 7.70 (d, J=8.1 Hz, 1H), 7.59 (d, J=8.1 Hz, 1H), 7.53 (ddd, J=1.5 Hz, 7.0 Hz, 8.4 Hz, 1H), 7.24~7.20 (m, 1H), 6.99 (d, J=9.2 Hz, 1H), 4.80 (s, 2H), 3.78 (t, J=5.1 Hz, 4H), 3.22~3.18 (m, 2H), 3.04 (t, J=7.3 Hz, 2H), 2.94 (t, J=7.3 Hz, 2H), 2.62 (t, J=5.1 Hz, 4H), 2.59~2.55 (m, 2H), 2.46 (q, J=7.0 Hz, 2H), 2.00 (q, J=7.3 Hz, 2H)

Mass, m/e: 492 (M$^+$), 157 (base)

Example 1-27

In the manner similar to Example 1-1, 3-amino-2-[3-[4-(4-methylquinolin-2-yl)piperazin-1-yl]propylthio]-3,4,5,6,7-pentahydro-4-oxa-8-thia-1,3-diaza-8H-cyclopenta[a]indene was obtained.

$^1$H-NMR(CDCl$_3$) δ: 7.77 (dd, J=1.3 Hz, 8.2 Hz, 1H), 7.72~7.70 (m, 1H), 7.53 (ddd, J=1.3 Hz, 3.0 Hz, 8.2 Hz, 1H), 7.25~7.22 (m, 1H), 6.85 (s, 1H), 4.80 (s, 2H), 3.78 (t, J=5.1 Hz, 4H), 3.22~3.18 (m, 2H), 3.04 (t, J=7.3 Hz, 2H), 2.94 (t, J=7.3 Hz, 2H), 2.61 (t, J=5.1 Hz, 4H), 2.60 (s, 3H), 2.56 (t, J=7.3 Hz, 2H), 2.50~2.42 (m, 2H), 2.00 (q, J=7.3 Hz, 2H)

Mass, m/e: 506 (M$^+$), 171 (base)

Example 1-28

In the manner similar to Example 1-1, 3-amino-2-[3-(4-benzothiazol-2-ylpiperazin-1-yl)propylthio]-3,4,5,6,7-pentahydro-4-oxa-8-thia-1,3-diaza-8H-cyclopenta[a]indene was obtained.

$^1$H-NMR (CDCl$_3$) δ: 7.60 (dd, J=0.7 Hz, 7.7 Hz, 1H), 7.56 (d, J=1.3 Hz, 1H), 7.32~7.28 (m, 1H), 7.10~7.06 (m, 1H), 4.80 (s, 2H), 3.69 (t, J=5.1 Hz, 4H), 3.21~3.17 (m, 2H), 3.06~3.02 (m, 2H), 2.94 (t, J=7.3 Hz, 2H), 2.62 (t, J=5.1 Hz, 4H), 2.56 (t, J=6.1 Hz, 4H), 2.46 (q, J=7.3 Hz, 2H), 1.98 (q, J=7.0 Hz, 2H)

Mass, m/e: 498 (M$^+$), 128 (base)

Example 1-29

In the manner similar to Example 1-1, 3-amino-5-methyl-2-[3-(4-quinolin-2-ylpiperazin-1-yl)propylthio]-5,6,7,8-tetrahydro-3H-benzo[4,5]thieno[2,3-d]pyrimidin-4-one was obtained.

$^1$H-NMR (CDCl$_3$) δ: 7.89 (d, J=9.2 Hz, 1H), 7.70 (d, J=8.4 Hz, 1H), 7.59 (d, J=8.1 Hz, 1H), 7.55~7.51 (m, 1H), 7.24~7.22 (m, 1H), 6.99 (d, J=9.2 Hz, 1H), 4.79 (s, 2H), 3.79 (t, J=5.1 Hz, 4H), 3.22~3.17 (m, 2H), 2.80~2.69 (m, 1H), 2.62 (t, J=5.1 Hz, 4H), 2.56 (t, J=7.0 Hz, 2H), 2.01~1.57 (m, 6H), 1.30 (d, J=6.0 Hz, 3H)

Mass, m/e: 520 (M$^+$), 157 (base)

Example 1-30

In the manner similar to Example 1-1, 3-amino-6-methyl-2-[3-(4-quinolin-2-ylpiperazin-1-yl)propylthio]-5,6,7,8-tetrahydro-3H-benzo[4,5]thieno[2,3-d]pyrimidin-4-one was obtained.

$^1$H-NMR (CDCl$_3$) δ: 7.89 (d, J=9.2 Hz, 1H), 7.70 (d, J=8.4 Hz, 1H), 7.60~7.58 (m, 1H), 7.53 (ddd, J=1.5 Hz, 7.0 Hz, 8.4 Hz, 1H), 7.22 (ddd, J=1.1 Hz, 7.0 Hz, 8.1 Hz, 1H), 6.99 (d, J=9.2 Hz, 1H), 4.77 (s, 2H), 3.79 (t, J=5.1 Hz, 4H), 3.19 (t, J=7.3 Hz, 2H), 2.63~2.62 (m, 1H), 2.62~2.60 (m, 4H), 2.56 (t, J=7.0 Hz, 2H), 2.04~1.92 (m, 6H), 1.00 (d, J=6.6 Hz, 3H)

Mass, m/e: 520 (M$^+$), 157 (base)

Example 1-31

In the manner similar to Example 1-1, 3-amino-7-methyl-2-[3-(4-quinolin-2-ylpiperazin-1-yl)propylthio]-5,6,7,8-tetrahydro-3H-benzo[4,5]thieno[2,3-d]pyrimidin-4-one was obtained.

$^1$H-NMR (CDCl$_3$) δ: 7.89 (d, J=9.2 Hz, 1H), 7.69 (m, 1H), 7.59 (d, J=7.9 Hz, 1H), 7.53 (d, J=7.9 Hz, 1H), 7.53 (m, 1H), 7.22 (m, 1H), 6.99 (d, J=9.2 Hz, 1H), 4.77 (s, 2H), 3.78 (t, J=5.1 Hz, 4H), 3.21~3.18 (m, 3H), 2.90~2.80 (m, 2H), 2.62 (t, J=5.1 Hz, 4H), 2.56 (t, J=7.0 Hz, 2H), 2.41~2.35 (m, 2H), 2.04~1.98 (m, 4H), 1.10 (d, J=6.6 Hz, 3H)

Mass, m/e: 520 (M$^+$), 157 (base)

Example 1-32

In the manner similar to Example 1-1, 3-amino-5,6-dimethyl-2-[3-[4-(4-methylquinolin-2-yl)piperazin-1-yl]propylthio]-3H-thieno[2,3-d]pyrimidin-4-one was obtained.

$^1$H-NMR (CDCl$_3$) δ: 7.77 (dd, J=1.1 Hz, 8.1 Hz, 1H), 7.71 (d, J=7.7 Hz, 1H), 7.53 (ddd, J=1.5 Hz, 7.0 Hz, 8.4 Hz, 1H), 7.25~7.22 (m, 1H), 6.84 (d, J=3.7 Hz, 1H), 4.78 (s, 2H), 3.78 (t, J=5.1 Hz, 4H), 3.20~3.17 (m, 2H), 2.62~2.60 (m, 4H), 2.60 (s, 3H), 2.58~2.54 (m, 2H), 2.44 (d, J=0.7 Hz, 3H), 2.36 (d, J=0.7 Hz, 3H), 1.99 (q, J=7.3 Hz, 2H)

Mass, m/e: 494 (M$^+$), 171 (base)

Example 1-33

In the manner similar to Example 1-1, 3-amino-2-[3-[4-(4-methylquinolin-2-yl)piperazin-1-yl]propylthio-5,6,7,8-tetrahydro-3H-benzo[4,5]thieno[2,3-d]pyrimidin-4-one was obtained.

¹H-NMR (CDCl₃) δ: 7.77 (dd, J=1.1 Hz, 8.4 Hz, 1H), 7.71 (d, J=8.4 Hz, 1H), 7.52 (ddd, J=1.5 Hz, 7.0 Hz, 8.4 Hz, 1H), 7.25~7.22 (m, 1H), 6.85 (s, 1H), 4.77 (s, 2H), 3.78 (t, J=5.1 Hz, 4H), 3.19 (t, J=7.3 Hz, 2H), 2.98~2.95 (m, 2H), 2.75 (t, J=5.9, 2H), 2.62~2.60 (m, 4H), 2.60 (s, 3H), 2.56 (t, J=7.3 Hz, 2H), 2.44 (d, J=0.7 Hz, 3H), 2.36 (d, J=0.7 Hz, 3H), 1.99 (q, J=7.3 Hz, 2H), 1.89~1.83 (m, 4H)

Mass, m/e: 520 (M⁺), 171 (base)

Example 1-34

In the manner similar to Example 1-1, 3-amino-2-[3-[4-(4-methylquinolin-2-yl)piperazin-1-yl]propylthio]-3,4,5,6,7,8-hexahydro-4,7-dioxa-9-thia-1,3-diaza-9H-fluorene was obtained.

¹H-NMR (CDCl₃) δ: 7.77 (dd, J=1.1 Hz, 8.0 Hz, 1H), 7.70 (d, J=8.4 Hz, 1H), 7.53 (ddd, J=1.5 Hz, 7.0 Hz, 8.4 Hz, 1H), 7.25~7.23 (m, 1H), 6.84 (s, 1H), 4.78 (br s, 4H), 4.13~3.99 (m, 2H), 3.78 (t, J=5.1 Hz, 4H), 3.22~3.18 (m, 2H), 3.10~3.07 (m, 2H), 2.63~2.55 (m, 6H), 2.60 (s, 3H), 2.04~1.97 (m, 2H)

Mass, m/e: 522 (M⁺), 171 (base)

Example 1-35

In the manner similar to Example 1-1, 3-amino-5,6-dimethyl-2-[3-[4-(5,6,7,8-tetrahydroquinolin-2-yl)piperazin-1-yl]propylthio]-3H-thieno[2,3-d]pyrimidin-4-one was obtained.

¹H-NMR (CDCl₃) δ: 7.17 (d, J=8.4 Hz, 1H), 6.43 (d, J=8.4 Hz, 1H), 4.77 (s, 2H), 3.50 (t, J=5.1 Hz, 4H), 3.17 (t, J=7.3 Hz, 2H), 2.75 (t, J=5.6 Hz, 2H), 2.63~2.52 (m, 8H), 2.44 (s, 3H), 2.35 (d, J=7.0 Hz, 3H), 1.97 (q, J=7.3 Hz, 1H), 1.86~1.80 (m, 2H), 1.78~1.75 (m, 2H)

Mass, m/e: 484 (M⁺), 161 (base)

Example 1-36

In the manner similar to Example 1-1, 3-amino-2-[3-[4-(5,6,7,8-tetrahydroquinolin-2-yl)piperazin-1-yl]propylthio]-5,6,7,8-tetrahydro-3H-benzo[4,5]thieno[2,3-d]pyrimidin-4-one was obtained.

¹H-NMR (CDCl₃) δ: 7.17 (d, J=8.4 Hz, 1H), 6.44 (d, J=8.4 Hz, 1H), 4.77 (s, 2H), 3.51 (t, J=5.1 Hz, 4H), 3.17 (t, J=7.3 Hz, 2H), 2.98~2.95 (m, 2H), 2.75~2.73 (m, 2H), 2.62~2.52 (m, 8H), 1.98 (q, J=7.3 Hz, 1H), 1.89~1.72 (m, 8H)

Mass, m/e: 510 (M⁺), 161 (base)

Example 1-37

In the manner similar to Example 1-1, 3-amino-2-[3-[4-(5,6,7,8-tetrahydroquinolin-2-yl)piperazin-1-yl]-propylthio]-3,4,5,6,7-pentahydro-4-oxa-8-thia-1,3-diaza-8H-cyclopenta[a]indene was obtained.

¹H-NMR (CDCl₃) δ: 7.18 (d, J=8.4 Hz, 1H), 6.44 (d, J=8.4 Hz, 1H), 4.81 (s, 2H), 3.52 (t, J=5.1 Hz, 4H), 3.18 (t, J=7.3 Hz, 2H), 2.95~2.91 (m, 2H), 2.76~2.57 (m, 6H), 2.46 (q, J=7.3 Hz, 2H), 2.01 (q, J=7.3 Hz, 2H), 1.86~1.68 (m, 8H)

Mass, m/e: 496 (M⁺), 161 (base)

Example 1-38

In the manner similar to Example 1-1, 3-amino-2-[3-[4-(7-methoxyisoquinolin-1-yl)piperazin-1-yl]propylthio]-5,6-dimethyl-3H-thieno[2,3-d]pyrimidin-4-one was obtained.

¹H-NMR (CDCl₃) δ: 8.07 (d, J=5.8 Hz, 1H), 7.68 (d, J=8.0 Hz, 1H), 7.40 (d, J=2.3 Hz, 1H), 7.30~7.27 (m, 1H), 7.21 (d, J=5.8 Hz, 1H), 4.78 (s, 2H), 3.94 (s, 3H), 3.44 (br s, 4H), 3.20 (t, J=7.3 Hz, 2H), 2.78 (br s, 4H), 2.64 (t, J=7.3 Hz, 2H), 2.44 (s, 3H), 2.35 (s, 3H), 2.02 (q, J=7.3 Hz, 2H)

Mass, m/e: 510 (M⁺), 187 (base)

Example 1-39

In the manner similar to Example 1-1, 3-amino-2-[3-[4-(7-methoxyisoquinolin-1-yl)piperazin-1-yl]propylthio]-5,6,7,8-tetrahydro-3H-benzo[4,5]thieno[2,3-d]-pyrimidin-4-one was obtained.

¹H-NMR (CDCl₃) δ: 8.07 (d, J=5.8 Hz, 1H), 7.68 (d, J=8.9 Hz, 1H), 7.40 (d, J=2.3 Hz, 1H), 7.30~7.27 (m, 1H), 7.21 (d, J=5.4 Hz, 1H), 4.78 (s, 2H), 3.94 (s, 3H), 3.45 (br s, 4H), 3.20 (t, J=7.0 Hz, 2H), 2.98~2.96 (m, 2H), 2.79 (br s, 4H), 2.73~2.71 (m, 2H), 2.65 (t, J=7.0 Hz, 2H), 2.03 (q, J=7.3 Hz, 2H), 1.86~1.82 (m, 4H)

Mass, m/e: 536 (M⁺), 187 (base)

Example 1-40

In the manner similar to Example 1-1, 3-amino-2-[3-[4-(7-methoxyisoquinolin-1-yl)piperazin-1-yl]-propylthio]-3H-pyrido[2,3-d]pyrimidin-4-one was obtained.

¹H-NMR (CDCl₃) δ: 8.70 (dd, J=1.5 Hz, 4.6 Hz, 1H), 7.92~7.91 (m, 1H), 7.69~7.66 (m, 1H), 7.63~7.57 (m, 1H), 7.40~7.34 (m, 1H), 7.30~7.20 (m, 2H), 4.93 (s, 2H), 3.91 (s, 3H), 3.48~3.44 (m, 4H), 3.30~3.26 (m, 2H)

Mass, m/e: 477 (M⁺), 187 (base)

Example 1-41

In the manner similar to Example 1-1, 3-amino-2-[3-[4-(7-methoxyisoquinolin-1-yl)piperazin-1-yl]-propylthio]-3H-pyrido[3,2-d]pyrimidin-4-one was obtained.

¹H-NMR (CDCl₃) δ: 8.99~8.90 (m, 1H), 8.56~8.54 (m, 1H), 8.06 (d, J=5.4 Hz, 1H), 7.69~7.67 (m, 2H), 7.40~7.21 (m, 3H), 4.84 (s, 2H), 3.94 (s, 3H), 3.45~3.38 (m, 6H), 2.79 (br s, 4H), 2.78~2.70 (m, 2H), 2.10~2.05 (m, 2H)

Mass, m/e: 477 (M⁺), 187 (base)

Example 1-42

In the manner similar to Example 1-1, 3-amino-2-[3-[4-(7-methoxy-3-methylisoquinolin-1-yl)piperazin-1-yl]propylthio]-5,6-dimethyl-3H-thieno[2,3-d]pyrimidin-4-one was obtained.

¹H-NMR (CDCl₃) δ: 7.58 (d, J=8.9 Hz, 1H), 7.34 (br s, 1H), 7.23 (dd, J=2.7 Hz, 8.9 Hz, 1H), 7.04 (s, 1H), 4.77 (s, 2H), 3.92 (s, 3H), 3.46 (br s, 4H), 3.21 (t, J=7.3 Hz, 2H), 2.78 (br s, 4H), 2.65~2.63 (m, 2H), 2.53 (s, 3H), 2.44 (s, 3H), 2.35 (s, 3H), 2.04 (br s, 2H)

Mass, m/e: 524 (M⁺), 188 (base)

Example 1-43

In the manner similar to Example 1-1, 3-amino-2-[3-[4-(7-methoxy-3-methylisoquinolin-1-yl)piperazin-1-yl]propylthio]-5,6,7,8-tetrahydro-3H-benzo[4,5]thieno[2,3-d]-pyrimidin-4-one was obtained.

¹H-NMR (CDCl₃) δ: 7.57 (d, J=8.7 Hz, 1H), 7.34 (d, J=1.5 Hz, 1H), 7.22 (dd, J=2.3 Hz, 8.9 Hz, 1H), 7.04 (s, 1H), 4.77 (s, 2H), 3.92 (s, 3H), 3.46 (br s, 4H), 3.20 (t, J=7.3 Hz, 2H), 2.96 (m, 2H), 2.77 (br s, 4H), 2.74~2.71 (m, 2H), 2.62~2.53 (m, 2H), 2.53 (s, 3H), 2.10 (br s, 2H), 1.86~1.85 (m, 2H)

Mass, m/e: 550 (M⁺), 188 (base)

Example 1-44

In the manner similar to Example 1-1, 3-amino-2-[3-[4-(5-methoxyisoquinolin-1-yl)piperazin-1-yl]-propylthio]-5,6-dimethyl-3H-thieno[2,3-d]pyrimidin-4-one was obtained.

$^1$H-NMR (CDCl$_3$) δ: 8.17 (d, J=5.8 Hz, 1H), 7.68~7.63 (m, 2H), 7.42 (d, J=8.1 Hz, 1H), 6.95 (d, J=7.7 Hz, 1H), 4.79 (s, 2H), 4.00 (s, 3H), 3.47 (br s, 4H), 3.21 (t, J=6.9 Hz, 2H), 2.77 (br s, 4H), 2.64 (t, J=7.3 Hz, 2H), 2.46 (s, 3H), 2.36 (s, 3H), 2.03 (q, J=7.3 Hz, 1H)

Mass, m/e: 510 (M$^+$), 187 (base)

Example 1-45

In the manner similar to Example 1-1, 3-amino-2-[3-[4-(5-methoxyisoquinolin-1-yl)piperazin-1-yl]-propylthio]-5,6,7,8-tetrahydro-3H-benzo[4,5]thieno[2,3-d]-pyrimidin-4-one was obtained.

$^1$H-NMR (CDCl$_3$) δ: 8.17 (d, J=5.8 Hz, 1H), 7.68~7.63 (m, 2H), 7.44~7.40 (m, 1H), 6.95 (d, J=7.7 Hz, 1H), 4.78 (s, 2H), 4.00 (s, 3H), 3.47 (br s, 4H), 3.21 (t, J=7.3 Hz, 2H), 2.99~2.96 (m, 2H), 2.76~2.74 (m, 6H), 2.64 (t, J=7.3 Hz, 2H), 2.06~2.00 (m, 2H)

Mass, m/e: 536 (M$^+$), 187 (base)

Example 1-46

In the manner similar to Example 1-1, 3-amino-2-[3-(4-furo[2,3-c]pyridin-7-ylpiperazin-1-yl)propylthio]-5,6-dimethyl-3H-thieno[2,3-d]pyrimidin-4-one was obtained.

$^1$H-NMR (CDCl$_3$) δ: 7.95 (d, J=5.4 Hz, 1H), 7.60 (d, J=2.3 Hz, 1H), 6.96 (d, J=5.4 Hz, 1H), 6.72 (d, J=1.9 Hz, 1H), 4.77 (s, 2H), 3.19 (t, J=7.3 Hz, 4H), 2.65 (t, J=5.0 Hz, 4H), 2.57 (t, J=0.8 Hz, 3H), 2.36 (d, J=0.8 Hz, 3H), 2.00 (q, J=7.3 Hz, 1H)

Mass, m/e: 470 (M$^+$), 147 (base)

Example 1-47

In the manner similar to Example 1-1, 3-amino-2-[3-(4-furo[3,2-c]pyridin-4-ylpiperazin-1-yl)propylthio]-5,6-dimethyl-3H-thieno[2,3-d]pyrimidin-4-one was obtained.

$^1$H-NMR (CDCl$_3$) δ: 8.04 (d, J=5.8 Hz, 1H), 7.53 (d, J=2.3 Hz, 1H), 6.94 (dd, J=0.8 Hz, 5.8 Hz, 1H), 6.82 (dd, J=1.2 Hz, 2.3 Hz, 1H), 4.77 (s, 2H), 3.76 (t, J=5.0 Hz, 4H), 3.19 (t, J=7.3 Hz, 2H), 2.65 (t, J=5.0 Hz, 4H), 2.57 (t, J=7.3 Hz, 2H), 2.45 (s, 3H), 2.36 (s, 3H), 2.05~1.96 (m, 2H)

Mass, m/e: 470 (M$^+$), 147 (base)

Example 1-48

In the manner similar to Example 1-1, 3-amino-2-[3-[4-(6-methoxyisoquinolin-1-yl)piperazin-1-yl]-propylthio]-5,6-dimethyl-3H-thieno[2,3-d]pyrimidin-4-one was obtained.

$^1$H-NMR (CDCl$_3$) δ: 8.09 (d, J=5.8 Hz, 1H), 8.00 (d, J=9.3 Hz, 1H), 7.16~7.10 (m, 2H), 7.02 (d, J=2.3 Hz, 1H), 4.78 (s, 2H), 3.93 (s, 3H), 3.45 (br s, 4H), 3.20 (t, J=7.3 Hz, 2H), 2.76 (br s, 4H), 2.63 (t, J=6.9 Hz, 2H), 2.44 (s, 3H), 2.35 (s, 3H), 2.03~2.00 (m, 1H)

Mass, m/e: 510 (M$^+$), 187 (base)

Example 1-49

In the manner similar to Example 1-1, 3-amino-2-[3-[4-(6-methoxyisoquinolin-1-yl)piperazin-1-yl]-propylthio]-5,6,7,8-tetrahydro-3H-benzo[4,5]thieno[2,3-d]pyrimidin-4-one was obtained.

1H-NMR (CDCl$_3$) δ: 8.09 (d, J=6.0 Hz, 1H), 7.99 (d, J=9.3 Hz, 1H), 7.16 (d, J=5.7 Hz, 1H), 7.12 (dd, J=2.7 Hz, 9.3 Hz, 1H), 7.02 (d, J=2.3 Hz, 1H), 4.78 (s, 2H), 3.93 (s, 3H), 3.45 (br s, 4H), 3.22~3.18 (m, 2H), 2.98~2.96 (m, 2H), 2.77 (br s, 4H), 2.73 (t, J=5.8 Hz, 2H), 2.66~2.62 (m, 2H), 2.05~2.00 (m, 2H), 1.88~1.75 (m, 4H)

Mass, m/e: 536 (M$^+$), 187 (base)

Example 1-50

In the manner similar to Example 1-1, 3-amino-2-[3-(4-quinolin-2-ylpiperazin-1-yl)propylthio]-5,6,7,8-tetrahydro-3H-quinazolin-4-one was obtained.

$^1$H-NMR (CDCl$_3$) δ: 7.89 (d, J=9.0 Hz, 1H), 7.70 (d, J=8.3 Hz, 1H), 7.59 (d, J=7.9 Hz, 1H), 7.53 (ddd, J=1.6 Hz, 7.0 Hz, 8.7 Hz, 1H), 7.24~7.20 (m, 1H), 6.98 (d, J=8.3 Hz, 1H), 4.80 (s, 2H), 3.77 (t, J=4.8 Hz, 4H), 3.14 (t, J=7.4 Hz, 4H), 2.62~2.60 (m, 4H), 2.58~2.45 (m, 6H), 1.99~1.95 (m, 2H), 1.80~1.72 (m, 4H)

Mass, m/e: 450 (M$^+$), 157 (base)

Example 1-51

In the manner similar to Example 1-1, 3-amino-2-[3-[4-(4-methylquinolin-2-yl)piperazin-1-yl]propylthio]-5,6,7,8-tetrahydro-3H-quinazolin-4-one was obtained.

$^1$H-NMR (CDCl$_3$) δ: 7.77 (m, 1H), 7.70 (d, J=8.1 Hz, 1H), 7.53 (ddd, J=1.5 Hz, 7.0 Hz, 8.4 Hz, 1H), 7.27~7.23 (m, 1H), 6.84 (d, J=0.7 Hz, 1H), 4.80 (s, 2H), 3.76 (t, J=5.1 Hz, 4H), 3.16~3.12 (m, 2H), 2.64~2.61 (m, 4H), 2.60~2.49 (m, 6H), 1.97 (q, J=7.3 Hz, 2H), 1.81~1.63 (m, 4H)

Mass, m/e: 464 (M$^+$), 171 (base)

Example 1-52

In the manner similar to Example 1-1, 3-amino-2-[3-[4-(3-chloroisoquinolin-1-yl)piperazin-1-yl]propylthio]-5,6-dimethyl-3H-thieno[2,3-d]pyrimidin-4-one was obtained.

$^1$H-NMR (CDCl$_3$) δ: 8.01 (d, J=8.1 Hz, 1H), 7.65 (d, J=8.1 Hz, 1H), 7.58 (dt, J=0.8 Hz, 6.6 Hz, 1H), 7.45 (ddd, J=1.2 Hz, 6.9 Hz, 8.1 Hz, 1H), 7.25~7.23 (m, 1H), 4.78 (s, 2H), 3.53 (br s, 4H), 3.18 (t, J=7.3 Hz, 2H), 2.75 (br s, 4H), 2.63 (t, J=7.3 Hz, 2H), 2.43 (s, 3H), 2.34 (s, 3H), 2.00 (q, J=7.3 Hz, 2H)

Mass, m/e: 514 (M$^+$), 128 (base)

Example 1-53

In the manner similar to Example 1-1, 3-amino-2-[3-[4-(3-chloroisoquinolin-1-yl)piperazin-1-yl]propylthio]-5,6,7,8-tetrahydro-3H-benzo[4,5]thieno[2,3-d]pyrimidin-4-one was obtained.

$^1$H-NMR (CDCl$_3$) δ: 8.99 (d, J=8.5 Hz, 1H), 7.65 (d, J=7.0 Hz, 1H), 7.59 (dt, J=1.2 Hz, 6.9 Hz, 1H), 7.45 (ddd, J=1.5 Hz, 6.9 Hz, 8.5 Hz, 1H), 7.24~7.22 (m, 1H), 4.78 (s, 2H), 3.59 (br s, 4H), 3.19 (t, J=7.3 Hz, 2H), 2.97~2.90 (m, 2H), 2.81 (br s, 4H), 2.72~2.69 (m, 2H), 2.06~2.03 (m, 2H), 1.87~1.82 (m, 2H)

Mass, m/e: 128 (base)

Example 1-54

In the manner similar to Example 1-1, 3-amino-5,6-dimethyl-2-[3-[4-(3-methylquinoxalin-2-yl)piperazin-1-yl]propylthio]-3H-thieno[2,3-d]pyrimidin-4-one was obtained.

$^1$H-NMR (CDCl$_3$) δ: 7.88 (dd, J=1.1 Hz, 8.4 Hz, 2H), 7.82 (dd, J=1.1 Hz, 8.4 Hz, 2H), 7.57 (ddd, J=1.1 Hz, 6.9 Hz, 8.4 Hz, 1H), 7.50 (ddd, J=1.1 Hz, 6.9 Hz, 8.4 Hz, 1H), 4.78 (s, 2H), 3.39~3.48 (m, 4H), 3.20 (t, J=7.0 Hz, 2H), 2.71 (s, 3H), 2.68~2.73 (m, 4H), 2.57~2.63 (m, 2H), 2.45 (s, 3H), 2.36 (s, 3H), 1.94~2.08 (m, 2H)

Mass, m/e: 495 ($M^+$), 268 (base), 128

Example 1-55

In the manner similar to Example 1-1, 3-amino-2-[3-[4-(3-methylquinoxalin-2-yl)piperazin-1-yl]propylthio]-5,6,7,8-tetrahydro-3H-benzo[4,5]thieno[2,3-d]pyrimidin-4-one was obtained.

$^1$H-NMR (CDCl$_3$) δ: 7.88 (dd, J=1.1 Hz, 8.1 Hz, 1H), 7.82 (dd, J=1.1 Hz, 8.1 Hz, 1H), 7.58 (ddd, J=1.1 Hz, 6.9 Hz, 8.1 Hz, 1H), 7.51 (ddd, J=1.1 Hz, 6.9 Hz, 8.1 Hz, 1H), 4.77 (s, 2H), 3.38~3.49 (m, 4H), 3.20 (t, J=7.1 Hz, 2H), 2.93~2.99 (m, 8H), 2.00 (q, J=7.1 Hz, 2H), 1.79~1.93 (m, 4H)

Mass, m/e: 521 ($M^{+)}$, 349, 294, 128 (base)

Example 1-56

In the manner similar to Example 1-1, 3-amino-5,6-dimethyl-2-[3-[4-(3-phenylquinoxalin-2-yl)piperazin-1-yl]propylthio]-3H-thieno[2,3-d]pyrimidin-4-one was obtained.

$^1$H-NMR (CDCl$_3$) δ: 7.96~8.01 (m, 2H), 7.84 (dd, J=1.5 Hz, 8.4 Hz, 1H), 7.60 (ddd, J=1.1 Hz, 6.9 Hz, 8.1 Hz, 1H), 7.41~7.52 (m, 5H), 4.75 (s, 2H), 3.29~3.37 (m, 4H), 3.14 (t, J=7.0 Hz, 2H), 2.47~2.53 (m, 4H), 2.43 (s, 3H), 2.35 (s, 3H), 1.91 (q, J=7.0 Hz, 2H), 1.24 (t, J=7.0 Hz, 2H)

Mass, m/e: 557 ($M^{+)}$, 128 (base)

Example 1-57

In the manner similar to Example 1-1, 3-amino-4-oxo-2-[3-(4-quinolin-2-ylpiperazin-1-yl)propylthio]-3,4-dihydroquinazoline-7-carboxylic acid was obtained.

$^1$H-NMR (DMSO-d$_6$) δ: 8.05~7.99 (m, 2H), 7.72~7.66 (m, 2H), 7.57~7.47 (m, 3H), 7.24~7.18 (m, 2H), 5.79 (br s, 2H), 3.68 (br s, 4H), 3.17~3.13 (m, 2H), 2.81~2.77 (m, 2H), 2.54~2.52 (m, 4H), 1.90~1.83 (m, 2H)

Mass, m/e: 490 ($M^{+)}$, 157 (base)

Example 1-58

In 10 ml of tert-butanol, 250 mg of 3-amino-4-oxo-2-[3-(4-quinolin-2-ylpiperazin-1-yl)propylthio]-3,4-dihydroquinazolin-7-carboxylic acid as synthesized in Example 1-57 was dissolved, to which 52 mg of triethylamine, and further 147 mg of DPPA, were added by the order stated. This mixture was heated under reflux for an overnight. Distilling the solvent off under reduced pressure, the residue was purified on silica gel column chromatography (chloroform:methanol=50:1). The purified product was added to 8 ml of 4N hydrochloric acid-dioxane solution, stirred for an hour, and an excessive amount of triethylamine was added. Distilling the solvent off under reduced pressure, the residue was purified on silica gel column chromatography (chloroform:methanol=50:1) to provide 20 mg (8%) of 3,7-diamino-2-[3-(4-quinolin-2-ylpiperazin-1-yl)propylthio]-3H-quinazolin-4-one.

$^1$H-NMR (CDCl$_3$) δ: 8.02 (d, J=9.2 Hz, 1H), 7.72~7.67 (m, 2H), 7.56~7.49 (m, 2H), 7.25~7.19 (m, 2H), 6.65~6.62 (m, 1H), 6.50 (d, J=2.2 Hz, 1H), 6.03 (br s, 2H), 5.51 (br s, 2H), 3.70 (br s, 2H), 3.05 (t, J=7.0 Hz, 2H), 2.53~2.45 (m, 6H), 1.98~1.87 (m, 2H)

Mass, m/e: 461 ($M^{+)}$, 157 (base)

Example 1-59

To 6 ml of 4N-hydrochloric acid-dioxane solution, 100 mg of 3-amino-7-tert-butoxycarbonyl-2-[3-(4-quinolin-2-ylpiperazin-1-yl)propylthio]-3,4,5,6,7,8-hexahydro-4-oxa-9-thia-1,3,7-triaza-9H-fluorene as synthesized in Example 1-13 was added and stirred for 2.5 hours. Distilling the solvent off under reduced pressure, 105 mg (100%) of 3-amino-2-[3-(4-quinolin-2-ylpiperazin-1-yl)propylthio]-3,4,5,6,7,8-hexahydro-4-oxa-9-thia-1,3,7-triaza-9H-fluorene trihydrochloride was obtained.

$^1$H-NMR (DMSO-d$_6$) δ: 9.82 (br s, 1H), 8.46 (d, J=9.5 Hz, 1H), 8.32 (br s, 1H), 7.93 (d, J=7.7 Hz, 1H), 7.78 (m, 1H), 7.58 (d, J=9.2 Hz, 1H), 7.50 (m, 1H), 4.87 (d, J=8.2 Hz, 2H), 4.33 (br s, 2H), 4.20~3.85 (m, 4H), 3.70 (d, J=5.4 Hz, 2H), 3.39 (br s, 2H), 3.26 (br s, 2H), 3.17~3.13 (m, 4H), 2.23~2.16 (m, 2H)

Mass, m/e: 507 ($M^{+)}$, 157 (base)

Example 1-60

In the manner similar to Example 1-59, 3-amino-2-[3-(4-benzothiazol-2-ylpiperazin-1-yl)propylthio]-3,4,5,6,7,8-hexahydro-4-oxa-9-thia-1,3,7-triaza-9H-fluorene was obtained from 3-amino-7-tert-butoxycarbonyl-2-[3-(4-benzothiazol-2-ylpiperazin-1-yl)propylthio]-3,4,5,6,7,8-hexahydro-4-oxa-9-thia-1,3,7-triaza-9H-fluorene which was synthesized in Example 1-20.

$^1$H-NMR (CDCl$_3$) δ: 7.60 (dd, J=1.0 Hz, 7.9 Hz, 1H), 7.56 (d, J=7.6 Hz, 1H), 7.32~7.28 (m, 1H), 7.10~7.06 (m, 1H), 4.79 (s, 2H), 4.03~4.02 (m, 2H), 3.70~3.67 (m, 4H), 3.21~3.12 (m, 4H), 3.02~3.00 (m, 2H), 2.62 (t, J=5.1 Hz, 4H), 2.57 (t, J=7.0 Hz, 2H), 1.98 (q, J=7.3 Hz, 2H)

Mass, m/e: 513 ($M^{+)}$, 163 (base)

Example 1-61

First, in the manner similar to Example 1-1, 3-amino-7-tert-butyoxycarbonyl-2-[3-[4-(4-methylquinolin-2-yl)-piperazin-1-yl]propylthio]-3,4,5,6,7,8-hexahydro-4-oxa-9-thia-1,3,7-triaza-9H-fluorene was obtained. Then, in the manner similar to Example 1-59, 3-amino-2-[3-[4-(4-methylquinolin-2-yl)piperazin-1-yl]propylthio]-3,4,5,6,7,8-hexahydro-4-oxa-9-thia-1,3,7-triaza-9H-fluorene trihydrochloride was prepared.

$^1$H-NMR (DMSO-d$_6$) δ: 8.05~7.05 (m, 5H), 4.34 (br s, 4H), 3.71~3.15 (m, 6H), 2.69 (m, 4H), 2.51~2.46 (m, 7H), 2.20 (m, 2H)

Mass, m/e: 521 ($M^{+)}$, 171 (base)

Example 1-62

To 10 ml of tetrahydrofuran, 203 mg of 3-amino-2-[3-(4-quinolin-2-ylpiperazin-1-yl)-propylthio]-3,4,5,6,7,8-hexahydro-4-oxa-9-thia-1,3,7-triaza-9H-fluorene trihydrochloride as synthesized in Example 1-59 was added and into which 133 mg of triethylamine was dropped. Acetyl chloride was added to the mixture under cooling with ice, followed by 30 minutes stirring and distillation under reduced pressure. The residue was purified on silica gel column chromatography (chloroform:methanol=25:1) to provide 150 mg (83%) of 7-acetyl-3-amino-2-[3-(4-quinolin-2-ylpiperazin-1-yl)propylthio]-3,4,5,6,7,8-hexahydro-4-oxa-9-thia-1,3,7-triaza-9H-fluorene.

$^1$H-NMR (CDCl$_3$) δ: 7.99 (d, J=8.9 Hz, 1H), 7.70 (d, J=8.5 Hz, 1H), 7.59 (d, J=7.7 Hz, 1H), 7.55~7.51 (m, 1H), 7.24~7.21 (m, 1H), 6.99 (d, J=9.2 Hz, 1H), 4.78 (br s, 4H), 3.79 (t, J=4.6 Hz, 4H), 3.75 (d, J=5.8 Hz, 2H), 3.22~3.19 (m, 2H), 3.15~3.07 (m, 2H), 2.67 (t, J=4.6 Hz, 4H), 2.58~2.55 (m, 2H), 2.21 (s, 3H), 2.04~1.96 (m, 2H)

Mass, m/e: 549 ($M^+$), 157 (base)

Example 1-63

To 10 ml of tetrahydrofuran, 310 mg of 3-amino-2-[3-(4-quinolin-2-ylpiperazin-1-yl)propylthio]-3,4,5,6,7,8-hexahydro-4-oxa-9-thia-1,3,7-triaza-9H-fluorene trihydrochloride as synthesized in Example 1-59 was added and further 50 mg of ethyl iodide was added. Into this mixture 200 mg of triethylamine was dropped, followed by 3 days' stirring at room temperature. Distilling the solvent off under reduced pressure, the residue was purified on silica gel column chromatography (chloroform:methanol=10:1) to provide 100 mg (37%) of 3-amino-7-ethyl-2-[3-(4-quinolin-2-ylpiperazin-1-yl)-propylthio]-3,4,5,6,7,8-hexahydro-4-oxa-9-thia-1,3,7-triaza-9H-fluorene.

$^1$H-NMR (CDCl$_3$) δ: 7.87 (d, J=8.9 Hz, 1H), 7.69 (d, J=8.5 Hz, 1H), 7.59~7.57 (m, 1H), 7.54~7.50 (m, 1H), 7.21 (ddd, J=1.2 Hz, 7.0 Hz, 8.5 Hz, 1H), 6.97 (d, J=9.3 Hz, 1H), 4.87 (s, 2H), 3.79~3.76 (m, 4H), 3.65 (br s, 2H), 3.18 (t, J=7.3 Hz, 2H), 3.08 (t, J=5.8 Hz, 2H), 2.81 (t, J=5.8 Hz, 2H), 2.67~2.60 (m, 6H), 2.55 (t, J=7.0 Hz, 2H), 2.02~1.95 (m, 2H), 1.20 (t, J=7.3 Hz, 3H)

Mass, m/e: 535 ($M^+$), 157 (base)

Example 2

Syntheses of Compounds of the Formula (I) in which $X^1$ stands for hydrogen and Y stands for sulfur Example 2-1

In 3 ml of ethanol, 75 mg of potassium 5,6-dimethyl-4-oxo-3,4-dihydrothieno[2,3-d]pyrimidine-2-thiolate, which was prepared from ethyl 2-amino-4,5-dimethylthiophene-3-carboxylate, and 87 mg of 2-[4-(3-chloropropyl)piperazin-1-yl]pyridine were heated under reflux for 5 hours. Cooling the reaction system off, chloroform was added, followed by washing with saturated brine. The organic layer was dried over anhydrous magnesium sulfate and the solvent was distilled off under reduced pressure. The residue was purified on silica gel column chromatography (chloroform:methanol=100:1) to provide 93 mg (75%) of 5,6-dimethyl-2-[3-(4-pyridin-2-ylpiperazin-1-yl)propylthio]-3H-thieno[2,3-d]-pyrimidin-4-one.

melting point: 209.0-209.4° C.

$^1$H-NMR (CDCl$_3$) δ: 8.20~8.18 (m, 1H), 7.47 (ddd, J=1.9 Hz, 7.1 Hz, 8.8 Hz, 1H), 6.65 (d, J=8.6 Hz, 1H), 6.61 (dd, J=5.0 Hz, 7.1 Hz, 1H), 3.63 (t, J=5.1 Hz, 4H), 3.28 (t, J=6.9 Hz, 2H), 2.63 (t, J=5.1 Hz, 4H), 2.59 (d, J=6.7 Hz, 2H), 2.43 (s, 3H), 2.35 (s, 3H), 2.01 (q, J=6.8 Hz, 2H)

IR (KBr) vmax: 3468, 1650, 1590 cm$^{-1}$

Mass, m/e: 415 ($M^+$), 107 (base)

Example 2-2

In the manner similar to Example 2-1, 2-[3-(4-pyridin-2-ylpiperazin-1-yl)propylthio]-5,6,7,8-tetrahydro-3H-benzo[4,5]thieno[2,3-d]pyrimidin-4-one was obtained.

melting point: 190.2-191.6° C.

$^1$H-NMR (CDCl$_3$) δ: 8.19 (ddd, J=0.8 Hz, 2.0 Hz, 4.9 Hz, 1H), 7.47 (ddd, J=2.0 Hz, 7.1 Hz, 8.6 Hz, 1H), 6.65 (d, J=8.6 Hz, 1H), 6.61 (ddd, J=0.8 Hz, 4.9 Hz, 7.1 Hz, 1H), 3.64 (t, J=6.9 Hz, 4H), 3.29 (t, J=6.9 Hz, 2H), 2.99~2.95 (m, 2H), 2.76~2.72 (m, 2H), 2.63 (t, J=5.0 Hz, 4H), 2.59 (d, J=6.8 Hz, 2H), 1.90~1.79 (m, 4H)

IR (KBr) vmax: 2932, 1666, 1594 cm$^{-1}$

Mass, m/e: 441 ($M^+$), 107 (base)

Example 2-3

In the manner similar to Example 2-1, 5-methyl-4-oxo-2-[3-(4-pyridin-2-ylpiperazin-1-yl)propylthio]-3,4-dihydrothieno[2,3-d]pyrimidine-6-carboxylic acid ethyl ester was obtained.

melting point: 160.1-161.8° C.

$^1$H-NMR (CDCl$_3$) δ: 8.19~8.17 (m, 1H), 7.48~7.45 (m, 1H), 6.65 (d, J=8.6 Hz, 1H), 6.62 (dd, J=4.9 Hz, 7.1 Hz, 1H), 4.34 (q, J=7.1 Hz, 2H), 3.66~3.63 (m, 4H), 3.27~3.20 (m, 2H), 2.84 (s, 3H), 2.73 (t, J=5.1 Hz, 4H), 2.68 (t, J=7.0 Hz, 2H), 2.12~2.06 (m, 2H), 1.39 (t, J=7.1 Hz, 3H)

IR (KBr) vmax: 3452, 2928, 1710, 1656, 1594 cm$^{-1}$

Mass, m/e: 473 ($M^+$), 107 (base)

Example 2-4

In the manner similar to Example 2-1, 5,6-dimethyl-2-[3-(4-quinolin-2-yl-piperazin-1-yl)propylthio]-3H-thieno[2,3-d]pyrimidin-4-one was obtained.

melting point: 224.8-225.9° C.

$^1$H-NMR (CDCl$_3$) δ: 7.88 (d, J=8.8 Hz, 1H), 7.70 (d, J=8.6 Hz, 1H), 7.59 (dd, J=1.2 Hz, 8.0 Hz, 1H), 7.54~7.50 (m, 1H), 7.22 (ddd, J=1.2 Hz, 6.9 Hz, 8.0 Hz, 1H), 6.98 (d, J=9.2 Hz, 1H), 3.89~3.80 (m, 4H), 3.29 (t, J=6.9 Hz, 2H), 2.67 (t, J=4.9 Hz, 4H), 2.62 (t, J=6.8 Hz, 2H), 2.43 (d, J=0.8 Hz, 3H), 2.43 (d, J=0.8 Hz, 3H), 2.08~1.98 (m, 2H)

IR (KBr) vmax: 3056, 2916, 1678, 1616, 1552 cm$^{-1}$

Mass, m/e: 465 ($M^+$), 157 (base)

Example 2-5

In the manner similar to Example 2-1, 2-[3-(4-quinolin-2-ylpiperazin-1-yl)propylthio]-5,6,7,8-tetrahydro-3H-benzo[4,5]thieno[2,3-d]pyrimidin-4-one was obtained.

$^1$H-NMR (CDCl$_3$) δ: 7.89 (d, J=9.0 Hz, 1H), 7.70 (d, J=8.0 Hz, 1H), 7.60 (d, J=7.8 Hz, 1H), 7.55~7.51 (m, 1H), 7.24~7.18 (m, 1H), 6.99 (d, J=9.0 Hz, 1H), 3.89 (br s, 4H), 3.30 (t, J=6.8 Hz, 2H), 3.01~2.92 (m, 2H), 2.78~2.70 (m, 2H), 2.66 (br s, 4H), 2.68~2.58 (m, 2H), 1.89~1.78 (m, 2H), 1.59~1.50 (m, 2H)

IR (KBr) vmax: 3056, 2932, 1678, 1616, 1604, 1550, 1504 cm$^{-1}$

Mass, m/e: 491 ($M^+$), 157 (base)

Example 2-6

In the manner similar to Example 2-1, 5-methyl-4-oxo-2-[3-(4-quinolin-2-ylpiperazin-1-yl)propylthio]-3,4-dihydrothieno[2,3-d]pyrimidine-6-carboxylic acid ethyl ester was obtained.

melting point: 200.1-201.4° C.

$^1$H-NMR (CDCl$_3$) δ: 7.89 (d, J=9.1 Hz, 1H), 7.69 (d, J=7.8 Hz, 1H), 7.59 (dd, J=1.1 Hz, 7.9 Hz, 1H), 7.53~7.51 (m, 1H), 7.23~7.21 (m, 1H), 6.98 (dd, J=2.7 Hz, 9.2 Hz, 1H), 4.34 (q, J=7.1 Hz, 2H), 3.86~3.85 (m, 4H), 3.27 (t, J=6.2 Hz, 2H), 2.84 (s, 3H), 2.78~2.76 (m, 4H), 2.70 (t, J=7.0 Hz, 2H), 2.12~2.11 (m, 2H), 1.39 (t, J=7.1 Hz, 3H)

IR (KBr) vmax: 3464, 3048, 2936, 1712, 1662, 1604 cm$^{-1}$

Mass, m/e: 523 ($M^+$), 157 (base)

Example 2-7

In the manner similar to Example 2-1, 2-[3-(4-benzothiazol-2-ylpiperazin-1-yl)propylthio]-3H-quinazolin-4-one was obtained.

$^1$H-NMR (DMSO-$d_6$) δ: 8.04 (dd, J=1.5 Hz, 8.1 Hz, 1H), 7.78~7.74 (m, 1H), 7.51 (d, J=8.1 Hz, 1H), 7.45 (d, J=8.1 Hz, 1H), 7.43~7.39 (m, 1H), 7.29~7.27 (m, 1H), 7.08~7.05 (m, 1H), 3.59 (t, J=5.0 Hz, 4H), 3.27~3.25 (m, 2H), 2.54 (t, J=5.0 Hz, 4H), 2.51~2.49 (m, 2H), 1.95~1.88 (m, 2H)

Mass, m/e: 437 ($M^+$), 163, 109 (base)

Example 2-8

In the manner similar to Example 2-1, 2-[3-(4-quinolin-2-ylpiperazin-1-yl)propylthio]-3H-quinazolin-4-one was obtained.

$^1$H-NMR (CDCl$_3$) δ: 8.16 (dd, J=1.5 Hz, 8.5 Hz, 1H), 7.88 (d, J=8.1 Hz, 1H), 7.70~7.66 (m, 2H), 7.60~7.50 (m, 3H), 7.35 (ddd, J=1.1 Hz, 6.9 Hz, 8.1 Hz, 1H), 7.21 (ddd, J=0.8 Hz, 6.9 Hz, 8.1 Hz, 1H), 6.98 (d, J=9.2 Hz, 1H), 3.88 (t, J=5.0 Hz, 4H), 3.34 (t, J=7.0 Hz, 2H), 2.68~2.63 (m, 6H), 2.07~2.04 (m, 2H)

Mass, m/e: 431 ($M^+$), 157 (base)

Example 2-9

In the manner similar to Example 2-1, 5,6-dimethyl-2-[3-(4-pyrrolo[1,2-a]quinoxalin-4-ylpiperazin-1-yl)-propylthio-3H-thieno[2,3-d]pyrimidin-4-one was obtained.

$^1$H-NMR (CDCl$_3$) δ: 7.87 (dd, J=1.4 Hz, 2.8 Hz, 1H), 7.79~7.76 (m, 1H), 7.70~7.69 (m, 2H), 7.36~7.28 (m, 2H), 6.82 (dd, J=1.4 Hz, 3.9 Hz, 1H), 6.79~6.78 (m, 1H), 3.85 (t, J=4.9 Hz, 4H), 3.29 (t, J=7.2 Hz, 2H), 2.72 (t, J=4.9 Hz, 4H), 2.63~2.60 (m, 2H), 2.42 (s, 3H), 2.37 (s, 3H), 2.05~2.01 (m, 2H)

IR (KBr) vmax: 2920, 2824, 1668, 1518 cm$^{-1}$

Mass, m/e: 504 ($M^+$), 196 (base)

Example 2-10

In the manner similar to Example 2-1, 2-[3-(4-pyrrolo[1,2-a]quinoxalin-4-ylpiperazin-1-yl)propylthio]-5,6,7,8-tetrahydro-3H-benzo[4,5]thieno[2,3-d]pyrimidin-4-one was obtained.

$^1$H-NMR (CDCl$_3$) δ: 7.87 (dd, J=1.2 Hz, 2.0 Hz, 1H), 7.79~7.76 (m, 1H), 7.69~7.67 (m, 1H), 7.35~7.28 (m, 1H), 6.83~6.82 (m, 1H), 6.78 (dd, J=2.8 Hz, 4.0 Hz, 1H), 3.86~3.84 (m, 4H), 3.29 (t, J=7.3 Hz, 2H), 2.94 (J=5.9 Hz, 2H), 2.76~2.71 (m, 6H), 2.63~2.60 (m, 2H), 1.89~1.82 (m, 2H)

IR (KBr) vmax: 2936, 1664, 1518 cm$^{-1}$

Mass, m/e: 530 ($M^+$), 196 (base)

Example 2-11

In the manner similar to Example 2-1, 2-[3-(4-benzothiazol-2-ylpiperazin-1-yl)propylthio]-5,6-dimethyl-3H-thieno[2,3-d]pyrimidin-4-one was obtained.

Mass, m/e: 471 ($M^+$), 163 (base)

Example 2-12

In the manner similar to Example 2-1, 2-[3-(4-quinolin-2-ylpiperazin-1-yl)propylthio]-3H-thieno[3,2-d]-pyrimidin-4-one was obtained.

$^1$H-NMR (CDCl$_3$) δ: 7.89 (d, J=9.2 Hz, 1H), 7.73 (d, J=5.1 Hz, 1H), 7.70 (d, J=8.1 Hz, 1H), 7.59 (d, J=7.7 Hz, 1H), 7.55~7.51 (m, 1H), 7.26~7.20 (m, 1H), 6.98 (d, J=9.2 Hz, 1H), 3.91 (t, J=4.8 Hz, 4H), 3.34~3.31 (m, 2H), 2.71~2.65 (m, 6H), 2.08~2.02 (m, 2H)

Mass, m/e: 437 ($M^+$), 157 (base)

Example 2-13

In the manner similar to Example 2-1, 5,6-dimethyl-2-[4-(4-quinolin-2-yl-piperazin-1-yl)but-2-enylthio]-3H-thieno[2,3-d]pyrimidin-4-one was obtained.

$^1$H-NMR (CDCl$_3$) δ: 7.87 (d, J=9.2 Hz, 1H), 7.69 (d, J=8.6 Hz, 1H), 7.60~7.57 (m, 1H), 7.54~7.50 (m, 1H), 7.23~7.20 (m, 1H), 6.94 (d, J=8.9 Hz, 1H), 5.88 (q, J=6.4 Hz, 1H), 5.78 (q, J=6.7 Hz, 1H), 3.89 (d, J=6.7 Hz, 1H), 3.71 (t, J=5.1 Hz, 4H), 3.05 (d, J=6.4 Hz, 1H), 2.54 (t, J=5.1 Hz, 4H), 2.46 (s, 3H), 2.35 (s, 3H)

Mass, m/e: 477 ($M^+$), 157 (base)

Example 2-14

In the manner similar to Example 2-1, 6-propyl-2-[3-(4-quinolin-2-ylpiperazin-1-yl)propylthio]-3H-pyrimidin-4-one was obtained.

$^1$H-NMR (CDCl$_3$) δ: 7.89 (d, J=9.2 Hz, 1H), 7.69 (d, J=9.4 Hz, 1H), 7.59 (d, J=8.1 Hz, 1H), 7.55~7.51 (m, 1H), 7.24~7.20 (m, 1H), 6.98 (d, J=9.2 Hz, 1H), 6.01 (s, 1H), 3.83 (t, J=4.8 Hz, 4H), 3.25 (t, J=7.0 Hz, 2H), 2.62 (t, J=4.8 Hz, 4H), 2.59~2.56 (m, 2H), 1.99 (q, J=6.9 Hz, 2H), 1.68 (q, J=7.3 Hz, 2H), 0.97 (t, J=7.3 Hz, 3H)

Mass, m/e: 423 ($M^+$), 157 (base)

Example 2-15

In the manner similar to Example 2-1, 5,6-dimethyl-2-[3-[4-(3-methylquinoxalin-2-yl)piperazin-1-yl]-propylsulfanyl]-3H-thieno[2,3-d]pyrimidin-4-one was obtained.

$^1$H-NMR (CDCl$_3$) δ: 7.88 (dd, J=1.1 Hz, 8.1 Hz, 1H), 7.81 (dd, J=1.1 Hz, 8.1 Hz, 1H), 7.57 (ddd, J=1.1 Hz, 6.9 Hz, 8.1 Hz, 1H), 7.51 (ddd, J=1.1 Hz, 6.9 Hz, 8.1 Hz, 1H), 3.49 (t, J=4.4 Hz, 4H), 3.29 (t, J=7.0 Hz, 2H), 2.75 (t, J=4.4 Hz, 4H), 2.71 (s, 3H), 2.65 (t, J=7.0 Hz, 2H), 2.42 (s, 3H), 2.33 (s, 3H), 2.04 (q, J=7.0 Hz, 2H)

Mass, m/e: 480 ($M^+$), 321, 253 (base)

Example 2-16

To 1N-aqueous sodium hydroxide solution, 105 mg of ethyl 5-methyl-4-oxo-2-[3-(4-quinolin-2-ylpiperazin-1-yl)propylthio]-3,4-dihydrothieno[2,3-d]pyrimidine-6-carboxylate which was synthesized in Example 2-6 was added and stirred at 70° C.-100° C. for an hour. The reaction mixture was cooled and washed with chloroform. The aqueous layer was neutralized with 2N-hydrochloric acid, and the precipitate was recovered by filtration and dried to provide 100 mg (100%) of 5-methyl-4-oxo-2-[3-(4-quinolin-2-ylpiperazin-1-yl)propylthio-3,4-dihydrothieno[2,3-d]-pyrimidine-6-carboxylic acid.

$^1$H-NMR (DMSO-$d_6$) δ: 8.16 (d, J=8.1 Hz, 1H), 7.76 (d, J=8.1 Hz, 1H), 7.66~7.75 (m, 1H), 7.60~7.59 (m, 1H), 7.36~7.29 (m, 2H), 4.65~4.64 (m, 4H), 3.64~3.62 (m, 4H), 3.39~3.27 (m, 7H), 2.19~2.16 (m, 2H)

IR (KBr) vmax: 3432, 1648, 1536 cm$^{-1}$

Mass, m/e: 451 ($M^+$), 157 (base)

Example 2-17

In the manner similar to Example 2-16, 5-methyl-4-oxo-2-[3-(4-pyridin-2-ylpiperazin-1-yl)propylthio]-3,4-dihydrothieno[2,3-d]pyrimidine-6-carboxylic acid was obtained from 5-methyl-4-oxo-2-[3-(4-pyridin-2-ylpiperazin-1-yl)propylthio]-3,4-dihydrothieno[2,3-d]pyrimidine-6-carboxylic acid ethyl ester which was synthesized in Example 2-3.

$^1$H-NMR (DMSO-$d_6$) δ: 8.11~8.09 (m, 1H), 7.52 (ddd, J=1.8 Hz, 7.0 Hz, 8.8 Hz, 1H), 6.81 (d, J=8.4 Hz, 1H), 6.64~6.61 (m, 1H), 3.53~5.49 (m, 4H), 3.21~3.20 (m, 2H), 2.76 (s, 3H), 2.66~2.54 (m, 4H), 2.52~2.47 (m, 4H), 1.92~1.85 (m, 2H)

IR (KBr) vmax: 3464, 2928, 1664, 1534 cm$^{-1}$

Mass, m/e: 445 (M$^{+)}$, 107 (base)

Example 2-18

In 20 ml of tert-butanol, 470 Milligrams of 5-methyl-4-oxo-2-[3-(4-pyridin-2-ylpiperazin-1-yl)propylthio]-3,4-dihydrothieno[2,3-d]pyrimidine-6-carboxylic acid as synthesized in Example 2-17 was dissolved to which 107 mg of triethylamine and 305 mg of DPPA were added by the order stated, followed by 9 hours' heating under reflux. Distilling the solvent off under reduced pressure, the residue was purified on silica gel column chromatography (chloroform:methanol=50:1). The purified product was added to 6 ml of 4N-hydrochloric acid-dioxane solution, stirred for an overnight and from which the solvent was distilled off under reduced pressure. To the residue chloroform was added, followed by washing with saturated aqueous sodium hydrogencarbonate solution, drying over anhydrous magnesium sulfate and removal of the solvent by distillation under reduced pressure. The residue was purified on silica gel column chromatography (chloroform:methanol=25:1) to provide 78 mg (18%) of 6-amino-5-methyl-2-[3-(4-pyridin-2-ylpiperazin-1-yl)propylthio]-3H-thieno[2,3-d]pyrimidin-4-one.

Example 2-19

In the manner similar to Example 2-18, 6-amino-5-methyl-2-[3-(4-quinolin-2-ylpiperazin-1-yl)propylthio]-3H-thieno[2,3-d]pyrimidin-4-one was obtained from 5-methyl-4-oxo-2-[3-(4-quinolin-2-ylpiperazin-1-yl)propylthio]-3,4-dihydrothieno[2,3-d]pyrimidine-6-carboxylic acid which was synthesized in Example 2-16.

$^1$H-NMR (CD$_3$OD) δ: 8.02 (d, J=9.0 Hz, 1H), 7.69 (d, J=8.1 Hz, 1H), 7.57~7.50 (m, 2H), 7.24~7.21 (m, 2H), 5.45 (br s, 1H), 3.34~3.28 (m, 6H), 2.53~2.48 (m, 4H), 2.44 (t, J=6.6 Hz, 2H), 1.89~1.81 (m, 2H)

Mass, m/e: 466 (M$^{+)}$, 157 (base)

Example 2-20

In the manner similar to Example 2-1, 2-[3-[4-(4-methylquinolin-2-yl)piperazin-1-yl]propylthio]-3,4,5,6,7,8-hexahydro-4-oxo-9-thia-1,3,7-triaza-9H-fluorene trihydrochloride was obtained.

$^1$H-NMR (DMSO-$d_6$) δ: 9.62 (br s, 1H), 8.13 (d, J=8.13 Hz, 1H), 7.78~7.76 (m, 1H), 7.54~7.51 (m, 3H), 4.83 (br s, 2H), 4.33 (s, 2H), 3.71~3.68 (m, 4H), 3.25~3.24 (m, 2H), 3.13~3.12 (m, 2H), 2.69 (s, 7H), 2.24~2.19 (m, 2H)

Mass, m/e: 506 (M$^{+)}$, 171 (base)

Example 2-21

In the manner similar to Example 2-1, 2-[3-(4-quinolin-2-ylpiperazin-1-yl)propylthio-3,4,5,6,7,8-hexahydro-4-oxa-9-thia-1,3,7-triaza-9H-fluorene trihydrochloride was obtained.

$^1$H-NMR (DMSO-$d_6$) δ: 11.86 (br s, 1H), 9.89 (br s, 1H), 8.50 (d, J=9.6 Hz, 1H), 8.42 (d, J=8.9 Hz, 1H), 7.95 (d, J=8.1 Hz, 1H), 7.80 (t, J=7.3 Hz, 1H), 7.61 (d, J=9.6 Hz, 1H), 7.53 (t, J=7.3 Hz, 1H), 4.91 (br s, 2H), 4.32 (br s, 2H), 3.93~3.87 (m, 2H), 3.36~3.24 (m, 6H), 3.17~3.13 (m, 2H), 2.51~2.49 (m, 2H), 2.21 (q, J=7.3 Hz, 2H)

Mass, m/e: 492 (M$^{+)}$, 157 (base)

Example 3

Syntheses of Compounds of the Formula (I) in which $X^1$ Stands for Hydrogen and Y is Direct Bond

Example 3-1

Step 3-1-A

To 10 ml of 4N-hydrochloric acid-dioxane solution, 996 mg of ethyl 2-amino-4,5-dimethylthiophene-3-carboxylate was added and into which 972 mg of 5-bromopentanenitrile was dropped. After 6 hours' stirring at room temperature, the reaction mixture was poured into ice water, neutralized with 25% ammonia water, and the precipitate was recovered by filtration. The precipitate was washed with chloroform-ethanol mixed solvent and dried to provide 750 mg (48%) of 2-(4-bromobutyl)-5,6-dimethyl-3H-thieno[2,3-c]pyrimidin-4-one.

$^1$H-NMR (CDCl$_3$): 3.45 (t, J=6.3 Hz, 2H), 2.77 (t, J=6.3 Hz, 2H), 2.45 (d, J=0.6 Hz, 3H), 2.01 (s, 3H), 2.00~1.98 (m, 4H)

Mass, m/e: 314 (M$^{+)}$, 235 (base)

Step 3-1-B

To 10 ml of tetrahydrofuran, 124 mg of 2-(4-bromobutyl)-5,6-dimethyl-3H-thieno-[2,3-c]pyrimidin-4-one as prepared in Step 3-1-A and 168 mg of 2-piperazin-1-ylquinoline were added and heated under reflux for 2 hours. Distilling the solvent off under reduced pressure, the residue was purified on silica gel column chromatography (chloroform:methanol=50:1) to provide 74 mg (42%) of 5,6-dimethyl-2-[4-(4-quinolin-2-ylpiperazin-1-yl)butyl]-3H-thieno[2,3-d]pyrimidin-4-one.

$^1$H-NMR (CDCl$_3$) δ: 7.89 (d, J=9.2 Hz, 1H), 7.69 (d, J=8.3 Hz, 1H), 7.59 (dd, J=1.3 Hz, 8.1 Hz, 1H), 7.53 (ddd, 1.5 Hz, 6.9 Hz, 9.9 Hz, 1H), 7.24~7.20 (m, 1H), 6.98 (d, J=9.2 Hz, 1H), 3.86~3.84 (m, 4H), 2.75 (t, J=7.2 Hz, 2H), 2.63 (t, J=5.0 Hz, 4H), 2.51~2.48 (m, 2H), 2.47 (d, J=0.6 Hz, 3H), 2.38 (d, J=0.6 Hz, 3H), 1.91~1.87 (m, 2H), 1.72~1.64 (m, 2H)

IR (KBr) vmax: 2924, 1664, 1594 cm$^{-1}$

Mass, m/e: 447 (M$^{+)}$, 157 (base)

Example 3-2

In the manner similar to Example 3-1, 5,6-dimethyl-2-(4-pyridin-2-ylpiperazin-1-ylmethyl)-3H-thieno-[2,3-d]pyrimidin-4-one was obtained.

$^1$H-NMR (CDCl$_3$) δ: 9.88 (br s, 1H), 8.23 (dd, J=1.8 Hz, 5.4 Hz, 1H), 7.53~7.48 (m, 1H), 6.68~6.62 (m, 2H), 3.62 (t, J=4.9 Hz, 4H), 3.59 (s, 2H), 2.69 (t, J=5.1 Hz, 4H), 2.49 (d, J=0.7 Hz, 3H), 2.39 (s, 3H)

Mass, m/e: 355 (M$^{+)}$, 107 (base)

Example 3-3

In the manner similar to Example 3-1, 5,6-dimethyl-2-(4-quinolin-2-ylpiperazin-1-ylmethyl)-3H-thieno-[2,3-d]pyrimidin-4-one was obtained.

¹H-NMR (CDCl₃) δ: 9.88 (br s, 1H), 7.92 (d, J=9.1 Hz, 1H), 7.71 (d, J=8.3 Hz, 1H), 7.61 (d, J=8.0 Hz, 1H), 7.56~7.53 (m, 1H), 7.26~7.20 (m, 1H), 6.99 (d, J=9.1 Hz, 1H), 3.83 (t, J=5.0 Hz, 4H), 3.60 (s, 2H), 2.72 (t, J=5.0 Hz, 4H), 2.50 (d, J=0.6 Hz, 3H), 2.39 (s, 3H)

Mass, m/e: 405 (M⁺), 157 (base)

Example 3-4

In the manner similar to Example 3-1, 5,6-dimethyl-2-(4-pyrrolo[1,2-a]quinoxalin-4-ylpiperazin-1-ylmethyl)-3H-thieno[2,3-d]pyrimidin-4-one was obtained.

¹H-NMR (CDCl₃) δ: 9.88 (br s, 1H), 7.83~7.82 (m, 1H), 7.74~7.72 (m, 1H), 7.36~7.28 (m, 2H), 6.78~6.75 (m, 2H), 3.87 (t, J=4.9 Hz, 4H), 3.63 (s, 2H), 2.79 (t, 4.9 Hz, 4H), 2.50 (d, J=0.8 Hz, 3H), 2.40 (s, 3H)

Mass, m/e: 444 (M⁺), 196 (base)

Example 3-5

In the manner similar to Example 3-1, 2-(4-pyridin-2-ylpiperazin-1-ylmethyl)-5,6,7,8-tetrahydro-3H-benzo[4,5]thieno[2,3-d]pyrimidin-4-one was obtained.

¹H-NMR (CDCl₃) δ: 9.86 (br s, 1H), 8.20~8.19 (m, 1H), 7.50 (ddd, J=1.8 Hz, 7.0 Hz, 8.4 Hz, 1H), 6.67~6.64 (m, 2H), 3.64~3.62 (m, 4H), 3.59 (s, 2H), 3.02~3.01 (m, 2H), 2.78 (t, J=5.9 Hz, 2H), 2.69 (t, J=5.1 Hz, 4H), 1.92~1.81 (m, 4H)

Mass, m/e: 381 (M⁺), 107 (base)

Example 3-6

In the manner similar to Example 3-1, 2-(4-quinolin-2-ylpiperazin-1-ylmethyl)-5,6,7,8-tetrahydro-3H-benzo[4,5]thieno[2,3-d]pyrimidin-4-one was obtained.

¹H-NMR (CDCl₃) δ: 9.91 (br s, 1H), 7.92 (d, J=9.0 Hz, 1H), 7.71 (d, J=8.5 Hz, 1H), 7.61~7.60 (m, 1H), 7.55 (ddd, J=1.4 Hz, 7.1 Hz, 8.5 Hz, 1H), 7.27~7.23 (m, 1H), 6.99 (d, J=9.3 Hz, 1H), 3.38 (t, J=4.9 Hz, 4H), 3.62 (s, 2H), 3.03~3.02 (m, 2H), 2.78~2.76 (m, 2H), 2.72 (t, J=4.9 Hz, 4H), 1.92~1.82 (m, 4H)

Mass, m/e: 431 (M⁺), 157 (base)

Example 3-7

In the manner similar to Example 3-1, 2-(4-pyrrolo[1,2-a]quinoxalin-4-ylpiperazin-1-ylmethyl)-5,6,7,8-tetrahydro-3H-benzo[4,5]thieno[2,3-d]pyrimidin-4-one was obtained.

¹H-NMR (CDCl₃) δ: 7.84~7.83 (m, 1H), 7.74 (dd, J=1.7 Hz, 8.0 Hz, 1H), 7.69 (dd, J=1.7 Hz, 7.7 Hz, 1H), 7.36~7.25 (m, 2H), 6.78~6.76 (m, 2H), 3.03 (s, 2H), 3.03~3.02 (m, 2H), 2.80~2.78 (m, 6H), 1.90~1.85 (m, 4H)

Mass, m/e: 470 (M⁺), 196 (base)

Example 3-8

In the manner similar to Example 3-1, 2-[4-(4-quinolin-2-ylpiperazin-1-yl)butyl]-5,6,7,8-tetrahydro-3H-benzo[4,5]thieno[2,3-d]pyrimidin-4-one was obtained.

¹H-NMR (CDCl₃) δ: 7.88 (d, J=9.2 Hz, 1H), 7.69 (d, J=8.6 Hz, 1H), 7.56 (d, J=7.3 Hz, 1H), 7.54~7.53 (m, 1H), 7.23~7.21 (m, 1H), 6.97 (d, J=9.2 Hz, 1H), 3.85~3.83 (m, 4H), 2.78~2.74 (m, 2H), 2.64~2.63 (m, 4H), 2.51~2.47 (m, 2H), 1.99~1.64 (m, 8H)

Mass, m/e: 473 (M⁺), 157 (base)

Example 3-9

In the manner similar to Example 3-1, 5,6-dimethyl-2-[4-(4-pyridin-2-ylpiperazin-1-yl)butyl]-3H-thieno[2,3-d]pyrimidin-4-one was obtained.

¹H-NMR (CDCl₃) δ: 8.18 (dd, J=1.2 Hz, 4.9 Hz, 1H), 7.47 (ddd, J=1.8 Hz, 7.3 Hz, 9.1 Hz, 1H), 6.64 (d, J=8.8 Hz, 1H), 6.62~6.60 (m, 1H), 3.63~3.61 (m, 4H), 2.75~2.74 (m, 4H), 2.49~2.45 (m, 5H), 2.38 (s, 3H), 1.92~1.84 (m, 2H), 1.70~1.62 (m, 2H)

IR (KBr) νmax: 2836, 1664, 1594 cm⁻¹

Mass, m/e: 397 (M⁺), 107 (base)

Example 3-10

In the manner similar to Example 3-1, 2-[4-(4-pyridin-2-ylpiperazin-1-yl)butyl]-5,6,7,8-tetrahydro-3H-benzo[4,5]thieno[2,3-d]pyrimidin-4-one was obtained.

melting point: 192.6-194.4° C.

¹H-NMR (CDCl₃) δ: 11.20 (br s, 1H), 8.18 (dd, J=1.2 Hz, 4.9 Hz, 1H), 7.49~7.45 (m, 1H), 6.64 (d, J=8.8 Hz, 1H), 6.63~6.60 (m, 1H), 3.62 (t, J=5.5 Hz, 4H), 3.01~2.98 (m, 2H), 2.78~2.73 (m, 4H), 2.59 (t, J=5.2 Hz, 4H), 2.47 (t, J=7.0 Hz, 2H), 1.92~1.82 (m, 4H), 1.69~1.59 (m, 4H)

IR (KBr) νmax: 2928, 1664, 1954, 1482 cm⁻¹

Mass, m/e: 423 (M⁺), 107 (base)

Example 3-11

In the manner similar to Example 3-1, 5,6-dimethyl-2-[4-(4-pyrrolo[1,2-a]quinoxalin-4-ylpiperazin-1-yl)butyl]-3H-thieno[2,3-d]pyrimidin-4-one was obtained.

¹H-NMR (CDCl₃) δ: 11.30 (br s, 1H), 7.81 (dd, J=1.2 Hz, 2.7 Hz, 1H), 7.72 (dd, J=1.5 Hz, 8.1 Hz, 1H), 7.67~7.65 (m, 1H), 7.34~7.24 (m, 2H), 6.79~6.74 (m, 2H), 3.90 (t, J=4.8 Hz, 4H), 2.76 (t, J=7.2 Hz, 2H), 2.67 (t, J=4.8 Hz, 4H), 2.51 (t, J=6.9 Hz, 2H), 2.48 (s, 3H), 2.38 (s, 3H), 1.94~1.86 (m, 2H), 1.72~1.65 (m, 2H)

Mass, m/e: 486 (M⁺), 196 (base)

Example 3-12

In the manner similar to Example 3-1, 5,6-dimethyl-2-[3-(4-quinolin-2-ylpiperazin-1-yl)propyl]-3H-thieno-[2,3-d]pyrimidin-4-one was obtained.

¹H-NMR (CDCl₃) δ: 12.92 (br s, 1H), 7.99 (d, J=9.3 Hz, 1H), 7.69 (d, J=8.1 Hz, 1H), 7.60 (dd, J=1.5 Hz, 8.1 Hz, 1H), 7.53 (ddd, J=1.5 Hz, 6.9 Hz, 8.5 Hz, 1H), 7.25~7.21 (m, 1H), 6.99 (d, J=9.3 Hz, 1H), 4.02 (t, J=5.0 Hz, 4H), 2.89 (t, J=6.2 Hz, 2H), 2.74 (t, J=5.0 Hz, 4H), 2.60~2.57 (m, 2H), 2.45 (s, 3H), 2.37 (d, J=0.8 Hz, 3H), 2.01 (t, J=6.2 Hz, 2H)

Mass, m/e: 433 (M⁺), 153 (base)

Example 3-13

In the manner similar to Example 3-1, 7-ethoxycarbonyl-2-[4-(4-quinolin-2-ylpiperazin-1-yl)butyl]-3,4,5,6,7,8-hexahydro-4-oxa-9-thia-1,3,7-triaza-9H-fluorene was obtained.

¹H-NMR (CDCl₃) δ: 7.87 (d, J=8.9 Hz, 1H), 7.68 (d, J=8.5 Hz, 1H), 7.58 (dd, J=1.2 Hz, 8.1 Hz, 1H), 7.51 (ddd, J=1.5 Hz, 6.9 Hz, 8.5 Hz, 1H), 7.21 (ddd, J=1.2 Hz, 6.9 Hz, 8.1 Hz, 1H), 6.96 (d, J=9.2 Hz, 1H), 4.67 (br s, 2H), 4.18 (q, J=6.9 Hz, 2H), 3.81 (t, J=5.0 Hz, 4H), 3.76~3.72 (m, 2H), 3.10 (br s, 2H), 2.78 (t, J=7.3 Hz, 2H), 2.60 (t, J=5.0 Hz, 4H), 2.47 (t, J=6.9 Hz, 2H), 1.98~1.86 (m, 2H), 1.70~1.63 (m, 4H)

Mass, m/e: 546 (M⁺), 157 (base)

Example 3-14

In the manner similar to Example 3-1, 7-benzyloxycarbonyl-2-[4-(4-quinolin-2-ylpiperazin-1-yl)butyl]-3,4,5,6,7,8-hexahydro-4-oxa-9-thia-1,3,7-triaza-9H-fluorene was obtained.

$^1$H-NMR (CDCl$_3$) δ: 7.87 (d, J=8.9 Hz, 1H), 7.68 (d, J=8.5 Hz, 1H), 7.58 (d, J=8.1 Hz, 1H), 7.53~7.49 (m, 1H), 7.36~7.29 (m, 5H), 7.23~7.19 (m, 1H), 6.96 (d, J=9.2 Hz, 1H), 5.17 (s, 2H), 4.69 (s, 2H), 3.82 (t, J=5.0 Hz, 4H), 3.79~3.75 (m, 2H), 3.11 (br s, 2H), 2.76 (t, J=6.9 Hz, 2H), 2.61 (t, J=5.1 Hz, 4H), 2.49~2.46 (m, 2H), 1.87 (q, J=7.3 Hz, 2H), 1.70~1.64 (m, 4H)

Mass, m/e: 395, 304 (base), 91

Example 3-15

In a mixture of 5 ml of acetic acid with 2 ml of water 60 mg of 3-amino-7-tert-butoxycarbonyl-2-[4-(4-quinolin-2-ylpiperazin-1-yl)butyl]-5,6,7,8-tetrahydro-3H-pyrido[4'3':4,5]thieno[2,3-d]pyrimidin-4-one was dissolved, and into the solution, a solution of 10 mg of sodium nitrite in 2 ml of water was dropped under cooling with ice. After 30 minutes' stirring, the reaction mixture was neutralized with saturated aqueous sodium hydrogencarbonate solution, and the resulting precipitate was extracted with chloroform, washed with water and dried over anhydrous sodium sulfate. Distilling the solvent off under reduced pressure, the residue was purified on silica gel column chromatography to provide 52 mg (99%) of 7-acetyl-2-[4-(4-quinolin-2-ylpiperazin-1-yl)butyl]-5,6,7,8-tetrahydro-3H-pyrido[4'3':4,5]thieno-[2,3-d]pyrimidin-4-one.

$^1$H-NMR (CDCl$_3$) δ: 11.54 (br s, 1H), 7.88 (d, J=9.2 Hz, 1H), 7.68 (d, J=8.5 Hz, 1H), 7.58 (dd, J=1.5 Hz, 8.5 Hz, 1H), 7.52 (ddd, J=1.5 Hz, 6.9 Hz, 8.5 Hz, 1H), 7.21 (ddd, J=1.5 Hz, 6.9 Hz, 8.5 Hz, 1H), 6.97 (d, J=9.2 Hz, 1H), 4.79 (br s, 2H), 3.83~3.81 (m, 4H), 3.73 (t, J=7.0 Hz, 2H), 3.17~3.12 (m, 2H), 2.81~2.73 (m, 2H), 2.65~2.60 (m, 4H), 2.49 (t, J=6.4 Hz, 2H), 2.19 (s, 3H), 1.89 (q, J=7.0 Hz, 2H), 1.67 (q, J=7.0 Hz, 2H)

Mass, m/e: 516 (M$^+$), 372, 157 (base)

Example 3-16

To 100 mg of 7-benzyloxycarbonyl-2-[4-(4-quinolin-2-ylpiperazin-1-yl)butyl]-3,4,5,6,7,8-hexahydro-4-oxa-9-thia-1,3,7-triaza-9H-fluorene as synthesized in Example 3-14, 5 ml of hydrogen bromide-acetic acid solution was added and stirred at room temperature. After neutralizing the system with saturated aqueous sodium hydrogencarbonate solution, the reaction product was extracted with chloroform, dried over anhydrous magnesium sulfate and concentrated to provide 78 mg (100%) of 2-[4-(4-quinolin-2-ylpiperazin-1-yl)butyl]-3,4,5,6,7,8-hexahydro-4-oxa-9-thia-1,3,7-triaza-9H-fluorene.

$^1$H-NMR (DMSO-d$_6$) δ: 8.01 (d, J=9.2 Hz, 1H), 7.68 (d, J=8.5 Hz, 1H), 7.54~7.49 (m, 2H), 7.35~7.32 (m, 1H), 7.29~7.20 (m, 1H), 4.03 (br s, 2H), 3.77~3.66 (m, 4H), 3.12~3.10 (m, 2H), 2.93 (br s, 2H), 2.67~2.64 (m, 2H), 2.49~2.46 (m, 4H), 2.36 (t, J=7.0 Hz, 2H), 1.76~1.70 (m, 2H), 1.55~1.50 (m, 2H)

Mass, m/e: 157 (base), 128

Example 3-17

First, in the manner similar to Example 3-1, 7-benzyloxycarbonyl-2-[4-[4-(4-methylquinolin-2-yl)piperazin-1-yl]butyl]-3,4,5,6,7,8-hexahydro-4-oxa-9-thia-1,3,7-triaza-9H-fluorene was obtained. Then from this compound 2-[4-[4-(4-methylquinolin-2-yl)piperazin-1-yl]butyl]-3,4,5,6,7,8-hexahydro-4-oxa-9-thia-1,3,7-triaza-9H-fluorene trihydrobromide was prepared in the manner similar to Example 3-16.

$^1$H-NMR (DMSO-d$_6$) δ: 12.47 (s, 1H), 10.16 (s, 1H), 9.20 (s, 2H), 8.12 (d, J=8.1 Hz, 1H), 8.05 (d, J=8.5 Hz, 1H), 7.86~7.82 (m, 1H), 7.63 (br s, 1H), 7.60~7.56 (m, 1H), 4.77~4.74 (m, 2H), 4.62~4.21 (m, 6H), 3.79~3.74 (m, 4H), 3.16~3.13 (m, 2H), 2.72 (s, 3H), 2.59~2.49 (m, 4H)

Mass, m/e: 488 (M$^+$), 171 (base)

Example 3-18

In the manner similar to Example 1-62, 7-acetyl-2-[4-[4-(4-methylquinolin-2-yl)piperazin-1-yl]butyl]-3,4,5,6,7,8-hexahydro-4-oxa-9-thia-1,3,7-triaza-9H-fluorene was obtained from 2-[4-[4-(4-methylquinolin-2-yl)piperazin-1-yl]butyl]-3,4,5,6,7,8-hexahydro-4-oxa-9-thia-1,3,7-triaza-9H-fluorene trihydrobromide as synthesized in Example 3-17.

$^1$H-NMR (CDCl$_3$) δ: 7.75 (d, J=7.7 Hz, 1H), 7.70 (d, J=8.5 Hz, 1H), 7.54~7.50 (m, 1H), 7.23~7.22 (m, 2H), 6.83 (s, 1H), 4.77 (br s, 4H), 3.78~3.72 (m, 6H), 3.19 (t, J=7.3 Hz, 2H), 3.13~3.04 (m, 2H), 2.61~2.53 (m, 6H), 2.59 (s, 3H), 2.20 (s, 3H), 1.98 (q, J=6.9 Hz, 2H)

Mass, m/e: 225, 171 (base), 142

Example 4

Syntheses of Compounds of the Formula (I) in which X$^1$ Stands for Amino, Lower Alkylamino, Di-Lower Alkylamino or Lower Alkylideneamino, and Y is Direct Bond

Example 4-1

Step 4-1-A

Into 7N-ammonia-methanol solution, 170 g of ethyl 2-oxo-cyclohexanecarboxylate was added and stirred for an overnight at room temperature. Distilling the solvent off under reduced pressure, the resulting crude crystalline product was recrystallized from ethyl acetate-n-hexane to provide 152 g (90%) of ethyl 2-aminocyclohex-1-enecarboxylate.

$^1$H-NMR (CDCl$_3$): 4.14 (q, J=7.3 Hz, 2H), 2.25 (d, J=5.9 Hz, 2H), 2.20 (d, J=5.9 Hz, 2H), 1.67~1.56 (m, 4H)

Mass, m/e: 169 (M$^+$), 96 (base)

Step 4-1-B

In 150 ml of tetrahydrofuran, 42.3 g of ethyl 2-aminocyclohex-1-enecarboxylate as synthesized in the above Step 4-1-A was dissolved, to which 40 g of pyridine was added, and into which 5-bromovaleryl chloride was dropped under cooling with ice. After stirring the reaction mixture overnight at room temperature, ethyl acetate was added, followed by washing with saturated aqueous sodium hydrogencarbonate solution, 10% aqueous citric acid and saturated brine, by the order stated. Drying the product over anhydrous magnesium sulfate, the solvent was distilled off under reduced pressure. The residue was purified on silica gel column chromatography (n-hexane:ethyl acetate=8:1), to provide 76.6 g (92%) of ethyl 2-(5-bromopentanoylamino)cyclohex-1-enecarboxylate.

$^1$H-NMR (CDCl$_3$): 11.62 (br s, 1H), 4.22~4.09 (m, 2H), 3.42 (t, J=6.9 Hz, 2H), 2.97~2.94 (m, 2H), 2.34 (t, J=7.0 Hz, 2H), 2.32~2.23 (m, 2H), 1.94~1.88 (m, 2H), 1.85~1.79 (m, 2H), 1.65~1.56 (m, 4H), 1.30 (t, J=7.0 Hz, 3H)

Mass, m/e: 333 (M$^+$), 55 (base)

Step 4-1-C

In 350 ml of toluene, 66.5 g of ethyl 2-(5-bromopentanoylamino)cyclohex-1-enecarboxylate as synthesized in above Step 4-1-B, 46.9 g of 2-piperazin-1-ylquinoline and 22.3 g of triethylamine were dissolved and heated under reflux for an overnight. The solvent was distilled off under reduced pressure, and ethyl acetate was added to the residue, followed by washing with saturated aqueous sodium hydrogencarbonate solution. The organic layer was dried over anhydrous magnesium sulfate, and from which the solvent was distilled off under reduced pressure. Purifying the residue on silica gel column chromatography (n-hexane:ethyl acetate:methanol=1:6:0.2) to provide 79.8 g (86%) of ethyl 2-[5-(4-quinolin-2-ylpiperazin-1-yl)pentanoylamino]cyclohex-1-enecarboxylate.

$^1$H-NMR (CDCl$_3$): 11.61 (br s, 1H), 7.87 (d, J=9.2 Hz, 1H), 7.69 (d, J=8.5 Hz, 1H), 7.58~7.56 (m, 1H), 7.51 (ddd, J=1.5 Hz, 6.9 Hz, 8.5 Hz, 1H), 7.20 (ddd, J=1.2 Hz, 6.9 Hz, 8.1 Hz, 1H), 6.97 (d, J=9.2 Hz, 1H), 4.16 (q, J=6.9 Hz, 2H), 3.74 (t, J=5.0 Hz, 4H), 2.97 (t, J=5.0 Hz, 2H), 2.56 (t, J=5.0 Hz, 4H), 2.43~2.90 (m, 6H), 1.74~1.70 (m, 2H), 1.68 (m, 4H), 1.28 (t, J=6.9 Hz, 2H)

Mass, m/e: 464 (M$^+$), 157 (base)

Step 4-1-D

In 120 ml of ethanol, 8.0 g of ethyl 2-[5-(4-quinolin-2-ylpiperazin-1-yl)pentanoylamino]cyclohex-1-enecarboxylate as synthesized in above Step 4-1-C was dissolved, and to the solution 60 ml of hydrazine monohydrate was added, followed by 4 hours' heating under reflux. Distilling the solvent off under reduced pressure, the residue was dissolved in chloroform, washed with saturated aqueous sodium hydrogencarbonate solution and saturated brine, and dried over anhydrous magnesium sulfate. Distilling the solvent off under reduced pressure, the residue was purified on silica gel column chromatography (chloroform:methanol=50:1) to provide 3.8 g (51%) of 3-amino-2-[4-(4-quinolin-2-ylpiperazin-1-yl)butyl]-5,6,7,8-tetrahydro-3H-quinazolin-4-one.

$^1$H-NMR (CDCl$_3$) δ: 7.87 (d, J=9.3 Hz, 1H), 7.69 (d, J=8.5 Hz, 1H), 7.58 (d, J=7.7 Hz, 1H), 7.52 (ddd, J=1.5 Hz, 6.9 Hz, 7.5 Hz, 1H), 7.25~7.19 (m, 1H), 6.97 (d, J=8.9 Hz, 1H), 4.93 (s, 2H), 3.74 (t, J=5.0 Hz, 4H), 2.92 (t, J=7.7 Hz, 2H), 2.58~2.55 (m, 6H), 2.52~2.49 (m, 2H), 2.44 (t, J=7.3 Hz, 2H), 1.81~1.63 (m, 8H)

Mass, m/e: 432 (M$^+$), 157 (base)

Example 4-2

In the manner similar to Example 4-1, 3-amino-2-[4-[4-(4-methylquinolin-2-yl)piperazin-1-yl]butyl]-5,6,7,8-tetrahydro-3H-quinazolin-4-one was obtained.

$^1$H-NMR (CDCl$_3$) δ: 7.74 (d, J=8.5 Hz, 1H), 7.69 (d, J=8.5 Hz, 1H), 7.51 (ddd, J=1.2 Hz, 7.0 Hz, 8.1 Hz, 1H), 7.22 (d, J=8.1 Hz, 1H), 6.82 (s, 1H), 4.94 (s, 2H), 3.74 (t, J=5.0 Hz, 4H), 2.92 (t, J=7.3 Hz, 2H), 2.57 (s, 3H), 2.56~2.54 (m, 6H), 2.53~2.50 (m, 2H), 2.44 (t, J=7.3 Hz, 2H), 1.82~1.62 (m, 8H)

Mass, m/e: 446 (M$^+$), 171 (base)

Example 4-3

In the manner similar to Example 4-1, 3-amino-2-[4-(4-quinolin-2-ylpiperazin-1-yl)butyl]-3H-quinazolin-4-one was obtained.

$^1$H-NMR (CDCl$_3$) δ: 8.24 (dd, J=1.2 Hz, 8.1 Hz, 1H), 7.88 (d, J=8.9 Hz, 1H), 7.73 (ddd, J=1.6 Hz, 6.9 Hz, 8.5 Hz, 1H), 7.71~7.65 (m, 2H), 7.59 (dd, J=1.2 Hz, 7.9 Hz, 1H), 7.52 (ddd, J=1.2 Hz, 6.9 Hz, 8.1 Hz, 1H), 7.44 (ddd, J=1.2 Hz, 6.9 Hz, 8.1 Hz, 1H), 7.21 (ddd, J=1.2 Hz, 6.4 Hz, 8.1 Hz, 1H), 6.97 (d, J=9.2 Hz, 1H), 4.91 (s, 2H), 3.75 (t, J=4.8 Hz, 4H), 3.07 (t, J=7.7 Hz, 2H), 2.58 (t, J=5.0 Hz, 4H), 2.48 (t, J=7.3 Hz, 2H), 1.95~1.87 (m, 2H), 1.76~1.69 (m, 2H)

Mass, m/e: 428 (M$^+$), 157 (base)

Example 4-4

In the manner similar to Example 4-1, 3-amino-2-[4-[4-(4-methylquinolin-2-yl)piperazin-1-yl]butyl]-3H-quinazolin-4-one was obtained.

$^1$H-NMR (CDCl$_3$) δ: 8.24 (dd, J=1.5 Hz, 8.1 Hz, 1H), 7.77~7.65 (m, 4H), 7.51 (ddd, J=1.5 Hz, 6.9 Hz, 8.5 Hz, 1H), 7.47~7.42 (m, 1H), 7.23~7.21 (m, 1H), 6.83 (s, 1H), 4.91 (s, 2H), 3.74 (t, J=5.0 Hz, 4H), 3.07 (t, J=7.3 Hz, 2H), 2.58 (t, J=5.4 Hz, 4H), 2.48 (t, J=7.3 Hz, 2H), 1.91 (q, J=7.7 Hz, 2H), 1.74 (q, J=7.7 Hz, 2H)

Mass, m/e: 428 (M$^+$), 157 (base)

Example 4-5

In the manner similar to Example 4-1, 3-amino-2-[4-[4-(3-methylquinolin-2-yl)piperazin-1 yl]butyl]-5,6,7,8-tetrahydro-3H-quinazolin-4-one was obtained.

$^1$H-NMR (CDCl$_3$) δ: 7.83 (d, J=8.5 Hz, 1H), 7.77 (s, 1H), 7.60 (d, J=8.1 Hz, 1H), 7.52 (ddd, J=1.5 Hz, 6.9 Hz, 8.5 Hz, 1H), 7.31 (ddd, J=1.1 Hz, 6.9 Hz, 8.1 Hz, 1H), 4.98 (s, 2H), 3.35~3.33 (m, 4H), 2.93 (t, J=7.3 Hz, 2H), 2.64 (br s, 4H), 2.59 (t, J=6.2 Hz, 2H), 2.53~2.50 (m, 2H), 2.47 (t, J=7.3 Hz, 2H), 2.42 (d, J=0.8 Hz, 3H), 1.83~1.65 (m, 8H)

Mass, m/e: 446 (M$^+$), 171 (base)

Example 4-6

In the manner similar to Example 4-1, 3-amino-2-[4-[4-(3,4-dimethylquinolin-2-yl)piperazin-1-yl]butyl]-5,6,7,8-tetrahydro-3H-quinazolin-4-one was obtained.

$^1$H-NMR (CDCl$_3$) δ: 7.87 (d, J=7.3 Hz, 1H), 7.83 (d, J=7.3 Hz, 1H), 7.53 (t, J=8.1 Hz, 1H), 7.37~7.35 (m, 1H), 4.99 (s, 2H), 3.27 (br s, 4H), 2.93 (t, J=7.7 Hz, 2H), 2.64 (br s, 4H), 2.59 (t, J=5.8 Hz, 2H), 2.55 (s, 3H), 2.52 (t, J=6.2 Hz, 2H), 2.47~2.46 (m, 2H), 2.37 (s, 3H), 1.81~1.67 (m, 8H)

Mass, m/e: 460 (M$^+$), 185 (base)

Example 4-7

In the manner similar to Example 4-1, 3-amino-2-[4-[4-(2,3-dihydro-1H-cyclopenta[c]quinolin-4-yl)-piperazin-1-yl]butyl]-5,6,7,8-tetrahydro-3H-quinazolin-4-one was obtained.

$^1$H-NMR (CDCl$_3$) δ: 7.80 (d, J=8.5 Hz, 1H), 7.64 (d, J=8.1 Hz, 1H), 7.53~7.49 (m, 1H), 7.30~7.26 (m, 1H), 4.96 (s, 2H), 3.57 (br s, 4H), 3.17 (t, J=7.3 Hz, 2H), 3.04 (t, J=7.3 Hz, 2H), 2.93 (t, J=7.7 Hz, 2H), 2.60~2.57 (m, 6H), 2.52 (t, J=6.2 Hz, 2H), 2.47~2.44 (m, 2H), 2.22 (q, J=7.3 Hz, 2H), 1.82~1.65 (m, 8H)

Mass, m/e: 472 (M$^+$), 197 (base)

Example 4-8

In the manner similar to Example 4-1, 3-amino-2-[4-[4-(7,8,9,10-tetrahydrophenanthridin-6-yl)piperazin-1-yl]butyl]-5,6,7,8-tetrahydro-3H-quinazolin-4-one was obtained.

$^1$H-NMR (CDCl$_3$) δ: 7.84~7.80 (m, 2H), 7.53 (t, J=8.1 Hz, 1H), 7.37~7.33 (m, 1H), 4.99 (s, 2H), 3.31 (br s, 4H), 3.10 (t,

J=6.6 Hz, 2H), 2.95~2.91 (m, 2H), 2.76 (t, J=5.8 Hz, 2H), 2.62 (br s, 4H), 2.60~2.57 (m, 2H), 2.52 (t, J=6.2 Hz, 2H), 2.49~2.45 (m, 2H), 1.98~1.93 (m, 2H), 1.82~1.65 (m, 10H)

Mass, m/e: 486 ($M^+$), 211 (base)

Example 4-9

In the manner similar to Example 4-1, 3-amino-2-[4-[4-(3,4-dimethylquinolin-2-yl)piperazin-1-yl]butyl]-3H-quinazolin-4-one was obtained.

$^1$H-NMR (CDCl$_3$) δ: 8.25~8.23 (m, 1H), 7.87 (dd, J=1.2 Hz, 8.5 Hz, 1H), 7.85~7.82 (m, 1H), 7.66 (d, J=7.7 Hz, 1H), 7.53 (ddd, J=1.2 Hz, 6.9 Hz, 8.5 Hz, 1H), 7.44 (ddd, J=1.2 Hz, 6.9 Hz, 8.0 Hz, 1H), 7.35 (ddd, J=1.2 Hz, 6.9 Hz, 8.0 Hz, 1H), 7.33 (ddd, J=1.5 Hz, 6.9 Hz, 8.5 Hz, 1H), 4.95 (s, 2H), 3.28 (br s, 4H), 3.10~3.06 (m, 2H), 2.65 (br s, 4H), 2.55 (s, 3H), 2.53~2.49 (m, 2H), 2.37 (s, 3H), 1.95~1.88 (m, 2H), 1.77~1.69 (m, 2H)

Mass, m/e: 456 ($M^+$), 185 (base)

Example 4-10

In the manner similar to Example 4-1, 3-amino-2-[4-[4-(2,3-dihydro-1H-cyclopenta[c]quinolin-4-yl)-piperazin-1-yl]butyl]-3H-quinazolin-4-one was obtained.

$^1$H-NMR (CDCl$_3$) δ: 8.24 (dd, J=1.2 Hz, 8.1 Hz, 1H), 7.80 (d, J=8.1 Hz, 1H), 7.73 (ddd, J=1.5 Hz, 6.9 Hz, 8.5 Hz, 1H), 7.67~7.63 (m, 2H), 7.51 (ddd, J=1.5 Hz, 6.9 Hz, 8.5 Hz, 1H), 7.47~7.42 (m, 2H), 7.28 (ddd, J=1.2 Hz, 6.9 Hz, 8.1 Hz, 1H), 4.93 (s, 2H), 3.58 (br s, 4H), 3.19~3.15 (m, 2H), 3.10~3.03 (m, 4H), 2.62 (br s, 4H), 2.49 (t, J=7.3 Hz, 2H), 2.23 (q, J=7.3 Hz, 2H), 1.91 (q, J=7.7 Hz, 2H), 1.75~1.71 (m, 2H)

Mass, m/e: 468 ($M^+$), 197 (base)

Example 4-11

In the manner similar to Example 4-1, 3-amino-2-[4-[4-(7,8,9,10-tetrahydrophenanthridin-6-yl)piperazin-1-yl]butyl]-3H-quinazolin-4-one was obtained.

$^1$H-NMR (CDCl$_3$) δ: 8.24 (dd, J=1.5 Hz, 8.5 Hz, 1H), 7.84~7.80 (m, 2H), 7.73 (ddd, J=1.5 Hz, 6.9 Hz, 8.5 Hz, 1H), 7.67 (d, J=8.1 Hz, 1H), 7.53 (ddd, J=1.5 Hz, 6.9 Hz, 8.5 Hz, 1H), 7.44 (ddd, J=1.2 Hz, 6.9 Hz, 8.1 Hz, 1H), 7.35 (ddd, J=1.5 Hz, 6.9 Hz, 8.5 Hz, 1H), 4.95 (s, 2H), 3.32 (br s, 4H), 3.11~3.06 (m, 4H), 2.76 (t, J=5.8 Hz, 2H), 2.64 (br s, 4H), 2.51 (t, J=7.3 Hz, 2H), 2.00~1.88 (m, 2H), 1.79~1.71 (m, 2H)

Mass, m/e: 482 ($M^+$), 211 (base)

Example 4-12

In the manner similar to Example 4-1, 3-amino-2-[4-(4-quinolin-2-ylpiperazin-1-yl)butyl]-3H-pyrido[3,2-d]-pyrimidin-4-one was obtained.

$^1$H-NMR (CDCl$_3$) δ: 8.83 (dd, J=1.5 Hz, 4.2 Hz, 1H), 8.01 (dd, J=1.5 Hz, 8.5 Hz, 1H), 7.88 (d, J=9.2 Hz, 1H), 7.70~7.64 (m, 2H), 7.58 (d, J=2.1 Hz, 1H), 7.54~7.50 (m, 1H), 7.23~7.19 (m, 1H), 6.97 (d, J=8.9 Hz, 1H), 5.03 (s, 2H), 3.76 (t, J=5.0 Hz, 4H), 3.10 (t, J=7.3 Hz, 2H), 2.59 (t, J=5.0 Hz, 4H), 2.48 (t, J=7.3 Hz, 2H), 1.92 (q, J=7.7 Hz, 2H), 1.76~1.71 (m, 2H)

Mass, m/e: 429 ($M^+$), 157 (base)

Example 4-13

In the manner similar to Example 4-1, 3-amino-2-[4-(4-pyrrolo[1,2-a]quinoxalin-4-ylpiperazin-1-yl)butyl]-3H-quinazolin-4-one was obtained.

$^1$H-NMR (CDCl$_3$) δ: 8.24 (dd, J=1.2 Hz, 7.7 Hz, 1H), 7.80 (m, 1H), 7.75~7.73 (m, 1H), 7.72 (dd, J=1.5 Hz, 5.4 Hz, 1H), 7.67~7.66 (m, 1H), 7.65~7.64 (m, 1H), 7.46~7.43 (m, 1H), 7.33~7.28 (m, 1H), 7.27~7.23 (m, 1H), 6.77 (dd, J=1.2 Hz, 3.9 Hz, 1H), 6.75~6.73 (m, 1H), 4.91 (s, 2H), 3.82 (t, J=5.0 Hz, 4H), 3.08 (t, J=7.7 Hz, 2H), 2.65 (t, J=5.0 Hz, 4H), 2.50 (t, J=7.3 Hz, 2H), 1.91 (q, J=7.7 Hz, 2H), 1.77~1.69 (m, 2H)

Mass, m/e: 429 ($M^+$), 157 (base)

Example 4-14

In the manner similar to Example 4-1, 3-amino-2-[4-(4-pyrrolo[1,2-a]quinoxalin-4-ylpiperazin-1-yl)butyl]-3H-pyrido[3,2-d]pyrimidin-4-one was obtained.

$^1$H-NMR (CDCl$_3$) δ: 8.84 (dd, J=1.5 Hz, 4.2 Hz, 1H), 8.00 (dd, J=1.5 Hz, 6.1 Hz, 1H), 7.80 (dd, J=1.5 Hz, 2.7 Hz, 1H), 7.71 (dd, J=1.5 Hz, 8.1 Hz, 1H), 7.66 (dd, J=1.5 Hz, 3.1 Hz, 1H), 7.65~7.64 (m, 1H), 7.33~7.22 (m, 2H), 6.77~6.73 (m, 2H), 5.04 (s, 2H), 3.82 (t, J=5.0 Hz, 4H), 3.10 (t, J=7.7 Hz, 2H), 2.65 (t, J=5.0 Hz, 4H), 2.51 (t, J=7.3 Hz, 2H), 1.92 (q, J=7.3 Hz, 2H), 1.73 (q, J=7.3 Hz, 2H)

Mass, m/e: 468 ($M^+$), 196 (base)

Example 4-15

In the manner similar to Example 4-1, 3-amino-7-chloro-2-[4-(4-quinolin-2-ylpiperazin-1-yl)butyl]-3H-quinazolin-4-one was obtained.

$^1$H-NMR (CDCl$_3$) δ: 8.16 (d, J=8.5 Hz, 1H), 7.88 (d, J=8.9 Hz, 1H), 7.69 (d, J=8.5 Hz, 1H), 7.67 (d, J=1.9 Hz, 1H), 7.58 (d, J=8.1 Hz, 1H), 7.52 (ddd, J=1.5 Hz, 6.9 Hz, 8.1 Hz, 1H), 7.43 (d, J=1.9 Hz, 1H), 7.38 (d, J=2.3 Hz, 1H), 7.21 (ddd, J=1.2 Hz, 6.9 Hz, 8.1 Hz, 1H), 6.97 (d, J=9.2 Hz, 1H), 4.89 (s, 2H), 3.76 (t, J=5.0 Hz, 4H), 3.06 (t, J=7.3 Hz, 2H), 2.58 (t, J=5.0 Hz, 4H), 2.48 (t, J=7.3 Hz, 2H), 1.90 (q, J=7.7 Hz, 2H), 1.71 (q, J=7.3 Hz, 2H)

Mass, m/e: 462 ($M^+$), 157 (base)

Example 4-16

In the manner similar to Example 4-1, 3-amino-6-bromo-2-[4-(4-quinolin-2-ylpiperazin-1-yl)butyl]-3H-quinazolin-4-one was obtained.

$^1$H-NMR (CDCl$_3$) δ: 8.37 (d, J=2.3 Hz, 1H), 7.88 (d, J=9.3 Hz, 1H), 7.80 (dd, J=2.3 Hz, 8.9 Hz, 1H), 7.79 (d, J=8.5 Hz, 1H), 7.58 (d, J=7.7 Hz, 1H), 7.54~7.50 (m, 2H), 7.23~7.19 (m, 1H), 6.97 (d, J=9.2 Hz, 1H), 4.91 (s, 2H), 3.75 (t, J=5.0 Hz, 4H), 3.06 (t, J=7.7 Hz, 2H), 2.58 (t, J=5.0 Hz, 4H), 2.48 (t, J=7.3 Hz, 2H), 1.90 (t, J=7.3 Hz, 2H), 1.71 (t, J=7.7 Hz, 2H)

Mass, m/e: 506 ($M^+$), 157 (base)

Example 4-17

In the manner similar to Example 4-1, 3-amino-6,7,8-trimethoxy-2-[4-(4-quinolin-2-ylpiperazin-1-yl)butyl]-3H-quinazolin-4-one was obtained.

$^1$H-NMR (CDCl$_3$) δ: 7.87 (d, J=9.2 Hz, 1H), 7.69 (d, J=8.5 Hz, 1H), 7.58 (dd, J=1.2 Hz, 8.5 Hz, 1H), 7.58 (ddd, J=1.5 Hz, 7.0 Hz, 8.5 Hz, 1H), 7.38 (s, 1H), 7.21 (ddd, J=1.2 Hz, 6.9 Hz, 8.1 Hz, 1H), 6.97 (d, J=9.2 Hz, 1H), 4.91 (s, 2H), 4.08 (s, 3H), 4.02 (s, 3H), 3.96 (s, 3H), 3.75 (t, J=5.0 Hz, 4H), 3.07 (t, J=7.7 Hz, 2H), 2.58 (t, J=5.0 Hz, 4H), 2.47 (t, J=7.7 Hz, 2H), 1.92 (q, J=7.7 Hz, 2H), 1.72 (q, J=7.7 Hz, 2H)

Mass, m/e: 157 (base)

Example 4-18

In the manner similar to Example 4-1, 3-amino-2-[4-(4-quinolin-2-ylpiperazin-1-yl)butyl]-3H-thieno[3,2-d]-pyrimidin-4-one was obtained.

$^1$H-NMR (CDCl$_3$) δ: 7.88 (d, J=9.2 Hz, 1H), 7.76 (d, J=5.0 Hz, 1H), 7.69 (d, J=7.3 Hz, 1H), 7.58 (dd, J=1.5 Hz, 8.0 Hz, 1H), 7.52 (ddd, J=1.5 Hz, 6.9 Hz, 8.1 Hz, 1H), 7.27 (d, J=5.4 Hz, 1H), 7.21 (ddd, J=1.2 Hz, 6.9 Hz, 8.1 Hz, 1H), 6.97 (d, J=9.2 Hz, 1H), 4.94 (s, 2H), 3.75 (t, J=5.0 Hz, 4H), 3.08 (t, J=7.7 Hz, 2H), 2.58 (t, J=5.0 Hz, 4H), 2.47 (t, J=7.7 Hz, 2H), 1.89 (q, J=7.7 Hz, 2H), 1.71 (q, J=7.7 Hz, 2H)

Mass, m/e: 434 (M$^+$), 157 (base)

Example 4-19

In the manner similar to Example 4-1, 3-amino-8-methyl-2-[4-(4-quinolin-2-ylpiperazin-1-yl)butyl]-3H-quinazolin-4-one was obtained.

$^1$H-NMR (CDCl$_3$) δ: 8.08 (dd, J=0.8 Hz, 8.1 Hz, 1H), 7.88 (d, J=8.9 Hz, 1H), 7.69 (d, J=8.5 Hz, 1H), 7.58 (ddd, J=1.5 Hz, 6.2 Hz, 7.7 Hz, 1H), 7.52 (ddd, J=1.5 Hz, 6.9 Hz, 8.5 Hz, 1H), 7.32 (t, J=7.7 Hz, 1H), 7.23~7.19 (m, 1H), 6.97 (d, J=9.2 Hz, 1H), 4.88 (s, 2H), 3.76 (t, J=5.0 Hz, 4H), 3.07 (t, J=7.7 Hz, 2H), 2.59 (t, J=5.4 Hz, 4H), 2.50 (t, J=7.7 Hz, 2H), 1.95 (q, J=7.3 Hz, 2H), 1.77~1.73 (m, 2H)

Mass, m/e: 442 (M$^+$), 157 (base)

Example 4-20

In the manner similar to Example 4-1, 3-amino-6-methyl-2-[4-(4-quinolin-2-ylpiperazin-1-yl)butyl]-3H-quinazolin-4-one was obtained.

$^1$H-NMR (CDCl$_3$) δ: 8.02 (s, 1H), 7.88 (d, J=8.9 Hz, 1H), 7.69 (d, J=8.5 Hz, 1H), 7.59~7.50 (m, 4H), 7.23~7.19 (m, 1H), 6.97 (d, J=9.2 Hz, 1H), 4.90 (s, 2H), 3.75 (t, J=5.0 Hz, 4H), 3.06 (t, J=1.7 Hz, 2H), 2.58 (t, J=5.0 Hz, 4H), 2.49~2.44 (m, 2H), 2.48 (s, 3H), 1.90 (q, J=7.7 Hz, 2H), 1.72 (q, J=7.7 Hz, 2H)

Mass, m/e: 442 (M$^+$), 157 (base)

Example 4-21

In the manner similar to Example 4-1, 3-amino-5-methyl-2-[4-(4-quinolin-2-ylpiperazin-1-yl)butyl]-3H-quinazolin-4-one was obtained.

$^1$H-NMR (CDCl$_3$) δ: 8.08 (d, J=8.1 Hz, 1H), 7.88 (d, J=9.2 Hz, 1H), 7.69 (d, J=8.1 Hz, 1H), 7.59~7.54 (m, 2H), 7.54~7.50 (m, 1H), 7.32 (t, J=7.7 Hz, 1H), 7.23~7.20 (m, 1H), 6.97 (d, J=9.2 Hz, 1H), 4.89 (s, 2H), 3.75 (t, J=5.0 Hz, 4H), 3.07 (t, J=7.3 Hz, 2H), 2.61 (s, 3H), 2.58 (t, J=5.0 Hz, 4H), 2.49 (t, J=7.7 Hz, 2H), 1.93 (q, J=7.7 Hz, 2H), 1.77~1.70 (m, 2H)

Mass, m/e: 442 (M$^+$), 157 (base)

Example 4-22

In the manner similar to Example 4-1, 3-amino-2-[4-(4-methoxyquinolin-2-yl)piperazin-1-yl]butyl-3H-quinazolin-4-one was obtained.

$^1$H-NMR (CDCl$_3$) δ: 8.28 (d, J=10.0 Hz, 1H), 8.25~8.23 (m, 1H), 7.66 (d, J=8.1 Hz, 1H), 7.47~7.40 (m, 2H), 7.32 (ddd, J=1.5 Hz, 6.9 Hz, 8.5 Hz, 1H), 7.29 (d, J=8.5 Hz, 1H), 6.91 (d, J=9.2 Hz, 1H), 6.56 (d, J=6.9 Hz, 1H), 4.91 (s, 2H), 3.94 (s, 3H), 3.75 (t, J=5.0 Hz, 4H), 3.07 (t, J=7.7 Hz, 2H), 2.58 (t, J=5.1 Hz, 4H), 2.48 (t, J=7.7 Hz, 2H), 1.91 (q, J=7.7 Hz, 2H), 1.76~1.69 (m, 2H)

Mass, m/e: 458 (M$^+$), 187 (base)

Example 4-23

In the manner similar to Example 4-1, 3-amino-2-[4-(4-quinolin-2-ylpiperazin-1-yl)butyl]-3H-thieno[2,3-d]-pyrimidin-4-one was obtained.

$^1$H-NMR (CDCl$_3$) δ: 7.88 (d, J=9.2 Hz, 1H), 7.79 (d, J=8.4 Hz, 1H), 7.58 (d, J=8.1 Hz, 1H), 7.52 (m, 1H), 7.42 (d, J=5.8, 1H), 7.23~7.18 (m, 2H), 6.97 (d, J=9.2 Hz, 1H), 6.56 (d, J=6.9 Hz, 1H), 4.93 (s, 2H), 3.75 (t, J=5.0 Hz, 4H), 3.07 (t, J=7.7 Hz, 2H), 2.58 (t, J=5.0 Hz, 4H), 2.48 (t, J=7.7 Hz, 2H), 1.89~1.87 (m, 2H), 1.72~1.70 (m, 2H)

Mass, m/e: 434 (M$^+$), 157 (base)

Example 4-24

In the manner similar to Example 4-1, 3-amino-8-chloro-2-[4-(4-quinolin-2-ylpiperazin-1-yl)butyl]-3H-quinazolin-4-one was obtained.

$^1$H-NMR (CDCl$_3$) δ: 8.16 (dd, J=1.5 Hz, 8.1 Hz, 1H), 7.88 (d, J=9.2 Hz, 1H), 7.81 (dd, J=1.5 Hz, 8.1 Hz, 1H), 7.69 (d, J=8.5 Hz, 1H), 7.58 (d, J=7.7 Hz, 1H), 7.52 (ddd, J=1.5 Hz, 6.9 Hz, 8.5 Hz, 1H), 7.38~7.34 (m, 1H), 7.23~7.19 (m, 1H), 6.97 (d, J=9.2 Hz, 1H), 4.93 (s, 2H), 3.76 (t, J=5.0 Hz, 4H), 3.12 (t, J=7.7 Hz, 2H), 2.60 (t, J=5.0 Hz, 4H), 2.50 (t, J=7.7 Hz, 2H), 1.95 (q, J=7.7 Hz, 2H), 1.75 (q, J=7.7 Hz, 2H)

Mass, m/e: 462 (M$^+$), 157 (base)

Example 4-25

In the manner similar to Example 4-1, 3-amino-5-chloro-2-[4-(4-quinolin-2-ylpiperazin-1-yl)butyl]-3H-quinazolin-4-one was obtained.

$^1$H-NMR (CDCl$_3$) δ: 7.88 (d, J=9.2 Hz, 1H), 7.69 (d, J=8.5 Hz, 1H), 7.59~7.50 (m, 4H), 7.44 (dd, J=2.7 Hz, 6.6 Hz, 1H), 7.23~7.19 (m, 1H), 6.97 (d, J=8.9 Hz, 1H), 4.86 (s, 2H), 3.76 (t, J=5.0 Hz, 4H), 3.05 (t, J=7.7 Hz, 2H), 2.59 (t, J=5.0 Hz, 4H), 2.48 (t, J=7.7 Hz, 2H), 1.89 (q, J=7.7 Hz, 2H), 1.75~1.69 (m, 2H)

Mass, m/e: 462 (M$^+$), 157 (base)

Example 4-26

In the manner similar to Example 4-1, 3-amino-2-[4-(4-quinolin-2-ylpiperazin-1-yl)butyl]-3H-benzo-[g]quinazolin-4-one was obtained.

$^1$H-NMR (CDCl$_3$) δ: 8.87 (s, 1H), 8.17 (s, 1H), 8.05 (d, J=7.7 Hz, 1H), 7.97 (d, J=8.1 Hz, 1H), 7.88 (d, J=8.3 Hz, 1H), 7.69 (d, J=8.5 Hz, 1H), 7.62~7.58 (m, 2H), 7.55~7.51 (m, 2H), 7.24~7.20 (m, 1H), 6.98 (d, J=9.2 Hz, 1H), 4.87 (s, 2H), 3.77 (t, J=5.0 Hz, 4H), 3.11 (t, J=7.7 Hz, 2H), 2.60 (t, J=5.0 Hz, 4H), 2.51 (t, J=7.7 Hz, 2H), 1.96 (q, J=7.7 Hz, 2H), 1.76 (q, J=7.7 Hz, 2H)

Mass, m/e: 478 (M$^+$), 157 (base)

Example 4-27

In the manner similar to Example 4-1, 3-amino-8-fluoro-2-[4-(4-quinolin-2-ylpiperazin-1-yl)butyl]-3H-quinazolin-4-one was obtained.

$^1$H-NMR (CDCl$_3$) δ: 7.88 (d, J=9.2 Hz, 1H), 7.69 (d, J=8.9 Hz, 1H), 7.66~7.62 (m, 1H), 7.59 (d, J=8.1 Hz, 1H), 7.54~7.51 (m, 1H), 7.45 (d, J=8.5 Hz, 1H), 7.23~7.19 (m, 1H), 7.11~7.06 (m, 1H), 6.97 (d, J=8.9 Hz, 1H), 4.86 (s, 2H), 3.76 (br s, 4H), 3.06 (t, J=7.7 Hz, 2H), 2.59 (br s, 4H), 2.50~2.46 (m, 2H), 1.92~1.87 (m, 2H), 1.72~1.70 (m, 2H)

Mass, m/e: 446 (M$^+$), 157 (base)

Example 4-28

In the manner similar to Example 4-1, 3-amino-5-hydrazino-2-[4-(4-quinolin-2-ylpiperazin-1-yl)butyl]-3H-quinazolin-4-one was obtained.

$^1$H-NMR (CDCl$_3$) δ: 9.15 (s, 2H), 7.88 (d, J=9.2 Hz, 1H), 7.69 (d, J=8.5 Hz, 1H), 7.58 (d, J=8.5 Hz, 1H), 7.55~7.50 (m, 2H), 7.23~7.19 (m, 1H), 7.00 (d, J=7.3 Hz, 1H), 6.97 (d, J=8.9 Hz, 1H), 6.87~6.85 (m, 1H), 4.73 (s, 2H), 3.76~3.74 (m, 4H), 3.63 (s, 2H), 3.00 (t, J=7.7 Hz, 2H), 2.58 (t, J=5.0 Hz, 4H), 2.47 (t, J=7.3 Hz, 2H), 1.87 (q, 2H), 1.72~1.68 (m, 2H)

Mass, m/e: 446 (M$^+$), 157 (base)

Example 4-29

In the manner similar to Example 4-1, 3-amino-7-methyl-2-[4-(4-quinolin-2-ylpiperazin-1-yl)butyl]-3H-quinazolin-4-one was obtained.

$^1$H-NMR (CDCl$_3$) δ: 8.11 (d, J=8.5 Hz, 1H), 7.88 (d, J=9.2 Hz, 1H), 7.69 (d, J=8.1 Hz, 1H), 7.58 (d, J=7.0 Hz, 1H), 7.52 (ddd, J=1.5 Hz, 6.9 Hz, 8.5 Hz, 1H), 7.27 (m, 1H), 7.23~7.19 (m, 2H), 6.97 (d, J=9.2 Hz, 1H), 4.88 (s, 2H), 3.76 (t, J=5.0 Hz, 4H), 3.07~3.04 (m, 2H), 2.61 (s, 3H), 2.58 (t, J=5.0 Hz, 4H), 2.49~2.46 (m, 2H), 2.48 (s, 3H), 1.90 (q, J=7.7 Hz, 2H), 1.72 (q, J=7.7 Hz, 2H)

Mass, m/e: 442 (M$^+$), 157 (base)

Example 4-30

In the manner similar to Example 4-1, 3-amino-5-methyl-4-oxo-2-[4-(4-quinolin-2-ylpiperazin-1-yl)butyl]-3,4-dihydrothieno[2,3-d]pyrimidine-6-carboxylic acid ethyl ester was obtained.

$^1$H-NMR (CDCl$_3$) δ: 7.88 (d, J=8.9 Hz, 1H), 7.69 (d, J=8.5 Hz, 1H), 7.58 (d, J=8.1 Hz, 1H), 7.54~7.52 (m, 1H), 7.23~7.21 (m, 1H), 6.97 (d, J=9.2 Hz, 1H), 4.88 (s, 2H), 3.75 (t, J=5.0 Hz, 4H), 3.06 (t, J=5.0 Hz, 2H), 2.93 (s, 3H), 2.58 (t, J=5.0 Hz, 4H), 2.48~2.45 (m, 2H), 1.88~1.86 (m, 2H), 1.71~1.69 (m, 2H), 1.39 (t, J=6.9 Hz, 3H)

Mass, m/e: 520 (M$^+$), 157 (base)

Example 4-31

In the manner similar to Example 4-1, 3-amino-2-[4-[4-(5-methoxyquinolin-2-yl)piperazin-1-yl]butyl-5,6,7,8-tetrahydro-3H-quinazolin-4-one was obtained.

$^1$H-NMR (CDCl$_3$) δ: 8.28 (d, J=9.6 Hz, 1H), 7.44~7.40 (m, 1H), 7.28 (d, J=7.7 Hz, 1H), 6.92 (d, J=9.2 Hz, 1H), 6.58 (d, J=7.3 Hz, 1H), 4.94 (s, 2H), 3.98 (s, 3H), 3.75 (t, J=5.0 Hz, 4H), 2.94~2.90 (s, 3H), 2.60~2.55 (m, 6H), 2.44 (t, J=7.7 Hz, 2H), 1.83~1.60 (m, 8H)

Mass, m/e: 462 (M$^+$), 187 (base)

Example 4-32

In the manner similar to Example 4-1, 3-amino-6-phenyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.88 (d, J=8.8 Hz, 1H), 7.79 (d, J=8.4 Hz, 1H), 7.58 (d, J=8.1 Hz, 1H), 7.52 (ddd, J=1.2 Hz, 6.9 Hz, 8.1 Hz, 1H), 7.34~7.19 (m, 6H), 6.98 (d, J=9.2 Hz, 1H), 4.96 (s, 2H), 3.76 (t, J=5.0 Hz, 4H), 2.95 (t, J=7.7 Hz, 2H), 2.75 (m, 2H), 2.58 (t, J=5.0 Hz, 4H), 2.46 (t, J=7.3 Hz, 2H), 2.16~2.12 (m, 1H), 1.96~1.61 (m, 8H)

Mass, m/e: 508 (M$^+$), 157 (base)

Example 4-33

In the manner similar to Example 4-1, 3-amino-2-[4-[4-(4,8-dimethylquinolin-2-yl)piperazin-1-yl]butyl]-5,6,7,8-tetrahydro-3H-quinazolin-4-one was obtained.

$^1$H-NMR (CDCl$_3$) δ: 7.63 (d, J=8.1 Hz, 1H), 7.40 (d, J=6.9 Hz, 1H), 7.15~7.12 (m, 1H), 6.82 (s, 1H), 4.95 (s, 2H), 3.75 (t, J=5.0 Hz, 4H), 2.93 (t, J=7.7 Hz, 2H), 2.64 (s, 3H), 2.60~2.56 (m, 6H), 2.58 (s, 3H), 2.53~2.50 (m, 2H), 2.44 (t, J=7.3 Hz, 2H), 1.84~1.61 (m, 8H)

Mass, m/e: 460 (M$^+$), 185 (base)

Example 4-34

In the manner similar to Example 4-1, 3-amino-2-[4-[4-(4,8-dimethylquinolin-2-yl)piperazin-1-yl]butyl]-3H-quinazolin-4-one was obtained.

$^1$H-NMR (CDCl$_3$) δ: 8.24 (dd, J=1.2 Hz, 8.1 Hz, 1H), 7.76~7.71 (m, 1H), 7.66 (d, J=7.7 Hz, 1H), 7.62 (d, J=7.7 Hz, 1H), 7.47~7.43 (m, 1H), 7.40 (d, J=6.9 Hz, 1H), 7.15~7.12 (m, 1H), 6.82 (s, 1H), 4.92 (s, 2H), 3.75 (t, J=5.0 Hz, 4H), 3.08 (t, J=7.7 Hz, 2H), 2.64 (s, 3H), 2.60~2.58 (m, 4H), 2.58 (s, 3H), 2.48 (t, J=7.7 Hz, 2H), 1.93~1.87 (m, 2H), 1.75~1.71 (m, 2H)

Mass, m/e: 456 (M$^+$), 185 (base)

Example 4-35

In the manner similar to Example 4-1, 3-amino-5,6-dimethyl-2-[4-(4-quinolin-2-ylpiperazin-1-yl)butyl]-3H-thieno[2,3-d]pyrimidin-4-one was obtained.

$^1$H-NMR (CDCl$_3$) δ: 7.88 (d, J=9.2 Hz, 1H), 7.79 (d, J=8.1 Hz, 1H), 7.58 (dd, J=1.2 Hz, 8.1 Hz, 1H), 7.52 (ddd, J=1.5 Hz, 6.9 Hz, 8.5 Hz, 1H), 7.23~7.19 (m, 1H), 6.97 (d, J=9.2 Hz, 1H), 4.88 (s, 2H), 3.76 (t, J=5.0 Hz, 4H), 3.04 (t, J=7.7 Hz, 2H), 2.57 (t, J=5.0 Hz, 4H), 2.46~2.44 (m, 2H), 2.46 (d, J=0.8 Hz, 3H), 2.37 (d, J=0.8 Hz, 3H), 1.88~1.82 (m, 2H), 1.72~1.66 (m, 2H)

Mass, m/e: 462 (M$^+$), 157 (base)

Example 4-36

In the manner similar to Example 4-1, 3-amino-8-methyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.88 (d, J=8.9 Hz, 1H), 7.69 (d, J=7.7 Hz, 1H), 7.58 (d, J=8.1 Hz, 1H), 7.54~7.50 (m, 1H), 7.23~7.19 (m, 1H), 6.97 (d, J=9.0 Hz, 1H), 4.92 (s, 2H), 3.75 (t, J=5.0 Hz, 4H), 2.92 (t, J=7.7 Hz, 2H), 2.66~2.65 (m, 1H), 2.57 (t, J=5.0 Hz, 4H), 2.56~2.40 (m, 4H), 1.87~1.57 (m, 11H)

Mass, m/e: 446 (M$^+$), 157 (base)

Example 4-37

In the manner similar to Example 4-1, 3-amino-2-[4-(4-quinolin-2-ylpiperazin-1-yl)butyl]-5,5a, 6,7,8,9,9a, 10-octahydro-3H-benzo[g]quinazolin-4-one was obtained.

$^1$H-NMR (CDCl$_3$) δ: 7.88 (d, J=8.9 Hz, 1H), 7.69 (d, J=8.9 Hz, 1H), 7.58 (d, J=8.1 Hz, 1H), 7.52 (ddd, J=1.5 Hz, 6.9 Hz, 8.5 Hz, 1H), 7.23~7.19 (m, 1H), 6.97 (d, J=9.2 Hz, 1H), 4.93 (s, 2H), 3.75 (t, J=5.0 Hz, 4H), 2.95~2.90 (m, 2H), 2.64~2.57 (m, 8H), 2.45 (t, J=7.7 Hz, 2H), 2.04~1.98 (m, 2H), 1.83~1.40 (m, 14H)

Mass, m/e: 486 (M$^+$), 157 (base)

Example 4-38

In the manner similar to Example 4-1, 3-amino-5,7-dimethyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.88 (d, J=9.2 Hz, 1H), 7.69 (d, J=8.1 Hz, 1H), 7.58 (d, J=7.7 Hz, 1H), 7.54~7.50 (m, 1H), 7.23~7.19 (m, 1H), 6.97 (d, J=9.2 Hz, 1H), 4.93 (s, 2H), 3.75 (t, J=5.0 Hz, 4H), 2.91 (t, J=7.7 Hz, 2H), 2.57 (m, 6H), 2.44 (t, J=7.7 Hz, 2H), 2.27~2.22 (m, 1H), 2.03~1.98 (m, 1H), 1.84~1.63 (m, 6H), 1.30 (d, J=6.6 Hz, 3H), 1.03 (d, J=6.6 Hz, 3H)

Mass, m/e: 460 (M$^+$), 157 (base)

Example 4-39

In the manner similar to Example 4-1, 3-amino-2-[4-(4-quinolin-2-ylpiperazin-1-yl)butyl]-5,6,7-trihydro-3H-cyclopenta[d]pyrimidin-4-one was obtained.

$^1$H-NMR (CDCl$_3$) δ: 7.88 (d, J=9.3 Hz, 1H), 7.69 (d, J=8.5 Hz, 1H), 7.58 (d, J=7.7 Hz, 1H), 7.52 (ddd, J=1.5 Hz, 6.9 Hz, 8.5 Hz, 1H), 7.21 (ddd, J=1.2 Hz, 7.0 Hz, 8.1 Hz, 1H), 6.97 (d, J=9.2 Hz, 1H), 4.97 (s, 2H), 3.75 (t, J=5.0 Hz, 4H), 2.97 (t, J=7.7 Hz, 2H), 2.86~2.80 (m, 4H), 2.57 (t, J=5.0 Hz, 4H), 2.45 (t, J=7.5 Hz, 2H), 2.08 (t, J=7.7 Hz, 2H), 1.84~1.78 (m, 2H), 1.70~1.61 (m, 2H)

Mass, m/e: 418 (M$^+$), 402, 157 (base)

Example 4-40

In the manner similar to Example 4-1, 3-amino-8-methoxy-2-[4-(4-quinolin-2-ylpiperazin-1-yl)butyl]-3H-quinazolin-4-one was obtained.

$^1$H-NMR (CDCl$_3$) δ: 7.87 (d, J=9.2 Hz, 1H), 7.81 (dd, J=0.8 Hz, 8.1 Hz, 1H), 7.69 (d, J=8.4 Hz, 1H), 7.58 (d, J=8.1 Hz, 1H), 7.52 (ddd, J=1.5 Hz, 6.9 Hz, 8.5 Hz, 1H), 7.39~7.36 (m, 1H), 7.22~7.20 (m, 1H), 7.17 (d, J=6.9 Hz, 1H), 6.97 (d, J=9.2 Hz, 1H), 4.96 (s, 2H), 4.00 (s, 3H), 3.75 (t, J=4.6 Hz, 4H), 3.12 (t, J=8.1 Hz, 2H), 2.58 (t, J=5.0 Hz, 4H), 2.47 (t, J=7.3 Hz, 2H), 1.94~1.86 (m, 2H), 1.75~1.68 (m, 2H)

Mass, m/e: 458 (M$^+$), 442, 157 (base)

Example 4-41

In the manner similar to Example 4-1, 3-amino-6,7-dimethoxy-2-[4-(4-quinolin-2-ylpiperazin-1-yl)butyl]-3H-quinazolin-4-one was obtained.

$^1$H-NMR (CDCl$_3$) δ: 7.88 (d, J=9.3 Hz, 1H), 7.69 (d, J=8.1 Hz, 1H), 7.59 (d, J=8.1 Hz, 1H), 7.53 (s, 1H), 7.52 (ddd, J=1.5 Hz, 6.9 Hz, 8.5 Hz, 1H), 7.22 (ddd, J=1.2 Hz, 6.9 Hz, 8.1 Hz, 1H), 7.06 (s, 1H), 6.97 (d, J=9.2 Hz, 1H), 4.90 (s, 2H), 3.99 (br s, 6H), 3.75 (m, 4H), 3.05 (t, J=7.7 Hz, 2H), 2.63 (m, 4H), 2.51 (t, J=6.9 Hz, 2H), 1.92~1.86 (m, 2H), 1.78~1.71 (m, 2H)

Mass, m/e: 488 (M$^+$), 472, 157 (base)

Example 4-42

In the manner similar to Example 4-1, 3-amino-2-[4-(4-quinolin-2-ylpiperazin-1-yl)butyl]-5,6,7,8,9-pentahydro-3H-cyclohepta[d]pyrimidin-4-one was obtained.

$^1$H-NMR (CDCl$_3$) δ: 7.88 (d, J=9.3 Hz, 1H), 7.69 (d, J=8.1 Hz, 1H), 7.58 (d, J=9.1 Hz, 1H), 7.52 (ddd, J=1.2 Hz, 6.9 Hz, 8.1 Hz, 1H), 7.22~7.20 (m, 1H), 6.97 (d, J=9.3 Hz, 1H), 5.00 (s, 2H), 3.75 (t, J=5.0 Hz, 4H), 2.91 (t, J=7.3 Hz, 2H), 2.75 (t, J=8.5 Hz, 2H), 2.58 (t, J=5.0 Hz, 4H), 2.45 (t, J=7.3 Hz, 2H), 1.83~1.78 (m, 4H), 1.70~1.60 (m, 6H)

Mass, m/e: 446 (M$^+$), 430, 157 (base)

Example 4-43

In the manner similar to Example 4-1, 4-amino-12-methyl-5-[4-(4-quinolin-2-ylpiperazin-1-yl)butyl]-4,6,12-triaza-tricyclo-[7.2.1.0*$^{2,7}$*]dodeca-2 (7), 5-dien-3-one was obtained.

$^1$H-NMR (CDCl$_3$) δ: 7.87 (d, J=9.2 Hz, 1H), 7.69 (d, J=7.5 Hz, 1H), 7.58 (d, J=8.1 Hz, 1H), 7.53~7.50 (m, 1H), 7.23~7.21 (m, 1H), 6.95 (d, J=9.2 Hz, 1H), 5.00 (s, 2H), 3.74 (t, J=5.0 Hz, 4H), 3.11 (s, 3H), 2.87 (t, J=5.3 Hz, 4H), 2.56~2.53 (m, 4H), 2.45~2.37 (m, 4H), 2.06~1.54 (m, 8H)

Mass, m/e: 281, 255, 171, 157 (base), 145, 128

Example 4-44

Step 4-44-A

In the manner similar to Example 4-1, 3-amino-6-tert-butoxycarbonyl-2-[4-(4-quinolin-2-ylpiperazin-1-yl)-butyl]-5,6,7,8-tetrahydro-3H-pyrido[4,3-d]pyrimidin-4-one was obtained.

$^1$H-NMR (CDCl$_3$) δ: 7.88 (d, J=9.3 Hz, 1H), 7.69 (d, J=8.1 Hz, 1H), 7.58 (d, J=8.1 Hz, 1H), 7.52 (ddd, J=1.5 Hz, 6.9 Hz, 8.5 Hz, 1H), 7.21 (ddd, J=1.2 Hz, 7.0 Hz, 8.1 Hz, 1H), 6.97 (d, J=8.8 Hz, 1H), 4.96 (s, 2H), 4.35 (s, 2H), 3.75 (t, J=5.0 Hz, 4H), 3.65 (t, J=5.7 Hz, 2H), 2.95 (t, J=7.7 Hz, 2H), 2.57 (t, J=5.0 Hz, 4H), 2.45 (t, J=7.4 Hz, 2H), 1.84~1.77 (m, 2H), 1.70~1.64 (m, 2H), 1.48 (s, 9H)

Mass, m/e: 533 (M$^+$), 433, 157 (base)

Step 4-44-B

To 10 ml of 4N-hydrochloric acid-dioxane solution, 53 mg of 3-amino-6-tert-butoxycarbonyl-2-[4-(4-quinolin-2-ylpiperazin-1-yl)butyl]-5,6,7,8-tetrahydro-3H-pyrido[4,3-d]pyrimidin-4-one as synthesized in above Step 4-44-A was added and stirred for 18 hours at room temperature. The solution was neutralized with saturated aqueous sodium hydrogencarbonate solution, extracted with ethyl acetate, dried over anhydrous magnesium sulfate, and the solvent was distilled off under reduced pressure. The residue was purified on silica gel column chromatography (chloroform:methanol=9:1) to provide 39 mg (90%) of 3-amino-2-[4-(4-quinolin-2-ylpiperazin-1-yl)butyl]-5,6,7,8-tetrahydro-3H-pyrido[4,3-d]pyrimidin-4-one.

$^1$H-NMR (CDCl$_3$) δ: 7.88 (d, J=8.7 Hz, 1H), 7.69 (d, J=8.1 Hz, 1H), 7.58 (d, J=8.1 Hz, 1H), 7.52 (ddd, J=1.5 Hz, 6.9 Hz, 8.5 Hz, 1H), 7.23~7.17 (m, 1H), 6.97 (d, J=9.3 Hz, 1H), 4.95 (s, 2H), 3.80 (s, 2H), 3.75 (t, J=4.6 Hz, 4H), 3.10 (t, J=5.8 Hz, 2H), 2.95 (t, J=7.7 Hz, 2H), 2.62 (t, J=5.8 Hz, 2H), 2.58 (t, J=5.2 Hz, 4H), 2.45 (t, J=7.4 Hz, 2H), 2.35 (s, 1H), 1.83~1.79 (m, 2H), 1.69~1.64 (m, 2H)

Mass, m/e: 433 (M$^+$, base), 417, 157

Example 4-45

In the manner similar to Example 4-1, 3-amino-2-[3-(4-quinolin-2-ylpiperazin-1-yl)propyl]-5,6,7,8-tetrahydro-3H-quinazolin-4-one was obtained.

$^1$H-NMR (CDCl$_3$) δ: 7.88 (d, J=9.2 Hz, 1H), 7.69 (d, J=8.1 Hz, 1H), 7.58 (d, J=7.7 Hz, 1H), 7.54~7.50 (m, 1H), 7.24~7.20 (m, 1H), 6.95 (d, J=9.2 Hz, 1H), 5.57 (s, 2H), 3.70 (t, J=5.0 Hz, 4H), 3.01~2.98 (m, 2H), 2.61~2.50 (m, 8H), 2.47~2.44 (m, 2H), 2.05 (q, J=6.9 Hz, 2H), 1.82~1.70 (m, 4H)

Mass, m/e: 418 (M$^+$), 157 (base)

Example 4-46

In the manner similar to Example 4-1, 3-amino-2-[2-(4-quinolin-2-ylpiperazin-1-yl)ethyl]-5,6,7,8-tetrahydro-3H-quinazolin-4-one was obtained.

$^1$H-NMR (CDCl$_3$) δ: 7.89 (d, J=9.2 Hz, 1H), 7.69 (d, J=8.5 Hz, 1H), 7.69 (d, J=8.9 Hz, 1H), 7.52 (ddd, J=1.5 Hz, 6.9 Hz, 8.5 Hz, 1H), 7.24~7.20 (m, 1H), 6.96 (d, J=9.2 Hz, 1H), 5.71 (s, 2H), 3.72 (t, J=5.0 Hz, 4H), 3.14 (t, J=6.5 Hz, 2H), 2.86 (t, J=6.5 Hz, 2H), 2.69 (t, J=5.0 Hz, 4H), 2.59 (t, J=6.2 Hz, 2H), 2.53 (t, J=6.2 Hz, 2H), 1.81~1.72 (m, 4H)

Mass, m/e: 404 (M$^+$), 157 (base)

Example 4-47

In the manner similar to Example 4-1, 3-amino-2-[5-(4-quinolin-2-ylpiperazin-1-yl)pentyl]-5,6,7,8-tetrahydro-3H-quinazolin-4-one was obtained.

$^1$H-NMR (CDCl$_3$) δ: 7.87 (d, J=8.9 Hz, 1H), 7.69 (d, J=8.5 Hz, 1H), 7.58 (d, J=8.2 Hz, 1H), 7.54~7.50 (m, 1H), 7.23~7.19 (m, 1H), 6.97 (d, J=8.9 Hz, 1H), 4.86 (s, 2H), 3.75 (t, J=5.0 Hz, 4H), 2.89 (t, J=7.7 Hz, 2H), 2.60~2.55 (m, 6H), 2.53~2.50 (m, 2H), 2.40 (t, J=7.7 Hz, 2H), 1.81~1.71 (m, 6H), 1.64~1.57 (m, 2H), 1.50~1.44 (m, 2H)

Mass, m/e: 446 (M$^+$), 157 (base)

Example 4-48

In the manner similar to Example 4-1, 3-amino-7-tert-butyloxycarbonyl-2-[4-(4-quinolin-2-ylpiperazin-1-yl)-butyl]-5,6,7,8-tetrahydro-3H-pyrido[4',3':4,5]thieno-[2,3-d]pyrimidin-4-one was obtained.

$^1$H-NMR (CDCl$_3$) δ: 7.88 (d, J=9.2 Hz, 1H), 7.69 (d, J=8.5 Hz, 1H), 7.56~7.60 (m, 1H), 7.52 (ddd, J=1.5 Hz, 6.9 Hz, 8.5 Hz, 1H), 7.21 (ddd, J=1.5 Hz, 6.9 Hz, 8.5 Hz, 1H), 6.97 (d, J=9.3 Hz, 1H), 4.88 (s, 2H), 4.60 (br s, 2H), 3.68~3.78 (m, 6H), 3.00~3.12 (m, 4H), 2.55~2.60 (m, 4H), 2.46 (t, J=7.0 Hz, 2H), 1.82~1.91 (m, 2H), 1.66~1.73 (m, 2H), 1.48 (s, 9H)

Mass, m/e: 589 (M$^+$), 489, 445, 157 (base)

Example 4-49

In the manner similar to Example 4-1, 7-acetyl-3-amino-2-[4-(4-quinolin-2-yl)butyl]-5,6,7,8-tetrahydro-3H-pyrido[4',3':4,5]thieno[2,3-d]pyrimidin-4-one was obtained.

$^1$H-NMR (CDCl$_3$) δ: 7.88 (d, J=9.2 Hz, 1H), 7.69 (d, J=8.5 Hz, 1H), 7.58 (dd, J=1.1 Hz, 8.5 Hz, 1H), 7.52 (ddd, J=1.1 Hz, 6.9 Hz, 8.5 Hz, 1H), 7.22 (ddd, J=1.1 Hz, 6.9 Hz, 8.5 Hz, 1H), 6.97 (d, J=9.2 Hz, 1H), 4.90 (br s, 2H), 4.79 (s, 2H), 3.72~3.80 (m, 6H), 3.13~3.18 (m, 2H), 3.04 (t, J=7.0 Hz, 4H), 2.60 (t, J=5.0 Hz, 4H), 2.48 (t, J=7.0 Hz, 2H), 2.20 (s, 3H), 1.87 (q, J=7.0 Hz, 2H), 1.70 (q, J=7.0 Hz, 2H)

Mass, m/e: 531 (M$^+$), 387, 157 (base)

Example 4-50

In the manner similar to Example 4-1, 3-amino-2-[4-(4-quinolin-2-ylpyperazin-1-yl)butyl]-5,6,7,8-tetrahydro-3H-benzo[4,5]thieno[2,3-d]pyrimidin-4-one was obtained.

$^1$H-NMR (CDCl$_3$) δ: 7.88 (d, J=9.2 Hz, 1H), 7.69 (d, J=8.5 Hz, 1H), 7.58 (dd, J=1.5 Hz, 8.5 Hz, 1H), 7.51 (ddd, J=1.5 Hz, 6.9 Hz, 8.5 Hz, 1H), 7.21 (ddd, J=1.5 Hz, 6.9 Hz, 8.5 Hz, 1H), 6.97 (d, J=9.2 Hz, 1H), 4.87 (s, 2H), 3.73~3.79 (m, 4H), 2.96~3.05 (m, 4H), 2.75 (t, J=5.9 Hz, 2H), 2.58 (br s, 4H), 2.46 (t, J=7.3 Hz, 2H), 1.81~1.92 (m, 6H), 1.65~1.74 (m, 2H)

Mass, m/e: 488 (M$^+$), 472, 344, 157 (base)

Example 4-51

In the manner similar to Example 4-1, 7-acetyl-3-amino-2-[4-[4-(4-phenylquinolin-2-yl)piperazin-1-yl]butyl]-5,6,7,8-tetrahydro-3H-pyrido[4',3':4,5]thieno[2,3-d]pyrimidin-4-one was obtained.

$^1$H-NMR (CDCl$_3$) δ: 7.75~7.77 (m, 2H), 7.70 (dd, J=3.1 Hz, 5.2 Hz, 1H), 7.61 (dd, J=1.1 Hz, 8.5 Hz, 2), 7.45~7.56 (m, 4H), 7.16 (ddd, J=1.1 Hz, 6.9 Hz, 8.5 Hz, 1H), 4.90 (s, 2H), 3.71~3.83 (m, 6H), 3.15 (t, J=5.7 Hz, 2H), 3.04 (t, J=7.7 Hz, 4H) 2.58 (t, J=5.0H, 4H), 2.46 (t, J=7.7 Hz, 2H), 2.20 (s, 3H), 1.87 (q, J=7.7 Hz, 2H), 1.62~1.74 (m, 2H)

Mass, m/e: 607 (M$^+$), 279, 149 (base)

Example 4-52

In the manner similar to Example 4-1, 3-amino-6-chloro-2-[4-(4-quinolin-2-ylpiperazin-1-yl)butyl]-3H-quinazolin-4-one was obtained.

$^1$H-NMR (CDCl$_3$) δ: 8.19 (d, J=2.3 Hz, 1H), 7.87 (d, J=9.2 Hz, 1H), 7.68 (d, J=9.2 Hz, 1H), 7.66 (dd, J=2.3 Hz, 8.4 Hz, 1H), 7.60 (d, J=8.4 Hz, 1H), 7.56~7.59 (m, 1H), 7.52 (ddd, J=1.5 Hz, 6.9 Hz, 8.5 Hz, 1H), 7.21 (ddd, J=1.5 Hz, 6.9 Hz, 8.5 Hz, 1H), 6.96 (d, J=9.2 Hz, 1H), 4.90 (br s, 2H), 3.75 (t, J=5.0 Hz, 4H), 3.05 (t, J=7.4 Hz, 2H), 2.58 (t, J=5.0 Hz, 4H), 2.47 (t, J=7.4 Hz, 2H), 1.89 (q, J=7.4 Hz, 2H), 1.71 (q, J=7.4 Hz, 2H)

Mass, m/e: 462 (M$^+$), 446, 157 (base)

Example 4-53

In the manner similar to Example 4-1, 3-amino-6-methoxy-2-[4-(4-quinolin-2-ylpiperazin-1-yl)butyl]-3H-quinazolin-4-one was obtained.

$^1$H-NMR (CDCl$_3$) δ: 7.88 (d, J=8.9 Hz, 1H), 7.69 (d, J=8.5 Hz, 1H), 7.59~7.61 (m, 1H), 7.58 (d, J=2.7 Hz, 1H), 7.52 (ddd, J=1.5 Hz, 6.9 Hz, 8.5 Hz, 1H), 7.34 (d, J=3.0 Hz, 1H), 7.32 (d, J=2.7 Hz, 1H), 7.21 (ddd, J=1.5 Hz, 6.9 Hz, 8.5 Hz, 1H), 6.97 (d, J=1.5 Hz, 1H), 4.92 (s, 2H), 3.19 (s, 3H), 3.73~3.77 (4H, m), 3.05 (t, J=7.7 Hz, 2H), 2.58 (t, J=7.7 Hz, 1H), 1.89 (q, J=7.7 Hz, 1H), 1.71 (q, J=7.7 Hz, 1H)

Mass, m/e: 458 (M$^+$), 442, 157 (base)

Example 4-54

In the manner similar to Example 4-1, 3-amino-2-[4-(4-quinolin-2-ylpiperazin-1-yl)butyl]-7-trifluoromethyl-3H-quinazolin-4-one was obtained.

$^1$H-NMR (CDCl$_3$) δ: 8.35 (d, J=8.9 Hz, 1H), 7.96 (s, 1H), 7.87 (d, J=9.2 Hz, 1H), 7.67 (d, J=8.5 Hz, 1H), 7.65 (dd, J=1.5 Hz, 8.5 Hz, 1H), 7.58 (dd, J=0.8 Hz, 7.7 Hz, 1H), 7.52 (ddd, J=1.5 Hz, 7.0 Hz, 8.5 Hz, 1H), 7.21 (ddd, J=1.5 Hz, 7.0 Hz, 8.5 Hz, 1H), 6.96 (d, J=9.2 Hz, 1H), 4.95 (s, 2H), 3.75 (t, J=5.0 Hz, 4H), 3.09 (t, J=7.7 Hz, 2H), 2.59 (t, J=5.0 Hz, 4H), 2.49 (t, J=7.7 Hz, 2H), 1.92 (q, J=7.7 Hz, 2H), 1.72 (q, J=7.7 Hz, 2H)

Mass, m/e: 496 (M$^+$), 480, 157

Example 4-55

In the manner similar to Example 4-1, 3-amino-2-[4-(4-quinolin-2-ylpiperazin-1-yl)butyl]-3H-pyrido-[3',2':4,5]thieno[3,2-d]pyridin-4-one was obtained.

$^1$H-NMR (CDCl$_3$) δ: 8.75 (dd, J=1.5 Hz, 4.5 Hz, 1H), 8.54 (dd, J=1.5 Hz, 8.1 Hz, 1H), 7.87 (d, J=8.9 Hz, 1H), 7.67 (d, J=8.5 Hz, 1H), 7.56~7.60 (m, 1H), 7.52 (ddd, J=1.5 Hz, 7.0H, 8.5 Hz, 1H), 7.45 (dd, J=4.6 Hz, 8.1 Hz, 1H), 7.21 (ddd, J=1.5

Hz, 7.0 Hz, 8.5 Hz, 1H), 6.96 (d, J=8.9 Hz, 1H), 5.09 (s, 2H), 3.71~3.79 (m, 4H), 3.14 (t, J=7.7 Hz, 2H), 2.59 (t, J=5.0 Hz, 4H), 2.50 (t, J=7.7 Hz, 2H), 1.95 (q, J=7.7 Hz, 2H), 1.74 (q, J=7.7 Hz, 2H)

Mass, m/e: 485 (M$^+$), 470, 341, 157 (base)

Example 4-56

In the manner similar to Example 4-1, 3-amino-6-fluoro-2-[4-(4-quinolin-2-ylpiperazin-1-yl)butyl]-3H-quinazolin-4-one was obtained.

$^1$H-NMR (CDCl$_3$) δ: 7.89 (d, J=9.2 Hz, 1H), 7.87 (dd, J=2.7 Hz, 8.5 Hz, 1H), 7.72~7.65 (m, 2H), 7.59 (dd, J=1.2 Hz, 8.1 Hz, 1H), 7.53 (ddd, J=1.5 Hz, 6.9 Hz, 8.5 Hz, 1H), 7.46 (dt, J=2.7 Hz, 8.5 Hz, 1H), 7.22 (ddd, J=1.2 Hz, 6.9 Hz, 8.1 Hz, 1H), 6.98 (d, J=9.2 Hz, 1H), 4.92 (s, 2H), 3.76 (t, J=5.0 Hz, 4H), 3.07 (t, J=7.7 Hz, 2H), 2.59 (t, J=5.0 Hz, 4H), 2.49 (t, J=7.7 Hz, 2H), 1.91 (q, J=7.7 Hz, 2H), 1.73 (q, J=7.7 Hz, 2H)

Mass, m/e: 446 (M$^+$), 157 (base)

Example 4-57

In the manner similar to Example 4-1, 3-amino-7-fluoro-2-[4-(4-quinolin-2-ylpiperazin-1-yl)butyl]-3H-quinazolin-4-one was obtained.

$^1$H-NMR (CDCl$_3$) δ: 8.25 (dd, J=6.2 Hz, 8.9 Hz, 1H), 7.89 (d, J=9.2 Hz, 1H), 7.70 (d, J=8.1 Hz, 1H), 7.59 (dd, J=1.2 Hz, 8.1 Hz, 1H), 7.53 (ddd, J=1.5 Hz, 6.9 Hz, 8.5 Hz, 1H), 7.31 (dd, J=2.7 Hz, 9.6 Hz, 1H), 7.22 (ddd, J=1.2 Hz, 6.9 Hz, 8.1 Hz, 1H), 7.16 (dt, J=2.3 Hz, 8.9 Hz, 1H), 6.98 (d, J=9.2 Hz, 1H), 4.89 (s, 2H), 3.76 (t, J=5.0 Hz, 4H), 3.07 (t, J=7.7 Hz, 2H), 2.59 (t, J=5.0 Hz, 4H), 2.49 (t, J=7.7 Hz, 2H), 1.91 (q, J=7.7 Hz, 2H), 1.73 (q, J=7.7 Hz, 2H)

Mass, m/e: 446 (M$^+$), 157 (base)

Example 4-58

In the manner similar to Example 4-1, 3-amino-2-[4-(4-quinolin-2-ylpiperazin-1-yl)butyl]-3H-thieno[3,4-d]-pyrimidin-4-one was obtained.

$^1$H-NMR (DMSO-d$_6$) δ: 8.02 (d, J=9.2 Hz, 1H), 7.69 (d, J=8.1 Hz, 1H), 7.58~7.48 (m, 2H), 7.35~7.28 (m, 2H), 7.25~7.18 (m, 2H), 5.51 (br s, 2H), 3.68 (br s, 4H), 3.27 (br s, 2H), 2.53~2.24 (m, 6H), 1.68~1.49 (m, 4H)

Mass, m/e: 434 (M$^+$), 157 (base)

Example 4-59

In the manner similar to Example 4-1, 3-amino-7-methyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 4.95 (s, 2H), 3.76 (t, J=5.0 Hz, 4H), 2.93 (t, J=6.9 Hz, 2H), 2.74~2.63 (m, 2H), 2.58 (t, J=5.0 Hz, 4H), 2.49~2.37 (m, 3H), 2.28~2.18 (m, 1H), 1.92~1.75 (m, 4H), 1.72~1.59 (m, 2H), 1.34~1.22 (m, 1H), 1.06 (d, J=6.6 Hz, 3H)

Mass, m/e: 446 (M$^+$), 157 (base)

Example 4-60

In the manner similar to Example 4-1, 3-amino-6-methyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.1 Hz, 1H), 7.59 (dd, J=1.2 Hz, 8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 4.95 (s, 2H), 3.76 (t, J=5.0 Hz, 4H), 2.93 (t, J=7.7 Hz, 2H), 2.77~2.69 (m, 2H), 2.67~2.60 (m, 2H), 2.58 (t, J=5.0 Hz, 4H), 2.45 (t, J=7.3 Hz, 2H), 2.09~1.98 (m, 1H), 1.92~1.62 (m, 6H), 1.45~1.32 (m, 1H), 1.08 (d, J=6.6 Hz, 3H)

Mass, m/e: 446 (M$^+$), 157 (base)

Example 4-61

In the manner similar to Example 4-1, 3-amino-6-ethyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (d, J=8.1 Hz, 1H), 7.53 (t, J=8.1 Hz, 1H), 7.22 (t, J=8.1 Hz, 1H), 6.98 (d, J=9.2 Hz, 1H), 4.95 (s, 2H), 3.76 (t, J=5.0 Hz, 4H), 2.93 (t, J=7.3 Hz, 2H), 2.80~2.72 (m, 1H), 2.66~2.53 (m, 6H), 2.45 (t, J=7.3 Hz, 2H), 2.09~1.98 (m, 1H), 1.98~1.89 (m, 1H), 1.81 (q, J=7.3 Hz, 2H), 1.72~1.30 (m, 6H), 0.98 (t, J=7.3 Hz, 3H)

Mass, m/e: 460 (M$^+$), 157 (base)

Example 4-62

In the manner similar to Example 4-1, 3-amino-6,7-dimethyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.1 Hz, 1H), 7.22 (ddd, J=1.2 Hz, 6.9 Hz, 8.1 Hz, 1H), 6.98 (d, J=9.2 Hz, 1H), 4.95 (s, 2H), 3.76 (t, J=5.0 Hz, 4H), 3.00~2.86 (m, 2H), 2.73~2.52 (m, 6H), 2.45 (t, J=7.3 Hz, 2H), 2.40~2.25 (m, 2H), 2.04~1.90 (m, 2H), 1.86~1.76 (m, 2H), 1.73~1.59 (m, 2H), 0.95~0.89 (m, 6H)

Mass, m/e: 460 (M$^+$), 157 (base)

Example 4-63

In the manner similar to Example 4-1, 3-amino-6-tert-butyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 4.96 (s, 2H), 3.76 (t, J=5.0 Hz, 4H), 2.94 (t, J=7.7 Hz, 2H), 2.76~2.54 (m, 7H), 2.45 (t, J=7.3 Hz, 2H), 2.20~2.10 (m, 1H), 2.04~1.96 (m, 1H), 1.86~1.76 (m, 2H), 1.72~1.57 (m, 2H), 1.39~1.23 (m, 2H), 0.96 (s, 9H)

Mass, m/e: 488 (M$^+$), 157 (base)

Example 4-64

In the manner similar to Example 4-1, 3-amino-5,7,7-trimethyl-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 4.94 (s, 2H), 3.76 (t, J=5.0 Hz, 4H), 3.00~2.80 (m, 3H), 2.58 (t, J=5.0 Hz, 4H), 2.52~2.42 (m, 3H), 2.32~2.25 (m, 1H), 1.87~1.62 (m, 5H), 1.33 (d, J=6.6 Hz, 3H), 1.23~1.15 (m, 1H), 1.06 (s, 3H), 0.85 (s, 3H)

Mass, m/e: 474 (M$^+$), 157 (base)

Example 4-65

In the manner similar to Example 4-1, 3-amino-2-[4-(4-benzothiazol-2-ylpiperazin-1-yl)butyl]-5,6,7,8-tetrahydro-3H-quinazolin-4-one was obtained.

$^1$H-NMR (CDCl$_3$) δ: 7.60 (d, J=8.5 Hz, 1H), 7.55 (d, J=8.1 Hz, 1H), 7.32~7.27 (m, 1H), 7.10~7.04 (m, 1H), 4.90 (s, 2H), 3.65 (t, J=5.0 Hz, 4H), 2.92 (t, J=7.7 Hz, 2H), 2.62~2.49 (m, 8H), 2.45 (t, J=7.3 Hz, 2H), 1.85~1.60 (m, 8H)

Mass, m/e: 438 (M$^+$), 422 (base)

Example 4-66

In the manner similar to Example 4-1, 3-amino-6,6-ethylenedioxy-2-[4-(4-quinolin-2-ylpiperazin-1-yl)butyl]-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.1 Hz, 1H), 7.59 (dd, J=1.2 Hz, 7.7 Hz, 1H), 7.53 (ddd, J=1.5 Hz, 6.9 Hz, 8.1 Hz, 1H), 7.22 (ddd, J=1.2 Hz, 6.9 Hz, 8.1 Hz, 1H), 6.98 (d, J=9.2 Hz, 1H), 4.94 (s, 2H), 4.07~3.98 (m, 4H), 3.76 (t, J=5.0 Hz, 4H), 2.94 (t, J=7.7 Hz, 2H), 2.85 (t, J=6.9 Hz, 2H), 2.75 (s, 2H), 2.58 (t, J=5.0 Hz, 4H), 2.45 (t, J=7.3 Hz, 2H), 1.96 (t, J=6.9 Hz, 2H), 1.80 (q, J=7.7 Hz, 2H), 1.72~1.59 (m, 2H)

Mass, m/e: 490 (M$^+$), 157 (base)

Example 4-67

To a mixed solution of 29 ml of acetone and 1 ml of water, 229 mg of 3-amino-6,6-ethylenedioxy-2-[4-(4-quinolin-2-ylpiperazin-1-yl)butyl]-5,6,7,8-tetrahydro-3H-quinazolin-4-one as synthesized in Example 4-66 and 59 mg of pyridinium p-toluenesulfonate were added and heated under reflux for 112 hours. After cooling, the reaction mixture was extracted with methylene chloride, washed with water, dried over anhydrous magnesium sulfate, and the solvent was distilled off under reduced pressure. Purifying the residue on silica gel column chromatography (methanol:methylene chloride=1:9) to provide 194 mg (78%) of 6,6-ethylenedioxy-3-isopropylideneamino-2-[4-(4-quinolin-2-ylpiperazin-1-yl)butyl]-5,6,7,8-tetrahydro-3H-quinazolin-4-one.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.5 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 4.08~3.99 (m, 4H), 3.76 (t, J=5.0 Hz, 4H), 2.86 (t, J=6.6 Hz, 2H), 2.75 (br s, 2H), 2.63 (t, J=7.3 Hz, 2H), 2.57 (t, J=5.0 Hz, 4H), 2.45~2.37 (m, 2H), 1.97 (t, J=6.9 Hz, 2H), 1.66~1.57 (m, 2H), 1.59 (s, 6H), 1.31~1.24 (m, 2H)

Mass, m/e: 530 (M$^+$), 157 (base)

Example 4-68

To 10 ml of methanol, 300 mg of sodium borohydride was added and into this mixture, a solution of 145 mg of 6,6-ethylenedioxy-3-isopropylideneamino-2-[4-(4-quinolin-2-ylpiperazin-1-yl)butyl]-5,6,7,8-tetrahydro-3H-quinazolin-4-one as synthesized in Example 4-67 in 10 ml of methanol was dropped under cooling with ice. Raising the temperature to room temperature, the reaction mixture was stirred for an hour. Distilling the system under reduced pressure, water was added to the distillation residue, extracted with methylene chloride, washed with water, dried over anhydrous magnesium sulfate and the solvent was distilled off under reduced pressure. The residue was purified on silica gel column chromatography (methanol:methylene chloride=2:23) to provide 89 mg (61%) of 6,6-ethylenedioxy-3-isopropylamino-2-[4-(4-quinolin-2-ylpiperazin-1-yl)butyl]-5,6,7,8-tetrahydro-3H-quinazolin-4-one.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=9.2 Hz, 1H), 5.33 (d, J=4.6 Hz, 1H), 4.09~3.99 (m, 4H), 3.76 (t, J=5.0 Hz, 4H), 3.41~3.32 (m, 1H), 2.84 (t, J=6.6 Hz, 2H), 2.74 (s, 2H), 2.58 (t, J=5.0 Hz, 4H), 2.43 (t, J=7.3 Hz, 2H), 1.96 (t, J=6.6 Hz, 2H), 1.82~1.72 (m, 2H), 1.67~1.56 (m, 4H), 1.16~1.01 (m, 6H)

Mass, m/e: 532 (M$^+$), 157 (base)

Example 4-69

To 40 ml of 6N-hydrochloric acid, 2.72 g of 3-amino-6,6-ethylenedioxy-2-[4-(4-quinolin-2-ylpiperazin-1-yl)butyl]-5,6,7,8-tetrahydro-3H-quinazolin-4-one as synthesized in Example 4-66 was added and heated under reflux for an hour. After cooling, the reaction mixture was neutralized with saturated aqueous sodium hydrogencarbonate solution, extracted with methylene chloride, dried over anhydrous magnesium sulfate, and the solvent was distilled off under reduced pressure. The residue was purified on silica gel column chromatography (methanol:methylene chloride=2:23) to provide 1.77 g (71%) of 3-amino-2-[4-(4-quinolin-2-ylpiperazin-1-yl)butyl]-3,4,5,6,7,8-hexahydro-4,6-dioxaquinazoline.

$^1$H-NMR (CDCl$_3$) δ: 7.89 (d, J=9.2 Hz, 1H), 7.70 (d, J=8.5 Hz, 1H), 7.60 (dd, J=1.2 Hz, 8.1 Hz, 1H), 7.53 (ddd, J=1.5 Hz, 6.9 Hz, 8.5 Hz, 1H), 7.23 (ddd, J=1.2 Hz, 6.9 Hz, 8.1 Hz, 1H), 6.98 (d, J=9.2 Hz, 1H), 5.01 (s, 2H), 3.76 (t, J=5.0 Hz, 4H), 3.39 (s, 2H), 3.06~2.95 (m, 4H), 2.66 (t, J=7.3 Hz, 2H), 2.59 (t, J=5.0 Hz, 4H), 2.47 (t, J=7.3 Hz, 2H), 1.89~1.79 (m, 2H), 1.74~1.64 (m, 2H)

Mass, m/e: 446 (M$^+$), 157 (base)

Example 4-70

To 25 ml of methanol, 500 mg of sodium borohydride was added, and into this mixture, a solution of 1.00 g of 3-amino-2-[4-(4-quinolin-2-ylpiperazin-1-yl)butyl]-3,4,5,6,7,8-hexahydro-4,6-dioxaquinazoline as synthesized in Example 4-69 in 25 ml of methanol was dropped under cooling with ice. Raising the temperature to room temperature, the system was stirred for 3 hours, followed by distillation under reduced pressure. After addition of water, the distillation residue was extracted with methylene chloride, washed with water, dried over anhydrous magnesium sulfate and the solvent was distilled off under reduced pressure. The residue was purified on silica gel column chromatography (methanol:methylene chloride=1:9) to provide 520 mg (52%) of 3-amino-6-hydroxy-2-[4-(4-quinolin-2-ylpiperazin-1-yl)butyl]-5,6,7,8-tetrahydro-3H-quinazolin-4-one.

$^1$H-NMR (CDCl$_3$) δ: 7.88 (d, J=9.2 Hz, 1H), 7.70 (d, J=8.5 Hz, 1H), 7.59 (d, J=8.1 Hz, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 6.97 (d, J=9.2 Hz, 1H), 4.97 (s, 2H), 4.24~4.16 (m, 1H), 3.75 (t, J=5.0 Hz, 4H), 2.93 (t, J=7.7 Hz, 2H), 2.88~2.76 (m, 2H), 2.69~2.49 (m, 6H), 2.45 (t, J=7.3 Hz, 2H), 2.01~1.61 (m, 6H)

Mass, m/e: 448 (M$^+$), 157 (base)

Example 4-71

In the manner similar to Example 4-1, 3-amino-2-[4-(4-quinolin-2-ylpiperazin-1-yl)butyl]-6-trifluoromethyl-5,6,7,8-tetrahydro-3H-quinazolin-4-one was obtained.

$^1$H-NMR (CDCl$_3$) δ: 7.89 (d, J=9.2 Hz, 1H), 7.70 (d, J=8.5 Hz, 1H), 7.59 (dd, J=1.2 Hz, 8.1 Hz, 1H), 7.53 (ddd, J=1.5 Hz, 6.9 Hz, 8.5 Hz, 1H), 7.23 (ddd, J=1.2 Hz, 6.9 Hz, 8.1 Hz, 1H), 6.98 (d, J=9.2 Hz, 1H), 4.97 (s, 2H), 3.79~3.74 (m, 4H), 2.98~2.90 (m, 3H), 2.82~2.32 (m, 10H), 2.23~2.15 (m, 1H), 1.86~1.62 (m, 5H)

Mass, m/e: 500 (M$^+$), 157 (base)

Example 5

Syntheses of Compounds of the Formula (I) in which X$^1$ Stands for Hydrogen and Y Stands for Nitrogen

Example 5-1

Step 5-1-A: To 14 ml of methanol, 256 mg of sodium was added at room temperature under stirring, then 1.04 g of nitroguanidine was added, followed by 45 minutes' heating under reflux. Successively, 1.70 g of ethyl 2-cyclohexanonecarboxylate was added, followed by 9 hours' heating under reflux. After cooling the reaction mixture, the solvent was distilled off under reduced pressure. Water was added to the residue, and the system was acidified with acetic acid. The precipitate was recovered by filtration and dried to provide 1.76 g (84%) of 2-nitroamino-5,6,7,8-tetrahydro-3H-quinazolin-4-one.

$^1$H-NMR (DMSO-d$_6$) δ: 2.56~2.45 (m, 2H) 2.30~2.19 (m, 2H), 1.74~1.58 (m, 4H)

Mass, m/e: 210 ((M+1)$^+$), 122 (base)

Step 5-1-B: To a solution of 1.52 g of 2-[3-(4-quinolin-2-ylpiperazin-1-yl)propyl]isoindol-1,3-dione in 30 ml of ethanol, another solution of 1.50 g of hydrazine monohydrate in 10 ml of ethanol was added, and heated under reflux for 7 hours. Cooling the reaction mixture, insoluble matter was separated by filtration, and the solvent was distilled off under reduced pressure. The residue was made alkaline with 5N-sodium hydroxide, extracted with chloroform, washed with saturated brine and dried over anhydrous sodium sulfate. Distilling the solvent off under reduced pressure, 0.99 g (96%) of 3-(4-quinolin-2-ylpiperazin-1-yl)propylamine was obtained.

$^1$H-NMR (CDCl$_3$) δ: 7.87 (d, J=8.9 Hz, 1H), 7.69 (d, J=8.5 Hz, 1H), 7.58 (d, J=8.1 Hz, 1H), 7.52 (ddd, J=1.5 Hz, 6.9 Hz, 8.5 Hz, 1H), 7.23 (ddd, J=1.2 Hz, 6.9 Hz, 8.1 Hz, 1H), 6.97 (d, J=8.9 Hz, 1H), 3.75 (t, J=5.4 Hz, 4H), 2.78 (t, J=6.9 Hz, 2H), 2.58 (t, J=5.4 Hz, 4H), 2.46 (t, J=7.3 Hz, 2H), 1.78~1.63 (m, 2H)

Mass, m/e: 270 (M$^+$), 157 (base)

Step 5-1-C: To 3 ml of pyridine, 210 mg of 2-nitroamino-5,6,7,8-tetrahydro-3H-quinazolin-4-one as obtained in above Step 5-1-A and 270 mg of 3-(4-quinolin-2-ylpiperazin-1-yl) propylamine as obtained in above step 5-1-B were added and heated under reflux for 16 hours. Cooling the system, the solvent was distilled off under reduced pressure. The residue was purified on silica gel column chromatography (25% aqueous ammonia:methanol:chloroform=0.5:5:45) to provide 301 mg (72%) of 2-[3-(4-quinolin-2-ylpiperazin-1-yl) propylamino]-5,6,7,8-tetrahydro-3H-quinazolin-4-one.

$^1$H-NMR (CDCl$_3$) δ: 7.87 (d, J=8.9 Hz, 1H), 7.68 (d, J=8.1 Hz, 1H), 7.58 (d, J=7.8 Hz, 1H), 7.52 (t, J=7.0 Hz, 1H), 7.21 (t, J=7.0 Hz, 1H), 6.97 (d, J=9.2 Hz, 1H), 5.73 (br s, 1H), 3.91 (br s, 4H), 3.39 (br s, 2H), 2.62 (t, J=5.0 Hz, 4H), 2.51 (t, J=6.2 Hz, 2H), 2.42 (t, J=6.2 Hz, 2H), 2.37 (t, J=6.2 Hz, 2H), 1.98~1.53 (m, 6H)

Mass, m/e: 418 (M$^+$), 157 (base)

Example 5-2

In the manner similar to Example 5-1, 2-[4-(4-quinolin-2-ylpiperazin-1-yl)butylamino]-5,6,7,8-tetrahydro-3H-quinazolin-4-one was obtained.

$^1$H-NMR (CDCl$_3$) δ: 7.87 (d, J=9.2 Hz, 1H), 7.68 (d, J=8.5 Hz, 1H), 7.58 (d, J=8.1 Hz, 1H), 7.52 (ddd, J=1.5 Hz, 6.9 Hz, 8.5 Hz, 1H), 7.21 (t, J=8.1 Hz, 1H), 6.96 (d, J=9.2 Hz, 1H), 6.05 (br s, 1H), 3.76 (t, J=5.0 Hz, 4H), 3.38 (br s, 2H), 2.58 (t, J=5.0 Hz, 4H), 2.52~2.28 (m, 6H), 1.95~1.51 (m, 8H)

Mass, m/e: 432 (M$^+$), 157 (base)

Example 5-3

In the manner similar to Example 5-1, 2-[3-[4-(4-methylquinolin-2-yl)piperazin-1-yl]propylamino]-5,6,7,8-tetrahydro-3H-quinazolin-4-one was obtained.

$^1$H-NMR (CDCl$_3$) δ: 7.77 (d, J=8.5 Hz, 1H), 7.69 (d, J=7.7 Hz, 1H), 7.52 (ddd, J=1.5 Hz, 6.9 Hz, 8.5 Hz, 1H), 7.24 (t, J=7.7 Hz, 1H), 6.84 (s, 1H), 3.95 (br s, 4H), 3.39 (br s, 2H), 2.62 (t, J=5.0 Hz, 4H), 2.59 (s, 3H), 2.52 (t, J=6.2 Hz, 2H), 2.46~2.36 (m, 4H), 1.87~1.64 (m, 6H)

Mass, m/e: 432 (M$^+$), 171 (base)

Example 5-4

In the manner similar to Example 5-1, 2-[3-[4-(7-methoxyisoquinolin-1-yl)piperazin-1-yl]propylamino]-5,6,7,8-tetrahydro-3H-quinazolin-4-one was obtained.

$^1$H-NMR (CDCl$_3$) δ: 8.04 (d, J=5.8 Hz, 1H), 7.66 (d, J=8.9 Hz, 1H), 7.37 (d, J=2.7 Hz, 1H), 7.27 (dd, J=2.7 Hz, 8.9 Hz, 1H), 7.20 (d, J=5.8 Hz, 1H), 6.00 (br s, 1H), 3.93 (s, 3H), 3.56 (br s, 4H), 3.41 (br s, 2H), 2.77 (br s, 4H), 2.59 (t, J=6.2 Hz, 2H), 2.48~2.41 (m, 2H), 2.40~2.33 (m, 2H), 1.91~1.80 (m, 2H), 1.78~1.63 (m, 4H)

Mass, m/e: 448 (M$^+$), 187 (base)

Example 5-5

In the manner similar to Example 5-1, 2-[3-(4-pyrrolo[1,2-a]quinoxalin-4-ylpiperazin-1-yl)propylamino]-5,6,7,8-tetrahydro-3H-quinazolin-4-one was obtained.

$^1$H-NMR (CDCl$_3$) δ: 7.81 (dd, J=1.2 Hz, 2.7 Hz, 1H), 7.72 (dd, J=1.5 Hz, 8.1 Hz, 1H), 7.65 (dd, J=1.5 Hz, 7.7 Hz, 1H), 7.35~7.23 (m, 2H), 6.80~6.73 (m, 2H), 4.01 (br s, 4H), 3.40 (br s, 2H), 3.69 (t, J=5.0 Hz, 4H), 2.54 (t, J=6.2 Hz, 2H), 2.44 (t, J=5.7 Hz, 2H), 2.39 (t, J=5.7 Hz, 2H), 1.88~1.63 (m, 6H)

Mass, m/e: 457 (M$^+$), 196 (base)

Example 5-6

In the manner similar to Example 5-1, 2-[3-(4-quinolin-2-ylpiperazin-1-yl)propylamino]-3H-quinazolin-4-one was obtained.

$^1$H-NMR (CDCl$_3$) δ: 8.09 (br s, 1H), 7.90 (d, J=9.2 Hz, 1H), 7.71 (d, J=8.5 Hz, 1H), 7.61 (d, J=8.1 Hz, 1H), 7.58~7.51 (m, 2H), 7.38~7.19 (m, 2H), 7.15 (br s, 1H), 6.99 (d, J=9.2 Hz, 1H), 3.92 (t, J=5.0 Hz, 4H), 3.55 (br s, 2H), 2.67 (br s, 4H), 2.60 (t, J=6.2 Hz, 2H), 1.95 (br s, 2H)

Mass, m/e: 414 (M$^+$), 157 (base)

Example 5-7

In the manner similar to Example 5-1, 2-[3-[4-(7-methoxyisoquinolin-1-yl)piperazin-1-yl]propylamino]-3H-quinazolin-4-one was obtained.

¹H-NMR (CDCl₃) δ: 8.13~8.03 (m, 2H), 7.69 (d, J=8.9 Hz, 1H), 7.55 (ddd, J=1.5 Hz, 6.9 Hz, 8.5 Hz, 1H), 7.39 (d, J=2.3 Hz, 1H), 7.35 (d, J=8.1 Hz, 1H), 7.29 (dd, J=2.3 Hz, 8.1 Hz, 1H), 7.27~7.21 (m, 1H), 7.14 (br s, 1H), 3.93 (s, 3H), 3.62~3.53 (m, 6H), 2.83 (br s, 4H), 2.69 (t, J=6.2 Hz, 2H), 2.07~1.94 (m, 2H)

Mass, m/e: 444 (M⁺), 187 (base)

Example 5-8

In the manner similar to Example 5-1, 2-[3-(4-pyrrolo[1,2-a]quinoxalin-4-ylpiperazin-1-yl)propylamino]-3H-quinazolin-4-one was obtained.

¹H-NMR (CDCl₃) δ: 8.09 (br s, 1H), 7.82 (s, 1H), 7.74 (d, J=7.7 Hz, 1H), 7.68 (d, J=7.7 Hz, 1H), 7.56 (ddd, J=1.5 Hz, 6.9 Hz, 8.5 Hz, 1H), 7.38~7.24 (m, 3H), 7.12 (br s, 1H), 6.81~6.73 (m, 2H), 3.99 (br s, 4H), 3.56 (br s, 2H), 2.73 (br s, 4H), 2.62 (t, J=6.2 Hz, 2H), 1.95 (br s, 2H)

Mass, m/e: 453 (M⁺), 196 (base)

Example 6

Syntheses of Compounds of the Formula (I) in which $X^1$ Stands for Amino, Lower Alkylamino, Di-Lower Alkylamino or Lower Alkylideneamino, and Y Stands for Nitrogen

Example 6-1

Step 6-1-A: To a solution 209 mg of potassium 3-amino-3H-quinazolin-4-one-2-thiolate in 5 ml of dimethylformamide, 141 mg of methyl iodide was added, and stirred for 20 minutes at room temperature. Water was added to the solution, followed by extraction with ethyl acetate and drying over anhydrous magnesium sulfate. Distilling the solvent off under reduced pressure, 161 mg (86%) of 3-amino-2-methylthio-3H-quinazolin-4-one was obtained.

Step 6-1-B: A mixture of 131 mg of 3-amino-2-methylthio-3H-quinazolin-4-one as synthesized in above Step 6-1-A and 172 mg 3-(4-quinolin-2-ylpiperazin-1-yl)propylamine was heated at 145° C. under stirring for 5 hours. The reaction mixture was cooled and purified on silica gel column chromatography (methanol:methylene chloride=1:19) to provide 198 mg (73%) of 3-amino-2-[3-(4-quinolin-2-ylpiperazin-1-yl)propylamino]-3H-quinazolin-4-one.

¹H-NMR (CDCl₃) δ: 8.06 (dd, J=1.5 Hz, 8.1 Hz, 1H), 7.90 (d, J=9.2 Hz, 1H), 7.71 (d, J=8.1 Hz, 1H), 7.62~7.51 (m, 3H), 7.50~7.45 (m, 1H), 7.37 (d, J=8.1 Hz, 1H), 7.23 (ddd, J=1.2 Hz, 6.9 Hz, 8.1 Hz, 1H), 7.13 (ddd, J=1.2 Hz, 6.9 Hz, 8.1 Hz, 1H), 6.99 (d, J=9.2 Hz, 1H), 4.51 (s, 2H), 3.81 (t, J=5.0 Hz, 4H), 3.64 (q, J=6.2 Hz, 2H), 2.65 (t, J=5.0 Hz, 4H), 2.60 (t, J=6.2 Hz, 2H), 1.91 (q, J=6.2 Hz, 2H)

Mass, m/e: 429 (M⁺), 157 (base)

Example 6-2

In the manner similar to Example 6-1, 3-amino-2-[3-(4-quinolin-2-ylpiperazin-1-yl)propylamino]-5,6,7,8-tetrahydro-3H-quinazolin-4-one was obtained.

¹H-NMR (CDCl₃) δ: 7.90 (d, J=9.2 Hz, 1H), 7.70 (d, J=8.5 Hz, 1H), 7.60 (dd, J=1.2 Hz, 8.1 Hz, 1H), 7.53 (ddd, J=1.5 Hz, 6.9 Hz, 8.5 Hz, 1H), 7.23 (ddd, J=1.2 Hz, 6.9 Hz, 8.1 Hz, 1H), 6.98 (d, J=9.2 Hz, 1H), 4.42 (br s, 2H), 3.80 (t, J=5.0 Hz, 4H), 3.52 (q, J=6.2 Hz, 2H), 2.63 (t, J=5.0 Hz, 4H), 2.56 (t, J=6.2 Hz, 2H), 2.50~2.40 (m, 4H), 1.89~1.80 (m, 2H), 1.78~1.66 (m, 4H)

Mass, m/e: 433 (M⁺), 157 (base)

Example 6-3

In the manner similar to Example 6-1, 3-amino-2-[3-(4-quinolin-2-ylpiperazin-1-yl)propylamino]-5,6,7,8-tetrahydro-3H-benzo[4,5]thieno[2,3-d]pyrimidin-4-one was obtained.

¹H-NMR (CDCl₃) δ: 7.90 (d, J=9.2 Hz, 1H), 7.70 (d, J=8.5 Hz, 1H), 7.60 (d, J=7.7 Hz, 1H), 7.54 (ddd, J=1.2 Hz, 6.9 Hz, 8.1 Hz, 1H), 7.46~7.41 (m, 1H), 7.23 (ddd, J=1.2 Hz, 6.9 Hz, 8.1 Hz, 1H), 6.99 (d, J=9.2 Hz, 1H), 4.41 (s, 2H), 3.81 (t, J=5.0 Hz, 4H), 3.57 (q, J=5.8 Hz, 2H), 2.93~2.88 (m, 2H), 2.69~2.55 (m, 8H), 1.92~1.76 (m, 6H)

Mass, m/e: 489 (M⁺), 157 (base)

Example 7-1

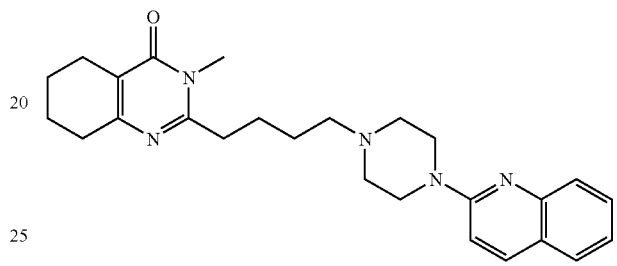

Step 7-1-A: Synthesis of 2-piperazin-1-ylquinoline

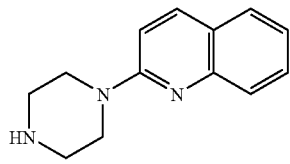

To a solution formed by dissolving 4.31 g of anhydrous piperazine in 30 ml of ethylene glycol, 818 mg of 2-chloroquinoline was added, and stirred at 140° C. for 2 hours. After cooling the reaction mixture, saturated aqueous sodium hydrogencarbonate solution was added, followed by extraction with chloroform. The organic layer was dried over anhydrous magnesium sulfate, and concentrated under reduced pressure. The residue was purified on silica gel column chromatography (chloroform:methanol=2:1) to provide 1.09 g (100%) of 2-piperazin-1-ylquinoline.

¹H-NMR (CDCl₃) δ: 7.89 (d, J=9.2 Hz, 1H), 7.70 (d, J=8.4 Hz, 1H), 7.59 (dd, J=1.5 Hz, 8.0 Hz, 1H), 7.53 (ddd, J=1.5 Hz, 7.0 Hz, 8.4 Hz, 1H), 7.26~7.22 (m, 1H), 6.97 (d, J=9.2 Hz, 1H), 3.70 (t, J=5.0 Hz, 4H), 3.01 (t, J=5.0 Hz, 4H)

Mass, m/e: 213 (M⁺), 145 (base)

Step 7-1-B: Synthesis of 2-aminocyclohex-1-enecarboxylic acid ethyl ester

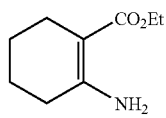

To 7N-ammonia-methanol solution, 170 g of ethyl 2-oxo-cyclohexanecarboxylate was added and stirred for an overnight at room temperature. Concentrating the solvent under reduced pressure, crude crystals were obtained, which were recrystallized from ethyl acetate-n-hexane to provide 152 g (90%) of 2-aminocyclohex-1-enecarboxylic acid ethyl ester.

¹H-NMR (CDCl₃) δ: 4.14 (q, J=7.3 Hz, 2H), 2.25 (d, J=5.9 Hz, 2H), 2.20 (d, J=5.9 Hz, 2H), 1.67~1.56 (m, 4H)

Mass, m/e: 169 (M⁺), 96 (base)

Step 7-1-C: Synthesis of 2-(5-bromopentanoylamino)cyclohex-1-enecarboxylic acid ethyl ester

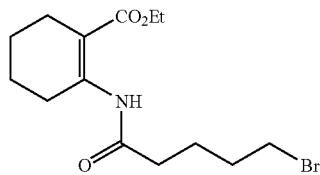

In 150 ml of tetrahydrofuran, 42.3 g of ethyl 2-aminocyclohex-1-enecarboxylate as synthesized in above Step 7-1-B was dissolved, to which 40 g of pyridine was added, and then 5-bromovaleryl chloride was dropped thereinto under cooling with ice. Stirring the system for an overnight at room temperature, ethyl acetate was added, followed by washing with saturated aqueous sodium hydrogencarbonate solution, 10% aqueous citric acid and saturated brine, and drying over anhydrous magnesium sulfate. Concentrating the solvent under reduced pressure, the residue was purified on silica gel column chromatography (n-hexane:ethyl acetate=8:1) to provide 76.6 g (92%) of 2-(5-bromopentanoylamino)-cyclohex-1-enecarboxylic acid ethyl ester.

¹H-NMR (CDCl₃) δ: 11.62 (br s, 1H), 4.22~4.09 (m, 2H), 3.42 (t, J=6.9 Hz, 2H), 2.97~2.94 (m, 2H), 2.34 (t, J=7.0 Hz, 2H), 2.32~2.23 (m, 2H), 1.94~1.88 (m, 2H), 1.85~1.79 (m, 2H), 1.65~1.56 (m, 4H), 1.30 (t, J=7.0 Hz, 3H)

Mass, m/e: 333 (M⁺), 55 (base)

Step 7-1-D: Synthesis of 2-[5-(4-quinolin-2-ylpiperazin-1-yl)pentanoylamino]cyclohex-1-enecarboxylic acid ethyl ester

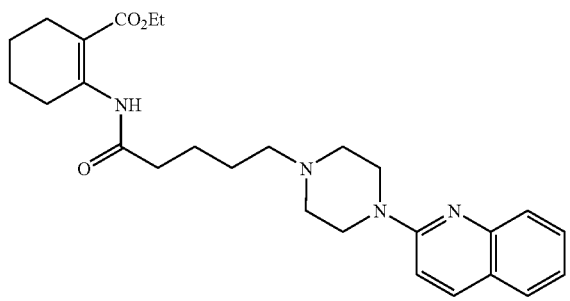

A mixture of 66.5 g of 2-(5-bromopentanoylamino)cyclohex-1-enecarboxylic acid ethyl ester as synthesized in above Step 7-1-C, 46.9 g of 2-piperazin-1-ylquinoline as synthesized in above Step 7-1-A, 22.3 g of triethylamine and 350 ml of toluene was heated under reflux for an overnight. The solvent was concentrated under reduced pressure, and ethyl acetate was added to the residue, followed by washing with saturated aqueous sodium hydrogencarbonate solution. The organic layer was dried over anhydrous magnesium sulfate and the solvent was concentrated under reduced pressure. The residue was purified on silica gel column chromatography (n-hexane:ethyl acetate:methanol=1:6:0.2) to provide 79.8 g (86%) of 2-[5-(4-quinolin-2-ylpiperazin-1-yl)pentanoylamino]cyclohex-1-enecarboxylic acid ethyl ester.

¹H-NMR (CDCl₃) δ: 11.61 (br s, 1H), 7.87 (d, J=9.2 Hz, 1H), 7.69 (d, J=8.5 Hz, 1H), 7.58~7.56 (m, 1H), 7.51 (ddd, J=1.5 Hz, 6.9 Hz, 8.5 Hz, 1H), 7.20 (ddd, J=1.2 Hz, 6.9 Hz, 8.1 Hz, 1H), 6.97 (d, J=9.2 Hz, 1H), 4.16 (q, J=6.9 Hz, 2H), 3.74 (t, J=5.0 Hz, 4H), 2.97 (t, J=5.0 Hz, 2H), 2.56 (t, J=5.0 Hz, 4H), 2.43~2.90 (m, 6H), 1.74~1.70 (m, 2H), 1.68 (m, 4H), 1.28 (t, J=6.9 Hz, 2H)

Mass, m/e: 464 (M⁺), 157 (base)

Step 7-1-E: Synthesis of 2-[5-(4-quinolin-2-ylpiperazin-1-yl)-pentanoylamino]cyclohex-1-enecarboxylic acid

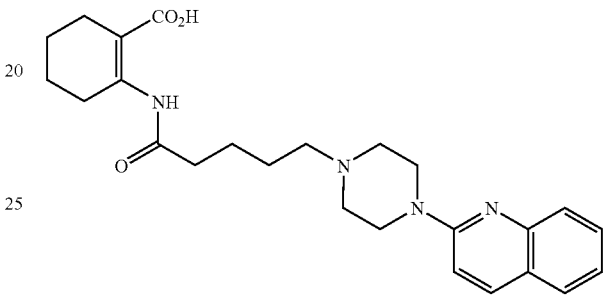

In 725 ml of 2-propanol and 365 ml of distilled water, 168.0 g of ethyl 2-[5-(4-quinolin-2-ylpiperazin-1-yl)pentanoylamino]cyclohex-1-enecarboxylate as synthesized in above Step 7-1-D was suspended. To the suspension 580 ml of 1N-aqueous sodium hydroxide was added and heated under reflux for 1.5 hours. After cooling, the reaction mixture was neutralized with 2N-hydrochloric acid. Whereupon precipitated crystals were recovered by filtration and dried to provide 131.8 g (83.4%) of 2-[5-(4-quinolin-2-ylpiperazin-1-yl)pentanoylamino]cyclohex-1-enecarboxylic acid.

¹H-NMR (CDCl₃) δ: 12.29 (br s, 1H), 7.92 (d, J=9.2 Hz, 1H), 7.70 (d, J=8.5 Hz, 1H), 7.61 (d, J=8.1 Hz, 1H), 7.57~7.53 (m, 1H), 7.18~7.15 (m, 1H), 6.96 (d, J=8.9 Hz, 1H), 3.89 (br s, 4H), 2.92~2.91 (m, 6H), 2.72~2.69 (m, 2H), 2.37~2.35 (m, 2H), 2.32~2.31 (m, 2H), 1.73~1.67 (m, 4H), 1.61~1.55 (m, 4H)

Mass, m/e: 418 (M⁺−18), 392 (M⁺−44), 157 (base)

Step 7-1-F: Synthesis of 3-methyl-2-[4-(4-quinolin-2-ylpiperazin-1-yl)-butyl]-5,6,7,8-tetrahydro-3H-quinazolin-4-one

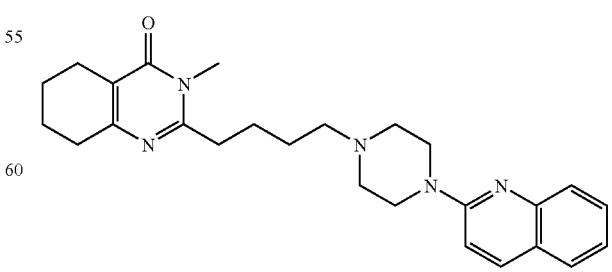

In 30 ml of tetrahydrofuran, 10.0 g of 2-[5-(4-quinolin-2-ylpiperazin-1-yl)-pentanoylamino]cyclohex-1-enecarboxylic acid as synthesized in above Step 7-1-E was suspended, and to the suspension, 7.0 g of 3 equivalent of acetic anhydride was added, followed by an hour's heating under reflux. The solution was cooled with ice, and while continuing the cooling, 35.6 ml of excessive 40% methylamine-methanol solution was gradually added. After about 10 minutes' refluxing under stirring, the temperature was cooled to room temperature and the solution was concentrated under reduced pressure. After addition of 80 ml of distilled water and 30 minutes' stirring, precipitated crystals were recovered by filtration and dried to provide 8.83 g (89.3%) of 3-methyl-2-[4-(4-quinolin-2-ylpiperazin-1-yl)butyl]-5,6,7,8-tetrahydro-3H-quinazolin-4-one.

$^1$H-NMR (CDCl$_3$) δ: 7.88 (d, J=9.1 Hz, 1H), 7.69 (d, J=8.5 Hz, 1H), 7.58 (d, J=8.1 Hz, 1H), 7.52 (dd, J=8.5 Hz, J=1.5 Hz, 1H), 7.23~7.20 (m, 1H), 6.97 (d, J=9.2 Hz, 1H), 3.75 (br s, 4H), 3.53 (s, 3H), 2.74 (t, J=7.7 Hz, 2H), 2.57~2.54 (m, 6H), 2.50~2.43 (m, 4H), 1.83~1.66 (m, 8H)

Mass, m/e: 431 (M$^+$), 157 (base)

Example 7-2

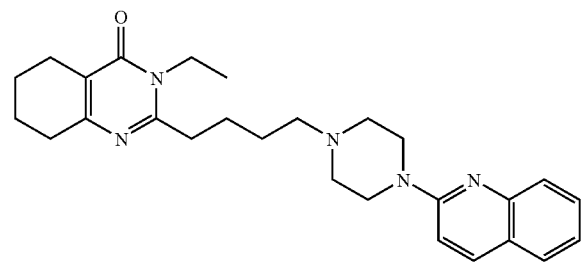

In the manner similar to Example 7-1, 3-2-[4-(4-quinolin-2-ylpiperazin-1-yl)butyl]-5,6,7,8-tetrahydro-3H-quinazolin-4-one was synthesized.

$^1$H-NMR (CDCl$_3$) δ: 7.88 (d, J=8.9 Hz, 1H), 7.69 (d, J=8.5 Hz, 1H), 7.58 (d, J=8.1 Hz, 1H), 7.54~7.50 (m, 1H), 7.23~7.19 (m, 1H), 6.97 (d, J=9.2 Hz, 1H), 4.11~4.06 (m, 2H), 3.75 (t, J=5.0 Hz, 4H), 2.76~2.72 (m, 2H), 2.58~2.53 (m, 6H), 2.49~2.43 (m, 4H), 1.83~1.65 (m, 8H), 1.33~1.30 (m, 3H)

Mass, m/e: 445 (M$^+$), 157 (base)

Example 7-3

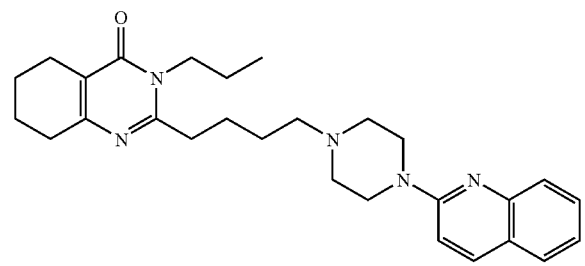

In the manner similar to Example 7-1, 3-propyl-2-[4-(4-quinolin-2-ylpiperazin-1-yl)butyl]-5,6,7,8-tetrahydro-3H-quinazolin-4-one was synthesized.

$^1$H-NMR (CDCl$_3$) δ: 7.89 (d, J=9.2 Hz, 1H), 7.70 (d, J=8.1 Hz, 1H), 7.59 (dd, J=1.2 Hz, 7.7 Hz, 1H), 7.53 (ddd, J=1.5 Hz, 6.9 Hz, 8.5 Hz, 1H), 7.22 (ddd, J=1.2 Hz, 6.9 Hz, 8.2 Hz, 1H), 6.98 (d, J=9.2 Hz, 1H), 3.95 (t, J=7.7 Hz, 2H), 3.76 (t, J=4.6 Hz, 4H), 2.74 (t, J=7.7 Hz, 2H), 2.59 (t, J=4.6 Hz, 4H), 2.56~2.53 (m, 2H), 2.51~2.42 (m, 4H), 1.86~1.58 (m, 11H)

Mass, m/e: 459 (M$^+$), 157 (base)

Example 7-4

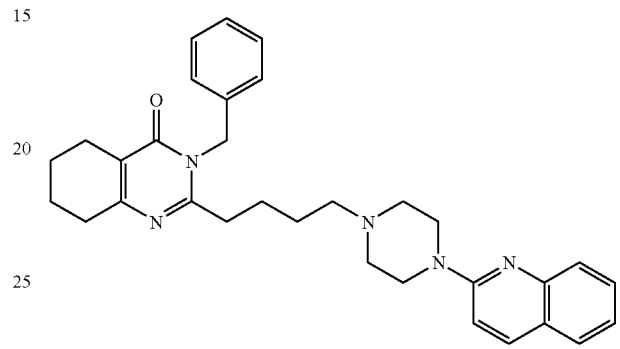

In the manner similar to Example 7-1, 3-benzyl-2-[4-(4-quinolin-2-ylpiperazin-1-yl)butyl]-5,6,7,8-tetrahydro-3H-quinazolin-4-one was synthesized.

$^1$H-NMR (CDCl$_3$) δ: 7.23~7.20 (m, 1H), 6.97 (d, J=9.2 Hz, 1H), 7.87 (d, J=8.9 Hz, 1H), 7.69 (d, J=8.9 Hz, 1H), 7.58 (dd, J=8.1 Hz, 1.2 Hz, 1H), 7.57~7.50 (m, 1H), 7.33~7.27 (m, 3H), 7.23~7.19 (m, 1H), 7.15 (d, J=6.9 Hz, 2H), 6.96 (d, J=8.9 Hz, 1H), 5.31 (s, 2H), 3.73~3.71 (m, 4H), 2.60~2.54 (m, 2H), 2.52~2.50 (m, 6H), 2.33 (t, J=7.3 Hz, 2H), 1.82~1.66 (m, 6H), 1.56~1.52 (m, 4H)

Mass, m/e: 507 (M$^+$), 157 (base)

Example 7-5

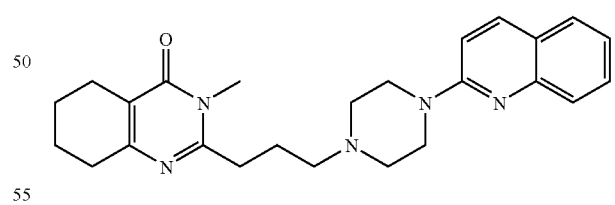

In the manner similar to Example 7-1, 3-methyl-2-[3-(4-quinolin-2-ylpiperazin-1-yl)propyl]-5,6,7,8-tetrahydro-3H-quinazolin-4-one was synthesized.

$^1$H-NMR (CDCl$_3$) δ: 7.88 (d, J=8.9 Hz, 1H), 7.69 (d, J=8.5 Hz, 1H), 7.59 (dd, J=1.1 Hz, 8.1 Hz, 1H), 7.52 (ddd, J=1.5 Hz, 6.9 Hz, 6.9 Hz, 1H), 7.22 (ddd, J=1.1 Hz, 6.9 Hz, 6.9 Hz, 1H), 6.96 (d, J=9.1 Hz, 1H), 3.75~3.70 (m, 4H), 3.55 (s, 3H), 2.77 (t, J=8.0 Hz, 2H), 2.62~2.56 (m, 10H), 1.99 (q, J=7.3 Hz, 2H), 1.81~1.68 (m, 4H)

Mass, m/e: 417 ((M+), 240, 178, 157 (base)

Example 7-6

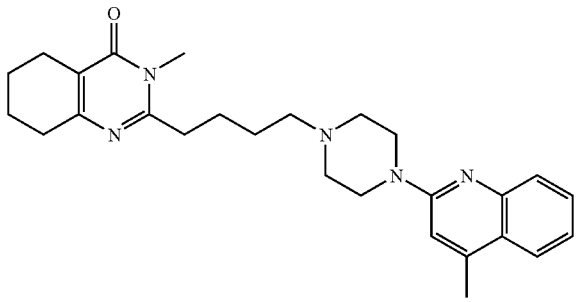

In the manner similar to Example 7-1, 3-methyl-2-[4-[4-(4-methylquinolin-2-yl)piperazin-1-yl]butyl]-5,6,7,8-tetrahydro-3H-quinazolin-4-one was synthesized.

$^1$H-NMR (CDCl$_3$) δ: 7.76 (dd, J=8.1 Hz, 1.2 Hz, 1H), 7.69 (d, J=8.5 Hz, 1H), 7.54~7.50 (m, 1H), 7.25~7.22 (m, 1H), 6.83 (s, 1H), 3.75 (t, J=5.0 Hz, 4H), 3.53 (s, 3H), 2.74 (t, J=8.1 Hz, 2H), 2.59~2.54 (m, 9H), 2.50~2.43 (m, 4H), 1.81~1.68 (m, 8H)

Mass, m/e: 445 (M$^+$), 171 (base)

Example 7-7

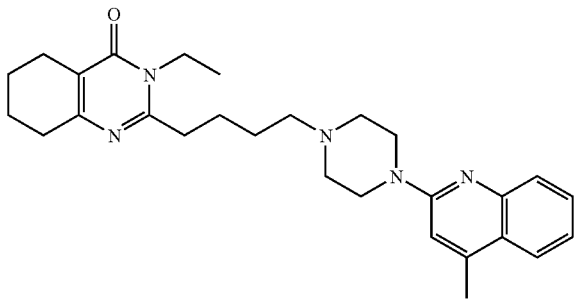

In the manner similar to Example 7-1, 3-ethyl-2-[4-[4-(4-methylquinolin-2-yl)piperazin-1-yl]butyl]-5,6,7,8-tetrahydro-3H-quinazolin-4-one was synthesized.

$^1$H-NMR (CDCl$_3$) δ: 7.76 (d, J=6.9 Hz, 1H), 7.69 (d, J=8.5 Hz, 1H), 7.54~7.50 (m, 1H), 7.26~7.22 (m, 1H), 6.83 (s, 1H), 4.12~4.05 (m, 2H), 3.77~3.74 (m, 4H), 2.74 (t, J=7.7 Hz, 2H), 2.62~2.59 (m, 4H), 2.59 (s, 3H), 2.56~2.53 (m, 2H), 2.49~2.45 (m, 4H), 1.83~1.67 (m, 8H), 1.33~1.29 (m, 3H)

Mass, m/e: 459 (M$^+$), 171 (base)

Example 7-8

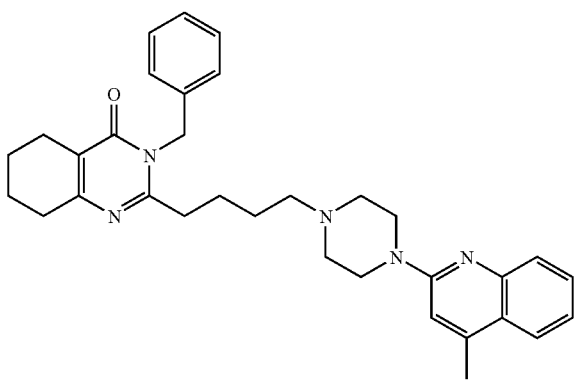

In the manner similar to Example 7-1, 3-benzyl-2-[4-[4-(4-methylquinolin-2-yl)piperazin-1-yl]butyl]-5,6,7,8-tetrahydro-3H-quinazolin-4-one was synthesized.

$^1$H-NMR (CDCl$_3$) δ: 7.76 (dd, J=8.1 Hz, J=1.2 Hz, 1H), 7.79 (d, J=7.7 Hz, 1H), 7.54~7.49 (m, 1H), 7.33~7.21 (m, 4H), 7.16 (s, 1H), 7.15 (s, 1H), 6.81 (s, 1H), 5.31 (s, 2H), 3.72~3.70 (m, 4H), 2.67~2.64 (m, 2H), 2.60~2.52 (m, 2H), 2.59 (s, 3H), 2.50 (t, J=5.0 Hz, 4H), 2.34~2.30 (m, 2H), 2.04~1.73 (m, 4H), 1.71~1.65 (m, 2H), 1.58~1.50 (m, 2H)

Mass, m/e: 521 (M$^+$), 171 (base)

Example 7-9

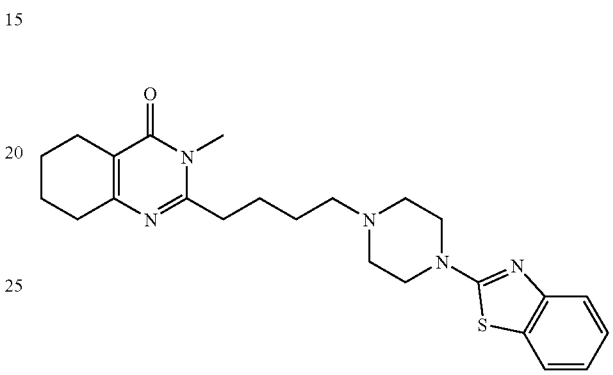

In the manner similar to Example 7-1, 2-[4-(4-benzothiazol-2-ylpiperazin-1-yl)butyl]-3-methyl-5,6,7,8-tetrahydro-3H-quinazolin-4-one was synthesized.

$^1$H-NMR (CDCl$_3$) δ:7.59 (d, J=7.3 Hz, 1H), 7.54 (d, J=8.1 Hz, 1H), 7.31~7.27 (m, 1H), 7.09~7.05 (m, 1H), 3.65~3.63 (m, 4H), 3.52 (s, 3H), 2.75~2.71 (m, 2H), 2.58~2.54 (m, 6H), 2.50~2.43 (m, 4H), 1.81~1.63 (m, 8H)

Mass, m/e: 437 (M$^+$), 96 (base)

Example 7-10

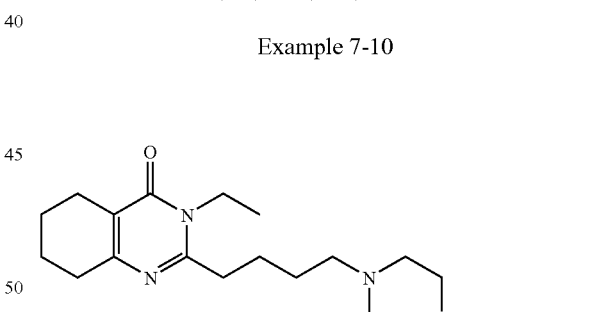

In the manner similar to Example 7~1, 2-[4-(4-benzothiazol-2-ylpiperazin-1-yl)butyl]-3-ethyl-5,6,7,8-tetrahydro-3H-quinazolin-4-one was synthesized.

$^1$H-NMR (CDCl$_3$) δ: 7.61~7.54 (m, 2H), 7.32~7.28 (m, 1H), 7.10~7.06 (m, 1H), 3.66~3.63 (m, 4H), 3.31~3.24 (m, 2H), 2.73~2.71 (m, 2H), 2.59 (t, J=5.0 Hz, 4H), 2.54~2.53 (m, 2H), 2.47~2.44 (m, 4H), 1.85~1.65 (m, 8H), 1.12 (t, J=7.3 Hz, 3H)

Mass, m/e: 451 (M$^+$), 96 (base)

Example 7-11

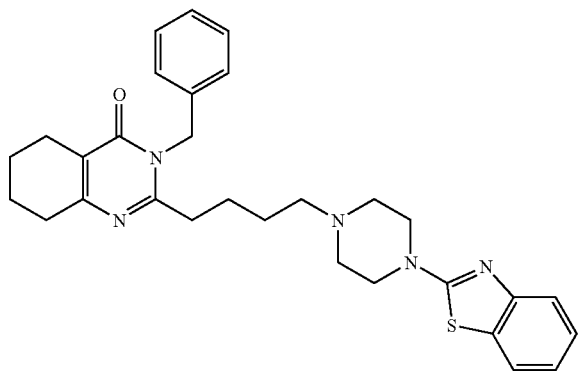

In the manner similar to Example 7-1, 2-[4-(4-benzothiazol-2-ylpiperazin-1-yl)butyl]-3-benzyl-5,6,7,8-tetrahydro-3H-quinazolin-4-one was synthesized.

$^1$H-NMR (CDCl$_3$) δ: 7.59 (d, J=6.9 Hz, 1H), 7.54 (d, 7.3 Hz, 1H), 7.33~7.27 (m, 6H), 7.09~7.05 (m, 1H), 4.43 (d, J=5.8 Hz, 2H), 3.61~3.59 (m, 4H), 2.65 (t, J=7.7 Hz, 2H), 2.58 (t, J=5.8 Hz, 2H), 2.55~2.52 (m, 2H), 2.51~2.48 (m, 4H), 2.32 (t, J=7.3 Hz, 2H), 1.81~1.64 (m, 6H), 1.55~1.49 (m, 2H)

Mass, m/e: 513 (M$^+$), 91 (base)

Example 7-12

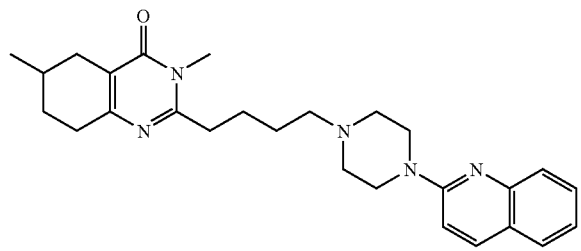

Using 5-methyl-2-oxo-cyclohexanecarboxlic acid ethyl ester (a compound disclosed in J. Am. Chem. Soc., 85, 207-222 (1963)) as the starting material, 3,6-dimethyl-2-[4-(4-quinolin-2-ylpiperazin-1-yl)butyl]-5,6,7,8-tetrahydro-3H-quinazolin-4-one was synthesized in the manner similar to Example 7-1.

$^1$H-NMR (CDCl$_3$) δ: 7.88 (d, J=8.9 Hz, 1H), 7.69 (d, J=8.5 Hz, 1H), 7.58 (d, J=7.7 Hz, 1H), 7.54~7.50 (m, 1H), 7.23~7.19 (m, 1H), 6.97 (d, J=9.2 Hz, 1H), 3.75 (t, J=5.0 Hz, 4H), 3.53 (s, 3H), 2.74~2.68 (m, 3H), 2.60~2.56 (m, 7H), 2.45 (t, J=7.3 Hz, 2H), 2.03~1.96 (m, 1H), 1.88~1.76 (m, 3H), 1.71~1.65 (m, 2H), 1.40~1.34 (m, 1H), 1.06 (d, J=6.6 Hz, 3H)

Mass, m/e: 445 (M$^+$), 157 (base)

Example 7-13

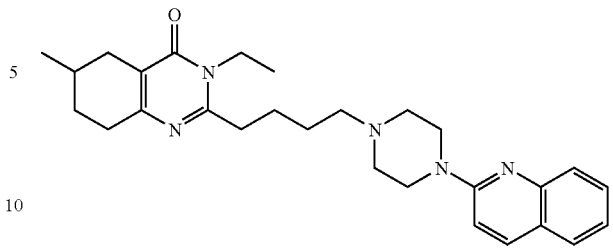

In the manner similar to Example 7-12, 3-ethyl-6-methyl-2-[4-(4-quinolin-2-ylpiperazin-1-yl)butyl]-5,6,7,8-tetrahydro-3H-quinazolin-4-one was synthesized.

$^1$H-NMR (CDCl$_3$) δ: 7.88 (d, J=9.0 Hz, 1H), 7.69 (d, J=8.5 Hz, 1H), 7.58 (dd, J=7.7 Hz, 1.2 Hz, 1H), 7.52 (ddd, J=8.5 Hz, 6.9 Hz, 1.5 Hz, 1H), 7.21 (ddd, J=8.1 Hz, 6.9 Hz, 1.2 Hz, 1H), 6.97 (d, J=9.2 Hz, 1H), 4.08 (q, J=7.3 Hz, 2H), 3.75 (t, J=5.0 Hz, 4H), 2.76~2.67 (m, 3H), 2.60~2.56 (m, 7H), 2.44 (t, J=7.3 Hz, 2H), 1.99 (dd, J=17.3 Hz, 10.0 Hz, 1H), 1.87~1.72 (m, 3H), 1.71~1.65 (m, 2H), 1.39~1.35 (m, 1H), 1.31 (t, J=6.9 Hz, 3H), 1.06 (d, J=6.7 Hz, 3H)

Mass, m/e: 459 (M$^+$), 157 (base)

Example 7-14

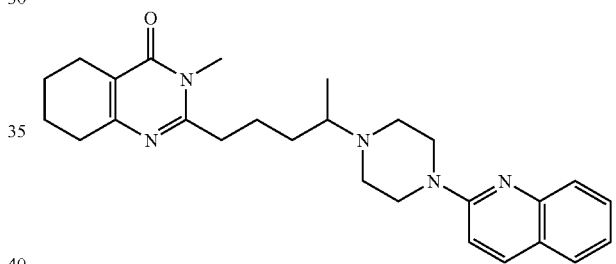

Step 7-14-A: Synthesis of 5-oxo-hexanoic acid methyl ester

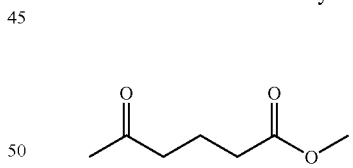

To a mixture of 30 ml of 4N aqueous sodium hydroxide and 30 ml of diethyl ether, 2.06 g of N-methyl-N-nitrosourea was added consuming 20 minutes under cooling with ice, followed by 20 minutes' stirring. The diethyl ether layer was separated, into which 1.30 g of 5-oxo-hexanoic acid was added and stirred at room temperature for 2 hours. The solution was washed with saturated aqueous sodium hydrogencarbonate solution, dried over anhydrous magnesium sulfate and the solvent was concentrated under reduced pressure. The residue was purified on silica gel column chromatography (ethyl acetate: n-hexane=1:3) to provide 1.15 g (80%) of 5-oxo-hexanoic acid methyl ester.

$^1$H-NMR (CDCl$_3$) δ: 3.66 (s, 3H), 2.49 (t, J=7.3 Hz, 2H), 2.33 (t, J=7.3 Hz, 2H), 2.13 (s, 3H), 1.89~1.84 (m, 2H)

Mass, m/e: 145, 59 (base)

Step 7-14-B: Synthesis of methyl 5-(4-quinolin-2-piperazin-1-yl)hexanoate

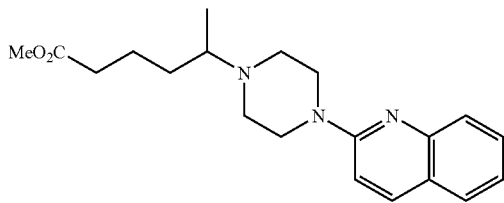

A mixture of 1.10 g of methyl 5-oxo-hexanoate as synthesized in above step 7-14-A, 1.36 g of 2-piperazin-1-ylquinoline, 20 mg of p-toluenesulfonic acid and 50 ml of toluene was heated under reflux for 16 hours, and the formed water was azeotropically removed. The solvent was concentrated under reduced pressure. The residue was dissolved in 50 ml of tetrahydrofuran, and the solution was stirred at room temperature for an hour while hydrogen chloride gas was introduced thereinto. Then 380 mg of sodium cyanotrihydroborate as dissolved in 10 ml of methanol was added, followed by 2 hours' stirring. To the solution, 0.1N aqueous potassium hydroxide was added, followed by extraction with ethyl acetate. The organic layer was dried over anhydrous magnesium sulfate and the solvent was concentrated under reduced pressure. The residue was purified on silica gel column chromatography (ethyl acetate:n-hexane=1:1) to provide 977 mg (45%) of methyl 5-(4-quinoline-2-ylpiperazin-1-yl)hexanoate.

$^1$H-NMR (CDCl$_3$) δ: 7.86 (d, J=9.3 Hz, 1H), 7.68 (d, J=8.1 Hz, 1H), 7.57 (d, J=8.1 Hz, 1H), 7.51 (ddd, J=1.5 Hz, 6.9 Hz, 8.5 Hz, 1H), 7.20 (ddd, J=1.5 Hz, 6.9 Hz, 8.1 Hz, 1H), 6.96 (d, J=8.9 Hz, 1H), 3.74~3.71 (m, 4H), 3.67 (s, 3H), 2.70~2.62 (m, 3H), 2.60~2.55 (m, 2H), 2.34 (t, J=7.3 Hz, 2H), 1.75~1.64 (m, 4H), 1.00 (d, J=6.6 Hz, 3H)

Mass, m/e: 341 (M$^+$), 157 (base)

Step 7-14-C: Synthesis of 5-(4-quinoline-2-ylpiperazin-1-yl)hexanoic acid

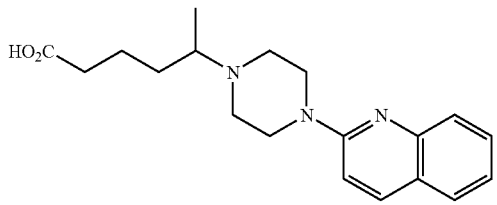

To 10 ml of 1N sodium hydroxide:ethanol=1:1 solution, 850 mg of methyl 5-(4-quinolin-2-ylpiperazin-1-yl)hexanoate as synthesized in above Step 7-14-B was added and heated under reflux for an hour. Cooling the system, 2N hydrochloric acid was added to make the pH7, and the precipitate was recovered by filtration and dried to provide 728 mg (89%) of 5-(4-quinoline-2-ylpiperazin-1-yl)hexanoic acid.

$^1$H-NMR (CDCl$_3$) δ: 7.91 (d, J=9.3 Hz, 1H), 7.70 (d, J=8.5 Hz, 1H), 7.60 (d, J=8.1 Hz, 1H), 7.54 (ddd, J=1.5 Hz, 6.9 Hz, 8.5 Hz, 1H), 7.27~7.23 (m, 1H), 6.95 (d, J=9.2 Hz, 1H), 4.05~3.95 (m, 4H), 3.06~3.00 (m, 3H), 2.98~2.94 (m, 2H), 2.34 (t, J=7.3 Hz, 2H), 1.98~1.93 (m, 1H), 1.75~1.64 (m, 2H), 1.54~1.49 (m, 1H), 1.16 (d, J=6.9 Hz, 3H)

Mass, m/e: 327 (M$^+$), 157 (base)

Step 7-14-D: Synthesis of ethyl 2-[5-(4-quinolin-2-ylpiperazin-1-yl)hexanoylamino]cyclohex-1-enecarboxylate

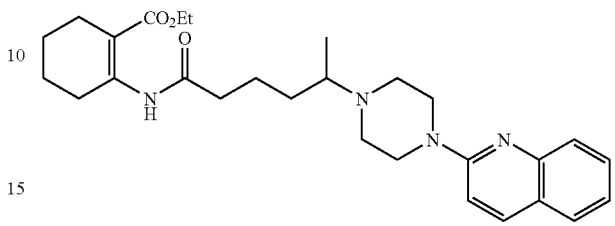

To a solution of 170 mg of ethyl 2-aminocyclohex-1-enecarboxylate as synthesized in Step 7-1-B in 5 ml of pyridine, 70 mg of phosphorus trichloride was added under cooling with ice, followed by 15 minutes' stirring. Raising the temperature to room temperature, 327 mg of 5-(4-quinoline-2-ylpiperazin-1-yl)hexanoic acid as synthesized in above Step 7-14-C was added to the solution and stirred for 3 hours. Distilling the pyridine off under reduced pressure, the residue was extracted with ethyl acetate and washed with water. The organic layer was dried over anhydrous magnesium sulfate, and the solvent was concentrated under reduced pressure. The residue was purified on silica gel column chromatography (ethyl acetate) to provide 182 mg (38%) of ethyl 2-[5-(4-quinolin-2-ylpiperazin-1-yl)hexanoylamino]cyclohex-1-enecarboxylate.

$^1$H-NMR (CDCl$_3$) δ: 11.61 (br s, 1H), 7.86 (d, J=8.9 Hz, 1H), 7.68 (d, J=8.5 Hz, 1H), 7.57 (d, J=7.7 Hz, 1H), 7.51 (ddd, J=1.2 Hz, 6.9 Hz, 8.1 Hz, 1H), 7.22~7.18 (m, 1H), 6.96 (d, J=9.3 Hz, 1H), 4.14 (q, J=6.9 Hz, 2H), 3.80~3.70 (m, 4H), 2.98~2.95 (m, 2H), 2.75~2.65 (m, 3H), 2.64~2.56 (m, 2H), 2.34 (t, J=7.3 Hz, 2H), 2.31~2.28 (m, 2H), 1.81~1.70 (m, 2H), 1.69~1.56 (m, 6H), 1.26 (t, J=6.9 Hz, 3H), 1.01 (d, J=6.6 Hz, 3H)

Mass, m/e: 478 (M$^+$), 157 (base)

Step 7-14-E: Synthesis of 2-[5-(4-quinolin-2-ylpiperazin-1-yl)hexanoylamino]-cyclohex-1-enecarboxylic acid

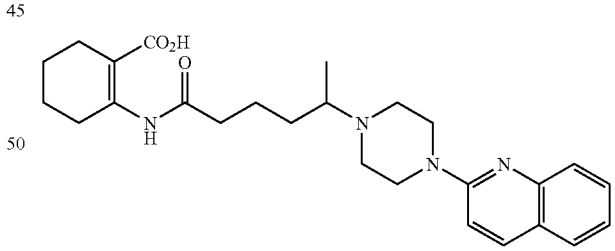

From ethyl 2-[5-(4-quinolin-2-ylpiperazin-1-yl)hexanoylamino]-cyclohex-1-enecarboxylate as synthesized in Step 7-14-D, 2-[5-(4-quinolin-2-ylpiperazin-1-yl)hexanoylamino]-cyclohex-1-enecarboxylic acid was synthesized in the manner similar to Step 7-1-E.

$^1$H-NMR (CDCl$_3$) δ: 12.32 (br s, 1H), 7.91 (d, J=9.3 Hz, 1H), 7.70 (d, J=8.5 Hz, 1H), 7.61 (d, J=8.1 Hz, 1H), 7.55 (ddd, J=1.5 Hz, 6.9 Hz, 8.5 Hz, 1H), 7.28~7.23 (m, 1H), 6.95 (d, J=8.9 Hz, 1H), 4.05~3.97 (m, 4H), 3.04~2.96 (m, 3H), 2.95~2.90 (m, 2H), 2.43~2.26 (m, 6H), 1.93~1.71 (m, 2H), 1.61~1.41 (m, 6H), 1.19 (d, J=6.9 Hz, 3H)

Mass, m/e: 406, 157 (base)

Step 7-14-F: Synthesis of 3-methyl-2-[4-(4-quinolin-2-ylpiperazin-1-yl)-pentyl]5,6,7,8-tetrahydro-3H-quinazolin-4-one

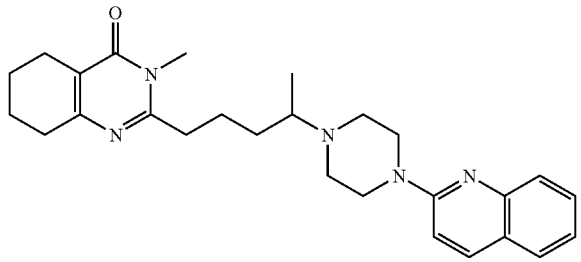

Using the 2-[5-(4-quinolin-2-ylpiperazin-1-yl)hexanoylamino]-cyclohex-1-enecarboxylic acid as synthesized in above Step 7-14-E, 3-methyl-2-[4-(4-quinolin-2-ylpiperazin-1-yl)pentyl]-5,6,7,8-tetrahydro-3H-quinazolin-4-one was synthesized in the manner similar to Step 7-1-F.

$^1$H-NMR (CDCl$_3$) δ: 7.87 (d, J=8.9 Hz, 1H), 7.69 (d, J=8.5 Hz, 1H), 7.58 (d, J=8.1 Hz, 1H), 7.52 (ddd, J=1.5 Hz, 6.9 Hz, 8.5 Hz, 1H), 7.23~7.19 (m, 1H), 6.96 (d, J=9.2 Hz, 1H), 3.77~3.71 (m, 4H), 3.54 (s, 3H), 2.74~2.68 (m, 5H), 2.59~2.54 (m, 4H), 2.50~2.47 (m, 2H), 1.83~1.68 (m, 8H), 1.01 (d, J=6.6 Hz, 3H)

Mass, m/e: 445, 157 (base)

Example 7-15

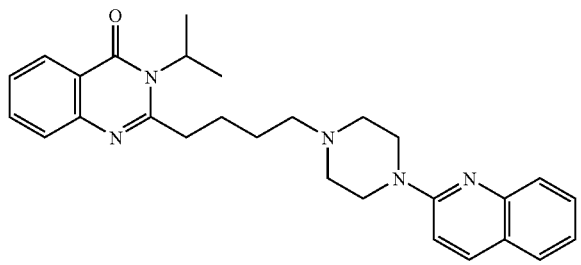

Step 7-15-A: Synthesis of 2-[4-(4-quinolin-2-ylpiperazin-1-yl)-pentanoylamino]benzoic acid

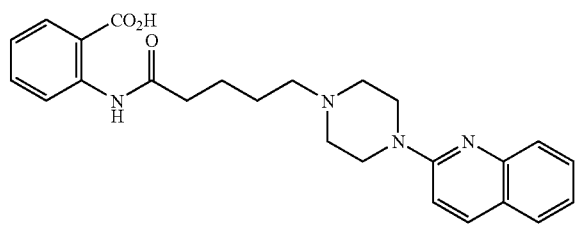

Using ethyl anthranilate as the starting material, 2-[4-(4-quinolin-2-ylpiperazin-1-yl)pentanoylamino]benzoic acid was synthesized in the manner similar to Steps 7-1-C to 7-1-E.

Because the product was difficultly soluble, no $^1$H-NMR was taken.

Mass, m/e: 432 (M$^+$), 414, 157 (base)

Step 7-15-B: Synthesis of 2-[4-(4-quinolin-2-ylpiperazin-1-yl)butyl]-3,1-benzoxazin-4-one

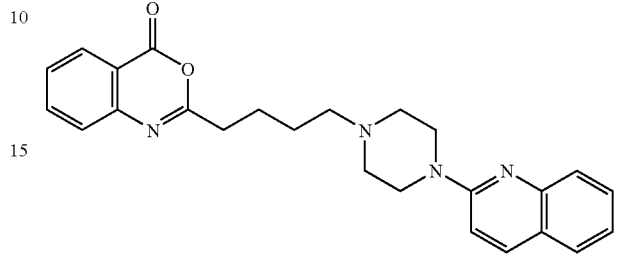

A mixture of 4.32 g of 2-[4-(4-quinolin-2-ylpiperazin-1-yl)-pentanoylamino]benzoic acid as synthesized in above Step 7-15-A and 3.06 g of acetic anhydride was stirred at 80° C. for an hour, and the solvent was distilled off under reduced pressure to provide 4.17 g (100%) of 2-[4-(4-quinolin-2-ylpiperazin-1-yl)butyl]-3,1-benzoxazin-4-one.

$^1$H-NMR (CDCl$_3$) δ: 8.19 (dd, J=1.5 Hz, 8.1 Hz, 1H), 7.87 (d, J=9.3 Hz, 1H), 7.79 (ddd, J=1.5 Hz, 6.9 Hz, 8.5 Hz, 1H), 7.69 (d, J=8.1 Hz, 1H), 7.61~7.54 (m, 2H), 7.55~7.48 (m, 2H), 7.21 (ddd, J=1.2 Hz, 6.9 Hz, 8.1 Hz, 1H), 6.97 (d, J=9.2 Hz, 1H), 3.75 (t, J=5.0 Hz, 4H), 2.74 (t, J=7.7 Hz, 2H), 2.58 (t, J=5.0 Hz, 4H), 2.46 (t, J=7.3 Hz, 2H), 1.90 (q, J=7.7 Hz, 2H), 1.74~1.65 (m, 2H)

Mass, m/e: 414 (M$^+$), 157 (base)

Step, 7-15-C: Synthesis of N-isopropyl-2-[5-(4-quinolin-2-ylpiperazin-1-yl)pentanoylamino]benzamide

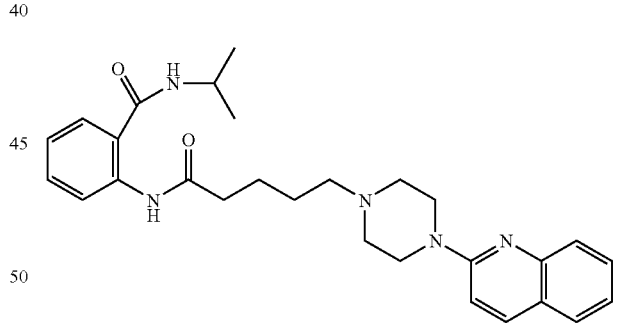

In a glass tube, 414 mg of 2-[4-(4-quinolin-2-ylpiperazin-1-yl)butyl]-3,1-benzoxazin-4-one as synthesized in above Step 7-15-B, 590 mg of isopropylamine and 5 ml of tetrahydrofuran were hermetically sealed and stirred for an hour at the exterior temperature of 80° C. Cooling the reaction mixture, the solvent was distilled off under reduced pressure, and the resulting residue was purified on silica gel column chromatography (dichloromethane:methanol=10:1) to provide 275 mg (58%) of N-isopropyl-2-[5-(4-quinolin-2-ylpiperazin-1-yl)pentanoylamino]benzamide.

$^1$H-NMR (CDCl$_3$) δ: 11.11 (br s, 1H), 8.61 (dd, J=0.8 Hz, 8.5 Hz, 1H), 7.87 (d, J=9.3 Hz, 1H), 7.68 (d, J=8.5 Hz, 1H), 7.58 (dd, J=1.2 Hz, 8.1 Hz, 1H), 7.51 (ddd, J=1.2 Hz, 6.9 Hz, 8.1 Hz, 1H), 7.45 (ddd, J=1.5 Hz, 6.9 Hz, 8.9 Hz, 1H), 7.41

(dd, J=1.5 Hz, 8.1 Hz, 1H), 7.20 (ddd, J=1.2 Hz, 6.9 Hz, 8.1 Hz, 1H), 7.05 (ddd, J=1.2 Hz, 7.3 Hz, 8.5 Hz, 1H), 6.96 (d, J=9.3 Hz, 1H), 5.99~5.97 (m, 1H), 4.26~4.21 (m, 1H), 3.74 (t, J=5.0 Hz, 4H), 2.61~2.57 (m, 4H), 2.45 (t, J=7.3 Hz, 2H), 1.81~1.75 (m, 2H), 1.69~1.59 (m, 2H), 1.26 (d, J=6.6 Hz, 6H)

Mass, m/e: 473 (M+), 157 (base)

Step 7-15-D: Synthesis of 3-isopropyl-2-[4-(4-quinolin-2-ylpiperazin-1-yl)butyl]-3H-quinazolin-4-one

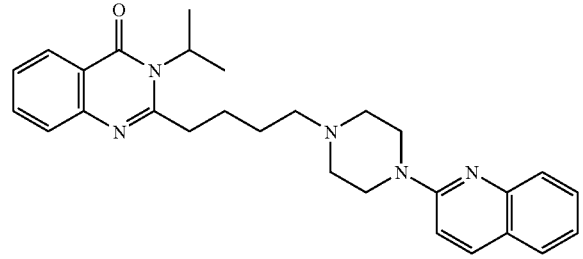

At 250° C., 200 mg of N-isopropyl-2-[5-(4-quinolin-2-ylpiperazin-1-yl)pentanoylamino]benzamide as synthesized in above Step 7-15-C was stirred for an hour. Cooling the system, the residue was purified on silica gel column chromatography (dichloromethane:methanol=15:1) to provide 25 mg (13%) of 3-isopropyl-2-[4-(4-quinolin-2-ylpiperazin-1-yl)butyl]-3H-quinazolin-4-one.

$^1$H-NMR (CDCl$_3$) δ: 8.21 (dd, J=1.2 Hz, 8.1 Hz, 1H), 7.88 (d, J=9.3 Hz, 1H), 7.70~7.66 (m, 2H), 7.64~7.62 (m, 1H), 7.60~7.57 (m, 2H), 7.52 (ddd, J=1.5 Hz, 6.9 Hz, 8.5 Hz, 1H), 7.40 (ddd, J=1.2 Hz, 6.9 Hz, 8.1 Hz, 1H), 7.24~7.19 (m, 1H), 6.97 (d, J=9.3 Hz, 1H), 4.64~4.56 (m, 1H), 3.78~3.74 (m, 4H), 2.90 (t, J=7.7 Hz, 2H), 2.61~2.57 (m, 4H), 2.50 (t, J=7.7 Hz, 2H), 1.93~1.85 (m, 2H), 1.79~1.69 (m, 2H), 1.68 (d, J=6.6 Hz, 6H)

Mass, m/e: 455 (M+), 157 (base)

Example 7-16

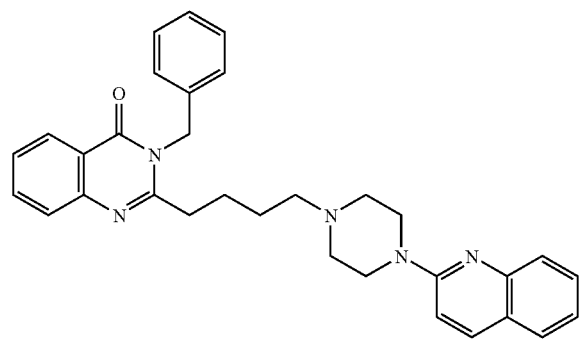

A mixture of 207 mg of 2-[4-(4-quinolin-2-ylpiperazin-1-yl)-butyl]-3,1-benzoxazin-4-one as synthesized in above Step 7-15-B and 150 mg of benzylamine was stirred at 250° C. for an hour. Cooling the solution, the residue was purified on silica gel column chromatography (dichloromethane: methanol=15:1) to provide 163 mg (65%) of 3-benzyl-2-[4-(4-quinolin-2-ylpiperazin-1-yl)butyl]-3H-quinazolin-4-one.

$^1$H-NMR (CDCl$_3$) δ: 8.30 (dd, J=1.2 Hz, 8.1 Hz, 1H), 7.88 (d, J=8.9 Hz, 1H), 7.74 (ddd, J=1.2 Hz, 6.9 Hz, 8.5 Hz, 1H), 7.72~7.57 (m, 2H), 7.53 (dd, J=1.1 Hz, 6.9 Hz, 1H), 7.35~7.16 (m, 7H), 7.46 (ddd, J=1.2 Hz, 6.9 Hz, 8.1 Hz, 1H), 6.96 (d, J=8.9 Hz, 1H), 5.43 (s, 3H), 3.74~3.70 (m, 4H), 2.79 (t, J=7.7 Hz, 2H), 2.54~2.50 (m, 4H), 2.38 (t, J=7.3 Hz, 2H), 1.86~1.79 (m, 2H), 1.63~1.55 (m, 2H)

Mass, m/e: 503 (M+), 157 (base), 91

Example 7-17

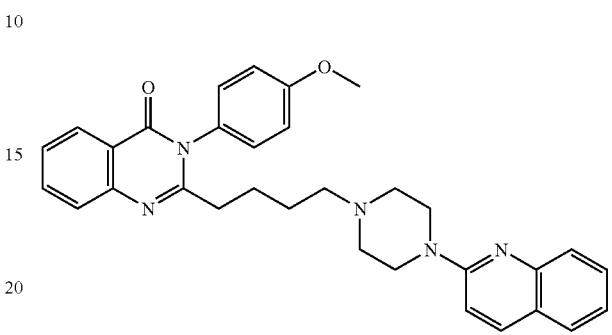

In the manner similar to Example 7-16, 3-(4-methoxyphenyl)-2-[4-(4-quinolin-2-ylpiperazin-1-yl)butyl]-3H-quinazolin-4-one was synthesized.

$^1$H-NMR (CDCl$_3$) δ: 8.26 (dd, J=1.5 Hz, 8.1 Hz, 1H), 7.87 (d, J=9.2 Hz, 1H), 7.78~7.76 (m, 1H), 7.73 (d, J=1.5 Hz, 1H), 7.69 (d, J=8.1 Hz, 1H), 7.58 (d, J=8.1 Hz, 1H), 7.52 (ddd, J=1.2 Hz, 6.9 Hz, 8.1 Hz, 1H), 7.45 (ddd, J=1.2 Hz, 6.9 Hz, 8.1 Hz, 1H), 7.23~7.19 (m, 1H), 7.16 (dd, J=2.3 Hz, 6.5 Hz, 2H), 7.05 (dd, J=2.3 Hz, 6.5 Hz, 2H), 6.96 (d, J=9.2 Hz, 1H), 3.86 (s, 3H), 3.72~3.70 (m, 4H), 2.52~2.48 (m, 6H), 2.32 (t, J=7.3 Hz, 2H), 1.80~1.71 (m, 2H), 1.53~1.49 (m, 2H)

Mass, m/e: 519 (M+), 307, 157 (base)

Example 7-18

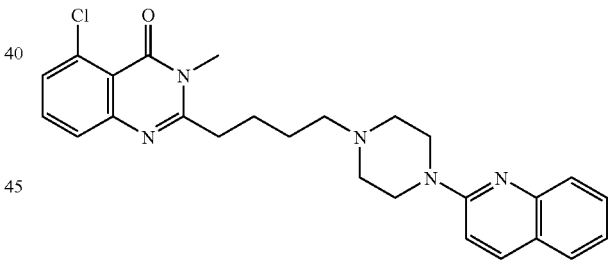

Step 7-18-A: Synthesis of methyl 2-amino-6-chlorobenzoate

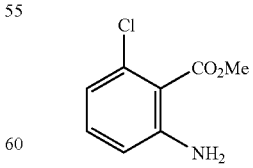

To a mixture of 20 ml of 4N sodium hydroxide and 50 ml of diethyl ether, 2.7 g of N-methyl-N-nitrosourea was added under cooling with ice and stirred for 30 minutes. The organic layer was separated and added to a solution of 915 mg of 2-amino-6-chloro-benzoic acid in 20 ml of diethyl ether, followed by an hour's stirring at room temperature. The solution was washed with saturated aqueous sodium hydrogencarbonate solution, dried over anhydrous magnesium sulfate and the solvent was distilled off under reduced pressure. The residue was purified on silica gel column chromatography (n-hexane: ethyl acetate=3:1) to provide 790 mg (80%) of methyl 2-amino-6-chlorobenzoate.

$^1$H-NMR (CDCl$_3$) δ: 7.07 (t, J=8.1 Hz, 1H), 6.74 (dd, J=0.8 Hz, 7.7 Hz, 1H), 6.57 (dd, J=0.8 Hz, 8.1 Hz, 1H), 4.86 (br s, 2H), 3.93 (s, 3H)

Mass, m/e: 185 (M$^+$), 153 (base), 126, 90

Step 7-18-B: Synthesis of methyl 2-(5-bromopentanoylamino-6-chloro-benzoate

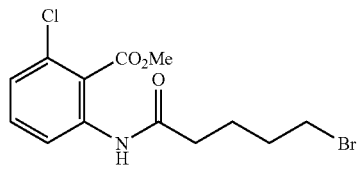

To a solution of 750 mg of methyl 2-amino-6-chlorobenzoate as synthesized in above Step 7-18-A in 10 ml of tetrahydrofuran, first 700 mg of pyridine and then 800 mg of 5-bromovaleryl chloride were added under cooling with ice. The solution was warmed to room temperature, stirred for an hour and the solvent was distilled off under reduced pressure. The residue was extracted with ethyl acetate, washed with saturated aqueous sodium hydrogencarbonate solution, 1N hydrochloric acid and saturated brine, dried over anhydrous magnesium sulfate and the solvent was distilled off under reduced pressure to provide 1.34 g (96%) of methyl 2-(5-bromopentanoylamino)-6-chlorobenzoate.

$^1$H-NMR (CDCl$_3$) δ: 9.07 (br s, 1H), 8.27 (d, J=8.1 Hz, 1H), 7.35 (t, J=8.1 Hz, 1H), 7.17 (dd, J=0.8 Hz, 8.1 Hz, 1H), 3.98 (s, 3H), 3.44 (t, J=6.6 Hz, 4H), 2.41 (t, J=7.3 Hz, 2H), 1.99~1.91 (m, 2H), 1.90~1.83 (m, 2H)

Mass, m/e: 347 (M$^+$), 185, 55 (base)

Step 7-18-C: Synthesis of methyl 2-chloro-6-[5-(4-quinolin-2-ylpiperazin-1-yl)pentanoylamino]benzoate

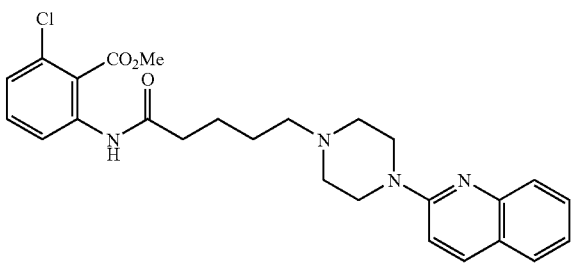

A mixture of 1.29 g of methyl 2-(5-bromopentanoylamino)-6-chloro-benzoate as synthesized in above Step 7-18-B, 800 mg of 2-piperazin-1-ylquinoline as synthesized in Step 7-1-A, 400 mg of triethylamine and 20 ml of toluene was heated under reflux for 3 hours. After cooling, the solution was washed with water, dried over anhydrous magnesium sulfate and the solvent was distilled off under reduced pressure. The residue was purified on silica gel column chromatography (ethyl acetate:methanol=15:1) to provide 1.13 g (64%) of methyl 2-chloro-6-[5-(4-quinolin-2-ylpiperazin-1-yl)pentanoylamino]benzoate.

$^1$H-NMR (CDCl$_3$) δ: 9.08 (br s, 1H), 8.28 (d, J=8.5 Hz, 1H), 7.87 (d, J=8.9 Hz, 1H), 7.69 (d, J=8.1 Hz, 1H), 7.58 (d, J=6.5 Hz, 1H), 7.56 (d, J=8.3 Hz, 1H), 7.52 (ddd, J=1.5 Hz, 6.9 Hz, 8.5 Hz, 1H), 7.35 (t, J=8.5 Hz, 1H), 7.23~7.15 (m, 2H), 6.97 (d, J=9.2 Hz, 1H), 3.97 (s, 3H), 3.74 (t, J=5.0 Hz, 4H), 2.57 (t, J=5.0 Hz, 4H), 2.45~2.40 (m, 4H), 1.81~1.73 (m, 2H), 1.66~1.59 (m, 2H)

Mass, m/e: 480 (M$^+$), 157 (base)

Step 7-18-D: Synthesis of 5-chloro-3-methyl-2-[4-(4-quinolin-2-ylpiperazin-1-yl)butyl]-3H-quinazolin-4-one

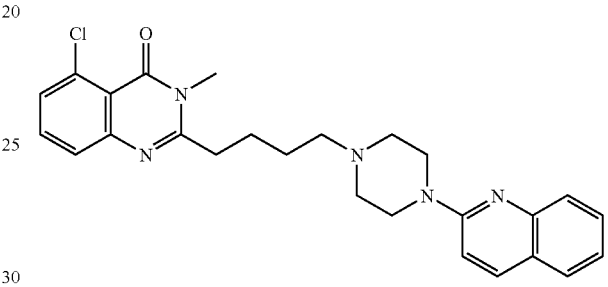

A mixture of 250 mg of methyl 2-chloro-6-[5-(4-quinolin-2-ylpiperazin-1-yl)pentanoylamino]benzoate as synthesized in the above Step 7-18-C and 5 ml of 40% methylamine-in-methanol solution was hermetically sealed in a glass tube and stirred for 18 hours at the exterior temperature of 100° C. After cooling, the solvent was distilled off from the solution, and the residue was purified on silica gel column chromatography (dichloro-methane:methanol=15:1) to provide 96 mg (40%) of 5-chloro-3-methyl-2-[4-(4-quinolin-2-ylpiperazin-1-yl)butyl]-3H-quinazolin-4-one.

$^1$H-NMR (CDCl$_3$) δ: 7.88 (d, J=8.9 Hz, 1H), 7.70 (d, J=8.5 Hz, 1H), 7.59 (dd, J=1.2 Hz, 8.1 Hz, 1H), 7.56~7.50 (m, 3H), 7.43 (d, J=2.3 Hz, 1H), 7.22 (ddd, J=1.2 Hz, 6.9 Hz, 8.1 Hz, 1H), 6.97 (d, J=9.2 Hz, 1H), 3.76 (t, J=5.0 Hz, 4H), 3.59 (s, 3H), 2.85 (t, J=7.7 Hz, 2H), 2.59 (t, J=5.0 Hz, 4H), 2.49 (t, J=7.3 Hz, 2H), 1.95~1.86 (m, 2H), 1.75~1.68 (m, 2H)

Mass, m/e: 461 (M$^+$), 157 (base)

Example 7-19

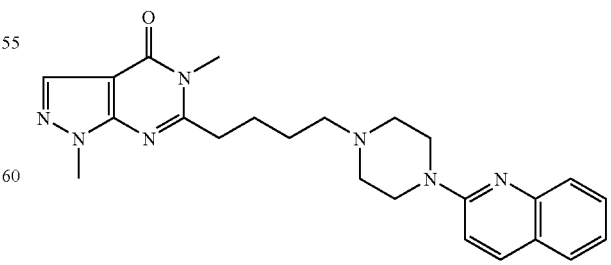

Using ethyl 5-amino-1-methyl-1H-pyrazole-4-carboxylate as the starting material, 1,5-dimethyl-6-[4-(4-quinolin-2- ylpiperazin-1-yl)butyl]-1,5-dihydropyrazolo[3,4-d]pyrimidin-4-one was synthesized in the manner similar to Example 7-18.

¹H-NMR(CDCl₃) δ: 8.01 (s, 1H), 7.89 (d, J=8.9 Hz, 1H), 7.70 (d, J=8.5 Hz, 1H), 7.62-7.58 (m, 1H), 7.54 (ddd, J=1.5 Hz, 6.9 Hz, 8.5 Hz, 1H), 7.23 (ddd, J=1.2 Hz, 6.9 Hz, 8.1 Hz, 1H), 6.98 (d, J=8.9 Hz, 1H), 3.77 (t, J=5.0 Hz, 4H), 3.61 (s, 3H), 3.59 (s, 3H), 2.86 (t, J=7.3 Hz, 2H), 2.60 (t, J=4.6 Hz, 4H), 2.50 (t, J=7.3 Hz, 2H), 1.94~1.86 (m, 2H), 1.75~1.70 (m, 2H)

Mass, m/e: 431 (M⁺), 157 (base)

Example 7-20

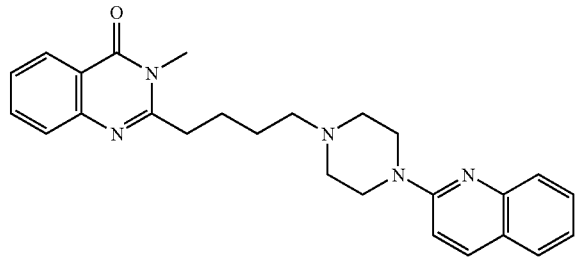

Using ethyl anthranilate as the starting material, 3-methyl-2-[4-(4-quinolin-2-ylpiperazin-1-yl)butyl]-3H-quinazolin-4-one was synthesized in the manner similar to Example 7-18.

¹H-NMR(CDCl₃) 5:8.26 (dd, J=1.2 Hz, 8.1 Hz, 1H), 7.89 (d, J=9.3 Hz, 1H), 7.72 (ddd, J=1.5 Hz, 6.9 Hz, 8.5 Hz, 1H), 7.71~7.69 (m, 1H), 7.64~7.62 (m, 1H), 7.62~7.58 (m, 1H), 7.53 (ddd, J=1.5 Hz, 6.9 Hz, 8.5 Hz, 1H), 7.44 (ddd, J=1.2 Hz, 6.9 Hz, 8.1 Hz, 1H), 7.22 (ddd, J=1.2 Hz, 6.9 Hz, 8.1 Hz, 1H), 6.98 (d, J=9.2 Hz, 1H), 3.76 (t, J=5.1 Hz, 4H), 3.64 (s, 3H), 2.89 (t, J=8.1 Hz, 2H), 2.59 (t, J=5.0 Hz, 4H), 2.49 (t, J=7.3 Hz, 2H), 1.93 (q, J=7.7 Hz, 2H), 1.79~1.70 (m, 2H)

Mass, m/e: 427 (M⁺), 157 (base)

Example 7-21

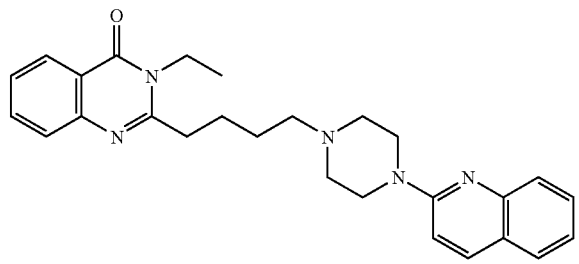

Using ethyl anthranilate as the starting material, 3-2-[4-(4-quinolin-2-ylpiperazin-1-yl)butyl]-3H-quinazolin-4-one was synthesized in the manner similar to Example 7-18.

H-NMR(CDCl₃) δ: 8.25 (dd, J=1.5 Hz, 8.1 Hz, 1H), 7.89 (d, J=9.2 Hz, 1H), 7.71 (ddd, J=1.5 Hz, 6.9 Hz, 8.5 Hz, 1H), 7.70 (dd, J=1.2 Hz, 8.5 Hz, 1H), 7.64~7.58 (m, 2H), 7.53 (ddd, J=1.5 Hz, 6.9 Hz, 8.5 Hz, 1H), 7.43 (ddd, J=1.5 Hz, 6.9 Hz, 8.5 Hz, 1H), 7.22 (ddd, J=1.2 Hz, 6.9 Hz, 8.1 Hz, 1H), 6.98 (d, J=8.9 Hz, 1H), 4.19 (q, J=6.9 Hz, 3H), 3.77 (t, J=5.0 Hz, 4H), 2.88 (t, J=7.7 Hz, 2H), 2.60 (t, J=5.0 Hz, 4H), 2.50 (t, J=7.3 Hz, 2H), 1.95 (q, J=7.7 Hz, 2H), 1.80~1.70 (m, 2H), 1.37 (t, J=6.9 Hz, 3H)

Mass, m/e: 441 (M⁺), 157 (base)

Example 7-22

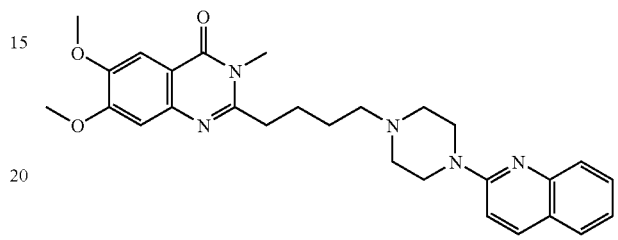

Using 2-amino-4,5-dimethoxybenzoic acid as the starting material, 6,7-dimethoxy-3-methyl-2-[4-(4-quinolin-2-ylpiperazin-1-yl) butyl]-3H-quinazolin-4-one was synthesized in the manner similar to Example 7-18.

¹H-NMR(CDCl₃) δ: 7.88 (d, J=8.9 Hz, 1H), 7.69 (d, J=8.5 Hz, 1H), 7.58 (dd, J=1.2 Hz, 8.1 Hz, 1H), 7.57 (s, 1H), 7.53 (ddd, J=1.5 Hz, 6.9 Hz, 8.5 Hz, 1H), 7.22 (ddd, J=1.2 Hz, 6.9 Hz, 8.1 Hz, 1H), 7.03 (s, 1H), 6.97 (d, J=9.2 Hz, 1H), 3.99 (s, 3H), 3.98 (s, 3H), 3.76 (t, J=5.0 Hz, 4H), 3.64 (s, 3H), 2.86 (t, J=7.3 Hz, 2H), 2.59 (t, J=5.0 Hz, 4H), 2.49 (t, J=7.3 Hz, 2H), 1.93~1.85 (m, 2H), 1.75~1.56 (m, 2H)

Mass, m/e: 487 (M⁺), 157 (base)

Example 7-23

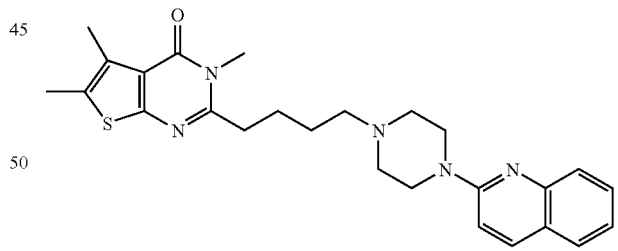

Using ethyl 2-amino-4,5-dimethylthiophene-3-carboxylate as the starting material, 3,5,6-trimethyl-2-[4-(4-quinolin-2-ylpiperazin-1-yl) butyl]-3H-thieno[2,3-d]pyrimidin-4-one was synthesized in the manner similar to Example 7-18.

¹H-NMR(CDCl₃) 5:7.88 (d, J=9.3 Hz, 1H), 7.69 (d, J=8.1 Hz, 1H), 7.58 (d, J=8.1 Hz, 1H), 7.54~7.50 (m, 1H), 7.23~7.19 (m, 1H), 6.97 (d, J=8.2 Hz, 1H), 3.76 (t, J=5.0 Hz, 4H), 3.58 (s, 3H), 2.83~2.79 (m, 2H), 2.59 (t, J=5.0 Hz, 4H), 2.50~2.38 (m, 2H), 2.46 (s, 3H), 2.36 (s, 3H), 1.89~1.83 (m, 2H), 1.73~1.68 (m, 2H)

Mass, m/e: 461 (M⁺), 157 (base)

Example 7-24

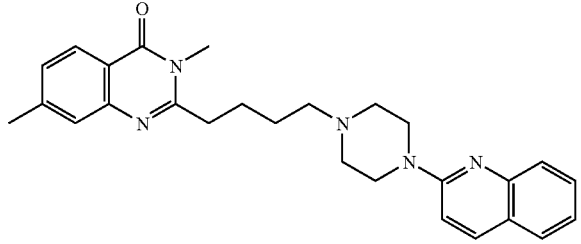

Using ethyl 2-amino-4-methylbenzoate as the starting material, 3,7-dimethyl-2-[4-(4-quinolin-2-ylpiperazin-1-yl) butyl]-3H-quinazolin-4-one was synthesized in the manner similar to Example 7-18.

$^1$H-NMR(CDCl$_3$) δ:8.13 (d, J=8.1 Hz, 1H), 7.88 (d, J=8.9 Hz, 1H), 7.69 (d, J=8.1 Hz, 1H), 7.59 (d, J=8.1 Hz, 1H), 7.54~7.50 (m, 1H), 7.42 (s, 1H), 7.24~7.19 (m, 2H), 6.97 (d, J=9.2 Hz, 1H), 3.76~3.75 (m, 4H), 3.63 (s, 3H), 2.88~2.84 (m, 2H), 2.60~2.58 (m, 4H), 2.51~2.48 (m, 5H), 1.93~1.89 (m, 2H), 1.74~1.71 (m, 2H)

Mass, m/e: 441 (M$^+$), 157 (base)

Example 7-25

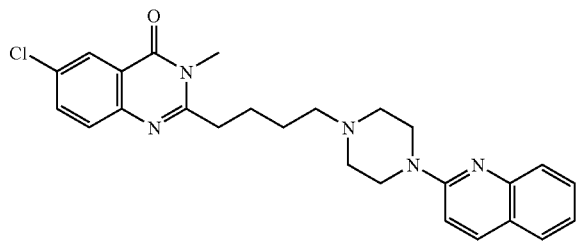

Using ethyl 2-amino-5-chlorobenzoate as the starting material, 6-chloro-3-methyl-2-[4-(4-quinolin-2-ylpiperazin-1-yl) butyl]-3H-quinazolin-4-one was synthesized in the manner similar to Example 7-18.

$^1$H-NMR(CDCl$_3$) δ: 8.21 (d, J=2.3 Hz, 1H), 7.89 (d, J=8.9 Hz, 1H), 7.69 (d, J=8.5 Hz, 1H), 7.65~7.62 (m, 1H), 7.60~7.51 (m, 3H), 7.24~7.20 (m, 1H), 6.98 (d, J=8.9 Hz, 1H), 3.76 (br s, 4H), 3.64 (s, 3H), 2.87 (t, J=7.7 Hz, 2H), 2.59 (br s, 4H), 2.51~2.47 (m, 2H), 1.94~1.88 (m, 2H), 1.75~1.71 (m, 2H)

Mass, m/e: 461 (M$^+$), 157 (base)

Example 7-26

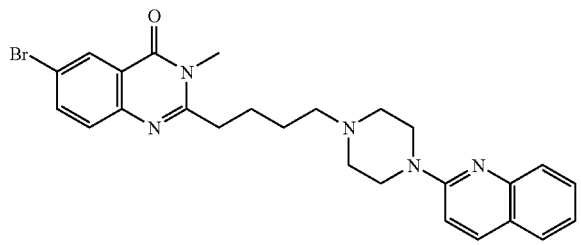

Using ethyl 2-amino-5-bromobenzoate as the starting material, 6-bromo-3-methyl-2-[4-(4-quinolin-2-ylpiperazin-1-yl) butyl]-3H-quinazolin-4-one was synthesized in the manner similar to Example 7-18.

$^1$H-NMR(CDCl$_3$) δ: 8.38 (d, J=2.3 Hz, 1H), 7.88 (d, J=9.2 Hz, 1H), 7.78 (dd, J=8.5 Hz, J=2.3 Hz, 1H), 7.69 (d, J=8.5 Hz, 1H), 7.60~7.58 (m, 1H), 7.55~7.49 (m, 2H), 7.24~7.20 (m, 1H), 6.97 (d, J=9.2 Hz, 1H), 3.76 (t, J=5.0 Hz, 4H), 3.63 (s, 3H), 2.86 (t, J=7.7 Hz, 2H), 2.59 (t, J=5.0 Hz, 4H), 2.51~2.47 (m, 2H), 1.97~1.87 (m, 2H), 1.77~1.64 (m, 2H)

Mass, m/e: 505 (M$^+$), 157 (base)

Example 7-27

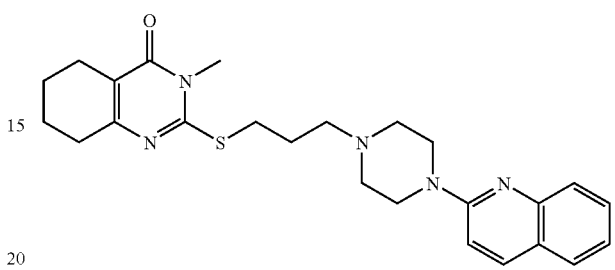

Step 7-27-A: Synthesis of 2-[4-(3-Chloropropyl)piperazin-1-yl]quinoline

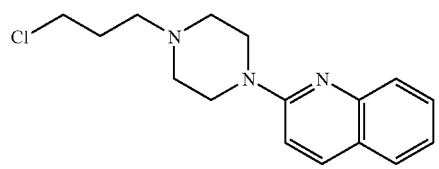

In 5 ml of acetone, 853 mg of 2-piperazin-1-ylquinoline as synthesized in Step 7-1-A was dissolved and to which 160 mg of sodium hydroxide as dissolved in 5 ml of water was added. Into the mixed liquid 0.5 ml of 1-bromo-3-chloropropane was dropped, followed by stirring for an overnight at room temperature. After addition of diethyl ether, the organic layer was washed with saturated aqueous sodium hydrogencarbonate solution, and the organic layer was dried over anhydrous magnesium sulfate. Distilling the solvent off under reduced pressure, the residue was purified on silica gel column chromatography (chloroform:methanol=50:1) to provide 1.10 g (95%) of 2-[4-(3-chloropropyl)piperazin-1-yl]quinoline.

$^1$H-NMR(CDCl$_3$): 7.89 (d, J=9.2 Hz, 1H), 7.70 (d, J=8.4 Hz, 1H), 7.59 (dd, J=1.4 Hz, 8.0 Hz, 1H), 7.53 (ddd, J=1.5 Hz, 7.1 Hz, 8.5 Hz, 1H), 7.22 (ddd, J=1.1 Hz, 6.9 Hz, 8.0 Hz, 1H), 6.98 (d, J=9.2 Hz, 1H), 3.75 (t, J=5.1 Hz, 4H), 3.61 (t, J=6.5 Hz, 2H), 2.63~2.43 (m, 6H), 2.04~1.97 (m, 2H)

Mass, m/e: 289 (M$^+$), 157 (base)

Step 7-27-B: Synthesis of 3-Methyl-2-[3-(4-quinolin-2-ylpiperazin-1-yl) Propylthio]-5,6,7,8-Tetrahydro-3H-quinazolin-4-one

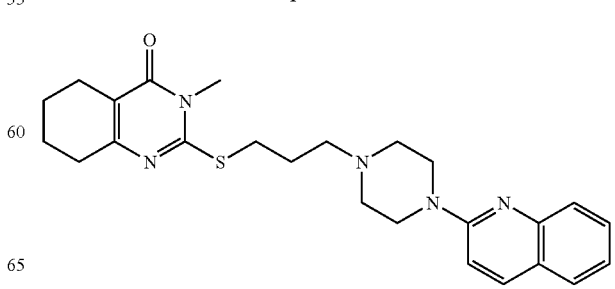

A mixture of 234 mg of potassium 3-methyl-4-oxo-3,4,5,6,7,8-hexahydroquinazoline-2-thiolate (a compound shown in J. Med. Chem., 40, 574-585 (1997)), 290 mg of 2-[4-(3-chloropropyl)-piperazin-1-yl]quinoline as synthesized in above Step 7-27-A and 5 ml of 2-propanol was heated under reflux for an overnight. The residue was purified on silica gel column chromatography (chloroform:methanol=10:1) to provide 467 mg (quantitative) of 3-methyl-2-[3-(4-quinolin-2-ylpiperazin-1-yl)propylthio-5,6,7,8-tetrahydro-3H-quinazolin-4-one.

$^1$H-NMR(CDCl$_3$) δ: 7.88 (d, J=9.3 Hz, 1H), 7.69 (d, J=8.5 Hz, 1H), 7.59 (dd, J=8.1 Hz, 1.2 Hz, 1H), 7.55~7.51 (m, 1H), 7.23~7.20 (m, 1H), 6.97 (d, J=9.3 Hz, 1H), 3.76 (t, J=5.0 Hz, 4H), 3.48 (s, 3H), 3.23 (t, J=7.3 Hz, 2H), 2.60 (t, J=5.0 Hz, 4H), 2.56~2.51 (m, 4H), 2.49~2.46 (m, 2H), 2.01~1.93 (m, 2H), 1.78~1.70 (m, 4H)

Mass, m/e: 449 (M$^+$), 157 (base)

Example 7-28

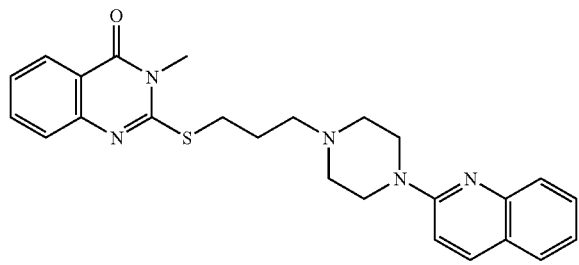

Using potassium 3-methyl-4-oxo-3,4-dihydroquinazoline-2-thiolate as the starting material, 3-methyl-2-[3-(4-quinolin-2-ylpiperazin-1-yl)propylthio-3H-quinazolin-4-one was synthesized in the manner similar to Example 7-27.

$^1$H-NMR(CDCl$_3$) δ: 8.21 (dd, J=8.1 Hz, 1.5 Hz, 1H), 7.88 (d, J=9.2 Hz, 1H), 7.71~7.66 (m, 2H), 7.59 (d, J=7.7 Hz, 1H), 7.55~7.51 (m, 2H), 7.39~7.35 (m, 1H), 7.24~7.20 (m, 1H), 6.98 (d, J=9.2 Hz, 1H), 3.79~3.77 (m, 4H), 3.65 (s, 3H), 3.39~3.35 (m, 2H), 2.64~2.57 (m, 6H), 2.09~2.02 (m, 2H)

Mass, m/e: 445 (M$^+$), 157 (base)

Example 7-29

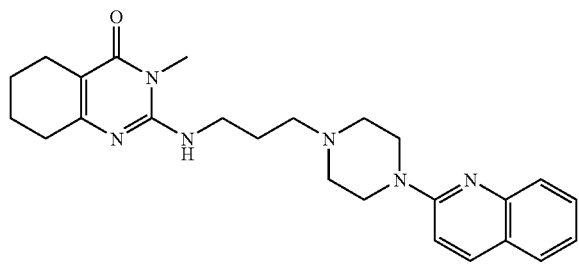

Step 7-29-A: Synthesis of 3-methyl-2methylthio-5,6,7,8-tetrahydro-3H-quinazolin-4-one

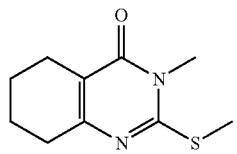

To a mixture of 10 ml of tetrahydrofuran and 5 ml of dimethylformamide, 340 mg of potassium 3-methyl-4-oxo-3,4,5,6,7,8-hexahydroquinazoline-2-thiolate was added, followed by addition of 210 mg of methyl iodide and an overnight's stirring at room temperature. The solution was concentrated, to which chloroform was added, followed by washing with saturated brine and drying over anhydrous magnesium sulfate. Distilling the solvent off under reduced pressure, 310 mg (quantitative) of 3-methyl-2-methylthio-5,6,7,8-tetrahydro-3H-quinazolin-4-one was obtained.

$^1$H-NMR(CDCl$_3$) δ: 3.49 (s, 3H), 2.56~2.54 (m, 2H), 2.54 (s, 3H), 2.49~2.46 (m, 2H), 1.77~1.70 (m, 4H)

Mass, m/e: 210 (M$^+$), 165 (base)

Step 7-29-B: Synthesis of 2-[4-(3-aminopropyl)piperazin-1-yl]quinoline

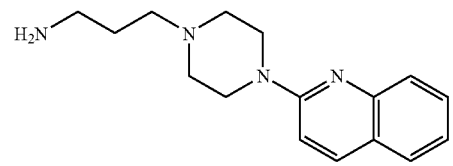

To 30 ml of ethanol, 1.52 g of 2-[3-(4-quinolin-2-ylpiperazin-1-yl) propyl]isoindol-1,3-dione (a compound shown in Pol. J. Chem., 75, 71-78 (2001)) was added, followed by addition of 1.50 g of hydrazine monohydrate as dissolved in 10 ml of ethanol and 7 hours' heating under reflux. After cooling the reaction system, insoluble matter was removed by filtration and the solvent was distilled off under reduced pressure. After being rendered to alkaline with 5N sodium hydroxide, the residue was extracted with chloroform, washed with saturated brine, dried over anhydrous sodium sulfate, and the solvent was distilled off under reduced pressure to provide 0.99 g (96%) of 2-[4-(3-aminopropyl)piperazin-1-yl]quinoline.

$^1$H-NMR(CDCl$_3$) δ: 7.87 (d, J=8.9 Hz, 1H), 7.69 (d, J=8.5 Hz, 1H), 7.58 (d, J=8.1 Hz, 1H), 7.52 (ddd, J=1.5 Hz, 6.9 Hz, 8.5 Hz, 1H), 7.23 (ddd, J=1.2 Hz, 6.9 Hz, 8.1 Hz, 1H), 6.97 (d, J=8.9 Hz, 1H), 3.75 (t, J=5.4 Hz, 4H), 2.78 (t, J=6.9 Hz, 2H), 2.58 (t, J=5.4 Hz, 4H), 2.46 (t, J=7.3 Hz, 2H), 1.78~1.63 (m, 2H)

Mass, m/e: 270 (M$^+$), 157 (base)

Step 7-29-C: Synthesis of 3-methyl-2-[3-(4-quinolin-2-ylpiperazin-1-yl) propylamino]-5,6,7,8-tetrahydro-3H-quinazolin-4-one

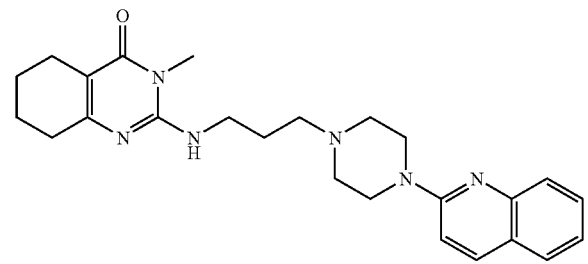

A mixture of 420 mg of 3-methyl-2-methylsulfanyl-5,6,7,8-tetrahydro-3H-quinazolin-4-one as synthesized in Step 7-29-A and 540 mg of 2-[4-(3-aminopropyl)piperazin-1-yl]quinoline as synthesized in above Step 7-29-B was heated under stirring at 140° C. for 6 hours. The residue was purified on silica gel column chromatography (chloroform:methanol=10:1) to provide 420 mg (48%) of 3-methyl-2-[3-(4-quinolin-2-ylpiperazin-1-yl)propylamino]-5,6,7,8-tetrahydro-3H-quinazolin-4-one.

$^1$H-NMR(CDCl$_3$) δ: 7.91 (d, J=9.3 Hz, 1H), 7.70 (d, J=8.5 Hz, 1H), 7.60 (d, J=8.1 Hz, 1H), 7.54 (ddd, J=8.5 Hz, 6.9 Hz, 1.5 Hz, 1H), 7.26~7.22 (m, 1H), 6.98 (d, J=8.9 Hz, 1H), 6.69 (br s, 1H), 3.77 (br s, 4H), 3.56~3.52 (m, 2H), 3.48 (s, 3H), 2.67 (br s, 4H), 2.64~2.61 (m, 2H), 2.54 (s, 3H), 2.49~2.40 (m, 4H), 1.88~1.87 (m, 2H), 1.77~1.70 (m, 4H)

Mass, m/e: 432 (M$^+$), 157 (base)

Example 7-30

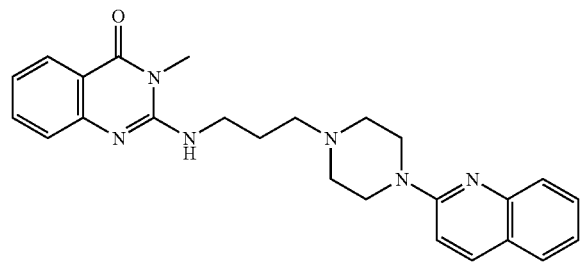

Step 7-30-A: Synthesis of 3-methyl-2-methylsulfanyl-3H-quinazolin-4-one

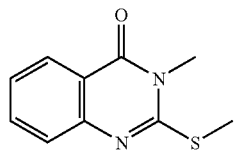

Using potassium 3-methyl-4-oxo-3,4-dihydroquinazoline-2-thiolate as the starting material, 3-methyl-2-methylsulfanyl-3H-quinazolin-4-one was synthesized in the manner similar to above Step 7-29-A.

$^1$H-NMR(CDCl$_3$) δ: 8.22~8.20 (m, 1H), 7.70~7.65 (m, 1H), 7.57~7.55 (m, 1H), 7.36 (ddd, J=8.1 Hz, J=6.9 Hz, J=1.2 Hz, 1H), 3.61 (s, 3H), 2.66 (s, 3H)

Mass, m/e: 206 (M$^+$), 161 (base)

Step 7-30-B: Synthesis of 3-methyl-2-[3-(4-quinolin-2-ylpiperazin-1-yl)propylamino]-3H-quinazolin-4-one

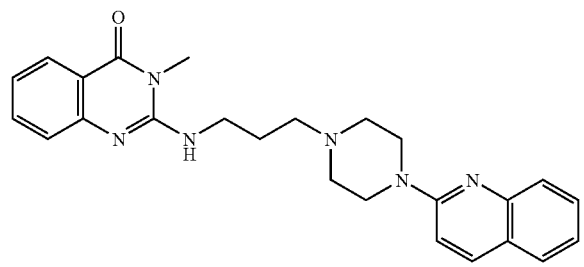

Using 3-methyl-2-methylsulfanyl-3H-quinazolin-4-one as synthesized in above Step 7-30A as the starting material, 3-methyl-2-[3-(4-quinolin-2-ylpiperazin-1-yl)propylamine]-3H-quinazolin-4-one was synthesized in the manner similar to Step 7-29-B.

$^1$H-NMR(CDCl$_3$) δ: 8.10 (dd, J=8.1 Hz, 1.2 Hz, 1H), 7.92 (d, J=9.2 Hz, 1H), 7.72 (d, J=8.5 Hz, 1H), 7.62 (dd, J=8.1 Hz, 1.2 Hz, 1H), 7.58~7.53 (m, 2H), 7.36 (d, J=7.7 Hz, 1H), 7.27~7.23 (m, 1H), 7.15~7.11 (m, 1H), 6.99 (d, J=8.9 Hz, 1H), 6.94 (br s, 1H), 3.79 (t, J=5.0 Hz, 4H), 3.69~3.65 (m, 2H), 3.51 (s, 3H), 2.70 (t, J=5.0 Hz, 4H), 2.68~2.65 (m, 2H), 1.95~1.92 (m, 2H)

Mass, m/e: 428 (M$^+$), 157 (base)

Production Example 1

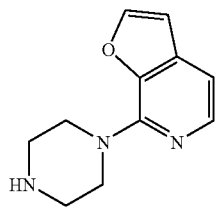

In 100 ml of ethylene glycol 8.6 g of anhydrous piperazine was dissolved, and to which 7-chlorofuro[2,3-c]pyridine was added, followed by an overnight's stirring at 140° C. After cooling, saturated aqueous sodium hydrogencarbonate solution was added to the solution, which was then extracted with chloroform. The organic layer was dried over anhydrous magnesium sulfate, and the solvent was distilled off under reduced pressure. The residue was purified on silica gel column chromatography to provide 1.52 g (75%) of 7-piperazin-1-ylfuro[2,3-c]pyridine.

$^1$H-NMR(CDCl$_3$) δ: 7.96 (d, J=5.5 Hz, 1H), 7.63 (d, J=2.3 Hz, 1H), 6.97 (d, J=5.4 Hz, 1H), 6.72 (d, J=1.9 Hz, 1H), 3.83~3.80 (m, 4H), 3.06 (t, J=5.0 Hz, 4H)

Mass, m/e: 203 (M$^+$), 135 (base)

Production Example 2

In the manner similar to Production Example 1, 7-(4-methylpiperazin-1-yl)furo[2,3-c]pyridine was obtained.

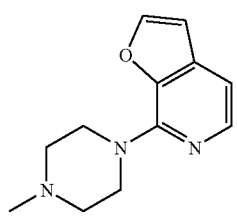

$^1$H-NMR(CDCl$_3$) δ: 7.95 (d, J=5.3 Hz, 1H), 7.62 (d, J=1.9 Hz, 1H), 6.96 (d, J=5.4 Hz, 1H), 6.72 (d, J=1.9 Hz, 1H), 3.88 (t, J=5.0 Hz, 4H), 2.59 (t, J=5.0 Hz, 4H), 2.38 (s, 3H)

Mass, m/e: 217 (M$^+$), 147 (base)

Production Example 3

In the manner similar to Production Example 1, 4-piperazin-1-ylfuro[3,2-c]pyridine was obtained.

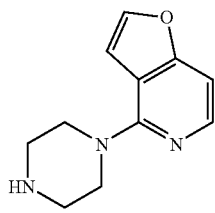

¹H-NMR(CDCl₃) δ: 8.05 (d, J=5.8 Hz, 1H), 7.53 (d, J=2.0 Hz, 1H), 6.94 (dd, J=0.8 Hz, 5.8 Hz, 1H), 6.81 (dd, J=1.2 Hz, 2.3 Hz, 1H), 3.67 (t, J=5.0 Hz, 4H), 3.05 (t, J=5.0 Hz, 4H)

Mass, m/e: 203 (M⁺), 135 (base)

Production Example 4

In the manner similar to Production Example 1, 4-(4-methylpiperazin-1-yl)furo[2,3-c]pyridine was obtained.

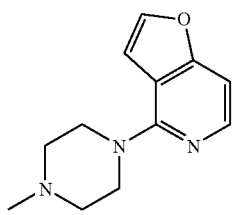

¹H-NMR(CDCl₃) δ: 8.05 (d, J=5.8 Hz, 1H), 7.53 (d, J=2.3 Hz, 1H), 6.94 (dd, J=1.2 Hz, 5.8 Hz, 1H), 6.81 (dd, J=1.2 Hz, 2.3 Hz, 1H), 3.74 (t, J=5.0 Hz, 4H), 2.59 (t, J=5.0 Hz, 4H), 2.37 (s, 3H)

Mass, m/e: 217 (M⁺), 147 (base)

Production Example 5

In the manner similar to Production Example 1, 7-piperazin-1-ylthieno[2,3-c]pyridine was obtained.

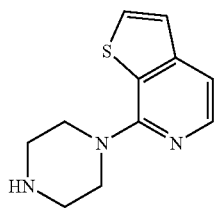

¹H-NMR(CDCl₃) δ: 8.14 (d, J=5.8 Hz, 1H), 7.58 (d, J=5.4 Hz, 1H), 7.32 (d, J=5.4 Hz, 1H), 7.25 (d, J=5.4 Hz, 1H), 3.64 (t, J=5.0 Hz, 4H), 3.09 (t, J=5.0 Hz, 4H)

Mass, m/e: 219 (M⁺), 151 (base)

Production Example 6

In the manner similar to Production Example 1, 7-(4-methylpiperazin-1-yl)thieno[2,3-c]pyridine was obtained.

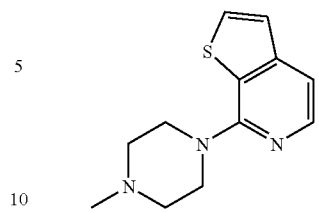

¹H-NMR(CDCl₃) δ: 8.13 (d, J=5.8 Hz, 1H), 7.57 (d, J=5.4 Hz, 1H), 7.31 (d, J=5.4 Hz, 1H), 7.24 (d, J=5.4 Hz, 1H), 3.71 (t, J=5.0 Hz, 4H), 2.63 (t, J=5.0 Hz, 4H), 2.38 (s, 3H)

Mass, m/e: 233 (M⁺), 163 (base)

Production Example 7

In the manner similar to Production Example 1, 4-piperazin-1-ylthieno[3,2-c]pyridine was obtained.

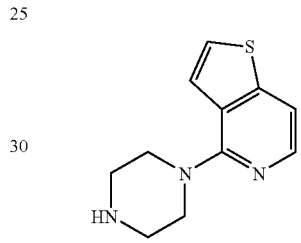

¹H-NMR(CDCl₃) δ: 8.09 (d, J=5.8 Hz, 1H), 7.42~7.35 (m, 3H), 3.50 (t, J=5.0 Hz, 4H), 3.11 (t, J=5.0 Hz, 4H)

Mass, m/e: 219 (M⁺), 151 (base)

Production Example 8

In the manner similar to Production Example 1, 4-(4-methylpiperazin-1-yl)thieno[3,2-c]pyridine was obtained.

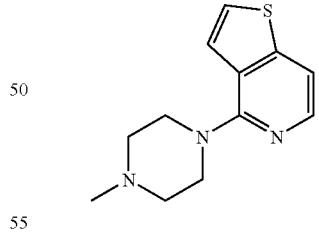

¹H-NMR(CDCl₃) δ: 8.08 (d, J=5.8 Hz, 1H), 7.41~7.33 (m, 3H), 3.57 (t, J=5.0 Hz, 4H), 2.64 (t, J=5.0 Hz, 4H), 2.39 (s, 3H)

Mass, m/e: 233 (M⁺), 163 (base)

Production Example 9

In the manner similar to Production Example 1, 2-bromo-4-piperazin-1-ylthieno[3,2-c]pyridine dihydrochloride was obtained.

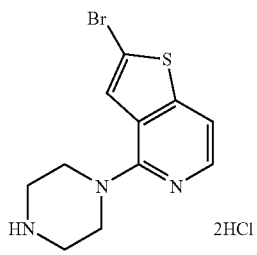

$^{1}$H-NMR (DMSO-$d_6$) δ: 8.03 (d, J=5.8 Hz, 1H), 7.90 (s, 1H), 7.67 (d, J=5.8 Hz, 1H), 3.72 (br s, 4H), 2.59 (br s, 4H)
Mass, m/e: 297 (M$^+$), 229 (base)

Production Example 10

In the manner similar to Production Example 1, 2-bromo-4-(methylpiperazin-1-yl)thieno[3,2-c]pyridine was obtained.

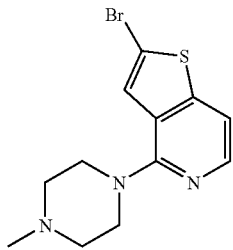

$^{1}$H-NMR(CDCl$_3$) δ: 8.05 (d, J=5.4 Hz, 1H), 7.36 (d, J=0.8 Hz, 1H), 7.19 (dd, J=0.8 Hz, 5.8 Hz, 1H), 3.53 (t, J=5.0 Hz, 4H), 2.63 (t, J=5.0 Hz, 4H), 2.39 (s, 3H)
Mass, m/e: 311 (M$^+$), 83 (base)

Production Example 11

In the manner similar to Production Example 1, 2-methyl-4-piperazin-1-ylthieno[3,2-c]pyridine dihydrochloride was obtained.

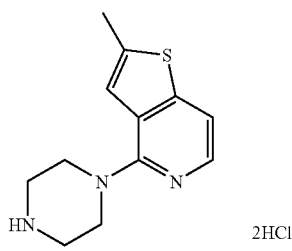

$^{1}$H-NMR (DMSO-$d_6$) δ: 7.94 (d, J=6.2 Hz, 1H), 7.76 (d, J=6.2 Hz, 1H), 7.55 (s, 1H), 3.91 (br s, 4H), 2.59 (br s, 4H), 2.64 (s, 3H)
Mass, m/e: 233 (M$^+$), 177 (base)

Production Example 12

In the manner similar to Production Example 1, 2-methyl-4-(4-methylpiperazin-1-ylthieno[3,2-c]pyridine dihydrochloride was obtained.

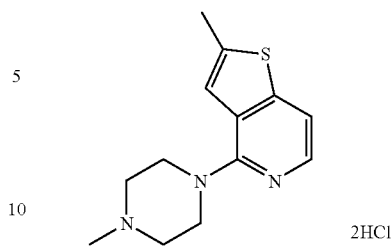

$^{1}$H-NMR (DMSO-$d_6$) δ: 7.96 (d, J=6.2 Hz, 1H), 7.73 (d, J=5.8 Hz, 1H), 7.50 (s, 1H), 4.20 (d, J=5.9 Hz, 3H), 3.57 (br s, 4H), 3.30~3.27 (m, 4H), 2.84 (d, J=4.3 Hz, 3H)
Mass, m/e: 247 (M$^+$), 177 (base)

Production Example 13

In the manner similar to Production Example 1, 3-bromo-4-piperazin-1-ylthieno[3,2-c]pyridine dihydrochloride was obtained.

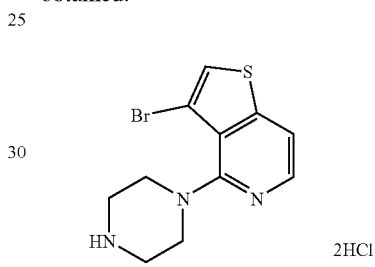

$^{1}$H-NMR (DMSO-$d_6$) δ: 8.17 (d, J=5.4 Hz, 1H), 8.02 (s, 1H), 7.83 (d, J=5.8 Hz, 1H), 3.56~3.32 (m, 8H)
Mass, m/e: 297 (M$^+$), 229 (base)

Production Example 14

In the manner similar to Production Example 1, 3-bromo-4-(4-methylpiperazin-1-yl)thieno[3,2-c]pyridine was obtained.

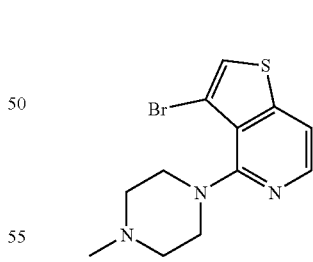

$^{1}$H-NMR (DMSO-$d_6$) δ: 8.17 (d, J=5.4 Hz, 1H), 8.03 (s, 1H), 7.84 (d, J=5.4 Hz, 1H), 3.59~3.51 (m, 4H), 3.37~3.27 (m, 4H), 2.87 (m, 3H)
Mass, m/e: 311 (M$^+$), 83 (base)

Production Example 15

In the manner similar to Production Example 1, 3-chloro-1-piperazin-1-ylisoquinoline dihydrochloride was obtained.

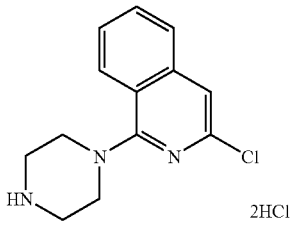

¹H-NMR (DMSO-d₆) δ: 8.08 (d, J=8.5 Hz, 1H), 7.90 (d, J=8.1 Hz, 1H), 7.78~7.75 (m, 1H), 7.64~7.62 (m, 1H), 7.60 (s, 1H), 3.60~3.57 (m, 4H), 3.29 (br s, 4H)

Mass, m/e: 247 (M⁺), 179 (base)

Production Example 16

In the manner similar to Production Example 1, 3-chloro-1-(4-methylpiperazin-1-yl)isoquinoline dihydrochloride was obtained.

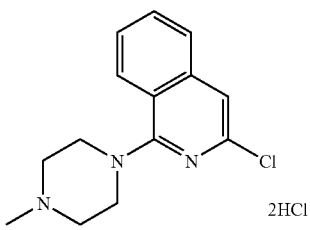

¹H-NMR(CDCl₃) δ: 8.02 (d, J=8.1 Hz, 1H), 7.90 (d, J=8.1 Hz, 1H), 7.79~7.75 (m, 1H), 7.64 (d, J=7.3 Hz, 1H), 7.61 (s, 1H), 3.98~3.52 (m, 4H), 3.52~3.32 (m, 4H), 2.86 (m, 3H)

Mass, m/e: 261 (M⁺), 83 (base)

Production Example 17

In the manner similar to Production Example 1, 7-(4-ethylpiperazin-1-yl)-thieno[2,3-c]pyridine was obtained.

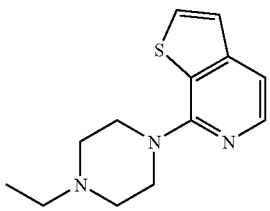

¹H-NMR(CDCl₃) δ: 8.12 (d, J=5.8 Hz, 1H), 7.57 (d, J=5.4 Hz, 1H), 7.31 (d, J=5.4 Hz, 1H), 7.23 (d, J=5.8 Hz, 1H), 3.73 (t, J=5.0 Hz, 4H), 2.67 (t, J=5.0 Hz, 4H), 2.52 (q, J=7.3 Hz, 2H), 1.53 (t, J=7.3 Hz, 3H)

Mass, m/e: 247 (M⁺), 163 (base)

Production Example 18

In the manner similar to Production Example 1, 4-(4-ethylpiperazin-1-yl)thieno[3,2-c]pyridine was obtained.

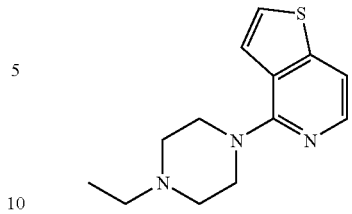

¹H-NMR(CDCl₃) δ: 8.08 (d, J=5.8 Hz, 1H), 7.41~7.33 (m, 3H), 3.59 (t, J=5.0 Hz, 4H), 2.68 (t, J=5.0 Hz, 4H), 2.52 (q, J=7.3 Hz, 2H), 1.15 (t, J=7.3 Hz, 3H)

Mass, m/e: 247 (M⁺), 163 (base)

Production Example 19

In the manner similar to Production Example 1, 5-piperazin-1-yl[1,6]naphthyridine was obtained.

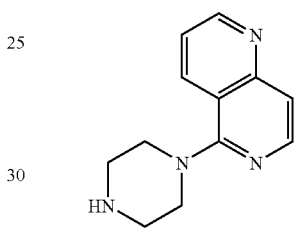

¹H-NMR(CDCl₃) δ: 8.99 (dd, J=1.9 Hz, 4.2 Hz, 1H), 8.39 (dd, J=1.2 Hz, 8.5 Hz, 1H), 8.34 (d, J=6.2 Hz, 1H), 7.48 (d, J=6.2 Hz, 1H), 7.42 (dd, J=4.2 Hz, 8.5 Hz, 1H), 3.42~3.39 (m, 4H), 3.16~3.14 (m, 4H)

Mass, m/e: 214 (M⁺), 146 (base)

Production Example 20

In the manner similar to Production Example 1, 5-(4-methylpiperazin-1-yl)[1,6]naphthyridine was obtained.

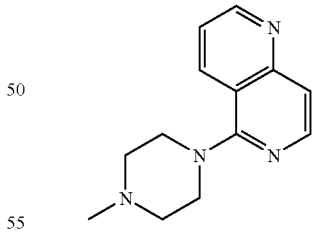

¹H-NMR(CDCl₃) δ: 8.98 (dd, J=1.9 Hz, 4.2 Hz, 1H), 8.39~8.36 (m, 1H), 8.33 (d, J=6.2 Hz, 1H), 7.48 (dd, J=0.8 Hz, 5.8 Hz, 1H), 7.41 (dd, J=4.3 Hz, 5.8 Hz, 1H), 3.49 (t, J=5.0 Hz, 4H), 2.69 (t, J=5.0 Hz, 4H), 2.41 (s, 3H)

Mass, m/e: 228 (M⁺), 158 (base)

Production Example 21

In the manner similar to Production Example 1, 5-(4-ethylpiperazin-1-yl)[1,6]naphthyridine was obtained.

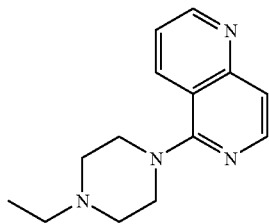

¹H-NMR(CDCl₃) δ:8.97 (dd, J=1.9 Hz, 4.2 Hz, 1H), 8.38~8.35 (m, 1H), 8.32 (d, J=5.8 Hz, 1H), 7.46~7.45 (m, 1H), 7.40 (dd, J=4.2 Hz, 8.5 Hz, 1H), 3.49 (t, J=5.0 Hz, 4H), 2.71 (t, J=5.0 Hz, 4H), 2.54 (q, J=7.3 Hz, 2H), 1.15 (t, J=7.3 Hz, 3H)

Mass, m/e: 242 (M⁺), 158 (base)

Production Example 22

In the manner similar to Production Example 1, 8-piperazin-1-yl[1,7]naphthyridine was obtained.

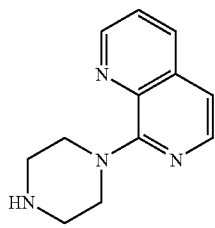

¹H-NMR(CDCl₃) δ: 8.82 (dd, J=1.9 Hz, 4.3 Hz, 1H), 8.13 (d, J=5.4 Hz, 1H), 8.00 (dd, J=1.9 Hz, 8.5 Hz, 1H), 7.47 (dd, J=4.2 Hz, 8.5 Hz, 1H), 7.04 (d, J=5.8 Hz, 1H), 3.93 (t, J=5.0 Hz, 4H), 3.13 (t, J=5.0 Hz, 4H)

Mass, m/e: 214 (M⁺), 146 (base)

Production Example 23

In the manner similar to Production Example 1, 8-(4-methylpiperazin-1yl)[1,7]naphthyridine was obtained.

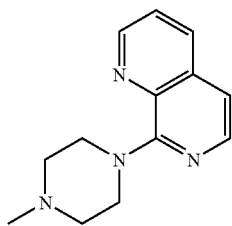

¹H-NMR (CDCl₃) δ: 8.82 (dd, J=1.9 Hz, 4.3 Hz, 1H), 8.12 (d, J=5.8 Hz, 1H), 7.80 (dd, J=1.9 Hz, 8.5 Hz, 1H), 7.47 (dd, J=4.2 Hz, 8.5 Hz, 1H), 7.04 (d, J=5.4 Hz, 1H), 4.01 (br s, 4H), 2.67 (t, J=5.0 Hz, 4H), 2.38 (s, 3H)

Mass, m/e: 228 (M⁺), 158 (base)

Production Example 24

In the manner similar to Production Example 1, 8-(4-ethylpiperazin-1yl)[1,7]naphthyridine was obtained.

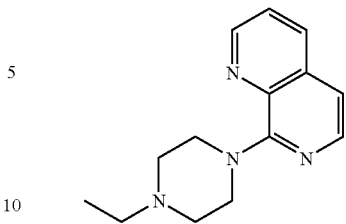

¹H-NMR (CDCl₃) δ: 8.81 (dd, J=1.9 Hz, 4.2 Hz, 1H), 8.16 (d, J=5.4 Hz, 1H), 7.99 (dd, J=1.9 Hz, 8.5 Hz, 1H), 7.47 (dd, J=4.2 Hz, 8.5 Hz, 1H), 7.03 (d, J=5.4 Hz, 1H), 4.03 (t, J=4.6 Hz, 4H), 2.71 (t, J=4.6 Hz, 4H), 2.51 (q, J=7.3 Hz, 2H), 1.15 (t, J=7.3 Hz, 3H)

Mass, m/e: 242 (M⁺), 158 (base)

Production Example 25

In the manner similar to Production Example 1, 2-methylpiperazin-1-ylfuro[3,2-c]pyridine was obtained.

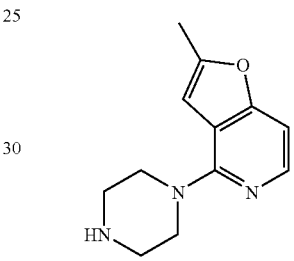

¹H-NMR (CDCl₃) δ: 7.93 (d, J=5.8 Hz, 1H), 6.86 (dd, J=1.2 Hz, 5.8 Hz, 1H), 6.38 (s, 1H), 3.60 (t, J=5.0 Hz, 4H), 3.03 (t, J=5.0 Hz, 4H), 2.43 (d, J=1.2 Hz, 3H)

Mass, m/e: 217 (M⁺), 161 (base)

Production Example 26

In the manner similar to Production Example 1, 7-methoxy-3-methyl-1-piperazin-1-ylisoquinoline was obtained.

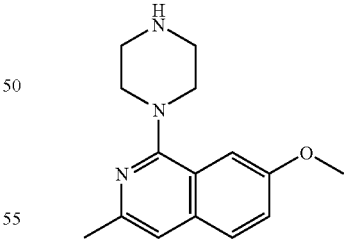

¹H-NMR (CDCl₃) δ: 7.58 (d, J=8.9 Hz, 1H), 7.36 (d, J=2.3 Hz, 1H), 7.23 (dd, J=2.3 Hz, 8.9 Hz, 1H), 7.05 (s, 1H), 3.92 (s, 3H), 3.36~3.32 (m, 4H), 3.18~3.14 (m, 4H), 2.54 (s, 3H)

Mass, m/e: 257 (M⁺), 188 (Base)

Production Example 27

In the manner similar to Production Example 1, 7-methoxy-3,4-dimethyl-1-(4-methylpiperazin-1-yl)isoquinoline was obtained.

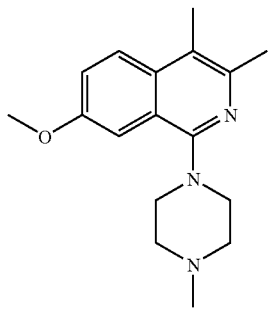

¹H-NMR (CDCl₃) δ: 7.82 (d, J=9.2 Hz, 1H), 7.41 (d, J=2.7 Hz, 1H), 7.27 (dd, J=2.7 Hz, 9.2 Hz, 1H), 3.93 (s, 3H), 3.41~3.34 (m, 4H), 2.73~2.68 (m, 4H), 2.56 (s, 3H), 2.46 (s, 3H), 2.41 (s, 3H)

Mass, m/e: 285 (M⁺), 215 (base), 202

Production Example 28

In the manner similar to Production Example 1, 7-methoxy-4-methyl-1-piperazin-1-ylisoquinoline was obtained.

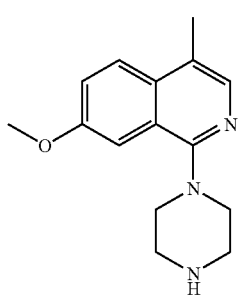

¹H-NMR (CDCl₃) δ: 7.92 (d, J=0.7 Hz, 1H), 7.81 (d, J=9.2 Hz, 1H), 7.49 (d, J=2.7 Hz, 1H), 7.40 (dd, J=2.7 Hz, 9.2 Hz, 1H), 3.95 (s, 3H), 3.31~3.26 (m, 4H), 3.18~3.14 (m, 4H), 2.49 (d, J=0.7 Hz, 3H)

Mass, m/e: 257 (M⁺), 201, 188 (base)

Production Example 29

In the manner similar to Production Example 1, 7-methoxy-4-methyl-1-(4-methylpiperazin-1-yl)isoquinoline was obtained.

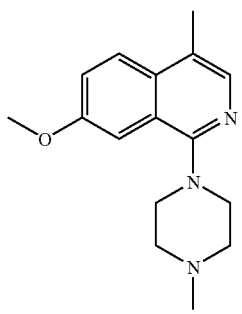

¹H-NMR (CDCl₃) δ: 7.90 (s, 1H), 7.80 (d, J=9.3 Hz, 1H), 7.45 (d, J=2.7 Hz, 1H), 7.33 (dd, J=2.7 Hz, 9.3 Hz, 1H), 3.95 (s, 3H), 3.48~3.39 (m, 4H), 2.75~2.66 (m, 4H), 2.49 (s, 3H), 2.41 (s, 3H)

Mass, m/e: 305 (M⁺), 235, 83 (base)

Production Example 30

In the manner similar to Production Example 1, 7-bromo-1-piperazin-1-ylisoquinoline was obtained.

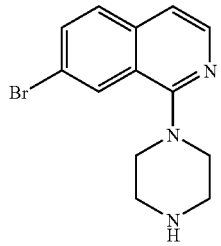

¹H-NMR (CDCl₃) δ: 8.24~8.22 (m, 1H), 8.16 (d, J=5.8 Hz, 1H), 7.67 (dd, J=1.9 Hz, 8.5 Hz, 1H), 7.61 (d, J=8.9 Hz, 1H), 7.26~7.19 (m, 1H), 3.36~3.32 (m, 4H), 3.16~3.12 (m, 4H)

Mass, m/e: 292 (M⁺), 235, 223 (base)

Production Example 31

In the manner similar to Production Example 1, 7-bromo-1-(4-methylpiperazin-1-yl)isoquinoline was obtained.

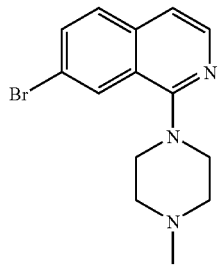

¹H-NMR (CDCl₃) δ: 8.23~8.21 (m, 1H), 8.16 (d, J=5.8 Hz, 1H), 7.67 (dd, J=1.9 Hz, 8.5 Hz, 1H), 7.61 (d, J=8.5 Hz, 1H), 7.20 (dd, J=0.8 Hz, 5.8 Hz), 3.47~3.39 (m, 4H), 2.76~2.26 (m, 4H), 2.41 (s, 3H)

Mass, m/e: 305 (M⁺), 235, 83 (base)

Production Example 32

In the manner similar to Production Example 1, 7-methoxy-1-(4-methylpiperazin-1-yl)isoquinoline was obtained.

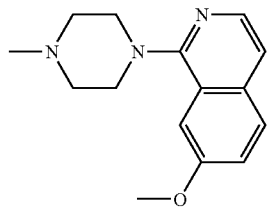

¹H-NMR (CDCl₃) δ: 8.07 (d, J=5.8 Hz, 1H), 7.68 (d, J=8.9 Hz, 1H), 7.39 (d, J=2.7 Hz, 1H), 7.29 (dd, J=2.7 Hz, 8.9 Hz, 1H), 7.22 (d, J=5.8 Hz, 1H), 3.94 (s, 3H), 3.48~3.40 (m, 4H), 2.77~2.69 (m, 4H)

Mass, m/e: 257 (M⁺), 187 (base)

Production Example 33

In the manner similar to Production Example 1, 1-(4-ethylpiperazin-1-yl)-7-methoxyisoquinoline was obtained.

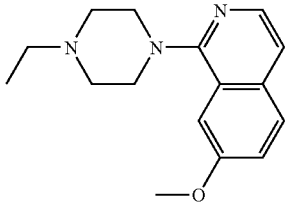

¹H-NMR (CDCl₃) δ: 8.07 (d, J=5.8 Hz, 1H), 7.68 (d, J=8.7 Hz, 1H), 7.40 (d, J=2.5 Hz, 1H), 7.31~7.25 (m, 1H), 7.21 (d, J=5.8 Hz, 1H), 3.48~3.39 (m, 4H), 2.79~2.69 (m, 4H), 2.55 (q, J=7.2 Hz, 2H), 1.17 (t, J=7.2 Hz, 3H)

Mass, m/e: 271 (M⁺), 187 (base)

Production Example 34

In the manner similar to Production Example 1, 7-methoxy-1-piperazin-1-ylisoquinoline was obtained.

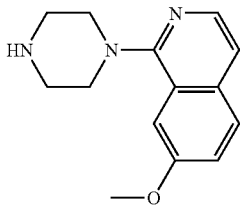

¹H-NMR (CDCl₃) δ: 8.08 (d, J=5.5 Hz, 1H), 7.68 (d, J=9.2 Hz, 1H), 7.42 (d, J=2.6 Hz, 1H), 7.29 (dd, J=2.6 Hz, 9.2 Hz, 1H), 7.23 (d, J=5.5 Hz, 1H), 3.94 (s, 3H), 3.37~3.30 (m, 4H), 3.20~3.13 (m, 4H)

Mass, m/e: 243 (M⁺), 174 (base)

Production Example 35

In the manner similar to Production Example 1, 1-piperazin-1-ylisoquinoline was obtained.

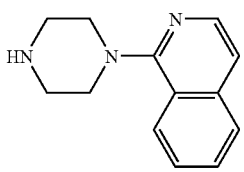

¹H-NMR (CDCl₃) δ: 8.15 (d, J=5.9 Hz, 1H), 8.11 (d, J=8.4 Hz, 1H), 7.75 (d, J=8.1 Hz, 1H), 7.61 (ddd, J=1.1 Hz, 7.0 Hz, 8.1 Hz, 1H), 7.51 (ddd, 1.1 Hz, 7.0 Hz, 8.4 Hz, 1H), 7.25 (d, J=5.9 Hz, 1H), 3.41~3.34 (m, 4H), 3.18~3.13 (m, 4H)

Mass, m/e: 213 (M⁺), 145 (base)

Production Example 36

In the manner similar to Production Example 1, 1-(4-methylpiperazin-1-yl)isoquinoline was obtained.

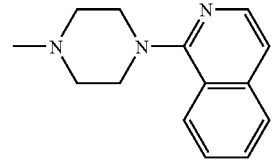

¹H-NMR (CDCl₃) δ: 8.15 (d, J=5.9 Hz, 1H), 8.09 (d, J=8.4 Hz, 1H), 7.75 (d, J=8.1 Hz, 1H), 7.60 (ddd, J=1.1 Hz, 7.0 Hz, 8.1 Hz, 1H), 7.50 (ddd, 1.1 Hz, 7.0 Hz, 8.4 Hz, 1H), 7.24 (d, J=5.9 Hz, 1H), 3.51~3.41 (m, 4H), 2.74~2.66 (m, 4H), 2.42 (s, 3H)

Mass, m/e: 227 (M⁺), 157 (base)

Production Example 37

In the manner similar to Production Example 1, 1-(4-ethylpiperazin-1-yl)isoquinoline was obtained.

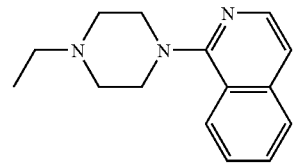

¹H-NMR (CDCl₃) δ: 8.14 (d, J=5.9 Hz, 1H), 8.09 (d, J=8.4 Hz, 1H), 7.74 (d, J=8.1 Hz, 1H), 7.60 (ddd, J=1.1 Hz, 7.0 Hz, 8.1 Hz, 1H), 7.50 (ddd, 1.1 Hz, 7.0 Hz, 8.4 Hz, 1H), 7.23 (d, J=5.9 Hz, 1H), 3.51~3.44 (m, 4H), 2.77~2.69 (m, 4H), 2.55 (q, J=7.3 Hz, 2H), 1.17 (t, J=7.3 Hz, 3H)

Mass, m/e: 241 (M⁺), 157 (base)

Production Example 38

In the manner similar to Production Example 1, 7-methoxy-1-(3-methylpiperazin-1-yl)isoquinoline was obtained.

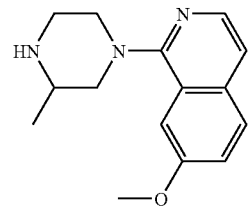

¹H-NMR (CDCl₃) δ: 8.07 (d, J=5.8 Hz, 1H), 7.68 (d, J=8.9 Hz, 1H), 7.40 (d, J=2.7 Hz, 1H), 7.29 (dd, J=2.7 Hz, 8.9 Hz, 1H), 7.23 (d, J=5.8 Hz, 1H), 3.94 (s, 3H), 3.70~3.62 (m, 2H), 3.30~3.17 (m, 3H), 3.08~2.99 (m, 1H), 2.80~2.71 (m, 1H), 1.20 (d, J=6.6 Hz, 3H)

Mass, m/e: 257 (M⁺), 175 (base)

Production Example 39

In the manner similar to Production Example 1, 1-(3,5-dimethylpiperazin-1-yl)-7-methoxyisoquinoline was obtained.

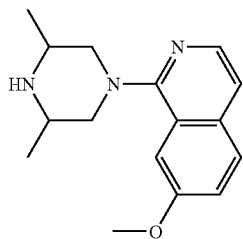

$^1$H-NMR (CDCl$_3$) δ: 8.07 (d, J=5.8 Hz, 1H), 7.68 (d, J=8.9 Hz, 1H), 7.40 (d, J=2.7 Hz, 1H), 7.29 (dd, J=2.7 Hz, 8.9 Hz, 1H), 7.21 (d, J=5.8 Hz, 1H), 3.93 (s, 3H), 3.70~3.62 (m, 2H), 3.33~3.23 (m, 2H), 2.66~2.57 (m, 2H), 1.17 (d, J=6.6 Hz, 6H)

Mass, m/e: 271 (M$^+$), 187 (base)

Production Example 40

In the manner similar to Production Example 1, 6-methoxy-1-piperazin-1-ylisoquinoline was obtained.

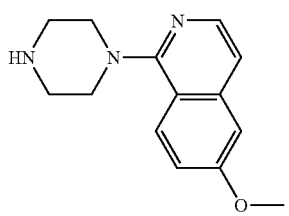

$^1$H-NMR (CDCl$_3$) δ: 8.10 (d, J=5.9 Hz, 1H), 8.01 (d, J=9.2 Hz, 1H), 7.16 (d, J=5.9 Hz, 1H), 7.13 (dd, J=2.6 Hz, 9.2 Hz, 1H), 7.02 (d, J=2.6 Hz, 1H), 3.93 (s, 3H), 3.38~3.32 (m, 4H), 3.18~3.12 (m, 4H)

Mass, m/e: 243 (M$^+$), 187 (base)

Production Example 41

In the manner similar to Production Example 1, 6-methoxy-1-(4-methylpiperazin-1-yl)isoquinoline was obtained.

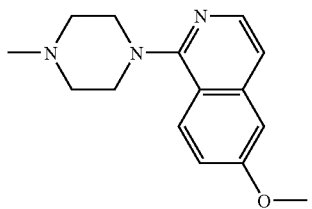

$^1$H-NMR (CDCl$_3$) δ: 8.09 (d, J=5.9 Hz, 1H), 7.99 (d, J=9.2 Hz, 1H), 7.15 (d, J=5.9 Hz, 1H), 7.12 (dd, J=2.6 Hz, 9.2 Hz, 1H), 7.02 (d, J=2.6 Hz, 1H), 3.93 (s, 3H), 3.48~3.38 (m, 4H), 2.74~2.64 (m, 4H), 2.41 (s, 3H)

Mass, m/e: 257 (M$^+$), 187 (base)

Production Example 42

In the manner similar to Production Example 1, 1-(4-ethylpiperazin-1-yl)-6-methoxyisoquinoline was obtained.

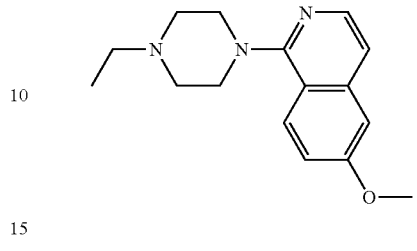

$^1$H-NMR (CDCl$_3$) δ: 8.09 (d, J=5.9 Hz, 1H), 7.99 (d, J=9.2 Hz, 1H), 7.14 (d, J=5.9 Hz, 1H), 7.11 (dd, J=2.6 Hz, 9.2 Hz, 1H), 7.01 (d, J=2.6 Hz, 1H), 3.93 (9s, 3H), 3.48~3.38 (m, 4H), 2.76~2.67 (m, 4H), 2.55 (q, J=7.3 Hz, 2H), 1.16 (t, J=7.3 Hz, 3H)

Mass, m/e: 271 (M$^+$), 187 (base)

Production Example 43

In the manner similar to Production Example 1, 5-methoxy-1-piperazin-1-ylisoquinoline was obtained.

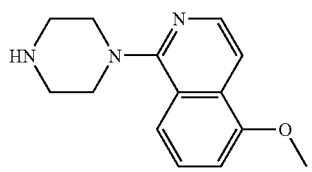

$^1$H-NMR (CDCl$_3$) δ: 8.16 (d, J=6.2 Hz, 1H), 7.67 (d, J=8.5 Hz, 1H), 7.63 (dd, J=0.8 Hz, 5.8 Hz, 1H), 7.41 (t, J=7.7 Hz, 1H), 6.94 (d, J=7.7 Hz, 1H), 3.99 (s, 3H), 3.39~3.31 (m, 4H), 3.18~3.11 (m, 4H)

Mass, m/e: 243 (M$^+$), 174 (base)

Production Example 44

In the manner similar to Production Example 1, 5-methoxy-1-(4-methylpiperazin-1-yl)isoquinoline was obtained.

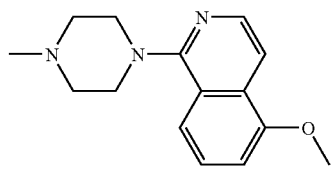

$^1$H-NMR (CDCl$_3$) δ: 8.16 (d, J=5.8 Hz, 1H), 7.65 (dd, J=0.8 Hz, 8.5 Hz, 1H), 7.62 (dd, J=0.8 Hz, 5.8 Hz, 1H), 7.41 (t, J=7.7 Hz, 1H), 6.94 (d, J=7.7 Hz, 1H), 3.98 (s, 3H), 3.50~3.38 (m, 4H), 2.74~2.63 (m, 4H), 2.41 (s, 3H)

Mass, m/e: 257 (M$^+$), 187 (base)

Production Example 45

In the manner similar to Production Example 1, 1-(4-ethylpiperazin-1-yl)-5-methoxyisoquinoline was obtained.

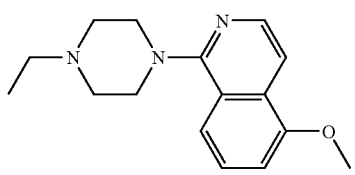

¹H-NMR (CDCl₃) δ: 8.15 (d, J=5.8 Hz, 1H), 7.65 (d, J=8.5 Hz, 1H), 7.62 (d, J=5.8 Hz, 1H), 7.40 (t, J=7.7 Hz, 1H), 6.93 (d, J=7.7 Hz, 1H), 3.98 (s, 3H), 3.50~3.40 (m, 4H), 2.77~2.68 (m, 4H), 2.55 (q, J=7.3 Hz, 2H), 1.16 (t, J=7.3 Hz, 3H)

Mass, m/e: 271 (M⁺), 187 (base)

Production Example 46

In the manner similar to Production Example 1, 7-methyl-1-piperazin-1-ylisoquinoline was obtained.

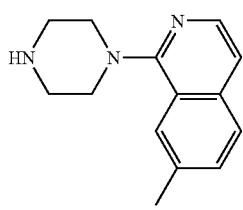

¹H-NMR (CDCl₃) δ: 8.10 (d, J=5.8 Hz, 1H), 7.88 (s, 1H), 7.66 (d, J=8.1 Hz, 1H), 7.45 (dd, J=1.5 Hz, 8.1 Hz, 1H), 7.22 (d, J=5.8 Hz, 1H), 3.39~3.32 (m, 4H), 3.20~3.13 (m, 4H)

Mass, m/e: 227 (M⁺), 159 (base)

Production Example 47

In the manner similar to Production Example 1, 7-methyl-1-(4-methylpiperazin-1-yl)isoquinoline was obtained.

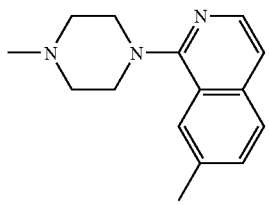

¹H-NMR (CDCl₃) δ: 8.09 (d, J=5.8 Hz, 1H), 7.85 (s, 1H), 7.65 (d, J=8.5 Hz, 1H), 7.44 (dd, J=1.5 Hz, 8.5 Hz, 1H), 7.21 (d, J=5.8 Hz, 1H), 3.51~3.38 (m, 4H), 2.77~2.64 (m, 4H), 2.54 (s, 3H), 2.42 (s, 3H)

Mass, m/e: 241 (M⁺), 171 (base)

Production Example 48

In the manner similar to Production Example 1, 1-(4-ethylpiperazin-1-yl)-7-methylisoquinoline was obtained.

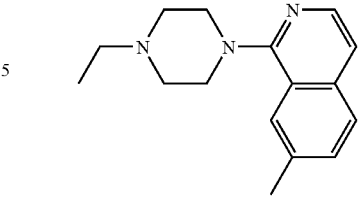

¹H-NMR (CDCl₃) δ: 8.09 (d, J=5.8 Hz, 1H), 7.85 (s, 1H), 7.65 (d, J=8.5 Hz, 1H), 7.44 (dd, J=1.5 Hz, 8.5 Hz, 1H), 7.20 (d, J=5.8 Hz, 1H), 3.50~3.40 (m, 4H), 2.80~2.69 (m, 4H), 2.59~2.52 (m, 5H), 1.17 (t, J=7.3 Hz, 3H)

Mass, m/e: 255 (M⁺), 171 (base)

Production Example 49

In the manner similar to Production Example 1, 7-chloro-1-piperazin-1-ylisoquinoline was obtained.

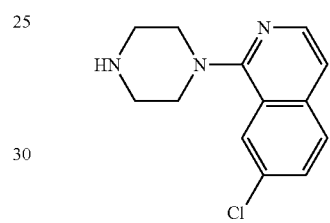

¹H-NMR (CDCl₃) δ: 8.16 (d, J=5.8 Hz, 1H), 8.07 (d, J=1.9 Hz, 1H), 7.70 (d, J=8.5 Hz, 1H), 7.55 (dd, J=1.9 Hz, 8.5 Hz, 1H), 7.23 (d, J=5.8 Hz, 1H), 3.41~3.33 (m, 4H), 3.20~3.14 (m, 4H)

Mass, m/e: 247 (M⁺), 179 (base)

Production Example 50

In the manner similar to Production Example 1, 7-chloro-1-(4-methylpiperazin-1-yl)isoquinoline was obtained.

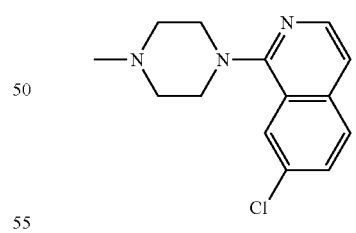

¹H-NMR (CDCl₃) δ: 8.15 (d, J=5.8 Hz, 1H), 8.05 (d, J=1.9 Hz, 1H), 7.70 (d, J=8.5 Hz, 1H), 7.55 (dd, J=1.9 Hz, 8.5 Hz, 1H), 7.22 (d, J=5.8 Hz, 1H), 3.48~3.40 (m, 4H), 2.77~2.70 (m, 4H), 2.42 (s, 3H)

Mass, m/e: 261 (M⁺), 83 (base)

Production Example 51

In the manner similar to Production Example 1, 7-chloro-1-(4-ethylpiperazin-1-yl)isoquinoline was obtained.

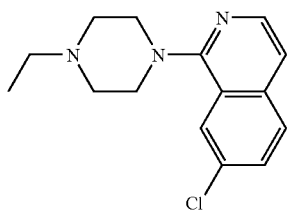

¹H-NMR (CDCl₃) δ: 8.15 (d, J=5.8 Hz, 1H), 8.05 (d, J=1.9 Hz, 1H), 7.70 (d, J=8.5 Hz, 1H), 7.55 (dd, J=1.9 Hz, 8.5 Hz, 1H), 7.21 (d, J=5.8 Hz, 1H), 3.49~3.40 (m, 4H), 2.79~2.69 (m, 4H), 2.56 (q, J=7.3 Hz, 2H), 1.17 (t, J=7.3 Hz, 3H)

Mass, m/e: 275 (M⁺), 97 (base)

Production Example 52

In the manner similar to Production Example 1, 7-fluoro-1-(4-methylpiperazin-1-yl)isoquinoline was obtained.

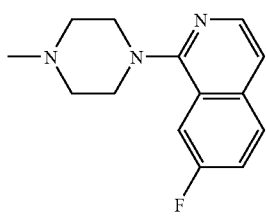

¹H-NMR (CDCl₃) δ: 8.14 (d, J=5.8 Hz, 1H), 7.78~7.73 (m, 1H), 7.73~7.66 (m, 1H), 7.42~7.35 (m, 1H), 7.24 (d, J=5.8 Hz, 1H), 3.48~3.37 (m, 4H), 2.76~2.64 (m, 4H), 2.42 (s, 3H)

Mass, m/e: 245 (M⁺), 175 (base)

Production Example 53

In the manner similar to Production Example 1, 1-(4-ethylpiperazin-1-yl)-7-fluoroisoquinoline was obtained.

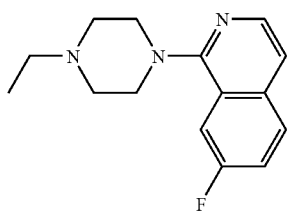

¹H-NMR (CDCl₃) δ: 8.14 (d, J=5.8 Hz, 1H), 7.78~7.73 (m, 1H), 7.73~7.67 (m, 1H), 7.42~7.36 (m, 1H), 7.24 (d, J=5.8 Hz, 1H), 3.49~3.39 (m, 4H), 2.79~2.70 (m, 4H), 2.56 (q, J=7.3 Hz, 2H), 1.17 (t, J=7.3 Hz, 3H)

Mass, m/e: 259 (M⁺), 175 (base)

Production Example 54

In the manner similar to Production Example 1, 1-(4-methylpiperazin-1-yl)-7-phenylisoquinoline was obtained.

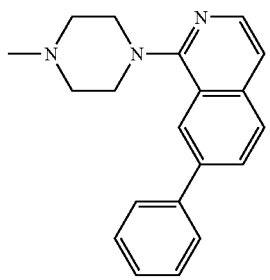

¹H-NMR (CDCl₃) δ: 8.30~8.27 (m, 1H), 8.16 (d, J=5.8 Hz, 1H), 7.90~7.80 (m, 2H), 7.72~7.67 (m, 2H), 7.55~7.48 (m, 2H), 7.44~7.39 (m, 1H), 7.29~7.25 (m, 1H), 3.55~3.49 (m, 4H), 2.76~2.66 (m, 4H), 2.42 (s, 3H)

Mass, m/e: 303 (M⁺), 233 (base)

Production Example 55

In the manner similar to Production Example 1, 1-(4-ethylpiperazin-1-yl)-7-phenylisoquinoline was obtained.

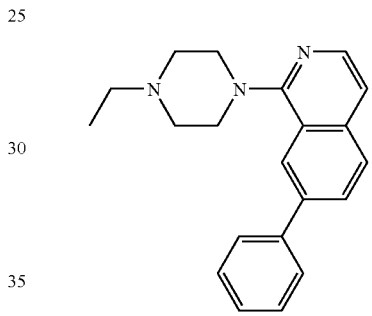

¹H-NMR (CDCl₃) δ: 8.30~8.27 (m, 1H), 8.16 (d, J=5.8 Hz, 1H), 7.89~7.80 (m, 2H), 7.72~7.67 (m, 2H), 7.55~7.49 (m, 2H), 7.44~7.39 (m, 1H), 7.28~7.24 (m, 1H), 3.58~3.48 (m, 4H), 2.81~2.72 (m, 4H), 2.56 (q, J=7.3 Hz, 2H), 1.17 (t, J=7.3 Hz, 3H)

Mass, m/e: 317 (M⁺), 233 (base)

Production Example 56

In the manner similar to Production Example 1, 7-phenyl-1-piperazin-1-ylisoquinoline was obtained.

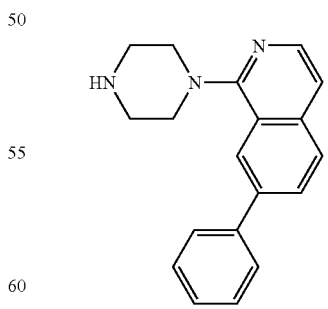

¹H-NMR (CDCl₃) δ: 8.30 (s, 1H), 8.16 (d, J=5.8 Hz, 1H), 7.90~7.80 (m, 2H), 7.72~7.67 (m, 2H), 7.54~7.48 (m, 2H), 7.44~7.39 (m, 1H), 7.28 (d, J=5.8 Hz, 1H), 3.47~3.38 (m, 4H), 3.21~3.14 (m, 4H)

Mass, m/e: 289 (M⁺), 220 (base)

Production Example 57

In the manner similar to Production Example 1, 6-chloro-1-piperazin-1-ylisoquinoline was obtained.

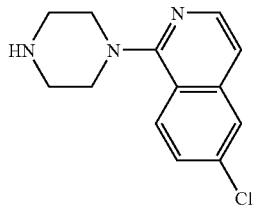

¹H-NMR (CDCl₃) δ: 8.16 (d, J=5.8 Hz, 1H), 8.03 (d, J=8.9 Hz, 1H), 7.73 (d, J=1.9 Hz, 1H), 7.44 (dd, J=1.9 Hz, 8.9 Hz, 1H), 7.16 (d, J=5.8 Hz, 1H), 3.40~3.34 (m, 4H), 3.17~3.12 (m, 4H)

Mass, m/e: 247 (M⁺), 179 (base)

Production Example 58

In the manner similar to Production Example 1, 6-chloro-1-(4-methylpiperazin-1-yl)isoquinoline was obtained.

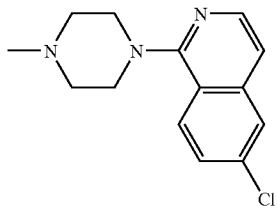

¹H-NMR (CDCl₃) δ: 8.15 (d, J=5.8 Hz, 1H), 8.01 (d, J=8.9 Hz, 1H), 7.72 (d, J=1.9 Hz, 1H), 7.43 (dd, J=1.9 Hz, 8.9 Hz, 1H), 7.14 (d, J=5.8 Hz, 1H), 3.45 (t, J=4.6 Hz, 4H), 2.69 (t, J=4.6 Hz, 4H), 2.41 (s, 3H)

Mass, m/e: 261 (M⁺), 83 (base)

Production Example 59

In the manner similar to Production Example 1, 6-chloro-1-(4-ethylpiperazin-1-yl)isoquinoline was obtained.

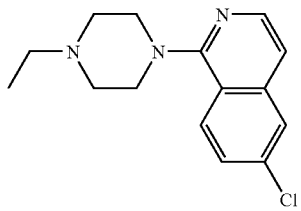

¹H-NMR (CDCl₃) δ: 8.15 (d, J=5.8 Hz, 1H), 8.01 (d, J=8.9 Hz, 1H), 7.72 (d, J=1.9 Hz, 1H), 7.42 (dd, J=1.9 Hz, 8.9 Hz, 1H), 7.14 (d, J=5.8 Hz, 1H), 3.46 (t, J=4.6 Hz, 4H), 2.72 (t, J=4.6 Hz, 4H), 2.55 (q, J=7.3 Hz, 2H), 1.16 (t, J=7.3 Hz, 3H)

Mass, m/e: 275 (M⁺), 83 (base)

Production Example 60

In the manner similar to Production Example 1, 5-chloro-1-piperazin-1-ylisoquinoline was obtained.

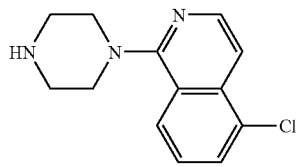

¹H-NMR (CDCl₃) δ: 8.25 (d, J=5.8 Hz, 1H), 8.04 (td, J=1.2 Hz, 8.5 Hz, 1H), 7.69 (dd, J=1.2 Hz, 7.3 Hz, 1H), 7.64 (dd, J=1.2 Hz, 5.8 Hz, 1H), 7.42 (dd, J=7.3 Hz, 8.5 Hz, 1H), 3.41~3.35 (m, 4H), 3.18~3.13 (m, 4H)

Mass, m/e: 247 (M⁺), 179 (base)

Production Example 61

In the manner similar to Production Example 1, 5-chloro-1-(4-methylpiperazin-1-yl)isoquinoline was obtained.

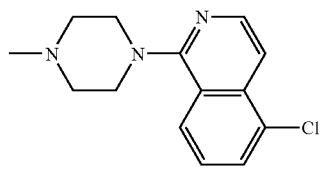

¹H-NMR (CDCl₃) δ: 8.24 (d, J=5.8 Hz, 1H), 8.02 (d, J=8.5 Hz, 1H), 7.68 (dd, J=1.2 Hz, 7.3 Hz, 1H), 7.62 (dd, J=1.2 Hz, 5.8 Hz, 1H), 7.41 (dd, J=7.3 Hz, 8.5 Hz, 1H), 3.45 (t, J=4.6 Hz, 4H), 2.69 (t, J=4.6 Hz, 4H), 2.41 (s, 3H)

Mass, m/e: 261 (M⁺), 83 (base)

Production Example 62

In the manner similar to Production Example 1, 5-chloro-1-(4-ethylpiperazin-1-yl)isoquinoline was obtained.

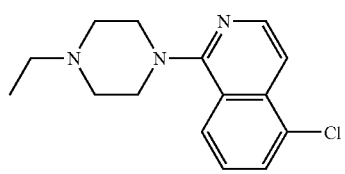

¹H-NMR (CDCl₃) δ: 8.24 (d, J=5.8 Hz, 1H), 8.02 (d, J=8.5 Hz, 1H), 7.68 (dd, J=0.8 Hz, 7.3 Hz, 1H), 7.61 (d, J=6.2 Hz, 1H), 7.40 (t, J=8.1 Hz, 1H), 3.47 (t, J=4.6 Hz, 4H), 2.73 (t, J=4.6 Hz, 4H), 2.55 (q, J=7.3 Hz, 2H), 1.16 (t, J=7.3 Hz, 3H)

Mass, m/e: 275 (M⁺), 97 (base)

Production Example 63

In the manner similar to Production Example 1, 7-fluoro-1-piperazin-1-ylisoquinoline was obtained.

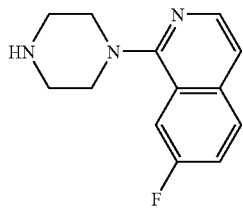

¹H-NMR (CDCl₃) δ: 8.14 (d, J=5.8 Hz, 1H), 7.79~7.69 (m, 2H), 7.43~7.37 (m, 1H), 7.27~7.24 (m, 1H), 3.38~3.32 (m, 4H), 3.19~3.14 (m, 4H)
Mass, m/e: 231 (M⁺), 163 (base)

Production Example 64

In the manner similar to Production Example 1, 1-(2,5-diazabicyclo[2.2.2]octan-1-yl)-7-methoxyisoquinoline was obtained.

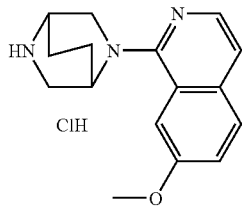

¹H-NMR (DMSO-d₆) δ: 7.97 (d, J=8.9 Hz, 1H), 7.79 (d, J=6.2 Hz, 1H), 7.59 (d, J=8.9 Hz, 1H), 7.48 (s, 1H), 7.42 (d, J=6.2 Hz, 1H), 4.63 (br s, 1H), 4.42~4.31 (m, 1H), 4.10~3.98 (m, 1H), 3.96 (s, 3H), 3.96~3.27 (m, 3H), 2.48~2.37 (m, 1H), 2.28~2.13 (m, 1H), 2.08~1.92 (m, 2H)
Mass, m/e: 269 (M⁺), 175 (base)

Production Example 65

In the manner similar to Production Example 1, 7-chloro-1-[4-[4-(3-methoxyphenyl)butyl]piperazin-1-yl]isoquinoline was obtained.

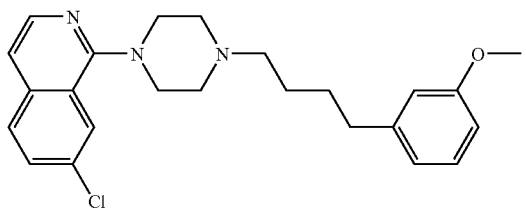

¹H-NMR (CDCl₃) δ: 8.15 (d, J=5.8 Hz, 1H), 8.06 (m, 1H), 7.67 (d, J=8.9 Hz, 1H), 7.56 (d, J=1.9 Hz, 1H), 7.52 (d, J=2.3 Hz, 1H), 7.26 (t, J=3.9 Hz, 1H), 6.82 (d, J=7.7 Hz, 1H), 6.75~6.69 (m, 2H), 3.86 (s, 3H), 3.39 (t, J=5.0 Hz, 4H), 2.69 (t, J=4.8 Hz, 4H), 2.59 (t, J=7.0 Hz, 2H), 2.41 (t, J=7.5 Hz, 2H), 1.75~1.50 (m, 4H)
Mass, m/e: 409 (M⁺), 191 (base), 121, 107

Production Example 66

In the manner similar to Production Example 1, 7-methoxy-1-[4-[4-(3-methoxyphenyl)butyl]piperazin-1-yl]-isoquinoline was obtained.

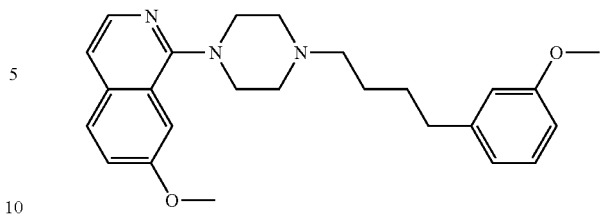

¹H-NMR (CDCl₃) δ: 8.17 (d, J=5.9 Hz, 1H), 8.08 (s, 1H), 7.20 (d, J=8.9 Hz, 1H), 7.13 (d, J=1.9 Hz, 1H), 7.10 (d, J=2.3 Hz, 1H), 7.04 (t, J=3.9 Hz, 1H), 6.80 (d, J=7.6 Hz, 1H), 6.79~6.65 (m, 2H) 3.96 (s, 3H), 3.89 (s, 3H), 3.42 (t, J=4.8 Hz, 4H), 2.73 (t, J=4.8 Hz, 4H), 2.63 (t, J=6.9 Hz, 2H), 2.43 (t, J=7.5 Hz, 2H), 1.78~1.47 (m, 4H)
Mass, m/e: 405 (M⁺), 187 (base), 121, 107

Production Example 67

In the manner similar to Production Example 1, 7-chloro-1-[4-[trans-4-(3-methoxyphenyl)cyclohexan-1-yl]piperazin-1-yl]isoquinoline was obtained.

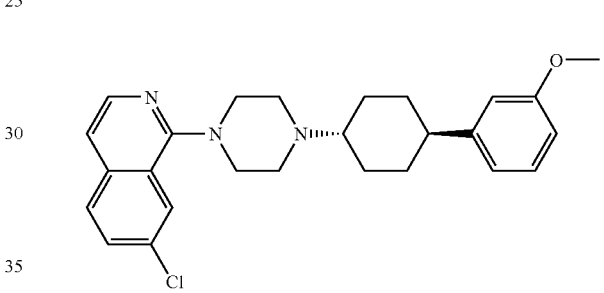

¹H-NMR (CDCl₃) δ: 8.14 (d, J=5.8 Hz, 1H), 8.03 (m, 1H), 7.69 (d, J=8.9 Hz, 1H), 7.55 (d, J=1.9 Hz, 1H), 7.53 (d, J=1.9 Hz, 1H), 7.22 (d, J=5.9 Hz, 1H), 6.81 (d, J=7.7 Hz, 1H), 6.76~6.72 (m, 2H), 3.80 (s, 3H), 3.59 (t, J=5.0 Hz, 4H), 2.97 (t, J=4.8 Hz, 4H), 2.53~2.47 (m, 2H), 2.21~2.10 (m, 4H), 2.09~2.00 (m, 4H)
Mass, m/e: 435 (M⁺), 420, 191 (base), 121, 107

Production Example 68

In the manner similar to Production Example 1, 7-methoxy-1-[4-[trans-4-(3-methoxyphenyl)cyclohexan-1-yl]-piperazin-1-yl]isoquinoline was obtained.

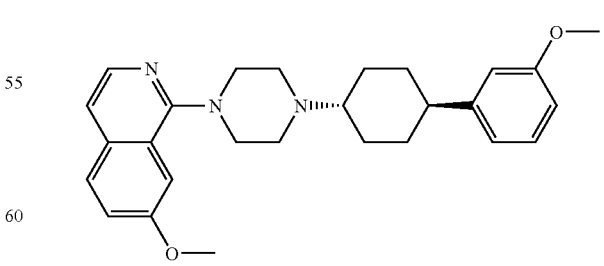

¹H-NMR (CDCl₃) δ: 8.08 (d, J=5.7 Hz, 1H), 8.00 (d, J=9.3 Hz, 1H), 7.20 (d, J=5.7 Hz, 1H), 7.14 (d, J=5.7 Hz, 1H), 7.11 (dd, J=2.7 Hz, 9.3 Hz, 1H), 7.01 (d, J=2.7 Hz, 1H), 6.82 (d, J=7.3 Hz, 1H), 6.78~6.72 (m, 2H), 3.92 (s, 3H), 3.80 (s, 3H), 3.43 (m, 4H), 2.87 (t, J=4.4 Hz, 4H), 2.50~2.47 (m, 2H), 2.16~2.10 (m, 4H), 2.06~1.98 (m, 4H)

Mass, m/e: 431 (M⁺), 416, 187 (base), 121

Production Example 69

In the manner similar to Production Example 1, 1-[4-(2,3-dihydrobenzo[1,4]dioxan-2-ylmethyl)piperazin-1-yl]-7-methoxyisoquinoline was obtained.

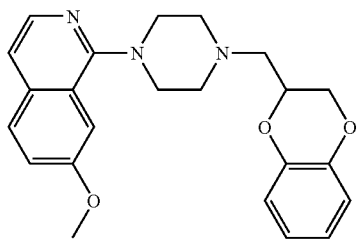

¹H-NMR (CDCl₃) δ: 8.06 (d, J=5.7 Hz, 1H), 7.66 (d, J=9.0 Hz, 1H), 7.39 (d, J=2.3 Hz, 1H), 7.22 (d, J=5.4 Hz, 1H), 7.28 (dd, J=2.3 Hz, 8.8 Hz, 1H), 6.89 (dd, J=4.6 Hz, 9.6 Hz, 1H), 6.84 (dd, J=3.4 Hz, 5.8 Hz, 1H), 4.41~4.35 (m, 2H), 4.05 (dd, J=7.4 Hz, 11.2 Hz, 1H), 3.94 (s, 3H), 3.41 (t, J=4.5 Hz, 4H), 2.92~2.85 (m, 2H), 2.83~2.73 (m, 4H)

Mass, m/e: 391 (M⁺), 376, 282, 187 (base), 174

Production Example 70

In the manner similar to Production Example 1, 1-[1,4]diazepan-1-yl-7-methoxyisoquinoline was obtained.

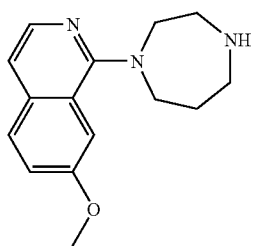

¹H-NMR (CDCl₃) δ: 8.02~7.99 (m, 2H), 7.11~7.09 (m, 2H), 7.00 (d, J=2.3 Hz, 1H), 3.92 (s, 3H), 3.76 (t, J=5.4 Hz, 2H), 3.72 (t, J=5.8 Hz, 2H), 3.27 (t, J=5.4 Hz, 2H), 3.16 (t, J=5.7 Hz, 2H), 2.75 (br s, 1H), 2.00~1.95 (m, 2H)

Mass, m/e: 257 (M⁺), 242, 201, 187 (base)

Production Example 71

In the manner similar to Production Example 1, 1-(4-benzo[1,3]dioxol-5-ylmethylpiperazin-1-yl)-7-methoxyisoquinoline was obtained.

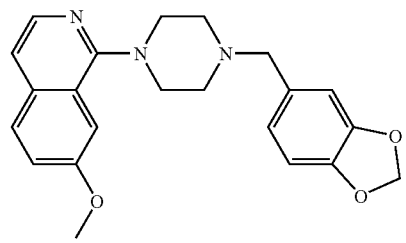

¹H-NMR (CDCl₃) δ: 8.07 (d, J=5.8 Hz, 1H), 7.97 (d, J=9.3 Hz, 1H), 7.13 (d, J=5.8 Hz, 1H), 7.09 (dd, J=2.7 Hz, 9.3 Hz, 1H), 7.00 (d, J=2.7 Hz, 1H), 6.91 (s, 1H), 6.77 (t, J=7.2 Hz, 2H), 5.94 (s, 2H), 3.91 (s, 3H), 3.53 (s, 2H), 3.39 (m, 4H), 2.69 (t, J=4.5 Hz, 4H)

Mass, m/e: 377 (M⁺), 187 (base), 174, 135

Production Example 72

In the manner similar to Production Example 1, 1-((8aS)-octahydropyrrolo[1,2-a]pyrazin-2-yl)-7-methoxyisoquinoline was obtained.

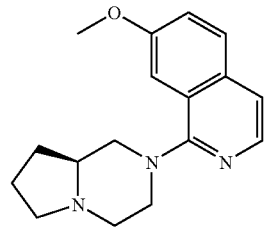

¹H-NMR (CDCl₃) δ: 8.07 (d, J=5.4 Hz, 1H), 7.68 (d, J=8.9 Hz, 1H), 7.40 (d, J=2.7 Hz, 1H), 7.29 (dd, J=2.3 Hz, 8.9 Hz, 1H), 7.21 (d, J=5.4 Hz, 1H), 3.94 (s, 3H), 3.87~3.84 (m, 1H), 3.79~3.75 (m, 2H), 3.22~3.16 (m, 2H), 2.93~2.88 (m, 1H), 2.64~2.58 (m, 1H), 2.40~2.38 (m, 1H), 2.29 (q, J=8.5 Hz, 1H), 1.94~1.76 (m, 3H), 1.65~1.52 (m, 1H)

Mass, m/e: 283 (M⁺), 96 (base)

Production Example 73

In the manner similar to Production Example 1, 7-chloro-1-((8aS)-octahydropyrrolo[1,2-a]pyrazin-2-yl)isoquinoline was obtained.

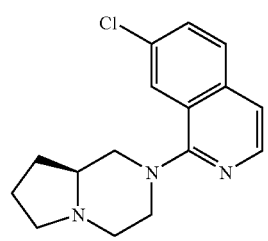

¹H-NMR (CDCl₃) δ: 8.14 (d, J=5.8 Hz, 1H), 8.04 (d, J=2.3 Hz, 1H), 7.68 (d, J=8.9 Hz, 1H), 7.55~7.52 (m, 1H), 7.19 (d, J=5.4 Hz, 1H), 3.87~3.83 (m, 1H), 3.78~3.73 (m, 1H), 3.24~3.16 (m, 3H), 2.93~2.87 (m, 1H), 2.63~2.60 (m, 1H), 2.38~2.25 (m, 2H), 1.93~1.83 (m, 3H), 1.63~1.51 (m, 1H)

Mass, m/e: 287 (M⁺), 96 (base)

Production Example 74

In the manner similar to Production Example 1, 8-((8aS)-octahydropyrrolo[1,2-a]pyrazin-2-yl)-1,7-naphthyridine was obtained.

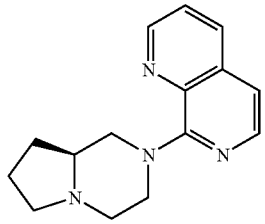

$^1$H-NMR (CDCl$_3$) δ: 8.83 (dd, J=1.9 Hz, 4.2 Hz, 1H), 8.13 (d, J=5.4 Hz, 1H), 8.01 (dd, J=1.9 Hz, 8.5 Hz, 1H), 7.48 (dd, J=4.3 Hz, 8.5 Hz, 1H), 7.04 (d, J=5.4 Hz, 1H), 4.96~4.90 (m, 2H), 3.32~3.25 (m, 1H), 3.19~3.15 (m, 2H), 2.97~2.92 (m, 1H), 2.62~2.56 (m, 1H), 2.34~2.33 (m, 1H), 2.25 (q, J=8.9 Hz, 1H), 1.96~1.85 (m, 2H), 1.82~1.75 (m, 1H), 1.56~1.50 (m, 1H)

Mass, m/e: 254 (M$^+$), 96 (base)

Production Example 75

In the manner similar to Production Example 1, 5-((8aS)-octahydropyrrolo[1,2-a]pyrazin-2-yl)-1,6-naphthyridine was obtained.

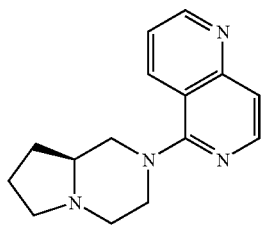

$^1$H-NMR (CDCl$_3$) δ: 8.98 (dd, J=1.9 Hz, 4.2 Hz, 1H), 8.40~8.37 (m, 1H), 8.33 (d, J=5.8 Hz, 1H), 7.47~7.40 (m, 2H), 3.93 (td, J=2.3 Hz, 8.3 Hz, 1H), 3.82 (dd, J=2.7 Hz, 11.8 Hz, 1H), 3.32~3.25 (m, 1H), 3.21~3.16 (m, 2H), 2.97~2.93 (m, 1H), 2.59 (dt, J=2.7 Hz, 11.2 Hz, 1H), 2.37~2.25 (m, 2H), 1.94~1.75 (m, 3H), 1.55~1.50 (m, 1H)

Mass, m/e: 254 (M$^+$), 96 (base)

Production Example 76

In the manner similar to Production Example 1, 7-chloro-1-((8aR)-octahydropyrrolo[1,2-a]pyrazin-2-yl)isoquinoline was obtained.

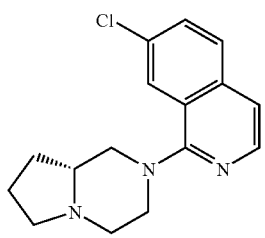

$^1$H-NMR (CDCl$_3$) δ: 8.15 (d, J=5.8 Hz, 1H), 8.06 (d, J=1.9 Hz, 1H), 7.69 (d, J=8.9 Hz, 1H), 7.55 (dd, J=1.9 Hz, 8.9 Hz, 1H), 7.21 (d, J=5.8 Hz, 1H), 3.86 (td, J=2.3 Hz, 11.6 Hz, 1H), 3.80~3.75 (m, 1H), 3.25~3.17 (m, 3H), 2.94~2.88 (m, 1H), 2.65~2.59 (m, 1H), 2.39~2.34 (m, 1H), 2.28 (t, J=8.9 Hz, 1H), 1.95~1.84 (m, 2H), 1.84~1.75 (m, 1H), 1.55~1.48 (m, 1H)

Mass, m/e: 287 (M$^+$), 96 (base)

Production Example 77

In the manner similar to Production Example 1, 1-((8aR)-octahydropyrrolo[1,2-a]pyrazin-2-yl)-7-methoxyisoquinoline was obtained.

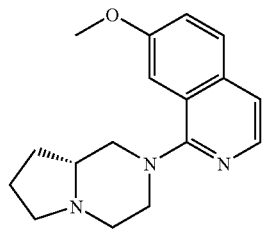

$^1$H-NMR (CDCl$_3$) δ: 8.06 (d, J=5.8 Hz, 1H), 7.66 (dd, J=3.4 Hz, 8.9 Hz, 1H), 7.39 (d, J=2.3 Hz, 1H), 7.27 (dd, J=2.3 Hz, 8.9 Hz, 1H), 7.19 (d, J=5.4 Hz, 1H), 3.93 (s, 3H), 3.85 (td, J=2.3 Hz, 12.0 Hz, 1H), 3.77~3.74 (m, 1H), 3.20~3.15 (m, 3H), 2.89 (t, J=10.8 Hz, 1H), 2.60 (t, J=11.2 Hz, 1H), 2.39~2.37 (m, 1H), 2.32~2.25 (m, 1H), 1.93~1.83 (m, 2H), 1.80~1.76 (m, 1H), 1.59~1.51 (m, 1H)

Mass, m/e: 283 (M$^+$), 96 (base)

Production Example 78

In the manner similar to Production Example 1, 3-chloro-1-((8aS)-octahydropyrrolo[1,2-a]pyrazin-2-yl)isoquinoline was obtained.

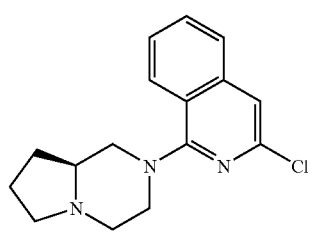

$^1$H-NMR (CDCl$_3$) δ: 8.00 (d, J=8.5 Hz, 1H), 7.64 (d, J=7.7 Hz, 1H), 7.60~7.56 (m, 1H), 7.46~7.42 (m, 1H), 7.22 (s, 1H), 3.99 (td, J=2.3 Hz, 12.3 Hz, 1H), 3.93~3.89 (m, 1H), 3.24 (dt, J=2.7 Hz, 12.0 Hz, 1H), 3.18~3.13 (m, 2H), 2.95~2.90 (m, 1H), 2.61~2.23 (m, 2H), 1.93~1.83 (m, 1H), 1.81~1.74 (m, 2H), 1.53~1.47 (m, 1H)

Mass, m/e: 287 (M$^+$), 96 (base)

Production Example 79

In the manner similar to Production Example 1, 3-chloro-1-((8aS)-octahydropyrrolo[1,2-a]pyrazin-2-yl)-7-methylisoquinoline was obtained.

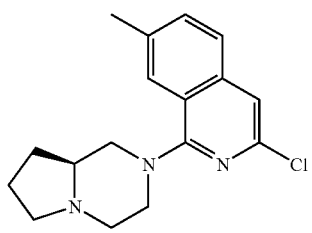

¹H-NMR (CDCl₃) δ: 7.55 (d, J=8.5 Hz, 1H), 7.42 (dd, J=1.5 Hz, 8.5 Hz, 1H), 7.19 (s, 1H), 3.95 (td, J=2.3 Hz, 12.3 Hz, 1H), 3.90~3.86 (m, 1H), 3.25~3.13 (m, 2H), 2.95~2.89 (m, 1H), 2.62~2.57 (m, 1H), 2.51 (s, 3H), 2.35~2.24 (m, 2H), 1.91~1.83 (m, 2H), 1.79~1.76 (m, 1H), 1.56~1.51 (m, 1H)

Mass, m/e: 301 (M⁺), 96 (base)

Production Example 80

In the manner similar to Production Example 1, 7-chloro-1-octahydropyrido[1,2-a]pyrazin-2-ylisoquinoline was obtained.

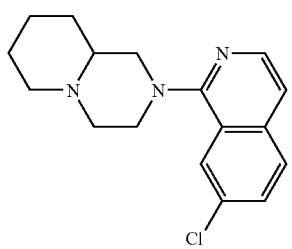

¹H-NMR (CDCl₃) δ: 8.15 (d, J=5.8 Hz, 1H), 8.05 (d, J=1.9 Hz, 1H), 7.69 (d, J=8.9 Hz, 1H), 7.55 (dd, J=1.9 Hz, 8.9 Hz, 1H), 7.21 (d, J=5.8 Hz, 1H), 3.72 (qd, J=2.7 Hz, 12.3 Hz, 1H), 3.56 (td, J=2.7 Hz, 12.3 Hz, 1H), 3.23 (dt, J=2.7 Hz, 12.3 Hz, 1H), 2.97~2.84 (m, 3H), 2.63 (dt, J=2.7 Hz, 11.6 Hz, 1H), 2.33~2.16 (m, 2H), 1.87~1.78 (m, 1H), 1.75~1.57 (m, 3H), 1.45~1.28 (m, 2H)

Mass, m/e: 301 (M⁺), 110 (base)

Production Example 81

In the manner similar to Production Example 1, 7-methoxy-1-octahydropyrido[1,2-a]pyrazin-2-ylisoquinoline was obtained.

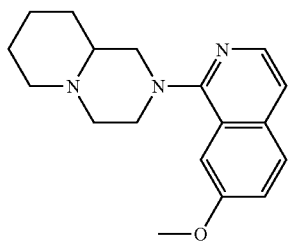

¹H-NMR (CDCl₃) δ: 8.07 (d, J=5.4 Hz, 1H), 7.67 (d, J=8.9 Hz, 1H), 7.40 (d, J=2.7 Hz, 1H), 7.28 (dd, J=2.7 Hz, 8.9 Hz, 1H), 7.20 (d, J=5.8 Hz, 1H), 3.94 (s, 3H), 3.72 (qd, J=2.7 Hz, 12.3 Hz, 1H), 3.57 (td, J=2.7 Hz, 12.3 Hz, 1H), 3.26~3.16 (m, 1H), 2.98~2.84 (m, 3H), 2.63 (dt, J=2.7 Hz, 11.6 Hz, 1H), 2.35~2.25 (m, 1H), 2.25~2.15 (m, 1H), 1.84~1.54 (m, 4H), 1.42~1.32 (m, 2H)

Mass, m/e: 297 (M⁺), 110 (base)

Production Example 82

In the manner similar to Production Example 1, 7-methylsulfanyl-1-(S)-octahydropyrido[1,2-a]pyran-2-ylisoquinoline was obtained.

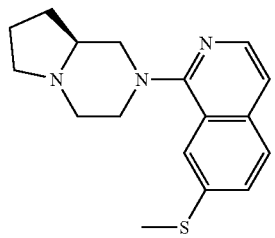

¹H-NMR (CDCl₃) δ: 8.10 (d, J=5.8 Hz, 1H), 7.85 (d, J=1.9 Hz, 1H), 7.65 (d, J=8.5 Hz, 1H), 7.50 (dd, J=1.9 Hz, 8.5 Hz, 1H), 7.18 (d, J=5.8 Hz, 1H), 3.91~3.84 (m, 1H), 3.82~3.75 (m, 1H), 3.25~3.15 (m, 3H), 2.94~2.85 (m, 1H), 2.59 (s, 3H), 2.43~2.24 (m, 2H), 1.97~1.73 (m, 3H), 1.66~1.47 (m, 2H)

Mass, m/e: 299 (M⁺), 96 (base)

Production Example 83

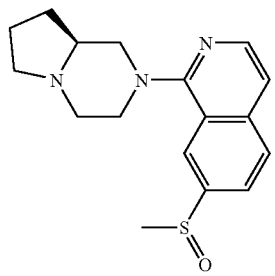

First, in the manner similar to Production Example 1, 285 mg of 7-methylsulfanyl-1-(S)-octahydropyrido[1,2-a]pyran-2-ylisoquinoline was obtained, to which 1 ml of 30% aqueous hydrogen peroxide and 0.5 ml of acetic acid were added, stirred at room temperature for 15 minutes, rendered alkaline with ammonia water, extracted with dichloromethane and dried over anhydrous magnesium sulfate. Distilling the solvent off under reduced pressure, the residue was purified on silica gel column chromatography (methanol:dichloromethane=1:4) to provide 235 mg (78%) of 7-methanesulfinyl-1-(S)-octahydropyrido[1,2-a]pyran-2-ylisoquinoline.

¹H-NMR (CDCl₃) δ: 8.43~8.40 (m, 1H), 8.23 (d, J=5.8 Hz, 1H), 7.89 (d, J=8.5 Hz, 1H), 7.77~7.73 (m, 1H), 7.28~7.25 (m, 1H), 3.94 (d, J=12.0 Hz, 1H), 3.89~3.81 (m, 1H), 3.33~3.23 (m, 1H), 3.23~3.14 (m, 2H), 3.02~2.91 (m, 1H), 2.79 (d, J=1.5 Hz, 3H), 2.70~2.60 (m, 1H), 2.46~2.25 (m, 2H), 1.97~1.75 (m, 3H), 1.62~1.46 (m, 1H)

Mass, m/e: 315 (M⁺), 96 (base)

Production Example 84

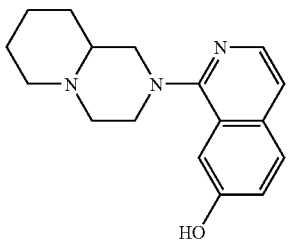

First, in the manner similar to Production Example 1, 610 mg of 7-methoxy-1-octahydropyrido[1,2-a]pyrazin-2-ylisoquinoline was obtained, to which 8 ml of 47% aqueous hydrobromic acid was added and heated under reflux for 2 hours. After cooling, the solution was neutralized with 5N aqueous sodium hydroxide, followed by extraction with chloroform, drying over anhydrous magnesium sulfate, and removal of the solvent by distillation under reduced pressure. The residue was purified on silica gel column chromatography (saturated aqueous ammonia:methanol: chloroform=0.5:5:45) to provide 500 mg (86%) of 7-hydroxy-1-octahydropyrido[1,2-a]pyrazin-2-ylisoquinoline.

$^1$H-NMR (CDCl$_3$) δ: 8.03 (dd, J=1.2 Hz, 5.8 Hz, 1H), 7.67 (d, J=8.9 Hz, 1H), 7.41 (d, J=2.3 Hz, 1H), 7.27~7.21 (m, 1H), 7.20 (d, J=5.8 Hz, 1H), 3.71~3.63 (m, 1H), 3.58~3.51 (m, 1H), 3.27~3.17 (m, 1H), 2.95~2.83 (m, 3H), 2.60~2.50 (m, 1H), 2.31~2.07 (m, 2H), 1.82~1.54 (m, 4H), 1.39~1.26 (m, 2H)

Mass, m/e: 283 (M$^+$), 110 (base)

Production Example 85

In the manner similar to Production Example 84, 1-(S)-octahydropyrido[1,2-a]pyran-2-yl-7-hydroxyisoquinoline was obtained.

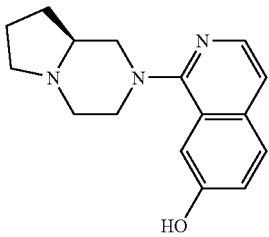

$^1$H-NMR (CDCl$_3$) δ: 8.02 (d, J=5.4 Hz, 1H), 7.68 (d, J=8.9 Hz, 1H), 7.42 (d, J=2.3 Hz, 1H), 7.29~7.25 (m, 1H), 7.23 (d, J=5.4 Hz, 1H), 3.71~3.58 (m, 2H), 3.32~3.23 (m, 1H), 3.21~3.13 (m, 2H), 3.01~2.85 (m, 3H), 2.55~2.46 (m, 1H), 1.98~1.79 (m, 3H), 1.59~1.49 (m, 1H)

Mass, m/e: 269 (M$^+$), 96 (base)

Production Example 86

In 3 ml of N-methylpyrrolidone, 105 mg of 7-hydroxy-1-octahydropyrido[1,2-a]pyrazin-2-ylisoquinoline as synthesized in Production Example 84 was dissolved, and to the solution 1.00 g of sulfamoyl chloride was added, followed by an hour's stirring at room temperature. The solution was neutralized with saturated aqueous sodium hydrogencarbonate solution, extracted with chloroform, dried over anhydrous magnesium sulfate, and the solvent was distilled off under reduced pressure. The residue was purified on silica gel column chromatography (25% aqueous ammonia:methanol: chloroform=1:10:90) to provide 85 mg (75%) of 1-octahydropyrido[1,2-a]pyrazin-2-yl-7-sulfamoylisoquinoline.

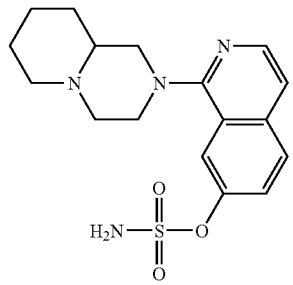

$^1$H-NMR (CDCl$_3$) δ: 8.05 (d, J=5.8 Hz, 1H), 7.97 (d, J=2.7 Hz, 1H), 7.75 (d, J=8.9 Hz, 1H), 7.57 (dd, J=2.7 Hz, 8.9 Hz, 1H), 7.14 (d, J=5.8 Hz, 1H), 3.62~3.49 (m, 2H), 3.05 (dt, J=2.7 Hz, 12.3 Hz, 1H), 2.94~2.72 (m, 3H), 2.54 (dt, J=3.1 Hz, 11.6 Hz, 1H), 2.27 (t, J=10.8 Hz, 1H), 2.21~2.12 (m, 1H), 1.83~1.54 (m, 4H), 1.43~1.21 (m, 2H)

Mass, m/e: 362 (M$^+$), 110 (base)

Production Example 87

In the manner similar to Production Example 86, 1-(S)-octahydropyrido[1,2-a]pyran-2-yl-7-sulfamoylisoquinoline was obtained.

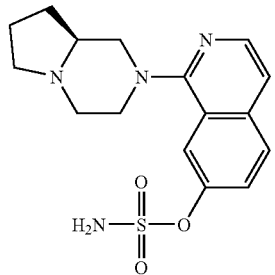

$^1$H-NMR (CDCl$_3$) δ: 8.08 (d, J=5.8 Hz, 1H), 7.98 (d, J=2.3 Hz, 1H), 7.77 (d, J=8.9 Hz, 1H), 7.57 (dd, J=2.3 Hz, 8.9 Hz, 1H), 7.17 (d, J=5.8 Hz, 1H), 3.85~3.78 (m, 1H), 3.73~3.65 (m, 1H), 3.18~3.05 (m, 3H), 2.86~2.78 (m, 1H), 2.63~2.54 (m, 1H), 2.43~2.24 (m, 2H), 1.95~1.74 (m, 3H), 1.53~1.41 (m, 1H)

Mass, m/e: 348 (M$^+$), 96 (base)

Production Example 88

Step 1: Synthesis of 1-(4-benzylpiperazin-1-yl)-7-chloroisoquinoline

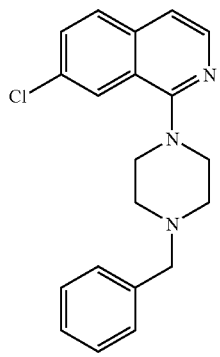

A mixture of 3.96 g 1,7-dichloroisoquinoline and 10.50 g of benzylpiperazine was stirred at 150° C. for 3 hours. To the residue water was added, followed by extraction with chloroform, washing with saturated aqueous sodium hydrogencarbonate solution and drying over anhydrous magnesium sulfate. Distilling the solvent off under reduced pressure, the residue was purified on silica gel column chromatography (ethyl acetate) to provide 4.78 g (71%) of 1-(4-benzylpiperazin-1-yl)-7-chloroisoquinoline.

1H-NMR (CDCl$_3$) δ: 8.14 (d, J=5.4 Hz, 1H), 8.04 (d, J=1.9 Hz, 1H), 7.68 (d, J=8.5 Hz, 1H), 7.53 (dd, J=2.3 Hz, 8.8 Hz, 1H), 7.39~7.23 (m, 5H), 7.20 (d, J=5.8 Hz, 1H), 3.64 (s, 2H), 3.41 (t, J=5.6 Hz, 4H), 2.73 (t, J=4.8 Hz, 4H)

Mass, m/e: 337 (M$^+$), 191, 159, 91 (base)

Step 2: Synthesis of 1-(4-benzylpiperazin-1-yl)-7-dimethylaminoisoquinoline

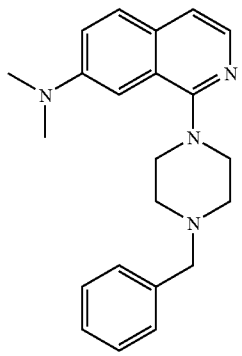

After dissolving 1.01 g of 1-(4-benzylpiperazin-1-yl)-7-chloroisoquinoline as synthesized in above Step 1 in 30 ml of tetrahydrofuran, 20 mg of palladium acetate, 48 mg of 2-(di-tert-butylphosphino)biphenyl, 450 mg of sodium-tert-butoxide and 5 ml of 2.0 M dimethylamine-tetrahydrofuran solution were added to the solution and sealed in a tube. This mixture was stirred at 80° C. for 16 hours. Removing the insoluble matter by filtration, the solvent was distilled off under reduced pressure and the residue was purified on silica gel column chromatography (methanol:chloroform=1:19) to provide 261 mg (25%) of 1-(4-benzylpiperazin-1-yl)-7-dimethylaminoisoquinoline.

$^1$H-NMR (CDCl$_3$) δ: 7.94 (d, J=5.7 Hz, 1H), 7.63 (d, J=9.0 Hz, 1H), 7.45~7.20 (m, 6H), 7.18 (d, J=5.4 Hz, 1H), 7.12 (d, J=2.3 Hz, 1H), 3.69 (s, 2H), 3.49 (t, J=4.8 Hz, 4H), 3.06 (s, 6H), 2.77 (t, J=5.0 Hz, 4H)

Mass, m/e: 346 (M$^+$), 330, 200 (base), 187, 91

Step 3: Synthesis of 7-dimethylamino-1-piperazin-1-ylisoquinoline

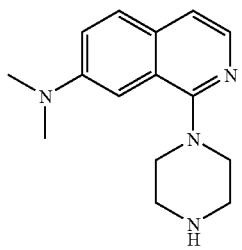

After dissolving 250 mg of 1-(4-benzylpiperazin-1-yl)-7-dimethylaminoisoquinoline as synthesized in above Step 2 in 20 ml of ethanol, 50 mg of 10% palladium-on carbon was added to the solution. This mixture was stirred for 16 hours at room temperature in hydrogen atmosphere. The insoluble matter was removed by filtration and the solvent was distilled off under reduced pressure. The residue was purified on silica gel column chromatography (methanol:chloroform=1:9) to provide 46 mg (25%) of 7-dimethylamino-1-piperazin-1-ylisoquinoline.

$^1$H-NMR (CDCl$_3$) δ: 7.95 (d, J=5.4 Hz, 1H), 7.64 (d, J=8.9 Hz, 1H), 7.27 (dd, J=2.3 Hz, 8.9 Hz, 1H), 7.16 (d, J=5.4 Hz, 1H), 7.12 (d, J=2.3 Hz, 1H), 3.39 (t, J=5.0 Hz, 4H), 3.19 (t, J=5.0 Hz, 4H), 3.07 (s, 6H)

Mass, m/e: 256 (M$^+$), 200, 187 (base)

Production Example 89

The compound as obtained in above Production Example 88 was methylated according to accepted practice to provide 7-dimethylamino-1-(4-methylpiperazin-1-yl)isoquinoline.

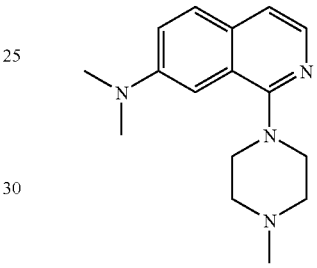

$^1$H-NMR (CDCl$_3$) δ: 7.95 (d, J=5.7 Hz, 1H), 7.63 (d, J=9.0 Hz, 1H), 7.32 (dd, J=2.8 Hz, 9.0 Hz, 1H), 7.21 (d, J=5.4 Hz, 1H), 7.12 (d, J=2.8 Hz, 1H), 3.45 (t, J=5.0 Hz, 4H), 3.07 (s, 6H), 2.71 (t, J=5.0 Hz, 4H), 2.42 (s, 3H)

Mass, m/e: 270 (M$^+$), 200, 187 (base)

Production Example 90

In the manner similar to Production Example 88, 7-methylamino-1-piperazin-1-ylisoquinoline was obtained.

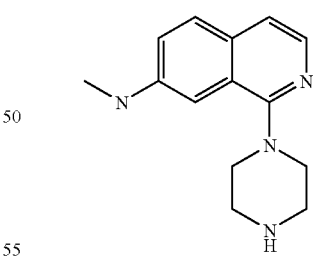

$^1$H-NMR (CDCl$_3$) δ: 7.93 (d, J=5.8 Hz, 1H), 7.57 (d, J=8.9 Hz, 1H), 7.17 (d, J=5.4 Hz, 1H), 7.01 (dd, J=1.3 Hz, 8.9 Hz, 1H), 6.90 (d, J=1.9 Hz, 1H), 3.56 (t, J=5.0 Hz, 4H), 3.33 (t, J=5.0 Hz, 4H), 2.94 (s, 3H)

Mass, m/e: 242 (M$^+$), 198, 186, 173 (base)

Production Example 91

In the manner similar to Production Example 89, 7-methylamino-1-(4-methylpiperazin-1-yl)isoquinoline was obtained.

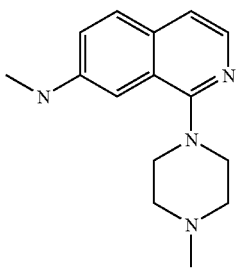

¹H-NMR (CDCl₃) δ: 7.94 (d, J=5.7 Hz, 1H), 7.55 (d, J=9.5 Hz, 1H), 7.21 (d, J=9.2 Hz, 1H), 7.07 (dd, J=2.6 Hz, 5.0 Hz, 1H), 6.97 (d, J=2.0 Hz, 1H), 3.44 (t, J=4.8 Hz, 4H), 2.95 (s, 3H), 2.72 (t, J=5.0 Hz, 4H), 2.42 (s, 3H)

Mass, m/e: 256 (M⁺), 186 (base), 173, 157

Production Example 92

Step 1: Synthesis of 2-benzo[1,3]dioxol-5-ylmethyl-1-tert-butoxycarbonyl-3-oxopiperazine

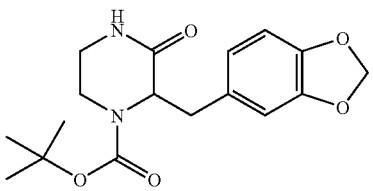

Under argon atmosphere, 17.5 ml of 1.58M n-butyl lithium-n-hexane solution was dropped into a mixture of 25 ml of tetrahydrofuran and 2.78 g of diisopropylamine under cooling ice, followed by 30 minutes' stirring under the same condition. Thereafter a solution of 2.50 g of 1-tert-butoxycarbonyl-3-oxopiperazine (which was prepared by following Tetrahedron Lett., 1980, 21, 3019-3020) in 60 ml of tetrahydrofuran was added by dropping under cooling with ice, followed by 3 hours' stirring under the same condition, further dropping of a solution of 2.30 g of 5-chloromethyl-benzo[1,3]dioxole in 20 ml of tetrahydrofuran under cooling with ice, and an hour's stirring under the same condition. The solution was warmed to room temperature and stirred for 18 hours. After addition of saturated aqueous ammonium chloride solution, the solution was extracted with ethyl acetate, dried over anhydrous magnesium sulfate and the solvent was distilled therefrom under reduced pressure. The residue was purified on silica gel column chromatography (ethyl acetate) to provide 2.84 g (68%) of 2-benzo[1,3]dioxol-5-ylmethyl-1-tert-butoxycarbonyl-3-oxopiperazine.

¹H-NMR (CDCl₃) δ: 6.67 (s, 1H), 6.65 (d, J=1.3 Hz, 2H), 5.90 (s, 2H), 4.52~4.43 (m, 1H), 4.12 (d, J=7.2 Hz, 2H), 3.23 (t, J=5.1 Hz, 2H), 2.57 (t, J=5.8 Hz, 2H), 1.45 (s, 9H)

Mass, m/e: 334 (M⁺), 278, 144, 57 (base)

Step 2: Synthesis of 2-benzo[1,3]dioxol-5-ylmethyl-1-tert-butoxycarbonylpiperazine

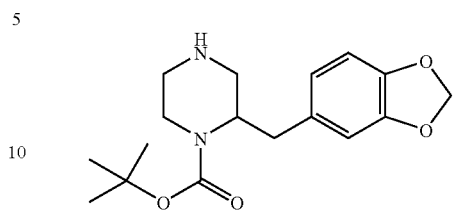

Dissolving 2.00 g of 2-benzo[1,3]dioxol-5-ylmethyl-1-tert-butoxycarbonyl-3-oxopiperazine as synthesized in the above step in 50 ml of tetrahydrofuran, 1.00 g of lithium aluminium hydride was added to the solution which then was heated under reflux for 16 hours. To the solution 10% aqueous potassium hydroxide solution was added, the insoluble matter was filtered off, extracted with ethyl acetate, the extract was dried over anhydrous magnesium sulfate and the solvent was distilled off under reduced pressure. The residue was purified on silica gel column chromatography (methanol:chloroform=1:19) to provide 1.27 g (66%) of 2-benzo[1,3]dioxol-5-ylmethyl-1-tert-butoxycarbonylpiperazine.

¹H-NMR (CDCl₃) δ: 6.68 (s, 1H), 6.65 (d, J=0.5 Hz, 2H), 5.90 (s, 2H), 4.02~3.87 (m, 3H), 3.78~3.54 (m, 2H), 2.96~2.77 (m, 2H), 2.65~2.51 (m, 2H), 1.45 (s, 9H)

Mass, m/e: 320 (M⁺), 219, 57 (base)

Step 3: Synthesis of 1-(2-benzo[1,3]dioxol-5-ylmethyl-1-tert-butoxycarbonylpiperazin-4-yl)-7-methoxyisoquinoline

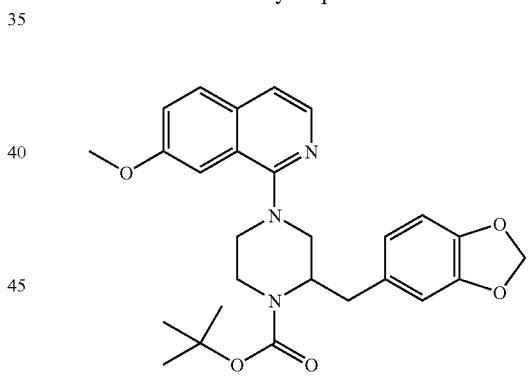

A mixture of 320 mg of 2-benzo[1,3]dioxol-5-ylmethyl-1-tert-butoxycarbonylpiperazine as synthesized in the above step, 200 mg of 1-chloro-7-methoxyisoquinoline and 100 mg of triethylamine was stirred in 2 ml of ethylene glycol at 150° C. for 18 hours. After addition of water, the solution was extracted with ethyl acetate, dried over anhydrous magnesium sulfate, and the solvent was distilled off under reduced pressure. The residue was purified on silica gel column chromatography (ethyl acetate:n-hexane=1:1) to provide 210 mg (44%) of 1-(2-benzo[1,3]dioxol-5-ylmethyl-1-tert-butoxycarbonylpiperazin-4-yl)-7-methoxyisoquinoline.

¹H-NMR (CDCl₃) δ: 8.05 (d, J=5.5 Hz, 1H), 7.64 (d, J=9.1 Hz, 1H), 7.26 (dd, J=2.1 Hz, 9.1 Hz, 1H), 7.22 (d, J=5.4 Hz, 1H), 7.08 (d, J=2.1 Hz, 1H), 6.92 (s, 1H), 6.79 (d, J=1.3 Hz, 1H), 5.94 (s, 2H), 3.93 (s, 3H), 3.33~3.26 (m, 2H), 3.21~3.14 (m, 2H), 2.80~2.66 (m, 3H), 1.45 (s, 9H)

Mass, m/e: 477 (M⁺), 342 (base), 187, 135

Step 4: Synthesis of 1-(3-benzo[1,3]dioxol-5-ylm-ethylpiperazin-1-yl)-7-methoxyisoquinoline

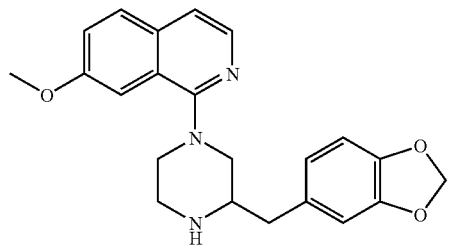

In 10 ml of 4N hydrochloric acid-dioxane solution, 150 mg of 1-(2-benzo[1,3]dioxol-5-ylmethyl-1-tert-butoxycarbonylpiperazin-4-yl)-7-methoxyisoquinoline as synthesized in the above step was added and stirred for 18 hours. The solution was neutralized with saturated aqueous sodium hydrogencarbonate solution, extracted with ethyl acetate, dried over anhydrous magnesium sulfate and the solvent was distilled off under reduced pressure. The residue was purified on silica gel column chromatography (methanol:chloroform=1:9) to provide 69 mg (58%) of 1-(3-benzo[1,3]dioxol-5-ylm-ethylpiperazin-1-yl)-7-methoxyisoquinoline.

$^1$H-NMR (CDCl$_3$) δ: 8.07 (d, J=5.5 Hz, 1H), 7.66 (d, J=9.2 Hz, 1H), 7.33~7.30 (m, 1H), 7.25~7.18 (m, 2H), 6.74 (s, 1H), 6.72 (d, J=0.8 Hz, 1H), 5.93 (s, 2H), 3.84 (s, 3H), 3.66~3.59 (m, 2H), 3.30~3.18 (m, 2H), 3.15~3.10 (m, 2H), 2.80~2.64 (m, 3H)

Mass, m/e: 377 (M$^+$), 242 (base), 187, 135

Production Example 93

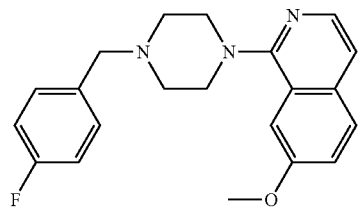

Into 10 ml of acetone, 50 mg of 7-methoxy-1-piperazin-1-ylisoquinoline, 100 mg of 4-fluorobenzyl bromide and 100 mg of triethylamine were added and heated under reflux for 5 hours. Distilling the solvent off under reduced pressure, the residue was purified on silica gel column chromatography (methanol:chloroform=1:19) to provide 52 mg (79%) of 1-[4-(4-fluorobenzyl)piperazin-1-yl]-7-methoxyisoquinoline.

$^1$H-NMR (CDCl$_3$) δ: 8.07 (d, J=5.5 Hz, 1H), 7.68 (d, J=9.2 Hz, 1H), 7.41~7.32 (m, 3H), 7.30~7.26 (m, 1H), 7.21 (d, J=5.5 Hz, 1H), 7.06~6.99 (m, 2H), 3.93 (s, 3H), 3.61 (s, 2H), 3.45~3.35 (m, 4H), 2.77~2.67 (m, 4H)

Mass, m/e: 351 (M$^+$), 187 (base)

Production Example 94

In the manner similar to Production Example 93, 1-[4-(4-fluorobenzyl)piperazin-1-yl]isoquinoline was obtained.

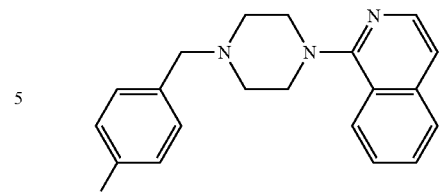

$^1$H-NMR (CDCl$_3$) δ: 8.14 (d, J=5.8 Hz, 1H), 8.08 (d, J=8.5 Hz, 1H), 7.74 (d, J=8.1 Hz, 1H), 7.59 (ddd, J=1.2 Hz, 6.9 Hz, 8.1 Hz, 1H), 7.49 (ddd, 1.2 Hz, 6.9 Hz, 8.5 Hz, 1H), 7.38~7.32 (m, 2H), 7.23 (d, J=5.8 Hz, 1H), 7.06~6.99 (m, 2H), 3.61 (s, 2H), 3.47~3.40 (m, 4H), 2.75~2.68 (m, 4H)

Mass, m/e: 321 (M$^+$), 157 (base)

Production Example 95

Step 1: Synthesis of 1-(4-tert-butoxycarbonylpiperazin-1-yl)-7-hydroxyisoquinoline

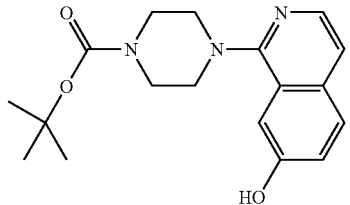

A mixture of 4.00 g of 7-methoxy-1-piperazin-1-ylisoquinoline and 40 ml of 47% aqueous hydrobromic acid was heated under reflux for 2 hours. After cooling, the residue was rendered alkaline with 5N aqueous sodium hydroxide solution, followed by addition of 30 ml of 1,4-dioxane and 3.94 g of di-tert-butyldicarbonate and an hour's stirring at room temperature. The solution was extracted with ethyl acetate, washed with saturated brine, dried over anhydrous magnesium sulfate and the solvent was distilled off under reduced pressure. The residue was purified on silica gel column chromatography (methanol:chloroform=1:19) to provide 4.63 g (85%) of 1-(4-tert-butoxycarbonylpiperazin-1-yl)-7-hydroxyisoquinoline.

$^1$H-NMR (CDCl$_3$) δ: 8.03 (d, J=5.5 Hz, 1H), 7.70 (d, J=8.8 Hz, 1H), 7.43 (d, J=2.6 Hz, 1H), 7.30~7.23 (m, 2H), 3.72~3.64 (m, 4H), 3.34~3.26 (m, 4H), 1.51 (s, 9H)

Mass, m/e: 329 (M$^+$), 173 (base)

Step 2: Synthesis of 7-hydroxy-1-piperazin-1-ylisoquinoline hydrochloride

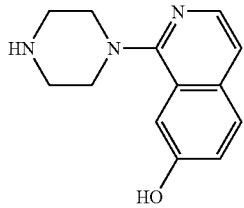

A mixture of 70 mg of 1-(4-tert-butoxycarbonylpiperazin-1-yl)-7-hydroxyisoquinoline as synthesized in the above step and 3 ml of 4N hydrochloric acid-ethyl acetate solution was stirred for an hour at room temperature. So formed crystalline product was recovered by filtration and washed with ethyl acetate to provide 43 mg (yield: 78%) of 7-hydroxy-1-piperazin-1-ylisoquinoline hydrochloride.

¹H-NMR (CD₃OD) δ: 8.02 (d, J=8.5 Hz, 1H), 7.78 (d, J=6.6 Hz, 1H), 7.72 (d, J=6.6 Hz, 1H), 7.64~7.56 (m, 2H), 4.06~3.98 (m, 4H), 3.68~3.59 (m, 4H)

Mass, m/e: 229 (M⁺), 173 (base)

Production Example 96

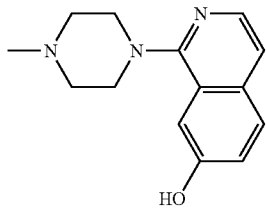

A mixture of 795 mg of 7-methoxy-(4-methylpiperazin-1-yl)-isoquinoline and 8 ml of 47% aqueous hydrobromic acid solution was heated under reflux for 2.5 hours. After cooling, the solution was neutralized with 20% aqueous sodium hydroxide solution, extracted with chloroform, dried over anhydrous magnesium sulfate and the solvent was distilled off under reduced pressure. The residue was purified on silica gel column chromatography (saturated ammonia water: methanol:chloroform=1:10:90) to provide 673 mg (80%) of 7-hydroxy-1-(4-methylpiperazin-1-yl)isoquinoline.

¹H-NMR (CDCl₃) δ: 8.01 (d, J=5.8 Hz, 1H), 7.66 (d, J=8.5 Hz, 1H), 7.36 (d, J=2.7 Hz, 1H), 7.26~7.19 (m, 2H), 3.48~3.35 (m, 4H), 2.70~2.55 (m, 4H), 2.33 (s, 3H)

Mass, m/e: 243 (M⁺), 173 (base)

Production Example 97

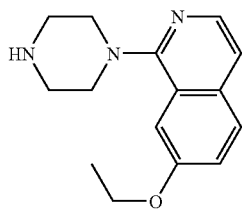

To a solution of 105 mg of 1-(4-tert-butoxycarbonylpiperazin-1-yl)-7-hydroxyisoquinoline in 10 ml of acetone, 93 mg of potassium carbonate and 55 mg of ethyl iodide were added and heated under reflux for 2 hours. Further adding 55 mg of ethyl iodide, the solution was heated under reflux for 2 hours, followed by addition of 48 mg of potassium carbonate and 55 mg of ethyl iodide, and an overnight's refluxing. Cooling the system off, the residue was extracted with ethyl acetate after addition of water, washed with saturated brine, dried over anhydrous magnesium sulfate and the solvent was distilled off under reduced pressure. The residue was purified on silica gel column chromatography (ethyl acetate:n-hexane=1:4) to provide 102 mg (90%) of 1-(4-tert-butoxycarbonylpiperazin-1-yl)-7-ethoxyisoquinoline.

Then the product was stirred in 3 ml of 4N hydrochloric acid-dioxane solution at room temperature for 30 minutes. The solution was rendered alkaline with 10% aqueous sodium hydroxide solution, extracted with ethyl acetate and the solvent was distilled off under reduced pressure. The residue was purified on silica gel column chromatography (methanol:chloroform=1:4) to provide 67 mg (93%) of 7-ethoxy-1-piperazin-1-ylisoquinoline.

¹H-NMR (CDCl₃) δ:8.07 (d, J=5.8 Hz, 1H), 7.67 (d, J=8.9 Hz, 1H), 7.40 (d, J=2.3 Hz, 1H), 7.28 (dd, J=2.3 Hz, 8.9 Hz, 1H), 7.22 (d, J=5.8 Hz, 1H), 4.17 (q, J=6.9 Hz, 2H), 3.38~3.32 (m, 4H), 3.20~3.14 (m, 4H), 1.51 (t, J=6.9 Hz, 3H)

Mass, m/e: 257 (M⁺), 188 (base)

Production Example 98

In the manner similar to Production Example 97, 7-(4-fluorobenzyloxy)-1-piperazin-1-ylisoquinoline was obtained.

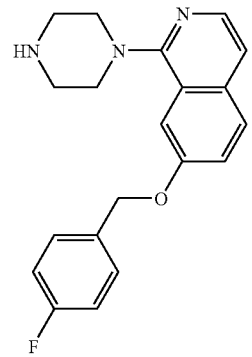

¹H-NMR (CDCl₃) δ:8.08 (d, J=5.8 Hz, 1H), 7.70 (d, J=8.8 Hz, 1H), 7.49~7.42 (m, 2H), 7.41~7.38 (m, 1H), 7.38~7.33 (m, 1H), 7.22 (d, J=5.8 Hz, 1H), 7.12~7.06 (m, 2H), 5.20 (s, 2H), 3.29~3.22 (m, 4H), 3.13~3.06 (m, 4H)

Mass, m/e: 337 (M⁺), 109 (base)

Production Example 99

In the manner similar to Production Example 97, 7-benzyloxy-1-piperazin-1-ylisoquinoline was obtained.

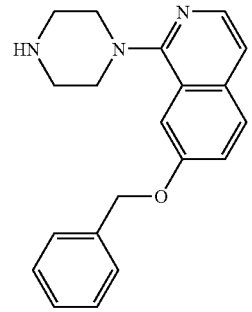

¹H-NMR(CDCl₃) δ: 8.06 (d, J=5.8 Hz, 1H), 7.69 (d, J=8.9 Hz, 1H), 7.50~7.29 (m, 7H), 7.21 (d, J=5.8 Hz, 1H), 5.25 (s, 2H), 3.24~3.18 (m, 4H), 3.08~3.02 (m, 4H)

Mass, m/e: 319 (M⁺), 91 (base)

Production Example 100

In the manner similar to Production Example 97, 7-[4-(1,3-dioxo-1,3-dihydroisoindol-2-yl)butoxy]-1-piperazin-1-yl-isoquinoline hydrochloride was obtained.

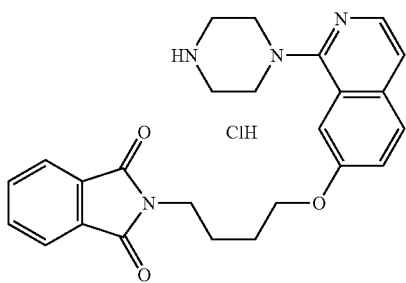

¹H-NMR (DMSO-d₆) δ: 7.97~7.91 (m, 2H), 7.89~7.80 (m, 4H), 7.57~7.48 (m, 2H), 7.38 (d, J=2.3 Hz, 1H), 4.25~4.16 (m, 4H), 3.79~3.63 (m, 8H), 1.87~1.77 (m, 4H)
Mass, m/e: 430 (M⁺), 160 (base)

Production Example 101

In the manner similar to Production Example 97, 7-sulfamoyloxy-1-piperazin-1-isoquinoline hydrochloride was obtained.

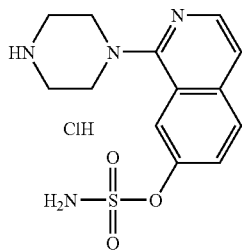

¹H-NMR (DMSO-d₆) δ: 8.19~8.11 (m, 3H), 8.07 (d, J=8.9 Hz, 1H), 7.98 (d, J=2.3 Hz, 1H), 7.69 (dd, J=2.3 Hz, 8.9 Hz, 1H), 7.57 (d, J=5.8 Hz, 1H), 3.65~3.57 (m, 4H), 3.40~3.31 (m, 4H)

Production Example 102

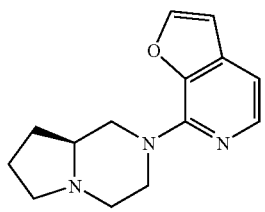

Step 102-A

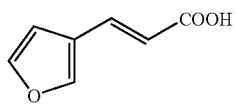

To 12 ml of pyridine, 10.0 g of 3-furaldehyde and 15.0 g of malonic acid were added, followed by heating under stirring at 80° C.-90° C. for 2 hours. The solution was poured into ice water, rendered weakly acidic with 1N hydrochloric acid. The precipitated crystals were recovered by filtration, dissolved in ethyl acetate and washed with 1N hydrochloric acid. The organic layer was dried over anhydrous magnesium sulfate and concentrated. The residue was recrystallized from ethyl acetate-n-hexane to provide 11.78 g (82%) of 3-furan-3-ylallylic acid.
¹H-NMR(CDCl₃): 7.70~7.67 (m, 2H), 7.45 (s, 1H), 6.62~6.61 (m, 1H), 6.16 (d, J=15.8 Hz, 1H)
Mass, m/e: 138 (M⁺, base)

Step 102-B

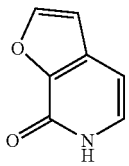

In 50 ml of acetone, 5.0 g of 3-furan-3-ylallylic acid as obtained in the above step 102-A and 4.3 g of triethylamine were dissolved, and to the solution 5.2 g of ethyl chlorocarbonate was dropped under cooling with ice, consuming 10 minutes, followed by 30 minutes' stirring under cooling with ice. Then an aqueous solution of sodium azide (formed by dissolving 3.5 g of sodium azide in 15 ml of purified water) was dropped, followed by another hour's stirring under cooling with ice. After addition of 150 ml of ice water, the solution was extracted with benzene, dried over anhydrous magnesium sulfate and concentrated to about 20 ml under reduced pressure, while maintaining the liquid temperature at not higher than 30° C. This solution was dropped into 40 ml of diphenylmethane and 7 ml of tributylamine which had been heated to 220° C. over 1.5 hours while distilling the benzene off to maintain the temperature of 220° C. After termination of the dropping, the liquid was cooled, to which n-hexane was added. Whereupon precipitated crystals were recovered by filtration, washed with ethyl acetate and dried to provide 3.15 g (64%) of 6H-furo[2,3-c]pyridin-7-one.
¹H-NMR (DMSO-d₆): 11.50 (br s, 1H), 8.07 (d, J=1.9 Hz, 1H), 6.86 (d, J=1.9 Hz, 1H), 6.50 (d, J=6.9 Hz, 1H)
Mass, m/e: 135 (M⁺, base)

Step 102-C

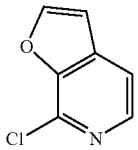

In 16.0 g of phosphorus oxychloride, 3.1 g of 6H-furo[2,3-c]-pyridin-7-one as obtained in above Step 102-B was heated under reflux for 1.5 hours. The solution was poured into ice, neutralized with saturated aqueous sodium hydrogencarbonate solution and extracted with chloroform. The extract was dried over anhydrous magnesium sulfate, and the solvent was distilled off under reduced pressure. The residue was purified on silica gel column chromatography (n-hexane:ethyl acetate=1:1) to provide 2.36 g (67%) of 7-chlorofuro[2,3-c]pyridine.
¹H-NMR(CDCl₃): 8.19 (d, J=5.4 Hz, 1H), 7.81 (d, J=1.9 Hz, 1H), 7.49 (d, J=5.4 Hz, 1H), 6.87 (d, J=2.3 Hz, 1H)
Mass, m/e: 153 (M⁺, base)

Step 102-D

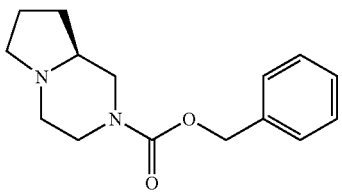

In 150 ml of tetrahydrofuran, 12.5 g of N-benzyloxycarbonyl-L-proline and 8.9 g of carbonyldiimidazole were dissolved and stirred for 30 minutes. Then 6.9 g of glycine methyl ester hydrochloride and 5.6 g of triethylamine were added to the solution and stirred for an overnight at room temperature. The solution was concentrated, and ethyl acetate was added, followed by washing with saturated aqueous sodium hydrogencarbonate solution, 10% aqueous citric acid and saturated brine, drying over anhydrous magnesium sulfate and concentration. The residue was dissolved in 100 ml of methanol, to which solution 2.0 g of 10% palladium-on-carbon was added and stirred for an overnight in gaseous hydrogen current. Filtering the catalyst off, the filtrate was concentrated. This residue was dissolved in 100 ml of methanol and following addition of triethylamine, the solution was heated under reflux for 14 hours. After concentration, a suitable amount of 2-propanol was added to the residue and the precipitated crystals were recovered by filtration and dried to provide 6.48 g (84%) of (8aS)-2-benzyloxycarbonylhexahydropyrrolo[1,2-a]pyrazin-1,4-dione. In 40 ml of tetrahydrofuran, 4.0 g of this product was dissolved and the solution was dropped into a suspension of 5.9 g of lithium aluminium hydride in 60 ml of tetrahydrofuran, followed by 14 hours' heating under reflux. The solution was cooled with ice, and excessive lithium aluminium hydride therein was decomposed by addition of saturated aqueous sodium hydrogencarbonate solution. After addition of benzyloxycarbonyl chloride, the solution was stirred for an hour under cooling with ice and for further 2 hours at room temperature, followed by extraction with chloroform, washing with saturated brine, drying over anhydrous magnesium sulfate and concentration. The residue was purified on silica gel column chromatography (chloroform:methanol=25:1) to provide 2.77 g (41%) of (8aS)-2-benzyloxycarbonyloctahydropyrrolo[1,2-a]pyrazine.
$^1$H-NMR(CDCl$_3$): 7.36~7.35 (m, 5H), 5.13 (s, 2H), 4.28~4.10 (m, 2H), 3.10~3.05 (m, 1H), 2.98 (br s, 2H), 2.61 (br s, 1H), 2.15~2.09 (m, 2H), 1.88~1.66 (m, 5H)
Mass, m/e: 260 (M$^+$), 91 (base)

Step 102-E

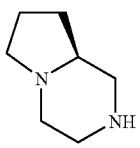

In 100 ml of methanol, 5.2 g of (8aS)-2-benzyloxycarbonyloctahydropyrrolo[1,2-a]pyrazine as obtained in above Step 102-D was dissolved, and to the solution 2.0 g of 20% palladium hydroxide on carbon was added, followed by an hour's stirring in hydrogen gaseous current. The catalyst was separated by filtration and the solution was concentrated to provide 4.65 g (100%) of (8aS)-octahydropyrrolo[1,2-a]pyrazine.

Step 102-F

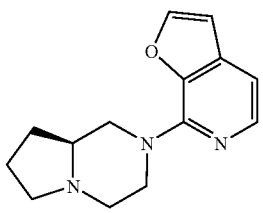

In 10 ml of ethylene glycol, 380 mg of (8aS)-octahydropyrrolo[1,2-a]pyrazine as obtained in above Step 102-E was dissolved and to which 270 mg of 7-chlorofuro[2,3-c]pyridine as obtained in Step 102-C and 202 mg of triethylamine were added, followed by an overnight's stirring at 140° C. After cooling, saturated aqueous sodium hydrogencarbonate solution was added to the mixture which then was extracted with chloroform and the organic layer was dried over anhydrous magnesium sulfate, and the solvent was distilled off under reduced pressure. The residue was purified on silica gel column chromatography (chloroform:methanol=20:1) to provide 190 mg (39%) of 7-((8aS)-octahydropyrrolo[1,2-a]pyrazin-2-yl)furo[2,3-c]-pyridine.
$^1$H-NMR(CDCl$_3$) δ: 7.95 (d, J=5.4 Hz, 1H), 7.63 (d, J=2.3 Hz, 1H), 6.95 (d, J=5.4 Hz, 1H), 6.72 (d, J=1.9 Hz, 1H), 4.80~4.76 (m, 1H), 4.71~4.66 (m, 1H), 3.325~3.14 (m, 3H), 2.87~2.81 (m, 1H), 2.44~2.40 (m, 1H), 2.38~2.13 (m, 2H), 1.96~1.84 (m, 2H), 1.82~1.74 (m, 1H), 1.56~1.51 (m, 1H)
Mass, m/e: 243 (M$^+$), 147 (base)

Production Example 103

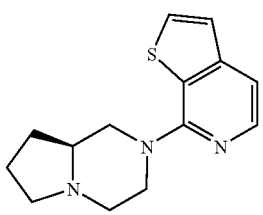

In the manner similar to Production Example 102, 7-((8aS)-octahydropyrrolo[1,2-a]pyrazin-2-yl)thieno[2,3-c]pyridine was obtained.
$^1$H-NMR(CDCl$_3$) δ: 8.12 (d, J=5.4 Hz, 1H), 7.57 (d, J=5.4 Hz, 1H), 7.31 (d, J=5.4 Hz, 1H), 7.23 (d, J=5.4 Hz, 1H), 4.44~4.40 (m, 1H), 4.34~4.31 (m, 1H), 3.27~3.26 (m, 1H), 3.23~3.11 (m, 2H), 2.92~2.86 (m, 1H), 2.50~2.45 (m, 1H), 2.27~2.21 (m, 2H), 1.95~1.86 (m, 2H), 1.83~1.76 (m, 1H), 1.59~1.51 (m, 1H)
Mass, m/e: 259 (M$^+$), 163 (base)

Production Example 104

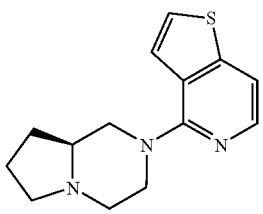

In the manner similar to Production Example 102, 4-((8aS)-octahydropyrrolo[1,2-a]pyrazin-2-yl)thieno[3,2-c]pyridine was obtained.

$^1$H-NMR(CDCl$_3$) δ: 8.04 (d, J=5.4 Hz, 1H), 7.43~7.29 (m, 3H), 4.17~4.12 (m, 1H), 4.07~4.02 (m, 1H), 3.28~3.22 (m, 1H), 3.19~3.14 (m, 2H), 2.94~2.88 (m, 1H), 2.51 (dt, J=2.7 Hz, 7.2 Hz, 1H), 2.29~2.22 (m, 2H), 1.94~1.85 (m, 2H), 1.85~1.75 (m, 1H), 1.56~1.50 (m, 1H)

Mass, m/e: 259 (M$^+$), 107 (base)

Production Example 105

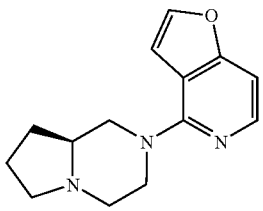

In the manner similar to Production Example 102, 4-((8aS)-octahydropyrrolo[1,2-a]pyrazin-2-yl)furo[3,2-c]pyridine was obtained.

$^1$H-NMR(CDCl$_3$) δ: 8.04 (d, J=5.8 Hz, 1H), 7.53 (d, J=2.3 Hz, 1H), 6.93 (d, J=5.8 Hz, 1H), 6.83 (dd, J=0.8 Hz, 2.3 Hz, 1H), 4.48 (ddd, J=1.9 Hz, 2.7 Hz, 12.3 Hz, 1H), 4.35~4.31 (m, 1H), 3.30~3.23 (m, 1H), 3.18~3.13 (m, 2H), 2.91~2.85 (m, 1H), 2.44~2.38 (m, 1H), 2.25~2.13 (m, 2H), 1.95~1.84 (m, 2H), 1.82~1.50 (m, 2H)

Mass, m/e: 243 (M$^+$), 147 (base)

Production Example 106

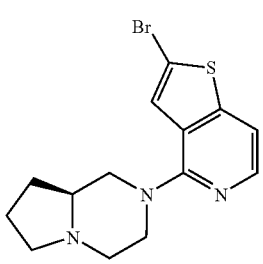

In the manner similar to Production Example 102, 2-bromo-4-((8aS)-octahydropyrrolo[1,2-a]pyrazin-2-yl)thieno[3,2-c]-pyridine was obtained.

1H-NMR(CDCl$_3$) δ: 8.05 (d, J=5.3 Hz, 1H), 7.38 (s, 1H), 7.17 (d, J=5.8 Hz, 1H), 4.06 (td, J=2.3 Hz, 12.3 Hz, 1H), 3.98~3.94 (m, 1H), 3.25~3.14 (m, 3H), 2.91~2.85 (m, 1H), 2.51~2.47 (m, 1H), 2.27~2.19 (m, 2H), 1.94~1.82 (m, 2H), 1.81~1.75 (m, 1H), 1.54~1.49 (m, 1H)

Mass, m/e: 337 (M$^+$), 96 (base)

Production Example 107

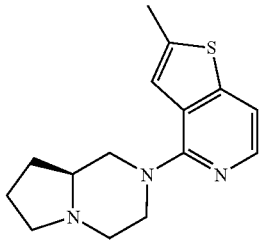

In the manner similar to Production Example 102, 4-((8aS)-octahydropyrrolo[1,2-a]pyrazin-2-yl)-2-methylthieno[3,2-c]-pyridine was obtained.

$^1$H-NMR(CDCl$_3$) δ: 8.01 (d, J=5.4 Hz, 1H), 7.23~7.22 (m, 1H), 7.03 (d, J=1.2 Hz, 1H), 4.07 (td, J=2.3 Hz, 12.0 Hz, 1H), 3.98 (d, J=11.8 Hz, 1H), 3.23~3.08 (m, 3H), 2.90~2.84 (m, 1H), 2.58 (dd, J=1.2 Hz, 4.3 Hz, 3H), 2.53~2.47 (m, 2H), 2.37~2.27 (m, 2H), 1.93~1.85 (m, 2H), 1.81~1.75 (m, 1H) 1.54~1.50 (m, 1H)

Mass, m/e: 273 (M$^+$), 177 (base)

Production Example 108

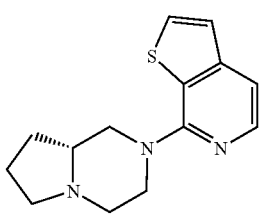

In the manner similar to Production Example 102, 7-((8aR)-octahydropyrrolo[1,2-a]pyrazin-2-yl)thieno[2,3-c]pyridine was obtained.

1H-NMR(CDCl$_3$) δ: 8.13 (d, J=5.4 Hz, 1H), 7.57 (d, J=5.4 Hz, 1H), 7.31 (d, J=5.4 Hz, 1H), 7.24 (d, J=5.4 Hz, 1H), 4.41 (td, J=2.3 Hz, 12.0 Hz, 1H), 4.3~4.31 (m, 1H), 3.24~3.15 (m, 3H), 2.93~2.87 (m, 1H), 2.51~2.45 (m, 1H), 2.28~2.22 (m, 2H), 1.94~1.87 (m, 2H), 1.81~1.73 (m, 1H), 1.56~1.52 (m, 1H)

Mass, m/e: 259 (M$^+$), 163 (base)

Production Example 109

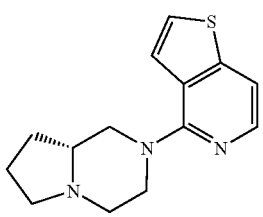

In the manner similar to Production Example 102, 4-((8aR)-octahydropyrrolo[1,2-a]pyrazin-2-yl)thieno[3,2-c]pyridine was obtained.

$^1$H-NMR(CDCl$_3$) δ: 8.07 (d, J=5.4 Hz, 1H), 7.43~7.41 (m, 1H), 7.37 (d, J=5.4 Hz, 1H), 7.33 (dd, J=0.8 Hz, 5.8 Hz, 1H), 4.17~4.13 (m, 1H), 4.05 (ddd, J=1.9 Hz, 5.0 Hz, 12.7 Hz, 1H), 3.26 (dt, J=2.7 Hz, 12.3 Hz, 1H), 3.19~3.15 (m, 2H), 2.95~2.89 (m, 1H), 2.52 (dt, J=2.7 Hz, 11.2 Hz, 1H), 2.30~2.23 (m, 2H), 1.94~1.87 (m, 2H), 1.82~1.76 (m, 1H), 1.56~1.49 (m, 1H)

Mass, m/e: 259 (M$^+$), 163 (base)

Production Example 110

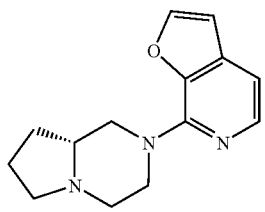

In the manner similar to Production Example 102, 7-((8aR)-octahydropyrrolo[1,2-a]pyrazin-2-yl)furo[2,3-c]pyridine was obtained.

$^1$H-NMR(CDCl$_3$) δ: 7.93 (d, J=5.0 Hz, 1H), 7.62 (d, J=1.9 Hz, 1H), 6.94 (d, J=5.4 Hz, 1H), 6.70 (d, J=2.3 Hz, 1H), 4.79~4.74 (m, 1H), 4.69~4.65 (m, 1H), 3.324~3.12 (m, 3H), 2.86~2.80 (m, 1H), 2.43~2.39 (m, 1H), 2.37~2.12 (m, 2H), 1.95~1.83 (m, 2H), 1.81~1.70 (m, 1H), 1.56~1.49 (m, 1H)

Mass, m/e: 243 (M$^+$), 147 (base)

Production Example 111

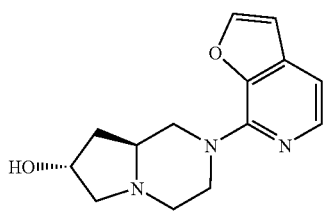

In the manner similar to Production Example 102, 7-((7R,8aS)-7-hydroxyoctahydropyrrolo[1,2-a]pyrazin-2-yl)furo[2,3-c]-pyridine was obtained.

$^1$H-NMR(CDCl$_3$) δ: 7.93 (d, J=5.4 Hz, 1H), 7.62 (d, J=2.3 Hz, 1H), 6.95 (d, J=5.4 Hz, 1H), 6.71 (d, J=2.3 Hz, 1H), 4.76~4.72 (m, 1H), 4.68~4.63 (m, 1H), 4.56~4.52 (m, 1H), 3.60~3.56 (m, 1H), 3.19~3.07 (m, 2H), 2.78 (dt, J=1.9 Hz, 10.4 Hz, 1H), 2.61~2.49 (m, 2H), 2.23~2.19 (m, 1H), 1.92~1.81 (m, 2H)

Mass, m/e: 259 (M$^+$), 147 (base)

Production Example 112

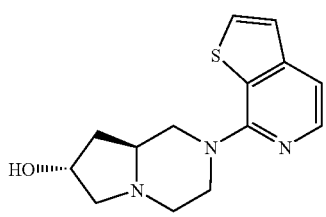

In the manner similar to Production Example 102, 7-((7R,8aS)-7-hydroxyoctahydropyrrolo[1,2-a]pyrazin-2-yl)thieno-[2,3-c]pyridine was obtained.

$^1$H-NMR(CDCl$_3$) δ: 8.11 (d, J=5.4 Hz, 1H), 7.57 (d, J=5.4 Hz, 1H), 7.30 (d, J=5.4 Hz, 1H), 7.23 (d, J=5.4 Hz, 1H), 4.57~4.52 (m, 1H), 4.38~4.34 (m, 1H), 4.30~4.25 (m, 1H), 3.61~3.56 (m, 1H), 3.18 (dt, J=3.1 Hz, 12.7 Hz, 1H), 3.10 (dt, J=2.7 Hz, 11.2 Hz, 1H), 2.86~2.81 (m, 1H), 2.72~2.59 (m, 2H), 2.28~2.24 (m, 1H), 1.93~1.81 (m, 2H)

Mass, m/e: 275 (M$^+$), 163 (base)

Production Example 113

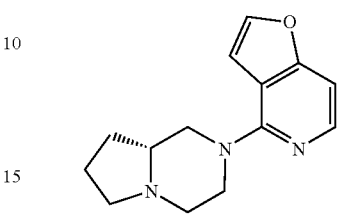

In the manner similar to Production Example 102, 4-((8aR)-octahydropyrrolo[1,2-a]pyrazin-2-yl)furo[3,2-c]pyridine was obtained.

$^1$H-NMR(CDCl$_3$) δ: 8.04 (d, J=5.8 Hz, 1H), 7.53 (d, J=2.3 Hz, 1H), 6.93 (dd, J=0.8 Hz, 5.8 Hz, 1H), 6.83~6.82 (m, 1H), 4.50~4.46 (m, 1H), 4.35~4.31 (m, 1H), 3.27 (dt, J=3.1 Hz, 12.3 Hz, 1H), 3.18~3.14 (m, 2H), 2.92~2.86 (m, 1H), 2.41 (dt, J=3.4 Hz, 11.2 Hz, 1H), 2.25~2.15 (m, 2H), 1.95~1.85 (m, 2H), 1.82~1.75 (m, 1H), 1.56~1.48 (m, 1H)

Mass, m/e: 243 (M$^+$), 147 (base)

Production Example 114

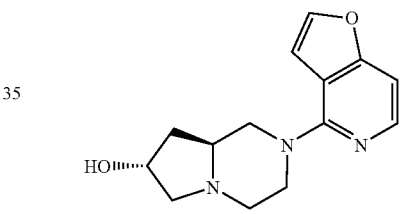

In the manner similar to Production Example 102, 4-((7R,8aS)-7-hydroxyoctahydropyrrolo[1,2-a]pyrazin-2-yl)furo[3,2-c]-pyridine was obtained.

$^1$H-NMR(CDCl$_3$) δ: 8.04 (d, J=5.8 Hz, 1H), 7.54 (d, J=2.3 Hz, 1H), 6.92 (dd, J=1.2 Hz, 5.8 Hz, 1H), 6.82 (dd, J=0.8 Hz, 2.3 Hz, 1H), 4.57~4.53 (m, 1H), 4.43 (ddd, J=1.9 Hz, 2.7 Hz, 11.9 Hz, 1H), 4.32~4.27 (m, 1H), 3.60~3.56 (m, 1H), 3.25~3.20 (m, 1H), 3.11~3.07 (m, 1H), 2.86~2.81 (m, 1H), 2.66~2.52 (m, 2H), 2.26~2.23 (m, 1H), 1.89~1.82 (m, 2H)

Mass, m/e: 259 (M$^+$), 147 (base)

Production Example 115

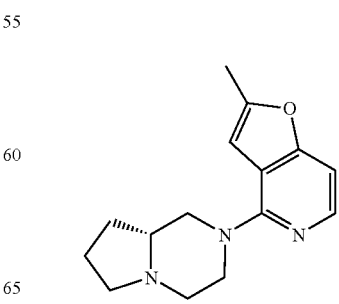

In the manner similar to Production Example 102, 4-((8aR)-octahydropyrrolo[1,2-a]pyrazin-2-yl)-2-methyl-furo[3,2-c]pyridine was obtained.

$^1$H-NMR(CDCl$_3$) δ: 7.97 (d, J=5.8 Hz, 1H), 6.84 (dd, J=0.8 Hz, 5.8 Hz, 1H), 6.40 (s, 1H), 4.42~4.38 (m, 1H), 4.28~4.21 (m, 1H), 3.24~3.12 (m, 3H), 2.86~2.80 (m, 1H), 2.43 (d, J=1.2 Hz, 3H), 2.42~2.35 (m, 1H), 2.26~2.13 (m, 2H), 1.93~1.85 (m, 2H), 1.80~1.73 (m, 1H), 1.55~1.48 (m, 1H)

Mass, m/e: 257 (M$^+$), 161 (base)

Production Example 116

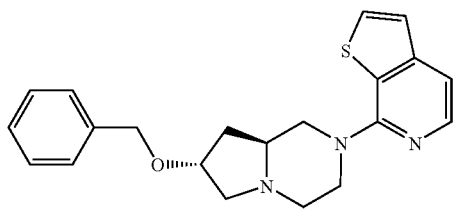

In the manner similar to Production Example 102, 7-((7R, 8aS)-7-benzyloxyoctahydropyrrolo[1,2-a]pyrazin-2-yl)thieno-[2,3-c]pyridine was obtained.

$^1$H-NMR(CDCl$_3$) δ: 8.11 (d, J=5.8 Hz, 1H), 7.56 (d, J=5.4 Hz, 1H), 7.34~7.22 (m, 7H), 4.49 (dd, J=1.6 Hz, 3.5 Hz, 2H), 4.39~4.35 (m, 1H), 4.30~4.26 (m, 1H), 3.56~3.52 (m, 1H), 3.20~3.08 (m, 2H), 2.85~2.80 (m, 1H), 2.62~2.53 (m, 2H), 2.38~2.34 (m, 1H), 1.99 (ddd, J=1.5 Hz, 7.2 Hz, 13.1 Hz, 1H), 1.81~1.75 (m, 1H)

Mass, m/e: 365 (M$^+$), 91 (base)

Production Example 117

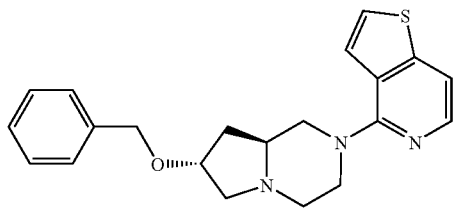

In the manner similar to Production Example 102, 4-((7R, 8aS)-7-benzyloxyoctahydropyrrolo[1,2-a]pyrazin-2-yl)thieno-[3,2-c]pyridine was obtained.

$^1$H-NMR(CDCl$_3$) δ: 8.06 (d, J=5.8 Hz, 1H), 7.41~7.26 (m, 8H), 4.53~4.4 (m, 2H), 4.25~4.22 (m, 1H), 4.10 (td, J=2.3 Hz, 11.9 Hz, 1H), 4.00 (dd, J=2.7 Hz, 12.7 Hz, 1H), 3.56~3.52 (m, 1H), 3.21~3.14 (m, 1H), 3.11~3.07 (m, 1H), 2.85~2.80 (m, 1H), 2.66~2.56 (m, 2H), 2.37 (dd, J=5.4 Hz, 9.6 Hz, 1H), 1.97 (ddd, J=1.5 Hz, 6.2 Hz, 13.1 Hz, 1H), 1.79~1.71 (m, 1H)

Mass, m/e: 365 (M$^+$), 163 (base)

Production Example 118

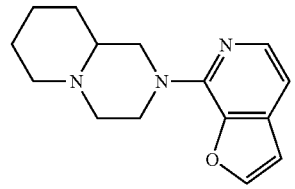

In the manner similar to Production Example 102, 7-octahydropyrido[1,2-a]pyrazin-2-ylfuro[2,3-c]pyridine was obtained.

$^1$H-NMR(CDCl$_3$) δ: 7.95 (d, J=5.4 Hz, 1H), 7.62 (d, J=2.3 Hz, 1H), 6.95 (d, J=5.4 Hz, 1H), 6.71 (d, J=2.3 Hz, 1H), 4.65~4.58 (m, 1H), 4.49~4.43 (m, 1H), 3.30~3.20 (m, 1H), 2.94~2.77 (m, 3H), 2.47~2.38 (m, 1H), 2.15~2.04 (m, 2H), 1.87~1.77 (m, 1H), 1.73~1.64 (m, 3H), 1.40~1.29 (m, 2H)

Mass, m/e: 257 (M$^+$), 110 (base)

Production Example 119

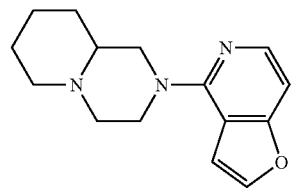

In the manner similar to Production Example 102, 4-octahydropyrido[1,2-a]pyrazin-2-ylfuro[3,2-c]pyridine was obtained.

$^1$H-NMR(CDCl$_3$) δ: 8.04 (d, J=5.8 Hz, 1H), 7.53 (d, J=2.3 Hz, 1H), 6.92 (dd, J=0.7 Hz, 5.8 Hz, 1H), 6.80 (dd, J=1.2 Hz, 2.3 Hz, 1H), 4.30~4.22 (m, 1H), 4.20~4.13 (m, 1H), 3.29 (dt, J=2.7 Hz, 12.3 Hz, 1H), 2.94~2.81 (m, 3H), 2.46~2.37 (m, 1H), 2.15~2.04 (m, 2H), 1.88~1.75 (m, 1H), 1.75~1.57 (m, 3H), 1.42~1.24 (m, 2H)

Mass, m/e: 257 (M$^+$), 110 (base)

Production Example 120

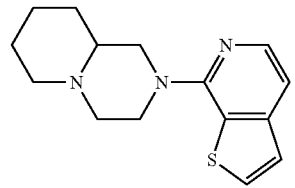

In the manner similar to Production Example 102, 7-octahydropyrido[1,2-a]pyrazin-2-ylthieno[2,3-c]pyridine was obtained.

$^1$H-NMR(CDCl$_3$) δ: 8.12 (d, J=5.4 Hz, 1H), 7.57 (d, J=5.4 Hz, 1H), 7.31 (d, J=5.4 Hz, 1H), 7.23 (d, J=5.4 Hz, 1H), 4.32~4.24 (m, 1H), 4.16~4.09 (m, 1H), 3.26 (dt, J=2.7 Hz, 12.3 Hz, 1H), 2.95~2.82 (m, 3H), 2.49 (dt, J=3.1 Hz, 12.0 Hz, 1H), 2.20~2.09 (m, 2H), 1.86~1.78 (m, 1H), 1.74~1.60 (m, 3H), 1.40~1.31 (m, 2H)

Mass, m/e: 273 (M$^+$), 110 (base)

Production Example 121

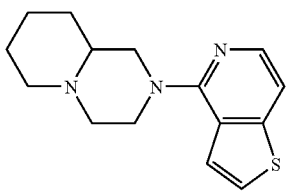

In the manner similar to Production Example 102, 4-octahydropyrido[1,2-a]pyrazin-2-ylthieno[3,2-c]pyridine was obtained.

$^1$H-NMR(CDCl$_3$) δ: 8.07 (d, J=5.4 Hz, 1H), 7.41 (d, J=5.4 Hz, 1H), 7.37 (d, J=5.4 Hz, 1H), 7.33 (d, J=5.4 Hz, 1H), 4.01~3.94 (m, 1H), 3.87~3.81 (m, 1H), 3.26 (dt, J=2.7 Hz, 12.3 Hz, 1H), 2.95~2.83 (m, 3H), 2.52 (dt, J=3.0 Hz, 11.6 Hz, 1H), 2.24~2.10 (m, 2H), 1.87~1.75 (m, 1H), 1.73~1.56 (m, 3H), 1.42~1.29 (m, 2H)

Mass, m/e: 273 (M$^+$), 110 (base)

Formulation Example: Tablets

|  | mg/tablet |
| --- | --- |
| Active ingredient | 5.0 |
| Starch | 10.0 |
| Lactose | 73.0 |
| Carboxymethyl cellulose-calcium | 10.0 |
| Talc | 1.0 |
| Magnesium stearate | 1.0 |
|  | 100.0 |

The active ingredient was pulverized to a particle size not greater than 70 μm, to which starch, lactose and carboxymethyl cellulose-calcium were added and mixed thoroughly. To the above powdery mixture, 10% starch paste was added, agitated and mixed to prepare granules. After drying, the particle size of the granules was dressed to around 1000 μm, with which talc and magnesium stearate were mixed and tabletted.

The invention claimed is:

1. A pyrimidine compound represented by the following formula (I)

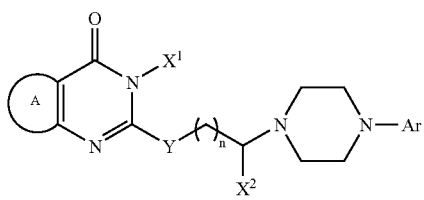

in which ring A stands for a carbocyclic group or heterocyclic group, $X^1$ stands for amino, lower alkylamino, di-lower alkylamino, lower alkylideneamino, lower alkyl or phenyl lower alkyl, $X^2$ stands for hydrogen or lower alkyl, Y stands for a direct bond, sulfur or nitrogen, n is 0 or an integer of 1-4, Ar stands for a group represented by any of the following formulae,

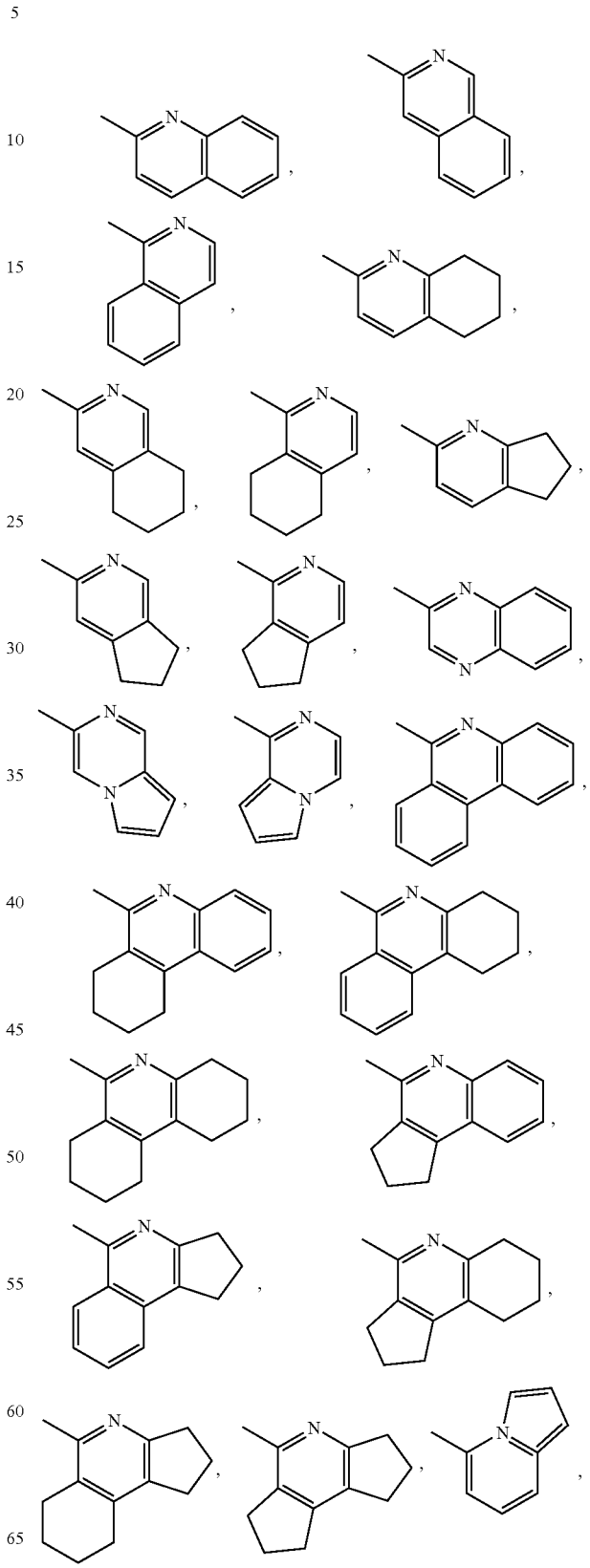

-continued
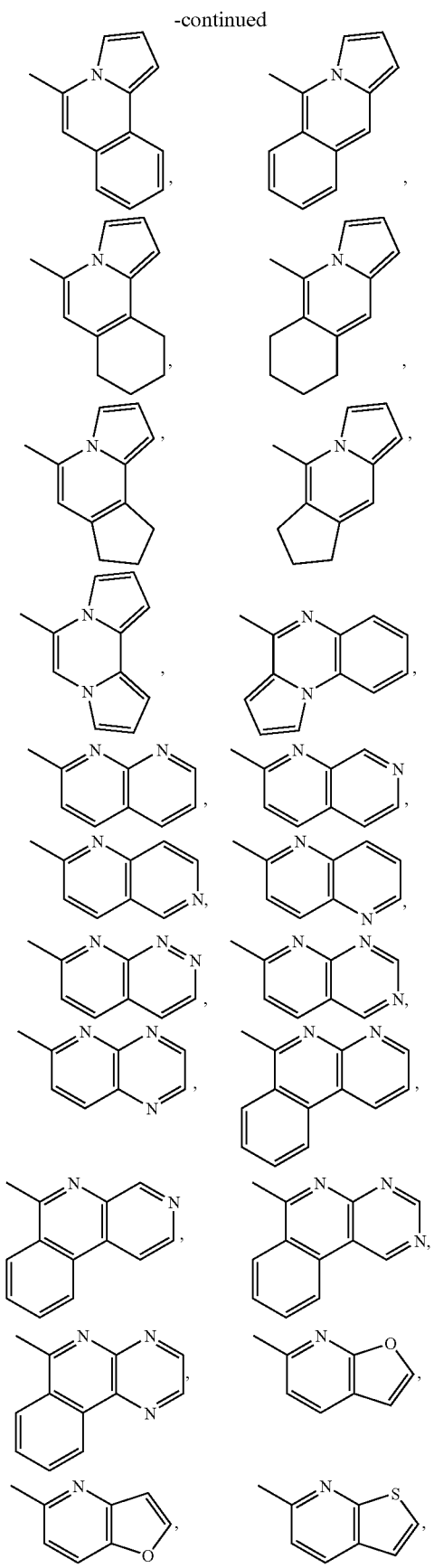
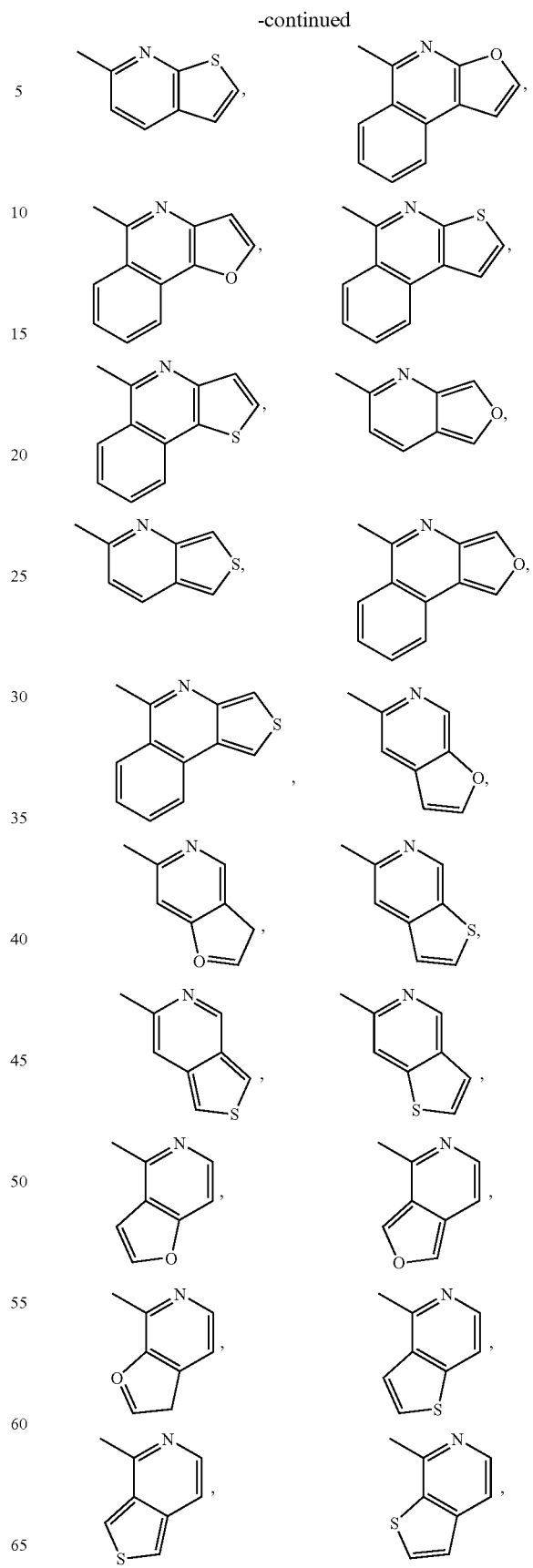

-continued

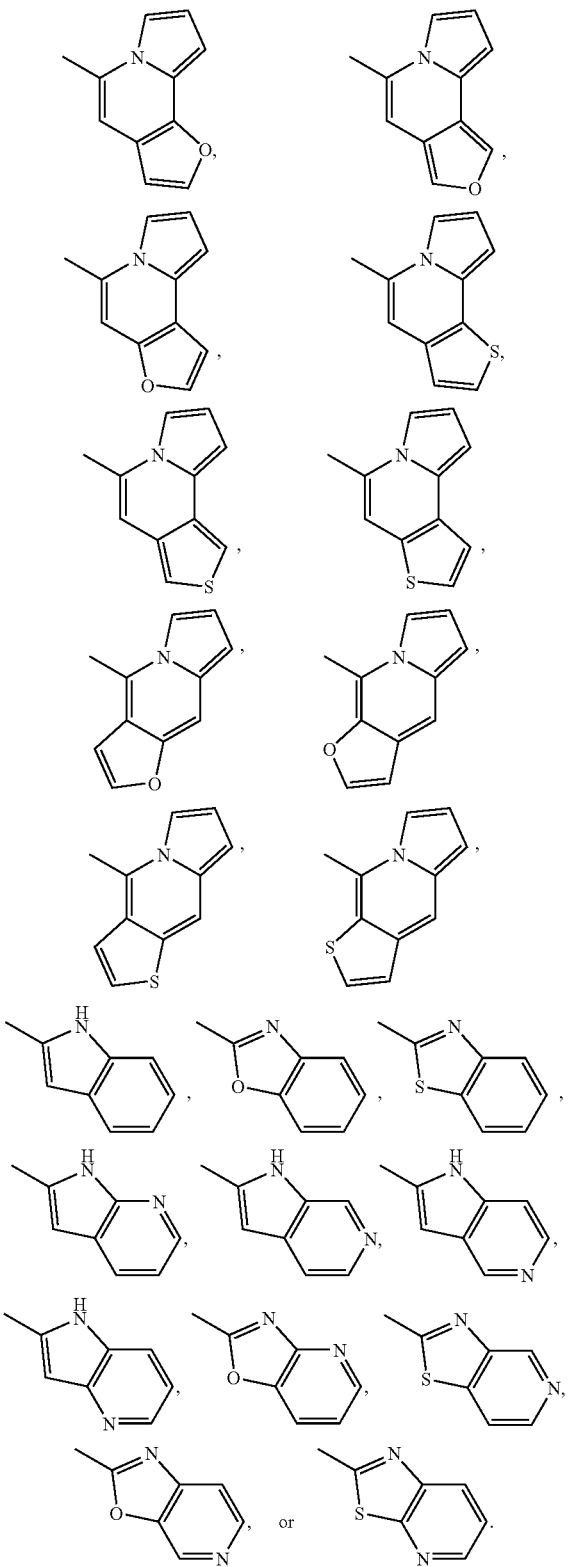

which are, independently from each other, either unsubstituted or substituted with substituent(s) selected from halogen, lower alkyl, hydroxyl, lower alkoxy and phenyl, or a pharmaceutically acceptable salt thereof.

2. The pyrimidine compound or pharmaceutically acceptable salt thereof as set forth in claim 1, in which the ring A stands for a carbocyclic group represented by any of the following formulae i)-iv):

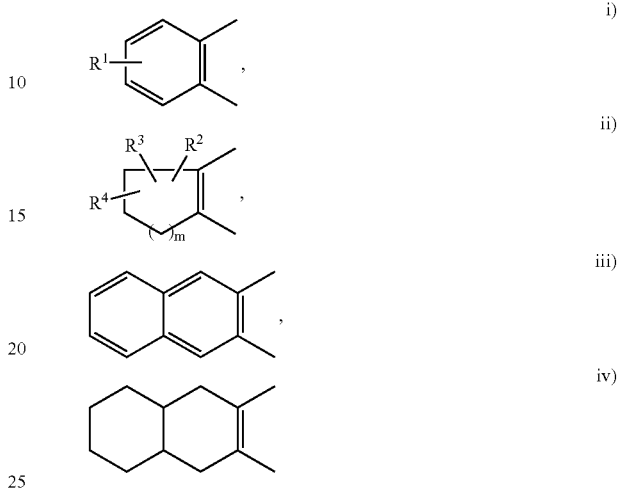

in which

R$^1$ stands for hydrogen, halogen, lower alkyl, halogenated lower alkyl, lower alkoxy, carboxyl, lower alkoxycarbonyl, phenyl, amino, hydrazino or nitro, R$^2$, R$^3$ and R$^4$ either stand for, independently from each other, hydrogen, halogen, lower alkyl, lower alkoxy, phenyl or hydroxyl; or two out of R$^2$, R$^3$ and R$^4$ together stand for oxo or lower alkylenedioxy, and m is an integer of 1-3.

3. The pyrimidine compound or pharmaceutically acceptable salt thereof as set forth in claim 2, in which the ring A stands for a carbocyclic group represented by the formula ii).

4. The pyrimidine compound or pharmaceutically acceptable salt thereof as set forth in claim 3, in which m is 2.

5. The pyrimidine compound or pharmaceutically acceptable salt thereof as set forth in claim 4, in which all of R$^2$, R$^3$ and R$^4$ stand for hydrogen atoms.

6. The pyrimidine compound or pharmaceutically acceptable salt thereof as set forth in claim 1, in which the ring A stands for a heterocyclic group represented by any of the following formulae v)-xv):

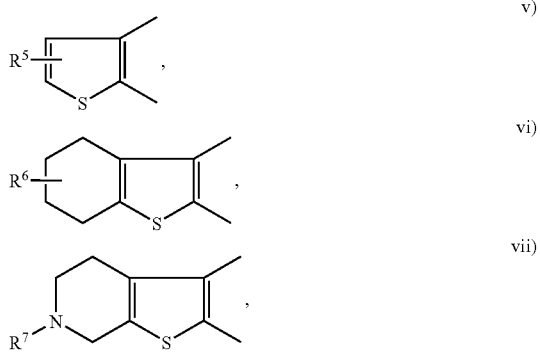

-continued

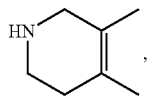 viii)

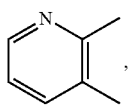 ix)

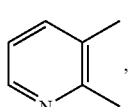 x)

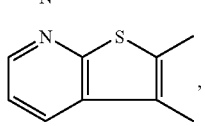 xi)

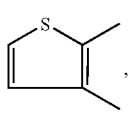 xii)

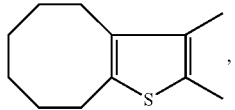 xiii)

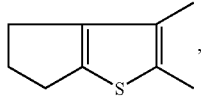, and xiv)

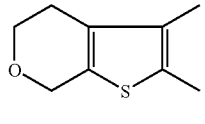 xv)

in which

R⁵ stands for hydrogen, lower alkyl, carboxyl or lower alkoxycarbonyl,

R⁶ stands for hydrogen or lower alkyl, and

R⁷ stands for hydrogen, lower alkyl, lower alkanoyl, lower alkoxycarbonyl or phenyl lower alkoxycarbonyl.

7. The pyrimidine compound or pharmaceutically acceptable salt thereof as set forth in claim 1, in which X¹ stands for amino or lower alkyl.

8. The pyrimidine compound or pharmaceutically acceptable salt thereof as set forth in claim 1, in which X² stands for hydrogen.

9. The pyrimidine compound or pharmaceutically acceptable salt thereof as set forth in claim 1, in which Y stands for a direct bond or sulfur.

10. The pyrimidine compound or pharmaceutically acceptable salt thereof as set forth in claim 1, in which n stands for 2 or 3.

11. The pyrimidine compound or pharmaceutically acceptable salt thereof as set forth in claim 1, in which Ar stands for quinolyl group which either unsubstituted or substituted with substituent(s) selected from halogen, lower alkyl, hydroxyl, lower alkoxy and phenyl.

12. A pyrimidine compound selected from the group consisting of the following compounds, or a pharmaceutically acceptable salt thereof:

3-amino-5,6-dimethyl-2-[3-(4-quinolin-2-ylpiperazin-1-yl)propylthio]-3H-thieno[2,3-d]pyrimidin-4-one,
3-amino-2-[3-(4-quinolin-2-ylpiperazin-1-yl)propylthio]-5,6,7,8-tetrahydro-3H-benzo[4,5]thieno[2,3-d]pyrimidin-4-one,
3-amino-5,6-dimethyl-2-[3-(4-pyrrolo[1,2-a]quinoxalin-4-ylpiperazin-1-yl)propylthio]-3H-thieno[2,3-d]pyrimidin-4-one,
3-amino-5-methyl-4-oxo-2-[3-(4-quinolin-2-ylpiperazin-1-yl)propylthio]-3,4-dihydrothieno[2,3-d]pyrimidine-6-carboxylic acid ethyl ester,
3-amino-2-[3-(4-quinolin-2-ylpiperazin-1-yl)propylthio]-5,6,7,8,9,10-hexahydro-3H-11-thia-1,3-diazacycloocta[a]inden-4-one,
3-amino-7-methyl-2-[3-(4-quinolin-2-ylpiperazin-1-yl)propylthio]-5,6,7,8-tetrahydro-3H-benzo[4,5]thieno[2,3-d]pyrimidin-4-one,
3-amino-2-[3-[4-(4-methylquinolin-2-yl)piperazin-1-yl]propylthio]-5,6,7,8-tetrahydro-3H-benzo[4,5]thieno[2,3-d]pyrimidin-4-one,
3-amino-2-[3-(4-quinolin-2-ylpiperazin-1-yl)propylthio]-5,6,7,8-tetrahydro-3H-9-thia-1,3,7-triazafluoren-4-one,
3-amino-2-[4-(4-quinolin-2-ylpiperazin-1-yl)butyl]-5,6,7,8-tetrahydro-3H-quinazolin-4-one,
3-amino-2-[4-(4-quinolin-2-ylpiperazin-1-yl)butyl]-3H-quinazolin-4-one,
3-amino-2-[4-[4-(4-methylquinolin-2-yl)piperazin-1-yl]butyl]-3H-quinazolin-4-one,
3-amino-2-[4-(4-quinolin-2-ylpiperazin-1-yl)butyl]-3H-thieno[3,2-d]pyrimidin-4-one,
3-amino-6-methyl-2-[4-(4-quinolin-2-ylpiperazin-1-yl)butyl]-3H-quinazolin-4-one,
3-amino-2-[4-[4-(5-methoxyquinolin-2-yl)piperazin-1-yl]butyl]-3H-quinazolin-4-one,
3-amino-2-[4-(4-quinolin-2-ylpiperazin-1-yl)butyl]-3H-thieno[2,3-d]pyrimidin-4-one,
3-amino-5-chloro-2-[4-(4-quinolin-2-ylpiperazin-1-yl)butyl]-3H-quinazolin-4-one,
3-amino-5-hydrazino-2-[4-(4-quinolin-2-ylpiperazin-1-yl)butyl]-3H-quinazolin-4-one,
3-amino-5,6-dimethyl-2-[4-(4-quinolin-2-ylpiperazin-1-yl)butyl]-3H-thieno[2,3-d]pyrimidin-4-one,
3-amino-8-methyl-2-[4-(4-quinolin-2-ylpiperazin-1-yl)butyl]-5,6,7,8-tetrahydro-3H-quinazolin-4-one,
3-amino-2-[4-(4-quinolin-2-ylpiperazin-1-yl)butyl]-3,5,6,7,8,9-hexahydro-cyclohepta[d]pyrimidin-4-one,
3-amino-6-fluoro-2-[4-(4-quinolin-2-ylpiperazin-1-yl)butyl]-3H-quinazolin-4-one,
3-amino-6-methyl-2-[4-(4-quinolin-2-ylpiperazin-1-yl)butyl]-5,6,7,8-tetrahydro-3H-quinazolin-4-one,
3-amino-6-ethyl-2-[4-(4-quinolin-2-ylpiperazin-1-yl)butyl]-5,6,7,8-tetrahydro-3H-quinazolin-4-one,
3-amino-6-hydroxy-2-[4-(4-quinolin-2-ylpiperazin-1-yl)butyl]-5,6,7,8-tetrahydro-3H-quinazolin-4-one,
3-amino-2-[3-(4-quinolin-2-ylpiperazin-1-yl)propylamine]-5,6,7,8-tetrahydro-3H-quinazolin-4-one,
3-methyl-2-[4-(4-quinolin-2-ylpiperazin-1-yl)butyl]-5,6,7,8-tetrahydro-3H-quinazolin-4-one,
3-ethyl-2-[4-(4-quinolin-2-ylpiperazin-1-yl)butyl]-5,6,7,8-tetrahydro-3H-quinazolin-4-one,
3-methyl-2-[4-[4-(4-methylquinolin-2-yl)piperazin-1-yl]butyl]-5,6,7,8-tetrahydro-3H-quinazolin-4-one,
3-ethyl-2-[4-[4-(4-methylquinolin-2-yl)piperazin-1-yl]butyl]-5,6,7,8-tetrahydro-3H-quinazolin-4-one,
3-benzyl-2-[4-[4-(4-methylquinolin-2-yl)piperazin-1-yl]butyl]-5,6,7,8-tetrahydro-3H-quinazolin-4-one, 3-methyl-2-[4-(4-quinolin-2-ylpiperazin-1-yl)butyl]-3H-quinazolin-4-one,
3-ethyl-2-[4-(4-quinolin-2-ylpiperazin-1-yl)butyl]-3H-quinazolin-4-one,
6-chloro-3-methyl-2-[4-(4-quinolin-2-ylpiperazin-1-yl)butyl]-3H-quinazolin-4-one,
3-methyl-2-[3-(4-quinolin-2-ylpiperazin-1-yl)propylthio]-5,6,7,8-tetrahydro-3H-quinazolin-4-one, and
3-methyl-2-[3-(4-quinolin-2-ylpiperazin-1-yl)propylthio]-3H-quinazolin-4-one.

13. A pharmaceutical composition comprising a pyrimidine derivative or pharmaceutically salt thereof as set forth in claim 1 and a pharmaceutically acceptable carrier.

14. A method for treating irritable bowel syndrome (IBS) by exerting $5\text{-}HT_{1A}$ agonistic activity and $5\text{-}HT_3$ antagonistic activity in vivo simultaneously and cooperatively, which comprises administering to a human being or other mammal who requires irritable bowel syndrome (IBS) therapy, a $5\text{-}HT_3$ antagonistic agent which concurrently exhibits $5\text{-}HT_{1A}$ agonistic activity, in which the $5\text{-}HT_3$ antagonistic agent which concurrently exhibits $5\text{-}HT_{1A}$ agonistic activity is a pyrimidine compound selected from the group consisting of the following compounds, or a pharmaceutically acceptable salt thereof:

3-amino-5,6-dimethyl-2-[3-(4-quinolin-2-ylpiperazin-1-yl)propylthio]-3Hthieno[2,3-d]pyrimidin-4-one,
3-amino-2-[3-(4-quinolin-2-ylpiperazin-1-yl)propylthio]-5,6,7,8-tetrahydro-3H-benzo[4,5]thieno[2,3-d]pyrimidin-4-one,
3-amino-5,6-dimethyl-2-[3-(4-pyrrolo[1,2-a]quinoxalin-4-ylpiperazin-1-yl)propylthio]-3H-thieno[2,3-d]pyrimidin-4-one,
3-amino-5-methyl-4-oxo-2-[3-(4-quinolin-2-ylpiperazin-1-yl)propylthio]3,4-dihydrothieno[2,3-d]pyrimidine-6-carboxylic acid ethyl ester,
3-amino-2-[3-(4-quinolin-2-ylpiperazin-1-yl)propylthio]-5,6,7,8,9,10-hexahydro-3H-11-thia-1,3-diazacycloocta[a]inden-4-one,
3-amino-7-methyl-2-[3-(4-quinolin-2-ylpiperazin-1-yl)propylthio]-5,6,7,8-tetrahydro-3H-benzo[4,5]thieno[2,3-d]pyrimidin-4-one,
3-amino-2-[3-[4-(4-methylquinolin-2-yl)piperazin-1-yl]propylthio]-5,6,7,8-tetrahydro-3H-benzo[4,5]thieno[2,3-d]pyrimidin-4-one,
3-amino-2-[3-(4-quinolin-2-ylpiperazin-1-yl)propylthio]-5,6,7,8-tetrahydro-3H-9-thia-1,3,7-triazafluoren-4-one,
3-amino-2-[4-(4-quinolin-2-ylpiperazin-1-yl)butyl]-5,6,7,8-tetrahydro-3H-quinazolin-4-one,
3-amino-2-[4-(4-quinolin-2-ylpiperazin-1-yl)butyl]-3H-quinazolin-4-one,
3-amino-2-[4-[4-(4-methylquinolin-2-yl)piperazin-1-yl]butyl]-3H-quinazolin-4-one,
3-amino-2-[4-(4-quinolin-2-ylpiperazin-1-yl)butyl]-3H-thieno[3,2-d]pyrimidin-4-one,
3-amino-6-methyl-2-[4-(4-quinolin-2-ylpiperazin-1-yl)butyl]-3H-quinazolin-4-one,
3-amino-2-[4-[4-(5-methoxyquinolin-2-yl)piperazin-1-yl]butyl]-3H-quinazolin-4-one,
3-amino-2-[4-(4-quinolin-2-ylpiperazin-1-yl)butyl]-3H-thieno[2,3-d]pyrimidin-4-one,
3-amino-5-chloro-2-[4-(4-quinolin-2-ylpiperazin-1-yl)butyl]-3H-quinazolin-4-one,
3-amino-5-hydrazino-2-[4-(4-quinolin-2-ylpiperazin-1-yl)butyl]-3Hquinazolin-4-one,
3-amino-5,6-dimethyl-2-[4-(4-quinolin-2-ylpiperazin-1-yl)butyl]-3H-thieno[2,3-d]pyrimidin-4-one,
3-amino-8-methyl-2-[4-(4-quinolin-2-ylpiperazin-1-yl)butyl]-5,6,7,8-tetrahydro-3H-quinazolin-4-one,
3-amino-2-[4-(4-quinolin-2-ylpiperazin-1-yl)butyl]-3,5,6,7,8,9-hexahydro-cyclohepta[d]pyrimidin-4-one,
3-amino-6-fluoro-2-[4-(4-quinolin-2-ylpiperazin-1-yl)butyl]-3H-quinazolin-4-one,
3-amino-6-methyl-2-[4-(4-quinolin-2-ylpiperazin-1-yl)butyl]-5,6,7,8-tetrahydro-3H-quinazolin-4-one,
3-amino-6-ethyl-2-[4-(4-quinolin-2-ylpiperazin-1-yl)butyl]-5,6,7,8-tetrahydro-3H-quinazolin-4-one,
3-amino-6-hydroxy-2-]-4-(4-quinolin-2-ylpiperazin-1-yl)butyl]-5,6,7,8-tetrahydro-3H-quinazolin-4-one,
3-amino-2-[3-(4-quinolin-2-ylpiperazin-1-yl)propylamine]-5,6,7,8-tetrahydro-3H-quinazolin-4-one,
3-methyl-2-[4-(4-quinolin-2-ylpiperazin-1-yl)butyl]-5,6,7,8-tetrahydro-3H-quinazolin-4-one,
3-ethyl-2-[4-(4-quinolin-2-ylpiperazin-1-yl)butyl]-5,6,7,8-tetrahydro-3H-quinazolin-4-one,
3-ethyl-2-[4-[4-(4-methylquinolin-2-yl)piperazin-1-yl]butyl]-5,6,7,8-tetrahydro-3H-quinazolin-4-one,
3-methyl-2-[4-[4-(4-methylquinolin-2-yl)piperazin-1-yl]butyl]-5,6,7,8-tetrahydro-3H-quinazolin-4-one,
3-benzyl-2-[4-[4-(4-methylquinolin-2-yl)piperazin-1-yl]butyl]-5,6,7,8-tetrahydro-3H-quinazolin-4-one,
3-methyl-2-[4-(4-quinolin-2-ylpiperazin-1-yl)butyl]-3H-quinazolin-4-one,
3-ethyl-2-[4-(4-quinolin-2-ylpiperazin-1-yl)butyl]-3H-quinazolin-4-one,
6-chloro,-3-methyl-2-[4-(4-quinolin-2-ylpiperazin-1-yl)butyl]-3H-quinazolin-4-one,
3-methyl-2-[3-(4-quinolin-2-ylpiperazin-1yl)propylthio]-5,6,7,8-tetrahydro-3H-quinazolin-4-one,
3-methyl-2-[3-(4-quinolin-2-ylpiperazin-1yl)propylthio]-3H-quinazolin-4-one,
3-propyl-2-[4-(4-quinolin-2-ylpiperazin-1-yl)butyl]-5,6,7,8-tetrahydro-3H-quinazolin-4-one,
3-benzyl-2-[4-(4-quinolin-2-ylpiperazin-1-yl)butyl]-5,6,7,8-tetrahydro-3H-quinazolin-4-one,
3-methyl-2-[3-(4-quinolin-2-ylpiperazin-1-yl)propyl]-5,6,7,8-tetrahydro-3H-quinazolin-4-one,
2-[4-(4-benzothiazol-2-ylpiperazin-1-yl)butyl]-3-methyl-5,6,7,8-tetrahydro-3H-quinazolin-4-one,
2-[4-(4-benzothiazol-2-ylpiperazin-1-yl)butyl]-3-ethyl-5,6,7,8-tetrahydro-3H-quinazolin-4-one,
2-[4-(4-benzothiazol-2-ylpiperazin-1-yl)butyl]-3-benzyl-5,6,7,8-tetrahydro-3H-quinazolin-4-one,
3,6-dimethyl-2-[4-(4-quinolin-2-ylpiperazin-1-yl)butyl]-5,6,7,8-tetrahydro-3H-quinazolin-4-one,
3-ethyl-6-methyl-2-[4-(4-quinolin-2-ylpiperazin-1-yl)butyl]-5,6,7,8-tetrahydro-3H-quinazolin-4-one,
3-methyl-2-[4-)4-quinolin-2-ylpiperazin-1-yl)pentyl]-5,6,7,8-tetrahydro-3H-quinazolin-4-one,
3-isopropyl-2-[4-(4-quinolin-2-ylpiperazin-1-yl)butyl]-3H-quinazolin-4-one,
3-benzyl-2-[4-(4-quinolin-2-ylpiperazin-1-yl)butyl]-3H-quinazolin-4-one,
3-(4-methoxyphenyl)-2-[4-(4-quinolin-2-ylpiperazin-1-yl)butyl]-3H-quinazolin-4-one,
5-chloro-3-methyl-2-[4-(4-quinolin-2-ylpiperazin-1-yl)butyl]-3H-quinazolin-4-one,
1,5-dimethyl-6-[4-(4-quinolin-2-ylpiperazin-1-yl)butyl]-1,5-dihydropyrazolo[3,4-d]pyrimidin-4-one,
6,7-dimethoxy-3-methyl-2-[4-(4-quinolin-2-ylpiperazin-1-yl)butyl]-3H-quinazolin-4-one, 3,5,6-trimethyl-2-[4-(4-quinolin-2-ylpiperazin-1-yl)butyl]-3H-thieno[2,3-d]pyrimidin-4-one,
3,7-dimethyl-2-[4-(4-quinolin-2-ylpiperazin-1-yl)butyl]-3H-quinazolin-4-one,
6-bromo-3-methyl-2-[4-(4-quinolin-2-ylpiperazin-1-yl)butyl]-3H-quinazolin-4-one,
3-methyl-2-[3-(4-quinolin-2-ylpiperazin-1-yl)propylamino]-5,6,7,8-tetrahydro-3H-quinazolin-4-one, and
3-methyl-2-[3-(4-quinolin-2-ylpiperazin-1-yl)propylamine]-3H-quinazolin-4-one.

15. A method for treating irritable bowel syndrome (IBS) by exerting 5-HT$_{1A}$ agonistic activity and 5-HT$_3$ antagonistic activity in vivo simultaneously and cooperatively, which comprises
administering to a human being or other mammal who requires irritable bowel syndrome (IBS) therapy, a 5-HT$_3$ antagonistic agent which concurrently exhibits 5-HT$_{1A}$ agonistic activity,
in which the 5-HT$_3$ antagonistic agent which concurrently exhibits 5-HT$_{1A}$ is a piperazinylpyridine compound selected from the group consisting of the following compounds, or a pharmaceutically acceptable salt thereof:
7-chloro-1-(4-methylpiperazin-1-yl)isoquinoline,
7-((8aS)-octahydropyrrolo[1,2-a]pyrazin-2-yl)thieno[2,3-c]-pyridine,
7-((8aS)-octahydropyrrolo[1,2-a]pyrazin-2-yl)furo[2,3-c]-pyridine,
2-methyl-4-((8aS)-octahydropyrrolo[1,2-a]pyrazin-2-yl)-thieno[3,2-c]pyridine,
7-methoxy-1-((8aR)-octahydropyrrolo[1,2-a]pyrazin-2-yl)-isoquinoline,
2-bromo-4-(4-methylpiperazin-1-yl)thieno[3,2-c]pyridine,
7-piperazin-1-ylfuro[2,3-c]pyridine,
4-(4-methylpiperazin-1-yl)furo[2,3-c]pyridine,
7-(4-methylpiperazin-1-yl)thieno[2,3-c]pyridine,
4-(4-methylpiperazin-1-yl)thieno[3,2-c]pyridine,
3-chloro-1-(4-methylpiperazin-1-yl)isoquinoline dihydrochloride,
7-(4-ethylpiperazin-1-yl)-thieno[2,3-c]pyridine,
8-(4-methylpiperazin-1-yl)[1,7]naphthyridine,
2-methylpiperazin-1-ylfuro[3,2-c]pyridine,
7-methoxy-4-methyl-1-piperazin-1-ylisoquinoline,
7-bromo-1-piperazin-1-ylisoquinoline,
7-methoxy-1-(4-methylpiperazin-1-yl)isoquinoline,
7-methoxy-1-piperazin-1-ylisoquinoline,
1-piperazin-1-ylisoquinoline,
7-methoxy-1-(3-methylpiperazin-1-yl)isoquinoline,
6-methoxy-1-piperazin-1-ylisoquinoline,
7-methyl-1-piperazin-1-ylisoquinoline,
7-methyl-1-(4-methylpiperazin-1-yl)isoquinoline,
7-chloro-1-piperazin-1-ylisoquinoline,
7-fluoro-1-(4-methylpiperazin-1-yl)isoquinoline,
6-chloro-1-piperazin-1-ylisoquinoline,
5-chloro-1-(4-methylpiperazin-1-yl)isoquinoline,
7-fluoro-1-piperazin 1-ylisoquinoline,
1-(4-benzo[1,3]dioxol-5-ylmethylpiperazin-1-yl)-7-methoxyisoquinoline,
1-((8aS)-octahydropyrrolo[1,2-a]pyrazin-2-yl)-7-methoxyisoquinoline,
7-chloro-1-((8aS)-octahydropyrrolo[1,2-a]pyrazin-2-yl)isoquinoline,
8-((8aS)-octahydropyrrolo[1,2-a]pyrazin-2-yl)-1,7-naphthyridine,
7-chloro-1-((8aR)-octahydlropyrrolo[1,2-a]pyrazin-2-yl)isoquinoline,
7-methoxy-1-octahydropyrido[1,2-a]pyrazin-2-ylisoquinoline,
7-methylsulfanyl-1-(S)-octahydropyrido[1,2-a]pyrazin-2-ylisoquinoline,
1-(S)-octahydropyrido[1,2-a]pyran-2-yl-7-hydroxyisoquinoline,
1-(S)-octahydropyrido[1,2-a]pyran-2-yl-7-sulfamoylisoquinoline,
7-dimethylamino-1-(4-methylpiperazin-1-yl)isoquinoline,
7-hydroxy-1-piperazin-1-ylisoquinoline hydrochloride,
7-(4-fluorobenzyloxy)-1-piperazin-1-ylisoquinoline,
4-((8aS)-octahydropyrrolo[1,2-a]pyrazin-2-yl)thieno[3,2-c]pyridine,
4-((8aS)-octahydropyrrolo[1,2-a]pyrazin-2-yl)furo[3,2-c]pyridine,
2-bromo-4-((8aS)-octahydropyrrolo[1,2-a]pyrazin-2-yl)thieno[3,2-c]-pyridine,
7-((8aR)-octahydropyrrolo[1,2-a]pyrazin-2-yl)thieno[2,3-c]pyridine,
4-((8aR)-octahydropyrrolo[1,2-a]pyrazin-2-yl)thieno[3,2-c]pyridine,
7-((8aR)-octahydropyrrolo[1,2-a]pyrazin-2-yl)furo[2,3-c]pyridine,
7-((7R,8aS)-7-hydlroxyoctahydropyrrolo[1,2-a]pyrazin-2-yl)furo[2,3-c]pyridine,
7-((7R,8aS)-7-hydroxyoctahydropyrrolo[1,2-a]pyrazin-2-yl)thieno[2,3-c]pyridine,
4-((8aR)-octahydropyrrolo[1,2-a]pyrazin-2-yl)furo[3,2-c]pyridine,
4-((7R,8aS)-7-hydroxyoctahydropyrrolo[1,2-a]pyrazin-2-yl)furo[3,2-c]-pyridine,
4-((8aR)-octahydropyrrolo[1,2-a]pyrazin-2-yl)-2-methylfuro[3,2-c]pyridine,
7-((7R,8aS)-7-benzyloxyoctahydropyrrolo[1,2-a]pyrazin-2-yl)thieno-[2,3-c]pyridine,
4-((7R,8aS)-7-benzyloxyoctahydropyrrolo[1,2-a]pyrazin-2-yl)thieno-[3,2-c]pyridine,
7-octahydropyrido[1,2-a]pyrazin-2-ylfuro[2,3-c]pyridine,
4-octahydropyrido[1,2-a]pyrazin-2-ylfuro[3,2-c]pyridine,
7-octahydropyrido[1,2-a]pyrazin-2-ylthieno[2,3-c]pyridine, and
4-octahydropyrido[1,2-a]pyrazin-2-ylthieno[3,2-c]pyridine.

16. The method as set forth in claim 15, in which the 5-HT$_3$ antagonistic agent which concurrently exhibits 5-HT$_{1A}$ agonistic activity is a piperazinylpyridine compound selected from the group consisting of the following compounds, or a pharmaceutically acceptable salt thereof:
7-chloro-1-(4-methylpiperazin-1-yl)isoquinoline,
7-((8aS)-octahydropyrrolo[1,2-a]pyrazin-2-yl)thieno[2,3-c]-pyridine,
7-((8aS)-octahydropyrrolo[1,2-a]pyrazin-2-yl)furo[2,3-c]-pyridine,
2-methyl-4-((8aS)-octahydropyrrolo[1,2-a]pyrazin-2-yl)-thieno[3,2-c]pyridine,
7-methoxy-1-((8aR)-octahydropyrrolo[1,2-a]pyrazin-2-yl)-isoquinoline, and
2-bromo-4-(4-methylpiperazin-1-yl)thieno[3,2-c]pyridine.

17. A method for treating irritable bowel syndrome (IBS) by exerting 5-HT$_{1A}$ agonistic activity and 5-HT$_3$ antagonistic activity in vivo simultaneously and cooperatively, which comprises
administering to a human being or other mammal who requires irritable bowel syndrome (IBS) therapy, a 5-HT$_{1A}$ agonistic agent and a 5-HT$_3$ antagonistic agent simultaneously, or in sequence, or at an interval, in which the 5-HT$_{1A}$ agonistic agent is tandospirone, and the 5-HT$_3$ antagonistic agent is a compound selected from alosetron, granisetron, azasetron, tropisetron, ramosetron, ondansetron, lerisetron, cilansetron, itasetron, indisetron, dolasetron and (R)-zacopride.

18. A combination of medical preparations for treating irritable bowel syndrome, which comprise 5-HT$_{1A}$ agonistic agent and 5-HT$_3$ antagonistic agent, in which the 5-HT$_{1A}$ agonistic agent is tandospirone, and the 5-HT$_3$ antagonistic agent is a compound selected from the group consisting of alosetron, granisetron, azasetron, tropisetron, ramosetron, ondansetron, lerisetron, cilansetron, itasetron, indisetron, dolasetron and (R)-zacopride.

19. A pharmaceutical composition comprising a pyrimidine compound or a pharmaceutically acceptable salt thereof as set forth in claim 12 and a pharmaceutically acceptable carrier.

* * * * *